United States Patent
Rosenthal et al.

(10) Patent No.: US 12,319,734 B2
(45) Date of Patent: Jun. 3, 2025

(54) ANTI-TMEM106B ANTIBODIES AND METHODS OF USE THEREOF

(71) Applicant: ALECTOR LLC, South San Francisco, CA (US)

(72) Inventors: Arnon Rosenthal, Woodside, CA (US); Eric Brown, South San Francisco, CA (US); Tina Schwabe, San Francisco, CA (US); Angie Yee, San Francisco, CA (US); Herve Rhinn, San Francisco, CA (US)

(73) Assignee: ALECTOR LLC, South San Francisco, CA (US)

( * ) Notice: Subject to any disclaimer, the term of this patent is extended or adjusted under 35 U.S.C. 154(b) by 388 days.

(21) Appl. No.: 17/820,686

(22) Filed: Aug. 18, 2022

(65) Prior Publication Data

US 2023/0303681 A1    Sep. 28, 2023

Related U.S. Application Data

(62) Division of application No. 16/959,081, filed as application No. PCT/US2018/067236 on Dec. 21, 2018, now Pat. No. 11,440,957.

(60) Provisional application No. 62/612,098, filed on Dec. 29, 2017.

(51) Int. Cl.
*C07K 16/18* (2006.01)
*C07K 16/28* (2006.01)

(52) U.S. Cl.
CPC .......... *C07K 16/28* (2013.01); *C07K 2317/34* (2013.01); *C07K 2317/56* (2013.01)

(58) Field of Classification Search
None
See application file for complete search history.

(56) References Cited

U.S. PATENT DOCUMENTS

| 11,440,957 B2 | 9/2022 | Rosenthal et al. |
| 2017/0355756 A1 | 12/2017 | Julien et al. |
| 2020/0339680 A1 | 10/2020 | Rosenthal et al. |

FOREIGN PATENT DOCUMENTS

| WO | WO-2008068048 A2 | 6/2008 |
| WO | WO-2019133512 A1 | 7/2019 |
| WO | WO-2022197947 A1 | 9/2022 |
| WO | WO-2022204274 A1 | 9/2022 |

OTHER PUBLICATIONS

Arnett, M.J., et al., "Pro-ngf, Sortilin, and P75ntr: Potential Mediators of Injury-induced Apoptosis in the Mouse Dorsal Root Ganglion," Brain Research 1183:32-42, Elsevier, Netherlands (Dec. 2007).

Beattie, M.S., et al., "Prongf Induces P75-mediated Death of Oligodendrocytes Following Spinal Cord Injury," Neuron 36(3):375-386, Cell Press, United States (Oct. 2002).

(Continued)

*Primary Examiner* — Aurora M Fontainhas

(74) *Attorney, Agent, or Firm* — Sterne, Kessler, Goldstein & Fox P.L.L.C.

(57) ABSTRACT

The present disclosure is generally directed to compositions that include antibodies, e.g., monoclonal antibodies, antibody fragments, etc., that specifically bind a TMEM106B polypeptide, e.g., a mammalian TMEM106B or human TMEM106B, and use of such compositions in preventing, reducing risk, or treating an individual in need thereof.

27 Claims, 2 Drawing Sheets

Specification includes a Sequence Listing.

(56) References Cited

OTHER PUBLICATIONS

Brady, O.A., et al., "The Frontotemporal Lobar Degeneration Risk Factor, TMEM106B, Regulates Lysosomal Morphology and Function," Human Molecular Genetics 22(4):685-695, IRL Press, United Kingdom (Feb. 2013).
Cherry, J.D., et al., "Variation in TMEM106B in Chronic Traumatic Encephalopathy," Acta Neuropathologica Communications 6:115, BioMed Central Ltd., United Kingdom (Nov. 2018), 9 pages.
Clayton, E.L., et al., "Frontotemporal Dementia Causative CHMP2B Impairs Neuronal Endolysosomal Traffic-rescue by TMEM106B Knockdown," Brain 141(12):3428-3442, Oxford University Press, United Kingdom (Dec. 2018).
Cortes, C.J., et al., "Polyglutamine-expanded Androgen Receptor Interferes With TFEB to Elicit Autophagy Defects in SBMA," Nature Neuroscience 17(9):1180-1189, Nature Publishing Group, United Kingdom (Sep. 2014).
Cruchaga, C., et al., "Association and Expression Analyses With SNPs in TOMM40 In Alzheimer's Disease," Archives of Neurology 68(8):1013-1019, American Medical Association, United States (Aug. 2011).
Fahnestock, M., et al., "The Precursor Pro-nerve Growth Factor is the Predominant Form of Nerve Growth Factor in Brain and is Increased in Alzheimer's Disease," Molecular and Cellular Neurosciences 18(2):210-220, Academic Press, United States (Aug. 2001).
Fan, Y.J., et al., "Differential Effects of Pro-BDNF on Sensory Neurons After Sciatic Nerve Transection in Neonatal Rats," European Journal of Neuroscience 27(9):2380-2390, Wiley-Blackwell Publishing Ltd., United Kingdom (May 2008).
Finch, N., et al., "TMEM106B Regulates Progranulin Levels and the Penetrance of FTLD in GRN Mutation Carriers," Neurology 76(5):467-474, Lippincott Williams & Wilkins, United States (Feb. 2011).
Harrington, A.W., et al., "Secreted ProNGF is a Pathophysiological Death-inducing Ligand After Adult CNS Injury," Proceedings of the National Academy of Sciences of the United States of America 101(16):6226-6230, National Academy of Sciences, United States (Apr. 2004).
International Search Report and Written Opinion for Application No. PCT/US2018/067236, European Patent Office, Netherlands, mailed on Jun. 4, 2019, 15 pages.
Maximov, Anton, et al. "Monitoring synaptic transmission in primary neuronal cultures using local extracellular stimulation." Journal of neuroscience methods 161(1): 75-87, Elsevier, Netherlands (Mar. 2007).
Jansen, P., et al., "Roles for the Pro-neurotrophin Receptor Sortilin in Neuronal Development, Aging and Brain Injury," Nature Neuroscience 10(11):1449-1457, Nature Publishing Group, United Kingdom (Nov. 2007).
Kundu, S.T., et al., "TMEM106B Drives Lung Cancer Metastasis by Inducing TFEB-dependent Lysosome Synthesis and Secretion of Cathepsins," Nature Communications, 9:2731, Nature Publishing Group, United Kingdom (Jul. 2018), 16 pages.
Lang, C.M., et al., "Membrane Orientation and Subcellular Localization of Transmembrane Protein 106B (TMEM106B), a Major Risk Factor for Frontotemporal Lobar Degeneration," The Journal of Biological Chemistry 287(23):19355-19365, American Society for Biochemistry and Molecular Biology, United States (Jun. 2012).
Timmerman, Peter, Wouter C. Puijk, and Rob H. Meloen. "Functional reconstruction and synthetic mimicry of a conformational epitope using CLIPS™ technology." Journal of Molecular Recognition: An Interdisciplinary Journal 20(5): 283-299, John Wiley & Sons, Inc., United States (Sep. 2007).
Klein, Z.A., et al., "Loss of TMEM106B Ameliorates Lysosomal and Frontotemporal Dementia-Related Phenotypes in Progranulin-Deficient Mice," Neuron 95(2):281-296, Cell Press, United States (Jul. 2017).
Nakamura, K., et al., "Intracellular Sortilin Expression Pattern Regulates ProNGF-induced Naturally Occurring Cell Death During Development," Cell Death and Differentiation 14(8):1552-1554, Nature Publishing Group, United Kingdom (Aug. 2007).
Nicholson, A.M., "TMEM106B P.T185S Regulates TMEM106B Protein Levels: Implications for Frontotemporal Dementia," Journal of Neurochemistry 126(6):781-791, Wiley-Blackwell Publishing Ltd., United Kingdom (Sep. 2013).
Nicholson, A.M., et al., "What we know about TMEM106B in neurodegeneration," Acta Neuropathologica 132(5):639-651, Springer Verlag, Germany (Nov. 2016).
Nykjaer, A., et al., "Sortilin is Essential for ProNGF-induced Neuronal Cell Death," Nature 427(6977):843-848, Nature Publishing Group, United Kingdom (Feb. 2004).
Nykjaer, A., et al., "P75NTR-live or Let Die," Current Opinion in Neurobiology 15(1):49-57, Elsevier Ltd., Netherlands (Feb. 2005).
Provenzano, M.J., et al., "P75NTR and Sortilin Increase After Facial Nerve Injury," Laryngoscope 118(1):87-93, Wiley-Blackwell, United States (Jan. 2008).
White C.C., et al., "Identification of Genes Associated With Dissociation of Cognitive Performance and Neuropathological Burden: Multistep Analysis of Genetic, Epigenetic, and Transcriptional Data," PLoS Medicine 14(4):e1002287, Public Library of Science, United States (Apr. 2017), 23 pages.
Satoh, J.I., et al., "TMEM106B Expression is Reduced in Alzheimer's Disease Brains," Alzheimers Res Ther 6(2):17 BioMed Central Ltd, United Kingdom (Mar. 2014), 14 pages.
Al-Shawi, R., et al., "Neurotoxic and Neurotrophic Roles of ProNGF and the Receptor Sortilin in the Adult and Ageing Nervous System," European Journal of Neuroscience 28(9):2103-2114, Wiley-Blackwell Publishing Ltd., United Kingdom (Dec. 2008).
Teng, H.K., et al., "ProBDNF Induces Neuronal Apoptosis via Activation of a Receptor Complex of p75NTR and Sortilin," The Journal of Neuroscience 25(22):5455-5463, Society for Neuroscience, United States (Jun. 2005).
Van Der Zee, H.H. et al., "Elevated Levels of Tumour Necrosis Factor (TNF)-α,Interleukin (IL)-1β And Il-10 in Hidradenitis Suppurativa Skin: A Rationale For Targeting TNF-α And IL-1β," British Journal of Dermatologists 164(6):1292-1298, Wiley-Blackwell Publishing Ltd., United Kingdom (Jun. 2011).
Volosin, M., et al., "Induction of Proneurotrophins and Activation of p75NTR-mediated Apoptosis via Neurotrophin Receptor-interacting Factor in Hippocampal Neurons After Seizures," The Journal of Neuroscience 28(39):9870-9879, Society for Neuroscience, United States (Sep. 2008).
Volosin, M., et al., "Interaction of Survival and Death Signaling in Basal Forebrain Neurons: Roles of Neurotrophins and Proneurotrophins," The Journal of Neuroscience 26(29):7756-7766, Society for Neuroscience, United States (Jul. 2006).
Wei, Y., et al., "Enhanced Protein Expressions of Sortilin and p75NTR in Retina of Rat Following Elevated Intraocular Pressure-induced Retinal Ischemia," Neuroscience Letters 429(2-3):169-174, Elsevier Ireland Ltd., Ireland (Dec. 2007).
Yano, H., et al., "Proneurotrophin-3 Is a Neuronal Apoptotic Ligand: Evidence for Retrograde-Directed Cell Killing," The Journal of Neuroscience 29(47):14790-14802, Society for Neuroscience, United States (Nov. 2009).
Ye, J., et al., "IgBLAST: an Immunoglobulin Variable Domain Sequence Analysis Tool," Nucleic Acids Research 41:W34-W40, Oxford University Press, United Kingdom (Jul. 2013).
Schwenk, B.M., et al., "The FTLD Risk Factor TMEM106B and MAP6 Control Dendritic Trafficking of Lysosomes," EMBO Journal 33:450-467, EMBO Press, Germany (Mar. 2014).
Chen-Plotkin, A.S., et al., "TMEM106B, the Risk Gene for Frontotemporal Dementia, Is Regulated by the microRNA-132/212 Cluster and Affects Progranulin Pathways" The Journal of Neuroscience 32(33):11213-11227, Society for Neuroscience, United States (Aug. 2012).
Van Deerlin, V.M., et al., "Common variants at 7p21 are associated with frontotemporal lobar degeneration with TDP-43 inclusions" Nature Genetics 42(3): 234-239, Nature Publishing Group, United Kingdom (Mar. 2010).

(56) References Cited

OTHER PUBLICATIONS

Gallagher, M.D., et al., "TMEM106B is a genetic modifier of frontotemporal lobar degeneration with C9orf72 hexanucleotide repeat expansions" Acta Neuropathologica 127(3): 407-418, Springer Verlag, Germany (Mar. 2014).

Van Blitterswijk, M., et al., "TMEM106B protects C9ORF72 expansion carriers against frontotemporal dementia" Acta Neuropathologica 127(3): 397-406, Springer Verlag, Germany (Mar. 2014).

Vass R., et al., "Risk genotypes at TMEM106B are associated with cognitive impairment in amyotrophic lateral sclerosis," Acta Neuropathol 121:373-380 Springer Verlag, Germany (Mar. 2011).

Zarow, C., et al., "Understanding Hippocampal Sclerosis in the Elderly: Epidemiology, Characterization, and Diagnostic Issues," Current Neurology and Neuroscience 8:363-370, Springer, Germany (Sep. 2008).

Yu, L., et al., "The TMEM106B Locus and TDP-43 Pathology in Older Persons Without FTLD," Neurology 84(9):927-934, Lippincott Williams & Wilkins, United States (Mar. 2015).

Rutherford, N.J., et al., "TMEM106B Risk Variant is Implicated in the Pathologic Presentation of Alzheimer Disease," Neurology 79(7):717-718, Lippincott Williams & Wilkins, United States (Aug. 2012).

Aoki, N., et al., "Hippocampal Sclerosis in Lewy Body Disease is a TDP-43 Proteinopathy Similar to FTLD-TDP Type A," Acta Neuropathologica 129(1):53-64, Springer Verlag, Germany (Jan. 2015).

Murray., M.E., et al., "Differential Clinicopathologic and Genetic Features of Late-Onset Amnestic Dementias," Acta Neuropathologica 128(3):411-421, Springer Verlag, Germany (Sep. 2014).

Rhinn, H and Abeliovich, A., "Differential Aging Analysis in Human Cerebral Cortex Identifies Variants in TMEM106B and GRN that Regulate Aging Phenotypes," Cell Systems 4(4):404-415, Cell Press, United States (Apr. 2017).

Amador-Ortiz, C. et al., "TDP-43 immunoreactivity in hippocampal sclerosis and Alzheimer's disease," Annals of Neurology 61(5):435-445, John Wiley & Sons, Inc., United States (May 2007).

Barger, S.W., "TMEM106B and frontotemporal lobar degeneration: Can overexpression tell us how reductions are beneficial?" J Neurochem 126(6):696-698, Wiley-Blackwell Publishing Ltd., United Kingdom (Sep. 2013).

Brady, O.A., et al., "Regulated intramembrane proteolysis of the frontotemporal lobar degeneration risk factor, TMEM106B, by signal peptide peptidase-like 2a (SPPL2a)," The Journal of Biological Chemistry 289(28):19670-19680, American Society for Biochemistry and Molecular Biology Inc., United States (Jul. 2014).

Busch, J.I., et al., "Increased expression of the frontotemporal dementia risk factor TMEM106B causes C9orf72-dependent alterations in lysosomes," Human Molecular Genetics 25(13):2681-2697, Oxford University Press, United Kingdom (Apr. 2016).

Debaisieux, S., and Schiavo, G., "Time for TMEM106B," The EMBO Journal 33(5):405-406, Wiley-Blackwell, Germany (Feb. 2014).

Harding, S.R., et al., "The TMEM106B risk allele is associated with lower cortical volumes in a clinically diagnosed frontotemporal dementia cohort," J Neurol Neurosurg Psychiatry 88(11):997-999, BMJ Publishing Group, United Kingdom (Apr. 2017).

Nelson, P.T., et al., "Reassessment of risk genotypes (GRN, TMEM106B, and ABCC9 variants) associated with hippocampal sclerosis of aging pathology," J Neuropathol Exp Neurol 74(1):75-84, Oxford University Press, United Kingdom (Jan. 2015).

Zhou, X., et al., "Elevated TMEM106B levels exaggerate lipofuscin accumulation and lysosomal dysfunction in aged mice with progranulin deficiency," Acta Neuropathologica Communications 5:9, BioMed Central Ltd., United Kingdom (Jan. 2017), 11 pages.

Baggen, J., et al., "Genome-wide CRISPR screening identifies TMEM106B as a proviral host factor for SARS-CoV-2," Nature Genetics 53:435-444, and Extended Figures and Methods, Nature Publishing Group, England (Apr. 2021).

Baggen, J., et al., "Identification of TMEM106B as proviral host factor for SARS-CoV-2," bioRxiv: pp. 1-28, CSHL Press, United States (Sep. 2020).

Wang, R., et al., "Functional genomic screens identify human host factors for SARS-CoV-2 and common cold coronaviruses," bioRxiv: pp. 1-52, CSHL, United States (Sep. 2020).

Wang, R., et al., "Genetic Screens Identify Host Factors for SARS-CoV-2 and Common Cold Coronaviruses," Cell 184:106-119, and Methods and Supplemental Figures, Cell Press, United States (Jan. 2021).

Edwards et al., "The remarkable flexibility of the human antibody repertoire; isolation of over one thousand different antibodies to a single protein, BLyS.," J. Mol. Biol. 334(1):103-118, Elsevier, Netherlands (Nov. 2003).

Kussie et al., "A single engineered amino acid substitution changes antibody fine specificity," J. Immunol. 152(1):146-152, American Association of Immunologists, United States (Jan. 1994).

Koenig et al. "Mutational landscape of antibody variable domains reveals a switch modulating the interdomain conformational dynamics and antigen binding," Proceedings of the National Academy of Sciences of the United States of America 114(4):E486-E495, National Academy of Sciences, United States (Jan. 2017).

Chen et al., "Enhancement and destruction of antibody function by somatic mutation: unequal occurrence is controlled by V gene combinatorial associations," The EMBO Journal 14(12):2784-2794, EMBO Press, Germany (Jun. 1995).

International Search Report and Written Opinion for Application No. PCT/US2022/020785, European Patent Office, Netherlands, mailed on Aug. 30, 2022, 22 pages.

Gershoni et al., "Epitope mapping—The first step in developing epitope-based vaccines", Biodrugs, 21(3):145-156, Springer Nature, Germany (May 2007).

International Search Report and Written Opinion for Application No. PCT/US2022/021533, European Patent Office, Netherlands, mailed on Jun. 22, 2022, 17 pages.

Kundu et al., "Abstract 688: Identifying TMEM106B as a novel metastasis driver in non-small cell lung cancers through an in vivo gain-of-function screen", Cancer Res 76(14_Supplement):688, 4 pages, American Association for Cancer Research, United States (2016).

Yune et al., "Minocycline Alleviates Death of Oligodendrocytes by Inhibiting Pro-Nerve Growth Factor Production in Microglia after Spinal Cord Injury," Journal of Neuroscience 27(29):7751-7761, Society for Neuroscience, United States (Jul. 2007).

Office Action mailed Nov. 8, 2021 in U.S. Appl. No. 16/959,081, inventors Rosenthal et al., 371(c) Date: Jun. 29, 2020, 17 pages.

```
                        SEQUENCE LISTING

Sequence total quantity: 349
SEQ ID NO: 1            moltype = AA  length = 274
FEATURE                 Location/Qualifiers
source                  1..274
                        mol_type = protein
                        organism = Homo sapiens
SEQUENCE: 1
MGKSLSHLPL HSSKEDAYDG VTSENMRNGL VNSEVHNEDG RNGDVSQFPY VEFTGRDSVT   60
CPTCQGTGRI PRGQENQLVA LIPYSDQRLR PRRTKLYVMA SVFVCLLLSG LAVFFLFPRS  120
IDVKYIGVKS AYVSYDVQKR TIYLNITNTL NITNNNYYSV EVENITAQVQ FSKTVIGKAR  180
LNNITIIGPL DMKQIDYTVP TVIAEEMSYM YDFCTLISIK VHNIVLMMQV TVTTTYFGHS  240
EQISQERYQY VDCGRNTTYQ LGQSEYLNVL QPQQ                             274

SEQ ID NO: 2            moltype = AA  length = 274
FEATURE                 Location/Qualifiers
source                  1..274
                        mol_type = protein
                        organism = Mus musculus
SEQUENCE: 2
GKSLSHLPLH SNKEDGYDGV TSTDNMRNGL VSSEVHNEDG RNGDVSQFPY VEFTGRDSVT   60
CPTCQGTGRI PRGQENQLVA LIPYSDQRLR PRRTKLYVMA SVFVCLLLSG LAVFFLFPRS  120
IEVKYIGVKS AYVSYDAEKR TIYLNITNTL NITNNNYYSV EVENITAQVQ FSKTVIGKAR  180
LNNITNIGPL DMKQIDYTVP TVIAEEMSYM YDFCTLLSIK VHNIVLMMQV TVTTAYFGHS  240
EQISQERYQY VDCGRNTTYQ LAQSEYLNVL QPQQ                             274

SEQ ID NO: 3            moltype = AA  length = 5
FEATURE                 Location/Qualifiers
REGION                  1..5
                        note = Synthetic Construct
source                  1..5
                        mol_type = protein
                        organism = synthetic construct
SEQUENCE: 3
NYLIE                                                               5

SEQ ID NO: 4            moltype = AA  length = 5
FEATURE                 Location/Qualifiers
```

```
REGION                    1..5
                          note = Synthetic Construct
source                    1..5
                          mol_type = protein
                          organism = synthetic construct
SEQUENCE: 4
EYPMH                                                                    5

SEQ ID NO: 5              moltype = AA  length = 7
FEATURE                   Location/Qualifiers
REGION                    1..7
                          note = Synthetic Construct
source                    1..7
                          mol_type = protein
                          organism = synthetic construct
SEQUENCE: 5
TLGRGVG                                                                  7

SEQ ID NO: 6              moltype = AA  length = 5
FEATURE                   Location/Qualifiers
REGION                    1..5
                          note = Synthetic Construct
source                    1..5
                          mol_type = protein
                          organism = synthetic construct
SEQUENCE: 6
DYYMN                                                                    5

SEQ ID NO: 7              moltype = AA  length = 5
FEATURE                   Location/Qualifiers
REGION                    1..5
                          note = Synthetic Construct
source                    1..5
                          mol_type = protein
                          organism = synthetic construct
SEQUENCE: 7
TYGIT                                                                    5

SEQ ID NO: 8              moltype = AA  length = 5
FEATURE                   Location/Qualifiers
REGION                    1..5
                          note = Synthetic Construct
source                    1..5
                          mol_type = protein
                          organism = synthetic construct
SEQUENCE: 8
EYTIH                                                                    5

SEQ ID NO: 9              moltype = AA  length = 5
FEATURE                   Location/Qualifiers
REGION                    1..5
                          note = Synthetic Construct
source                    1..5
                          mol_type = protein
                          organism = synthetic construct
SEQUENCE: 9
DYYIH                                                                    5

SEQ ID NO: 10             moltype = AA  length = 5
FEATURE                   Location/Qualifiers
REGION                    1..5
                          note = Synthetic Construct
source                    1..5
                          mol_type = protein
                          organism = synthetic construct
SEQUENCE: 10
DYPMH                                                                    5

SEQ ID NO: 11             moltype = AA  length = 5
FEATURE                   Location/Qualifiers
REGION                    1..5
                          note = Synthetic Construct
source                    1..5
                          mol_type = protein
                          organism = synthetic construct
SEQUENCE: 11
GYGMS                                                                    5

SEQ ID NO: 12             moltype = AA  length = 5
```

```
                            -continued

FEATURE              Location/Qualifiers
REGION               1..5
                     note = Synthetic Construct
source               1..5
                     mol_type = protein
                     organism = synthetic construct
SEQUENCE: 12
SYWMN                                                                5

SEQ ID NO: 13        moltype = AA  length = 5
FEATURE              Location/Qualifiers
REGION               1..5
                     note = Synthetic Construct
source               1..5
                     mol_type = protein
                     organism = synthetic construct
SEQUENCE: 13
DYGVH                                                                5

SEQ ID NO: 14        moltype = AA  length = 5
FEATURE              Location/Qualifiers
REGION               1..5
                     note = Synthetic Construct
source               1..5
                     mol_type = protein
                     organism = synthetic construct
SEQUENCE: 14
DYYMY                                                                5

SEQ ID NO: 15        moltype = AA  length = 5
FEATURE              Location/Qualifiers
REGION               1..5
                     note = Synthetic Construct
source               1..5
                     mol_type = protein
                     organism = synthetic construct
SEQUENCE: 15
TFPIE                                                                5

SEQ ID NO: 16        moltype = AA  length = 5
FEATURE              Location/Qualifiers
REGION               1..5
                     note = Synthetic Construct
source               1..5
                     mol_type = protein
                     organism = synthetic construct
SEQUENCE: 16
NYWIT                                                                5

SEQ ID NO: 17        moltype = AA  length = 5
FEATURE              Location/Qualifiers
REGION               1..5
                     note = Synthetic Construct
source               1..5
                     mol_type = protein
                     organism = synthetic construct
SEQUENCE: 17
DYYMH                                                                5

SEQ ID NO: 18        moltype = AA  length = 5
FEATURE              Location/Qualifiers
REGION               1..5
                     note = Synthetic Construct
source               1..5
                     mol_type = protein
                     organism = synthetic construct
SEQUENCE: 18
DYLIE                                                                5

SEQ ID NO: 19        moltype = AA  length = 5
FEATURE              Location/Qualifiers
REGION               1..5
                     note = Synthetic Construct
source               1..5
                     mol_type = protein
                     organism = synthetic construct
SEQUENCE: 19
NYAMS                                                                5
```

```
SEQ ID NO: 20         moltype = AA  length = 5
FEATURE               Location/Qualifiers
REGION                1..5
                      note = Synthetic Construct
source                1..5
                      mol_type = protein
                      organism = synthetic construct
SEQUENCE: 20
SYYIH                                                                    5

SEQ ID NO: 21         moltype = AA  length = 5
FEATURE               Location/Qualifiers
REGION                1..5
                      note = Synthetic Construct
source                1..5
                      mol_type = protein
                      organism = synthetic construct
SEQUENCE: 21
DYYIN                                                                    5

SEQ ID NO: 22         moltype = AA  length = 5
FEATURE               Location/Qualifiers
REGION                1..5
                      note = Synthetic Construct
source                1..5
                      mol_type = protein
                      organism = synthetic construct
SEQUENCE: 22
NYDVN                                                                    5

SEQ ID NO: 23         moltype = AA  length = 5
FEATURE               Location/Qualifiers
REGION                1..5
                      note = Synthetic Construct
source                1..5
                      mol_type = protein
                      organism = synthetic construct
SEQUENCE: 23
DYNMN                                                                    5

SEQ ID NO: 24         moltype = AA  length = 5
FEATURE               Location/Qualifiers
REGION                1..5
                      note = Synthetic Construct
source                1..5
                      mol_type = protein
                      organism = synthetic construct
SEQUENCE: 24
DSGMD                                                                    5

SEQ ID NO: 25         moltype = AA  length = 5
FEATURE               Location/Qualifiers
REGION                1..5
                      note = Synthetic Construct
source                1..5
                      mol_type = protein
                      organism = synthetic construct
SEQUENCE: 25
RHWMQ                                                                    5

SEQ ID NO: 26         moltype = AA  length = 5
FEATURE               Location/Qualifiers
REGION                1..5
                      note = Synthetic Construct
source                1..5
                      mol_type = protein
                      organism = synthetic construct
SEQUENCE: 26
SYWMH                                                                    5

SEQ ID NO: 27         moltype = AA  length = 5
FEATURE               Location/Qualifiers
REGION                1..5
                      note = Synthetic Construct
source                1..5
                      mol_type = protein
                      organism = synthetic construct
SEQUENCE: 27
DYWMH                                                                    5
```

```
SEQ ID NO: 28          moltype = AA   length = 5
FEATURE                Location/Qualifiers
REGION                 1..5
                       note = Synthetic Construct
source                 1..5
                       mol_type = protein
                       organism = synthetic construct
SEQUENCE: 28
DCYMH                                                                      5

SEQ ID NO: 29          moltype = AA   length = 5
FEATURE                Location/Qualifiers
REGION                 1..5
                       note = Synthetic Construct
source                 1..5
                       mol_type = protein
                       organism = synthetic construct
SEQUENCE: 29
NYWMH                                                                      5

SEQ ID NO: 30          moltype = AA   length = 5
FEATURE                Location/Qualifiers
REGION                 1..5
                       note = Synthetic Construct
source                 1..5
                       mol_type = protein
                       organism = synthetic construct
SEQUENCE: 30
DYGMH                                                                      5

SEQ ID NO: 31          moltype = AA   length = 5
FEATURE                Location/Qualifiers
REGION                 1..5
                       note = Synthetic Construct
source                 1..5
                       mol_type = protein
                       organism = synthetic construct
SEQUENCE: 31
SFWMN                                                                      5

SEQ ID NO: 32          moltype = AA   length = 5
FEATURE                Location/Qualifiers
REGION                 1..5
                       note = Synthetic Construct
source                 1..5
                       mol_type = protein
                       organism = synthetic construct
SEQUENCE: 32
NYGVH                                                                      5

SEQ ID NO: 33          moltype = AA   length = 5
FEATURE                Location/Qualifiers
REGION                 1..5
                       note = Synthetic Construct
source                 1..5
                       mol_type = protein
                       organism = synthetic construct
SEQUENCE: 33
SYDIN                                                                      5

SEQ ID NO: 34          moltype = AA   length = 5
FEATURE                Location/Qualifiers
REGION                 1..5
                       note = Synthetic Construct
source                 1..5
                       mol_type = protein
                       organism = synthetic construct
SEQUENCE: 34
RFWMH                                                                      5

SEQ ID NO: 35          moltype = AA   length = 5
FEATURE                Location/Qualifiers
REGION                 1..5
                       note = Synthetic Construct
source                 1..5
                       mol_type = protein
                       organism = synthetic construct
SEQUENCE: 35
```

TYWID                                                                        5

SEQ ID NO: 36         moltype = AA  length = 17
FEATURE               Location/Qualifiers
REGION                1..17
                      note = Synthetic Construct
source                1..17
                      mol_type = protein
                      organism = synthetic construct
SEQUENCE: 36
VINPGSGGTK YNEKLKG                                                          17

SEQ ID NO: 37         moltype = AA  length = 17
FEATURE               Location/Qualifiers
REGION                1..17
                      note = Synthetic Construct
source                1..17
                      mol_type = protein
                      organism = synthetic construct
SEQUENCE: 37
MIYTNTGEPT YAAEFKG                                                          17

SEQ ID NO: 38         moltype = AA  length = 16
FEATURE               Location/Qualifiers
REGION                1..16
                      note = Synthetic Construct
source                1..16
                      mol_type = protein
                      organism = synthetic construct
SEQUENCE: 38
KIWWNDDKFY YPALKS                                                           16

SEQ ID NO: 39         moltype = AA  length = 17
FEATURE               Location/Qualifiers
REGION                1..17
                      note = Synthetic Construct
source                1..17
                      mol_type = protein
                      organism = synthetic construct
SEQUENCE: 39
VINPYNGGTS YHQKFKG                                                          17

SEQ ID NO: 40         moltype = AA  length = 17
FEATURE               Location/Qualifiers
REGION                1..17
                      note = Synthetic Construct
source                1..17
                      mol_type = protein
                      organism = synthetic construct
SEQUENCE: 40
EIYPRSDNTY YNEKFKD                                                          17

SEQ ID NO: 41         moltype = AA  length = 17
FEATURE               Location/Qualifiers
REGION                1..17
                      note = Synthetic Construct
source                1..17
                      mol_type = protein
                      organism = synthetic construct
SEQUENCE: 41
WFYPGSTYID YNEKFKD                                                          17

SEQ ID NO: 42         moltype = AA  length = 17
FEATURE               Location/Qualifiers
REGION                1..17
                      note = Synthetic Construct
source                1..17
                      mol_type = protein
                      organism = synthetic construct
SEQUENCE: 42
LVYPYNGDTD YNQKFKG                                                          17

SEQ ID NO: 43         moltype = AA  length = 17
FEATURE               Location/Qualifiers
REGION                1..17
                      note = Synthetic Construct
source                1..17
                      mol_type = protein
                      organism = synthetic construct

```
SEQUENCE: 43
VIYTDTGEPK YAEVFKG                                                              17

SEQ ID NO: 44           moltype = AA  length = 17
FEATURE                 Location/Qualifiers
REGION                  1..17
                        note = Synthetic Construct
source                  1..17
                        mol_type = protein
                        organism = synthetic construct
SEQUENCE: 44
TISSGSFYIY YPDSVKG                                                              17

SEQ ID NO: 45           moltype = AA  length = 17
FEATURE                 Location/Qualifiers
REGION                  1..17
                        note = Synthetic Construct
source                  1..17
                        mol_type = protein
                        organism = synthetic construct
SEQUENCE: 45
QIYPGDGDTN YNGKFKG                                                              17

SEQ ID NO: 46           moltype = AA  length = 16
FEATURE                 Location/Qualifiers
REGION                  1..16
                        note = Synthetic Construct
source                  1..16
                        mol_type = protein
                        organism = synthetic construct
SEQUENCE: 46
VIWNNGNTDY NAAFIS                                                               16

SEQ ID NO: 47           moltype = AA  length = 17
FEATURE                 Location/Qualifiers
REGION                  1..17
                        note = Synthetic Construct
source                  1..17
                        mol_type = protein
                        organism = synthetic construct
SEQUENCE: 47
RIDPEDGDAE YAPKFQG                                                              17

SEQ ID NO: 48           moltype = AA  length = 17
FEATURE                 Location/Qualifiers
REGION                  1..17
                        note = Synthetic Construct
source                  1..17
                        mol_type = protein
                        organism = synthetic construct
SEQUENCE: 48
NFHPYNDDTK YNEKFKG                                                              17

SEQ ID NO: 49           moltype = AA  length = 17
FEATURE                 Location/Qualifiers
REGION                  1..17
                        note = Synthetic Construct
source                  1..17
                        mol_type = protein
                        organism = synthetic construct
SEQUENCE: 49
VINPGGGNTD YSEKFKD                                                              17

SEQ ID NO: 50           moltype = AA  length = 17
FEATURE                 Location/Qualifiers
REGION                  1..17
                        note = Synthetic Construct
source                  1..17
                        mol_type = protein
                        organism = synthetic construct
SEQUENCE: 50
DIYPGSGNSN YNESFKR                                                              17

SEQ ID NO: 51           moltype = AA  length = 17
FEATURE                 Location/Qualifiers
REGION                  1..17
                        note = Synthetic Construct
source                  1..17
                        mol_type = protein
```

```
                        organism = synthetic construct
SEQUENCE: 51
RIDPEDGETK YAPEFQG                                                       17

SEQ ID NO: 52           moltype = AA  length = 17
FEATURE                 Location/Qualifiers
REGION                  1..17
                        note = Synthetic Construct
source                  1..17
                        mol_type = protein
                        organism = synthetic construct
SEQUENCE: 52
VINPGSGGTN YNEKFKG                                                       17

SEQ ID NO: 53           moltype = AA  length = 17
FEATURE                 Location/Qualifiers
REGION                  1..17
                        note = Synthetic Construct
source                  1..17
                        mol_type = protein
                        organism = synthetic construct
SEQUENCE: 53
NINPNNGDAF YNQKFKG                                                       17

SEQ ID NO: 54           moltype = AA  length = 17
FEATURE                 Location/Qualifiers
REGION                  1..17
                        note = Synthetic Construct
source                  1..17
                        mol_type = protein
                        organism = synthetic construct
SEQUENCE: 54
RIDPEDGDTE NAPKFRG                                                       17

SEQ ID NO: 55           moltype = AA  length = 17
FEATURE                 Location/Qualifiers
REGION                  1..17
                        note = Synthetic Construct
source                  1..17
                        mol_type = protein
                        organism = synthetic construct
SEQUENCE: 55
FISDGGGYIY YADNVKD                                                       17

SEQ ID NO: 56           moltype = AA  length = 17
FEATURE                 Location/Qualifiers
REGION                  1..17
                        note = Synthetic Construct
source                  1..17
                        mol_type = protein
                        organism = synthetic construct
SEQUENCE: 56
WIYPGNGITN YNEKFKG                                                       17

SEQ ID NO: 57           moltype = AA  length = 17
FEATURE                 Location/Qualifiers
REGION                  1..17
                        note = Synthetic Construct
source                  1..17
                        mol_type = protein
                        organism = synthetic construct
SEQUENCE: 57
VINPGSGITN YNEKFKG                                                       17

SEQ ID NO: 58           moltype = AA  length = 17
FEATURE                 Location/Qualifiers
REGION                  1..17
                        note = Synthetic Construct
source                  1..17
                        mol_type = protein
                        organism = synthetic construct
SEQUENCE: 58
TISSGGRYTV YPDSVKG                                                       17

SEQ ID NO: 59           moltype = AA  length = 17
FEATURE                 Location/Qualifiers
REGION                  1..17
                        note = Synthetic Construct
source                  1..17
```

```
                        mol_type = protein
                        organism = synthetic construct
SEQUENCE: 59
VINPGSGSTK YNEKFKG                                                    17

SEQ ID NO: 60           moltype = AA  length = 17
FEATURE                 Location/Qualifiers
REGION                  1..17
                        note = Synthetic Construct
source                  1..17
                        mol_type = protein
                        organism = synthetic construct
SEQUENCE: 60
LVYPYNGGTN YNQNFKG                                                    17

SEQ ID NO: 61           moltype = AA  length = 17
FEATURE                 Location/Qualifiers
REGION                  1..17
                        note = Synthetic Construct
source                  1..17
                        mol_type = protein
                        organism = synthetic construct
SEQUENCE: 61
RIYPGSGYTY YNEKFKG                                                    17

SEQ ID NO: 62           moltype = AA  length = 17
FEATURE                 Location/Qualifiers
REGION                  1..17
                        note = Synthetic Construct
source                  1..17
                        mol_type = protein
                        organism = synthetic construct
SEQUENCE: 62
WIYPRDGTTI YNEKFKG                                                    17

SEQ ID NO: 63           moltype = AA  length = 17
FEATURE                 Location/Qualifiers
REGION                  1..17
                        note = Synthetic Construct
source                  1..17
                        mol_type = protein
                        organism = synthetic construct
SEQUENCE: 63
YINPTSGYTR YNQKFKD                                                    17

SEQ ID NO: 64           moltype = AA  length = 17
FEATURE                 Location/Qualifiers
REGION                  1..17
                        note = Synthetic Construct
source                  1..17
                        mol_type = protein
                        organism = synthetic construct
SEQUENCE: 64
RIDPEDGDTE YVPKFQG                                                    17

SEQ ID NO: 65           moltype = AA  length = 17
FEATURE                 Location/Qualifiers
REGION                  1..17
                        note = Synthetic Construct
source                  1..17
                        mol_type = protein
                        organism = synthetic construct
SEQUENCE: 65
VINPNYGTTS YNQKFKG                                                    17

SEQ ID NO: 66           moltype = AA  length = 17
FEATURE                 Location/Qualifiers
REGION                  1..17
                        note = Synthetic Construct
source                  1..17
                        mol_type = protein
                        organism = synthetic construct
SEQUENCE: 66
YISSGSSTTH YADTVKG                                                    17

SEQ ID NO: 67           moltype = AA  length = 17
FEATURE                 Location/Qualifiers
REGION                  1..17
                        note = Synthetic Construct
```

```
source                  1..17
                        mol_type = protein
                        organism = synthetic construct
SEQUENCE: 67
EILPGSNNIY YNEKVKG                                                     17

SEQ ID NO: 68           moltype = AA  length = 17
FEATURE                 Location/Qualifiers
REGION                  1..17
                        note = Synthetic Construct
source                  1..17
                        mol_type = protein
                        organism = synthetic construct
SEQUENCE: 68
YVNPSSGYTK NNQKFKD                                                     17

SEQ ID NO: 69           moltype = AA  length = 17
FEATURE                 Location/Qualifiers
REGION                  1..17
                        note = Synthetic Construct
source                  1..17
                        mol_type = protein
                        organism = synthetic construct
SEQUENCE: 69
FINPSSGYTK YNQNFKD                                                     17

SEQ ID NO: 70           moltype = AA  length = 17
FEATURE                 Location/Qualifiers
REGION                  1..17
                        note = Synthetic Construct
source                  1..17
                        mol_type = protein
                        organism = synthetic construct
SEQUENCE: 70
RIDPEDGTTN FAPKFQD                                                     17

SEQ ID NO: 71           moltype = AA  length = 17
FEATURE                 Location/Qualifiers
REGION                  1..17
                        note = Synthetic Construct
source                  1..17
                        mol_type = protein
                        organism = synthetic construct
SEQUENCE: 71
YINPSSGYTK YNQKFKD                                                     17

SEQ ID NO: 72           moltype = AA  length = 17
FEATURE                 Location/Qualifiers
REGION                  1..17
                        note = Synthetic Construct
source                  1..17
                        mol_type = protein
                        organism = synthetic construct
SEQUENCE: 72
YISSGSSTIY YADTVKG                                                     17

SEQ ID NO: 73           moltype = AA  length = 17
FEATURE                 Location/Qualifiers
REGION                  1..17
                        note = Synthetic Construct
source                  1..17
                        mol_type = protein
                        organism = synthetic construct
SEQUENCE: 73
QIYPGDGDTD YNGKFKD                                                     17

SEQ ID NO: 74           moltype = AA  length = 16
FEATURE                 Location/Qualifiers
REGION                  1..16
                        note = Synthetic Construct
source                  1..16
                        mol_type = protein
                        organism = synthetic construct
SEQUENCE: 74
VIWAGGNTNY NSALMS                                                      16

SEQ ID NO: 75           moltype = AA  length = 17
FEATURE                 Location/Qualifiers
REGION                  1..17
```

```
                        note = Synthetic Construct
source                  1..17
                        mol_type = protein
                        organism = synthetic construct
SEQUENCE: 75
WIYPRDGNTQ YIEKLKG                                                      17

SEQ ID NO: 76           moltype = AA  length = 17
FEATURE                 Location/Qualifiers
REGION                  1..17
                        note = Synthetic Construct
source                  1..17
                        mol_type = protein
                        organism = synthetic construct
SEQUENCE: 76
NIDPSDSQTH YNQKFKD                                                      17

SEQ ID NO: 77           moltype = AA  length = 17
FEATURE                 Location/Qualifiers
REGION                  1..17
                        note = Synthetic Construct
source                  1..17
                        mol_type = protein
                        organism = synthetic construct
SEQUENCE: 77
NMFPGSSRTN YNEKFKS                                                      17

SEQ ID NO: 78           moltype = AA  length = 17
FEATURE                 Location/Qualifiers
REGION                  1..17
                        note = Synthetic Construct
source                  1..17
                        mol_type = protein
                        organism = synthetic construct
SEQUENCE: 78
NIDPSDSETH YNQKFKD                                                      17

SEQ ID NO: 79           moltype = AA  length = 13
FEATURE                 Location/Qualifiers
REGION                  1..13
                        note = Synthetic Construct
source                  1..13
                        mol_type = protein
                        organism = synthetic construct
SEQUENCE: 79
RGYTIYDFYA MDY                                                          13

SEQ ID NO: 80           moltype =     length =
SEQUENCE: 80
000

SEQ ID NO: 81           moltype = AA  length = 9
FEATURE                 Location/Qualifiers
REGION                  1..9
                        note = Synthetic Construct
source                  1..9
                        mol_type = protein
                        organism = synthetic construct
SEQUENCE: 81
IAGGTGAAY                                                               9

SEQ ID NO: 82           moltype = AA  length = 10
FEATURE                 Location/Qualifiers
REGION                  1..10
                        note = Synthetic Construct
source                  1..10
                        mol_type = protein
                        organism = synthetic construct
SEQUENCE: 82
AATVVAGFDY                                                              10

SEQ ID NO: 83           moltype = AA  length = 9
FEATURE                 Location/Qualifiers
REGION                  1..9
                        note = Synthetic Construct
source                  1..9
                        mol_type = protein
                        organism = synthetic construct
SEQUENCE: 83
```

-continued

```
SKGSGTGDY                                                                            9

SEQ ID NO: 84           moltype = AA  length = 11
FEATURE                 Location/Qualifiers
REGION                  1..11
                        note = Synthetic Construct
source                  1..11
                        mol_type = protein
                        organism = synthetic construct
SEQUENCE: 84
HEEDYSNWFP F                                                                        11

SEQ ID NO: 85           moltype = AA  length = 9
FEATURE                 Location/Qualifiers
REGION                  1..9
                        note = Synthetic Construct
source                  1..9
                        mol_type = protein
                        organism = synthetic construct
SEQUENCE: 85
TYYANSPDY                                                                            9

SEQ ID NO: 86           moltype = AA  length = 4
FEATURE                 Location/Qualifiers
REGION                  1..4
                        note = Synthetic Construct
source                  1..4
                        mol_type = protein
                        organism = synthetic construct
SEQUENCE: 86
RLAY                                                                                 4

SEQ ID NO: 87           moltype = AA  length = 10
FEATURE                 Location/Qualifiers
REGION                  1..10
                        note = Synthetic Construct
source                  1..10
                        mol_type = protein
                        organism = synthetic construct
SEQUENCE: 87
QNFYYGCEDY                                                                          10

SEQ ID NO: 88           moltype = AA  length = 10
FEATURE                 Location/Qualifiers
REGION                  1..10
                        note = Synthetic Construct
source                  1..10
                        mol_type = protein
                        organism = synthetic construct
SEQUENCE: 88
WGHYDEAMDD                                                                          10

SEQ ID NO: 89           moltype = AA  length = 9
FEATURE                 Location/Qualifiers
REGION                  1..9
                        note = Synthetic Construct
source                  1..9
                        mol_type = protein
                        organism = synthetic construct
SEQUENCE: 89
SLRPLHFDY                                                                            9

SEQ ID NO: 90           moltype = AA  length = 13
FEATURE                 Location/Qualifiers
REGION                  1..13
                        note = Synthetic Construct
source                  1..13
                        mol_type = protein
                        organism = synthetic construct
SEQUENCE: 90
RVIYDGYYRT MDC                                                                      13

SEQ ID NO: 91           moltype = AA  length = 8
FEATURE                 Location/Qualifiers
REGION                  1..8
                        note = Synthetic Construct
source                  1..8
                        mol_type = protein
                        organism = synthetic construct
```

```
SEQUENCE: 91
YFYGGMDY                                                                                8

SEQ ID NO: 92           moltype = AA  length = 13
FEATURE                 Location/Qualifiers
REGION                  1..13
                        note = Synthetic Construct
source                  1..13
                        mol_type = protein
                        organism = synthetic construct
SEQUENCE: 92
SPYSSYVGYA VDY                                                                         13

SEQ ID NO: 93           moltype = AA  length = 8
FEATURE                 Location/Qualifiers
REGION                  1..8
                        note = Synthetic Construct
source                  1..8
                        mol_type = protein
                        organism = synthetic construct
SEQUENCE: 93
KAYGGFPY                                                                                8

SEQ ID NO: 94           moltype = AA  length = 6
FEATURE                 Location/Qualifiers
REGION                  1..6
                        note = Synthetic Construct
source                  1..6
                        mol_type = protein
                        organism = synthetic construct
SEQUENCE: 94
SQPFTY                                                                                  6

SEQ ID NO: 95           moltype = AA  length = 13
FEATURE                 Location/Qualifiers
REGION                  1..13
                        note = Synthetic Construct
source                  1..13
                        mol_type = protein
                        organism = synthetic construct
SEQUENCE: 95
SSYGVYVAYP MDY                                                                         13

SEQ ID NO: 96           moltype = AA  length = 14
FEATURE                 Location/Qualifiers
REGION                  1..14
                        note = Synthetic Construct
source                  1..14
                        mol_type = protein
                        organism = synthetic construct
SEQUENCE: 96
EGQLRLRRVY AMDY                                                                        14

SEQ ID NO: 97           moltype = AA  length = 11
FEATURE                 Location/Qualifiers
REGION                  1..11
                        note = Synthetic Construct
source                  1..11
                        mol_type = protein
                        organism = synthetic construct
SEQUENCE: 97
RIGNLYHVMD Y                                                                           11

SEQ ID NO: 98           moltype = AA  length = 8
FEATURE                 Location/Qualifiers
REGION                  1..8
                        note = Synthetic Construct
source                  1..8
                        mol_type = protein
                        organism = synthetic construct
SEQUENCE: 98
DGGTGFTY                                                                                8

SEQ ID NO: 99           moltype = AA  length = 12
FEATURE                 Location/Qualifiers
REGION                  1..12
                        note = Synthetic Construct
source                  1..12
                        mol_type = protein
```

```
                                                       -continued

SEQUENCE: 99
PYYGIRNCYF DV                                                    12

SEQ ID NO: 100         moltype = AA   length = 11
FEATURE                Location/Qualifiers
REGION                 1..11
                       note = Synthetic Construct
source                 1..11
                       mol_type = protein
                       organism = synthetic construct
SEQUENCE: 100
SDFITTVVAD Y                                                     11

SEQ ID NO: 101         moltype = AA   length = 10
FEATURE                Location/Qualifiers
REGION                 1..10
                       note = Synthetic Construct
source                 1..10
                       mol_type = protein
                       organism = synthetic construct
SEQUENCE: 101
DNFYSYAMDY                                                       10

SEQ ID NO: 102         moltype = AA   length = 11
FEATURE                Location/Qualifiers
REGION                 1..11
                       note = Synthetic Construct
source                 1..11
                       mol_type = protein
                       organism = synthetic construct
SEQUENCE: 102
IIYDHDWYFD V                                                     11

SEQ ID NO: 103         moltype = AA   length = 9
FEATURE                Location/Qualifiers
REGION                 1..9
                       note = Synthetic Construct
source                 1..9
                       mol_type = protein
                       organism = synthetic construct
SEQUENCE: 103
SYFSNPIGY                                                         9

SEQ ID NO: 104         moltype = AA   length = 8
FEATURE                Location/Qualifiers
REGION                 1..8
                       note = Synthetic Construct
source                 1..8
                       mol_type = protein
                       organism = synthetic construct
SEQUENCE: 104
HYTNPFAY                                                          8

SEQ ID NO: 105         moltype = AA   length = 8
FEATURE                Location/Qualifiers
REGION                 1..8
                       note = Synthetic Construct
source                 1..8
                       mol_type = protein
                       organism = synthetic construct
SEQUENCE: 105
TLPQAMDY                                                          8

SEQ ID NO: 106         moltype = AA   length = 13
FEATURE                Location/Qualifiers
REGION                 1..13
                       note = Synthetic Construct
source                 1..13
                       mol_type = protein
                       organism = synthetic construct
SEQUENCE: 106
SPPTVVLIGY FDY                                                   13

SEQ ID NO: 107         moltype = AA   length = 11
FEATURE                Location/Qualifiers
REGION                 1..11
                       note = Synthetic Construct
source                 1..11
```

```
                                mol_type = protein
                                organism = synthetic construct
SEQUENCE: 107
RTWDLYYAVD N                                                              11

SEQ ID NO: 108       moltype =    length =
SEQUENCE: 108
000

SEQ ID NO: 109       moltype = AA   length = 10
FEATURE              Location/Qualifiers
REGION               1..10
                     note = Synthetic Construct
source               1..10
                     mol_type = protein
                     organism = synthetic construct
SEQUENCE: 109
RDGNYWYFDV                                                                10

SEQ ID NO: 110       moltype = AA   length = 11
FEATURE              Location/Qualifiers
REGION               1..11
                     note = Synthetic Construct
source               1..11
                     mol_type = protein
                     organism = synthetic construct
SEQUENCE: 110
SLYDYDGVFA Y                                                              11

SEQ ID NO: 111       moltype = AA   length = 12
FEATURE              Location/Qualifiers
REGION               1..12
                     note = Synthetic Construct
source               1..12
                     mol_type = protein
                     organism = synthetic construct
SEQUENCE: 111
EGGSISDWYF DV                                                             12

SEQ ID NO: 112       moltype = AA   length = 12
FEATURE              Location/Qualifiers
REGION               1..12
                     note = Synthetic Construct
source               1..12
                     mol_type = protein
                     organism = synthetic construct
SEQUENCE: 112
EAGSISDWYF DV                                                             12

SEQ ID NO: 113       moltype = AA   length = 7
FEATURE              Location/Qualifiers
REGION               1..7
                     note = Synthetic Construct
source               1..7
                     mol_type = protein
                     organism = synthetic construct
SEQUENCE: 113
EWDSGAY                                                                    7

SEQ ID NO: 114       moltype = AA   length = 10
FEATURE              Location/Qualifiers
REGION               1..10
                     note = Synthetic Construct
source               1..10
                     mol_type = protein
                     organism = synthetic construct
SEQUENCE: 114
NYGSPYAMDY                                                                10

SEQ ID NO: 115       moltype = AA   length = 9
FEATURE              Location/Qualifiers
REGION               1..9
                     note = Synthetic Construct
source               1..9
                     mol_type = protein
                     organism = synthetic construct
SEQUENCE: 115
GDGFSYFDY                                                                  9
```

```
SEQ ID NO: 116          moltype = AA   length = 12
FEATURE                 Location/Qualifiers
REGION                  1..12
                        note = Synthetic Construct
source                  1..12
                        mol_type = protein
                        organism = synthetic construct
SEQUENCE: 116
EAKLLRSYAM DY                                                              12

SEQ ID NO: 117          moltype = AA   length = 8
FEATURE                 Location/Qualifiers
REGION                  1..8
                        note = Synthetic Construct
source                  1..8
                        mol_type = protein
                        organism = synthetic construct
SEQUENCE: 117
WIFYAMDY                                                                    8

SEQ ID NO: 118          moltype = AA   length = 10
FEATURE                 Location/Qualifiers
REGION                  1..10
                        note = Synthetic Construct
source                  1..10
                        mol_type = protein
                        organism = synthetic construct
SEQUENCE: 118
LITVDYAMDY                                                                 10

SEQ ID NO: 119          moltype = AA   length = 17
FEATURE                 Location/Qualifiers
REGION                  1..17
                        note = Synthetic Construct
source                  1..17
                        mol_type = protein
                        organism = synthetic construct
SEQUENCE: 119
KEGLWTYGYD GGAWFAY                                                         17

SEQ ID NO: 120          moltype = AA   length = 11
FEATURE                 Location/Qualifiers
REGION                  1..11
                        note = Synthetic Construct
source                  1..11
                        mol_type = protein
                        organism = synthetic construct
SEQUENCE: 120
RGYYGRSPFA Y                                                               11

SEQ ID NO: 121          moltype = AA   length = 16
FEATURE                 Location/Qualifiers
REGION                  1..16
                        note = Synthetic Construct
source                  1..16
                        mol_type = protein
                        organism = synthetic construct
SEQUENCE: 121
RSSQSIVYNN GNTYLE                                                          16

SEQ ID NO: 122          moltype = AA   length = 10
FEATURE                 Location/Qualifiers
REGION                  1..10
                        note = Synthetic Construct
source                  1..10
                        mol_type = protein
                        organism = synthetic construct
SEQUENCE: 122
RASSSVSYIH                                                                 10

SEQ ID NO: 123          moltype = AA   length = 16
FEATURE                 Location/Qualifiers
REGION                  1..16
                        note = Synthetic Construct
source                  1..16
                        mol_type = protein
                        organism = synthetic construct
SEQUENCE: 123
RSSKSLLHSN GITYLY                                                          16
```

```
SEQ ID NO: 124         moltype = AA   length = 14
FEATURE                Location/Qualifiers
REGION                 1..14
                       note = Synthetic Construct
source                 1..14
                       mol_type = protein
                       organism = synthetic construct
SEQUENCE: 124
RSSTGAVTTS NYAN                                                              14

SEQ ID NO: 125         moltype = AA   length = 11
FEATURE                Location/Qualifiers
REGION                 1..11
                       note = Synthetic Construct
source                 1..11
                       mol_type = protein
                       organism = synthetic construct
SEQUENCE: 125
RASENIYIYL A                                                                 11

SEQ ID NO: 126         moltype = AA   length = 11
FEATURE                Location/Qualifiers
REGION                 1..11
                       note = Synthetic Construct
source                 1..11
                       mol_type = protein
                       organism = synthetic construct
SEQUENCE: 126
KASDHINNWL A                                                                 11

SEQ ID NO: 127         moltype = AA   length = 17
FEATURE                Location/Qualifiers
REGION                 1..17
                       note = Synthetic Construct
source                 1..17
                       mol_type = protein
                       organism = synthetic construct
SEQUENCE: 127
KSSQSLLNSG NQRNYLA                                                           17

SEQ ID NO: 128         moltype = AA   length = 11
FEATURE                Location/Qualifiers
REGION                 1..11
                       note = Synthetic Construct
source                 1..11
                       mol_type = protein
                       organism = synthetic construct
SEQUENCE: 128
KASQDINSYL S                                                                 11

SEQ ID NO: 129         moltype = AA   length = 16
FEATURE                Location/Qualifiers
REGION                 1..16
                       note = Synthetic Construct
source                 1..16
                       mol_type = protein
                       organism = synthetic construct
SEQUENCE: 129
RSSQSLVHSN GKTYLH                                                            16

SEQ ID NO: 130         moltype = AA   length = 17
FEATURE                Location/Qualifiers
REGION                 1..17
                       note = Synthetic Construct
source                 1..17
                       mol_type = protein
                       organism = synthetic construct
SEQUENCE: 130
KSSQSLLNSN NLQNYLA                                                           17

SEQ ID NO: 131         moltype = AA   length = 16
FEATURE                Location/Qualifiers
REGION                 1..16
                       note = Synthetic Construct
source                 1..16
                       mol_type = protein
                       organism = synthetic construct
SEQUENCE: 131
```

RSSQTIVHSN GNTYLE                                                     16

SEQ ID NO: 132          moltype = AA  length = 11
FEATURE                 Location/Qualifiers
REGION                  1..11
                        note = Synthetic Construct
source                  1..11
                        mol_type = protein
                        organism = synthetic construct
SEQUENCE: 132
RASENIYSSL G                                                          11

SEQ ID NO: 133          moltype = AA  length = 11
FEATURE                 Location/Qualifiers
REGION                  1..11
                        note = Synthetic Construct
source                  1..11
                        mol_type = protein
                        organism = synthetic construct
SEQUENCE: 133
RASQDIGSNL N                                                          11

SEQ ID NO: 134          moltype = AA  length = 11
FEATURE                 Location/Qualifiers
REGION                  1..11
                        note = Synthetic Construct
source                  1..11
                        mol_type = protein
                        organism = synthetic construct
SEQUENCE: 134
RVSENIYNNL A                                                          11

SEQ ID NO: 135          moltype = AA  length = 10
FEATURE                 Location/Qualifiers
REGION                  1..10
                        note = Synthetic Construct
source                  1..10
                        mol_type = protein
                        organism = synthetic construct
SEQUENCE: 135
SASSSLNYMY                                                            10

SEQ ID NO: 136          moltype = AA  length = 15
FEATURE                 Location/Qualifiers
REGION                  1..15
                        note = Synthetic Construct
source                  1..15
                        mol_type = protein
                        organism = synthetic construct
SEQUENCE: 136
RASKSVSISV YTYVH                                                      15

SEQ ID NO: 137          moltype = AA  length = 16
FEATURE                 Location/Qualifiers
REGION                  1..16
                        note = Synthetic Construct
source                  1..16
                        mol_type = protein
                        organism = synthetic construct
SEQUENCE: 137
RSSQSIVHSN GNTYLE                                                     16

SEQ ID NO: 138          moltype = AA  length = 16
FEATURE                 Location/Qualifiers
REGION                  1..16
                        note = Synthetic Construct
source                  1..16
                        mol_type = protein
                        organism = synthetic construct
SEQUENCE: 138
RSSKSLLHSN GITYLF                                                     16

SEQ ID NO: 139          moltype = AA  length = 16
FEATURE                 Location/Qualifiers
REGION                  1..16
                        note = Synthetic Construct
source                  1..16
                        mol_type = protein
                        organism = synthetic construct

```
SEQUENCE: 139
RSGQSIVHSN GNTYLE                                                          16

SEQ ID NO: 140         moltype = AA  length = 16
FEATURE                Location/Qualifiers
REGION                 1..16
                       note = Synthetic Construct
source                 1..16
                       mol_type = protein
                       organism = synthetic construct
SEQUENCE: 140
RSSQSLTNYY GNTYLS                                                          16

SEQ ID NO: 141         moltype = AA  length = 17
FEATURE                Location/Qualifiers
REGION                 1..17
                       note = Synthetic Construct
source                 1..17
                       mol_type = protein
                       organism = synthetic construct
SEQUENCE: 141
KSSQSLLNSN NQQNYLA                                                         17

SEQ ID NO: 142         moltype = AA  length = 10
FEATURE                Location/Qualifiers
REGION                 1..10
                       note = Synthetic Construct
source                 1..10
                       mol_type = protein
                       organism = synthetic construct
SEQUENCE: 142
SASSSISYMY                                                                 10

SEQ ID NO: 143         moltype = AA  length = 17
FEATURE                Location/Qualifiers
REGION                 1..17
                       note = Synthetic Construct
source                 1..17
                       mol_type = protein
                       organism = synthetic construct
SEQUENCE: 143
KSSQSLLNSG NQKNYLA                                                         17

SEQ ID NO: 144         moltype = AA  length = 16
FEATURE                Location/Qualifiers
REGION                 1..16
                       note = Synthetic Construct
source                 1..16
                       mol_type = protein
                       organism = synthetic construct
SEQUENCE: 144
RSSKSLLHYN GITYLY                                                          16

SEQ ID NO: 145         moltype = AA  length = 16
FEATURE                Location/Qualifiers
REGION                 1..16
                       note = Synthetic Construct
source                 1..16
                       mol_type = protein
                       organism = synthetic construct
SEQUENCE: 145
RSSQTIVHRN GNTYLE                                                          16

SEQ ID NO: 146         moltype = AA  length = 16
FEATURE                Location/Qualifiers
REGION                 1..16
                       note = Synthetic Construct
source                 1..16
                       mol_type = protein
                       organism = synthetic construct
SEQUENCE: 146
RSSQNIVHSN GNTYLE                                                          16

SEQ ID NO: 147         moltype = AA  length = 11
FEATURE                Location/Qualifiers
REGION                 1..11
                       note = Synthetic Construct
source                 1..11
                       mol_type = protein
```

```
                        -continued organism = synthetic construct
SEQUENCE: 147
KASQNVGTAV A                                                            11

SEQ ID NO: 148          moltype = AA   length = 10
FEATURE                 Location/Qualifiers
REGION                  1..10
                        note = Synthetic Construct
source                  1..10
                        mol_type = protein
                        organism = synthetic construct
SEQUENCE: 148
RATSSVTYMH                                                              10

SEQ ID NO: 149          moltype = AA   length = 16
FEATURE                 Location/Qualifiers
REGION                  1..16
                        note = Synthetic Construct
source                  1..16
                        mol_type = protein
                        organism = synthetic construct
SEQUENCE: 149
RSSQSIVHRN GNTYLE                                                       16

SEQ ID NO: 150          moltype = AA   length = 16
FEATURE                 Location/Qualifiers
REGION                  1..16
                        note = Synthetic Construct
source                  1..16
                        mol_type = protein
                        organism = synthetic construct
SEQUENCE: 150
RSSKSLLHSN GNTYSY                                                       16

SEQ ID NO: 151          moltype = AA   length = 16
FEATURE                 Location/Qualifiers
REGION                  1..16
                        note = Synthetic Construct
source                  1..16
                        mol_type = protein
                        organism = synthetic construct
SEQUENCE: 151
RSSKTLLNSN GNTYLY                                                       16

SEQ ID NO: 152          moltype = AA   length = 17
FEATURE                 Location/Qualifiers
REGION                  1..17
                        note = Synthetic Construct
source                  1..17
                        mol_type = protein
                        organism = synthetic construct
SEQUENCE: 152
KSSQSLLYSS NQKNYLA                                                      17

SEQ ID NO: 153          moltype = AA   length = 16
FEATURE                 Location/Qualifiers
REGION                  1..16
                        note = Synthetic Construct
source                  1..16
                        mol_type = protein
                        organism = synthetic construct
SEQUENCE: 153
RSSKSLLHSN GNTYLY                                                       16

SEQ ID NO: 154          moltype = AA   length = 10
FEATURE                 Location/Qualifiers
REGION                  1..10
                        note = Synthetic Construct
source                  1..10
                        mol_type = protein
                        organism = synthetic construct
SEQUENCE: 154
CASSRVNYMH                                                              10

SEQ ID NO: 155          moltype = AA   length = 17
FEATURE                 Location/Qualifiers
REGION                  1..17
                        note = Synthetic Construct
source                  1..17
```

```
                        mol_type = protein
                        organism = synthetic construct
SEQUENCE: 155
KSSQSLLNSG NQKNYLT                                              17

SEQ ID NO: 156          moltype = AA   length = 16
FEATURE                 Location/Qualifiers
REGION                  1..16
                        note = Synthetic Construct
source                  1..16
                        mol_type = protein
                        organism = synthetic construct
SEQUENCE: 156
RSSQSIVHGN GNTYLE                                               16

SEQ ID NO: 157          moltype = AA   length = 10
FEATURE                 Location/Qualifiers
REGION                  1..10
                        note = Synthetic Construct
source                  1..10
                        mol_type = protein
                        organism = synthetic construct
SEQUENCE: 157
SASSSVSYMY                                                      10

SEQ ID NO: 158          moltype = AA   length = 11
FEATURE                 Location/Qualifiers
REGION                  1..11
                        note = Synthetic Construct
source                  1..11
                        mol_type = protein
                        organism = synthetic construct
SEQUENCE: 158
RASQDINNYL Y                                                    11

SEQ ID NO: 159          moltype = AA   length = 17
FEATURE                 Location/Qualifiers
REGION                  1..17
                        note = Synthetic Construct
source                  1..17
                        mol_type = protein
                        organism = synthetic construct
SEQUENCE: 159
KSSQSLRNSR TRKNYLA                                              17

SEQ ID NO: 160          moltype = AA   length = 10
FEATURE                 Location/Qualifiers
REGION                  1..10
                        note = Synthetic Construct
source                  1..10
                        mol_type = protein
                        organism = synthetic construct
SEQUENCE: 160
SASSSVSYMH                                                      10

SEQ ID NO: 161          moltype = AA   length = 7
FEATURE                 Location/Qualifiers
REGION                  1..7
                        note = Synthetic Construct
source                  1..7
                        mol_type = protein
                        organism = synthetic construct
SEQUENCE: 161
KVSNRFS                                                         7

SEQ ID NO: 162          moltype = AA   length = 7
FEATURE                 Location/Qualifiers
REGION                  1..7
                        note = Synthetic Construct
source                  1..7
                        mol_type = protein
                        organism = synthetic construct
SEQUENCE: 162
ATSNLAS                                                         7

SEQ ID NO: 163          moltype = AA   length = 7
FEATURE                 Location/Qualifiers
REGION                  1..7
                        note = Synthetic Construct
```

```
source                    1..7
                          mol_type = protein
                          organism = synthetic construct
SEQUENCE: 163
QMSSLAS                                                                  7

SEQ ID NO: 164            moltype = AA  length = 7
FEATURE                   Location/Qualifiers
REGION                    1..7
                          note = Synthetic Construct
source                    1..7
                          mol_type = protein
                          organism = synthetic construct
SEQUENCE: 164
GTNNRAP                                                                  7

SEQ ID NO: 165            moltype = AA  length = 7
FEATURE                   Location/Qualifiers
REGION                    1..7
                          note = Synthetic Construct
source                    1..7
                          mol_type = protein
                          organism = synthetic construct
SEQUENCE: 165
NGKMLAE                                                                  7

SEQ ID NO: 166            moltype = AA  length = 7
FEATURE                   Location/Qualifiers
REGION                    1..7
                          note = Synthetic Construct
source                    1..7
                          mol_type = protein
                          organism = synthetic construct
SEQUENCE: 166
GATSLET                                                                  7

SEQ ID NO: 167            moltype = AA  length = 7
FEATURE                   Location/Qualifiers
REGION                    1..7
                          note = Synthetic Construct
source                    1..7
                          mol_type = protein
                          organism = synthetic construct
SEQUENCE: 167
GASTRES                                                                  7

SEQ ID NO: 168            moltype = AA  length = 7
FEATURE                   Location/Qualifiers
REGION                    1..7
                          note = Synthetic Construct
source                    1..7
                          mol_type = protein
                          organism = synthetic construct
SEQUENCE: 168
RANRLVD                                                                  7

SEQ ID NO: 169            moltype = AA  length = 7
FEATURE                   Location/Qualifiers
REGION                    1..7
                          note = Synthetic Construct
source                    1..7
                          mol_type = protein
                          organism = synthetic construct
SEQUENCE: 169
QMSNLAS                                                                  7

SEQ ID NO: 170            moltype = AA  length = 7
FEATURE                   Location/Qualifiers
REGION                    1..7
                          note = Synthetic Construct
source                    1..7
                          mol_type = protein
                          organism = synthetic construct
SEQUENCE: 170
KISNRFS                                                                  7

SEQ ID NO: 171            moltype = AA  length = 7
FEATURE                   Location/Qualifiers
REGION                    1..7
```

```
                        note = Synthetic Construct
source                  1..7
                        mol_type = protein
                        organism = synthetic construct
SEQUENCE: 171
FASIRES                                                                 7

SEQ ID NO: 172          moltype = AA  length = 7
FEATURE                 Location/Qualifiers
REGION                  1..7
                        note = Synthetic Construct
source                  1..7
                        mol_type = protein
                        organism = synthetic construct
SEQUENCE: 172
AATNLAD                                                                 7

SEQ ID NO: 173          moltype = AA  length = 7
FEATURE                 Location/Qualifiers
REGION                  1..7
                        note = Synthetic Construct
source                  1..7
                        mol_type = protein
                        organism = synthetic construct
SEQUENCE: 173
ATSSLDS                                                                 7

SEQ ID NO: 174          moltype = AA  length = 7
FEATURE                 Location/Qualifiers
REGION                  1..7
                        note = Synthetic Construct
source                  1..7
                        mol_type = protein
                        organism = synthetic construct
SEQUENCE: 174
DTSNLAS                                                                 7

SEQ ID NO: 175          moltype = AA  length = 7
FEATURE                 Location/Qualifiers
REGION                  1..7
                        note = Synthetic Construct
source                  1..7
                        mol_type = protein
                        organism = synthetic construct
SEQUENCE: 175
LASNLES                                                                 7

SEQ ID NO: 176          moltype = AA  length = 7
FEATURE                 Location/Qualifiers
REGION                  1..7
                        note = Synthetic Construct
source                  1..7
                        mol_type = protein
                        organism = synthetic construct
SEQUENCE: 176
KVFNRFS                                                                 7

SEQ ID NO: 177          moltype = AA  length = 7
FEATURE                 Location/Qualifiers
REGION                  1..7
                        note = Synthetic Construct
source                  1..7
                        mol_type = protein
                        organism = synthetic construct
SEQUENCE: 177
GISNRFS                                                                 7

SEQ ID NO: 178          moltype = AA  length = 7
FEATURE                 Location/Qualifiers
REGION                  1..7
                        note = Synthetic Construct
source                  1..7
                        mol_type = protein
                        organism = synthetic construct
SEQUENCE: 178
RTSTLAS                                                                 7

SEQ ID NO: 179          moltype = AA  length = 7
FEATURE                 Location/Qualifiers
```

```
REGION                      1..7
                            note = Synthetic Construct
source                      1..7
                            mol_type = protein
                            organism = synthetic construct
SEQUENCE: 179
RGNGLVD                                                                  7

SEQ ID NO: 180              moltype = AA  length = 7
FEATURE                     Location/Qualifiers
REGION                      1..7
                            note = Synthetic Construct
source                      1..7
                            mol_type = protein
                            organism = synthetic construct
SEQUENCE: 180
SASNRYT                                                                  7

SEQ ID NO: 181              moltype = AA  length = 7
FEATURE                     Location/Qualifiers
REGION                      1..7
                            note = Synthetic Construct
source                      1..7
                            mol_type = protein
                            organism = synthetic construct
SEQUENCE: 181
RMSNLAS                                                                  7

SEQ ID NO: 182              moltype = AA  length = 7
FEATURE                     Location/Qualifiers
REGION                      1..7
                            note = Synthetic Construct
source                      1..7
                            mol_type = protein
                            organism = synthetic construct
SEQUENCE: 182
WASTRES                                                                  7

SEQ ID NO: 183              moltype = AA  length = 7
FEATURE                     Location/Qualifiers
REGION                      1..7
                            note = Synthetic Construct
source                      1..7
                            mol_type = protein
                            organism = synthetic construct
SEQUENCE: 183
DTSKLAS                                                                  7

SEQ ID NO: 184              moltype = AA  length = 7
FEATURE                     Location/Qualifiers
REGION                      1..7
                            note = Synthetic Construct
source                      1..7
                            mol_type = protein
                            organism = synthetic construct
SEQUENCE: 184
RTSNLAS                                                                  7

SEQ ID NO: 185              moltype = AA  length = 7
FEATURE                     Location/Qualifiers
REGION                      1..7
                            note = Synthetic Construct
source                      1..7
                            mol_type = protein
                            organism = synthetic construct
SEQUENCE: 185
YTSMLHS                                                                  7

SEQ ID NO: 186              moltype = AA  length = 9
FEATURE                     Location/Qualifiers
REGION                      1..9
                            note = Synthetic Construct
source                      1..9
                            mol_type = protein
                            organism = synthetic construct
SEQUENCE: 186
FQVSHVPFT                                                                9

SEQ ID NO: 187              moltype = AA  length = 9
```

```
FEATURE            Location/Qualifiers
REGION             1..9
                   note = Synthetic Construct
source             1..9
                   mol_type = protein
                   organism = synthetic construct
SEQUENCE: 187
QQWSSNPST                                                                 9

SEQ ID NO: 188     moltype = AA  length = 9
FEATURE            Location/Qualifiers
REGION             1..9
                   note = Synthetic Construct
source             1..9
                   mol_type = protein
                   organism = synthetic construct
SEQUENCE: 188
AQNLELPWT                                                                 9

SEQ ID NO: 189     moltype = AA  length = 9
FEATURE            Location/Qualifiers
REGION             1..9
                   note = Synthetic Construct
source             1..9
                   mol_type = protein
                   organism = synthetic construct
SEQUENCE: 189
VLWYSNHLV                                                                 9

SEQ ID NO: 190     moltype = AA  length = 9
FEATURE            Location/Qualifiers
REGION             1..9
                   note = Synthetic Construct
source             1..9
                   mol_type = protein
                   organism = synthetic construct
SEQUENCE: 190
QHHYGSPPA                                                                 9

SEQ ID NO: 191     moltype = AA  length = 9
FEATURE            Location/Qualifiers
REGION             1..9
                   note = Synthetic Construct
source             1..9
                   mol_type = protein
                   organism = synthetic construct
SEQUENCE: 191
QQYWSSPYT                                                                 9

SEQ ID NO: 192     moltype = AA  length = 9
FEATURE            Location/Qualifiers
REGION             1..9
                   note = Synthetic Construct
source             1..9
                   mol_type = protein
                   organism = synthetic construct
SEQUENCE: 192
QNDHSYPLT                                                                 9

SEQ ID NO: 193     moltype = AA  length = 9
FEATURE            Location/Qualifiers
REGION             1..9
                   note = Synthetic Construct
source             1..9
                   mol_type = protein
                   organism = synthetic construct
SEQUENCE: 193
LQYDEFPLT                                                                 9

SEQ ID NO: 194     moltype = AA  length = 9
FEATURE            Location/Qualifiers
REGION             1..9
                   note = Synthetic Construct
source             1..9
                   mol_type = protein
                   organism = synthetic construct
SEQUENCE: 194
SQITHVPWT                                                                 9
```

| | | |
|---|---|---|
| SEQ ID NO: 195<br>FEATURE<br>REGION<br>source | moltype = AA  length = 9<br>Location/Qualifiers<br>1..9<br>note = Synthetic Construct<br>1..9<br>mol_type = protein<br>organism = synthetic construct | |
| SEQUENCE: 195<br>QQHYNTPFT | | 9 |
| SEQ ID NO: 196<br>FEATURE<br>REGION<br>source | moltype = AA  length = 9<br>Location/Qualifiers<br>1..9<br>note = Synthetic Construct<br>1..9<br>mol_type = protein<br>organism = synthetic construct | |
| SEQUENCE: 196<br>FQGSHVPYT | | 9 |
| SEQ ID NO: 197<br>FEATURE<br>REGION<br>source | moltype = AA  length = 9<br>Location/Qualifiers<br>1..9<br>note = Synthetic Construct<br>1..9<br>mol_type = protein<br>organism = synthetic construct | |
| SEQUENCE: 197<br>QHLWSIPWT | | 9 |
| SEQ ID NO: 198<br>FEATURE<br>REGION<br>source | moltype = AA  length = 9<br>Location/Qualifiers<br>1..9<br>note = Synthetic Construct<br>1..9<br>mol_type = protein<br>organism = synthetic construct | |
| SEQUENCE: 198<br>LQYASSPRT | | 9 |
| SEQ ID NO: 199<br>FEATURE<br>REGION<br>source | moltype = AA  length = 9<br>Location/Qualifiers<br>1..9<br>note = Synthetic Construct<br>1..9<br>mol_type = protein<br>organism = synthetic construct | |
| SEQUENCE: 199<br>QHFWDTPFT | | 9 |
| SEQ ID NO: 200<br>FEATURE<br>REGION<br>source | moltype = AA  length = 9<br>Location/Qualifiers<br>1..9<br>note = Synthetic Construct<br>1..9<br>mol_type = protein<br>organism = synthetic construct | |
| SEQUENCE: 200<br>QQWTSFPPT | | 9 |
| SEQ ID NO: 201<br>FEATURE<br>REGION<br>source | moltype = AA  length = 9<br>Location/Qualifiers<br>1..9<br>note = Synthetic Construct<br>1..9<br>mol_type = protein<br>organism = synthetic construct | |
| SEQUENCE: 201<br>QHSRELPYT | | 9 |
| SEQ ID NO: 202<br>FEATURE<br>REGION<br>source | moltype = AA  length = 9<br>Location/Qualifiers<br>1..9<br>note = Synthetic Construct<br>1..9<br>mol_type = protein<br>organism = synthetic construct | |
| SEQUENCE: 202<br>FQGSHVPFT | | 9 |

```
SEQ ID NO: 203          moltype = AA   length = 9
FEATURE                 Location/Qualifiers
REGION                  1..9
                        note = Synthetic Construct
source                  1..9
                        mol_type = protein
                        organism = synthetic construct
SEQUENCE: 203
VQNLELPYT                                                                    9

SEQ ID NO: 204          moltype = AA   length = 9
FEATURE                 Location/Qualifiers
REGION                  1..9
                        note = Synthetic Construct
source                  1..9
                        mol_type = protein
                        organism = synthetic construct
SEQUENCE: 204
FQGSHVPWT                                                                    9

SEQ ID NO: 205          moltype = AA   length = 9
FEATURE                 Location/Qualifiers
REGION                  1..9
                        note = Synthetic Construct
source                  1..9
                        mol_type = protein
                        organism = synthetic construct
SEQUENCE: 205
LQGTHQPRT                                                                    9

SEQ ID NO: 206          moltype = AA   length = 9
FEATURE                 Location/Qualifiers
REGION                  1..9
                        note = Synthetic Construct
source                  1..9
                        mol_type = protein
                        organism = synthetic construct
SEQUENCE: 206
QQHYSTPFT                                                                    9

SEQ ID NO: 207          moltype = AA   length = 8
FEATURE                 Location/Qualifiers
REGION                  1..8
                        note = Synthetic Construct
source                  1..8
                        mol_type = protein
                        organism = synthetic construct
SEQUENCE: 207
AQNLELWT                                                                     8

SEQ ID NO: 208          moltype = AA   length = 9
FEATURE                 Location/Qualifiers
REGION                  1..9
                        note = Synthetic Construct
source                  1..9
                        mol_type = protein
                        organism = synthetic construct
SEQUENCE: 208
QQYHSYPRT                                                                    9

SEQ ID NO: 209          moltype = AA   length = 9
FEATURE                 Location/Qualifiers
REGION                  1..9
                        note = Synthetic Construct
source                  1..9
                        mol_type = protein
                        organism = synthetic construct
SEQUENCE: 209
AQNLELPYT                                                                    9

SEQ ID NO: 210          moltype = AA   length = 9
FEATURE                 Location/Qualifiers
REGION                  1..9
                        note = Synthetic Construct
source                  1..9
                        mol_type = protein
                        organism = synthetic construct
SEQUENCE: 210
```

-continued

```
FQGSHLPWT                                                                        9

SEQ ID NO: 211          moltype = AA  length = 9
FEATURE                 Location/Qualifiers
REGION                  1..9
                        note = Synthetic Construct
source                  1..9
                        mol_type = protein
                        organism = synthetic construct
SEQUENCE: 211
LQYDEFPFT                                                                        9

SEQ ID NO: 212          moltype = AA  length = 9
FEATURE                 Location/Qualifiers
REGION                  1..9
                        note = Synthetic Construct
source                  1..9
                        mol_type = protein
                        organism = synthetic construct
SEQUENCE: 212
QQYSSYPYT                                                                        9

SEQ ID NO: 213          moltype = AA  length = 9
FEATURE                 Location/Qualifiers
REGION                  1..9
                        note = Synthetic Construct
source                  1..9
                        mol_type = protein
                        organism = synthetic construct
SEQUENCE: 213
QQWSSNPYT                                                                        9

SEQ ID NO: 214          moltype = AA  length = 9
FEATURE                 Location/Qualifiers
REGION                  1..9
                        note = Synthetic Construct
source                  1..9
                        mol_type = protein
                        organism = synthetic construct
SEQUENCE: 214
MQHLEYPYT                                                                        9

SEQ ID NO: 215          moltype = AA  length = 9
FEATURE                 Location/Qualifiers
REGION                  1..9
                        note = Synthetic Construct
source                  1..9
                        mol_type = protein
                        organism = synthetic construct
SEQUENCE: 215
MQHLDYPYT                                                                        9

SEQ ID NO: 216          moltype = AA  length = 9
FEATURE                 Location/Qualifiers
REGION                  1..9
                        note = Synthetic Construct
source                  1..9
                        mol_type = protein
                        organism = synthetic construct
SEQUENCE: 216
QQYYSYPYT                                                                        9

SEQ ID NO: 217          moltype = AA  length = 8
FEATURE                 Location/Qualifiers
REGION                  1..8
                        note = Synthetic Construct
source                  1..8
                        mol_type = protein
                        organism = synthetic construct
SEQUENCE: 217
QQYYSYPT                                                                         8

SEQ ID NO: 218          moltype = AA  length = 9
FEATURE                 Location/Qualifiers
REGION                  1..9
                        note = Synthetic Construct
source                  1..9
                        mol_type = protein
                        organism = synthetic construct
```

```
SEQUENCE: 218
QQWSSNPPT                                                                        9

SEQ ID NO: 219         moltype = AA  length = 9
FEATURE                Location/Qualifiers
REGION                 1..9
                       note = Synthetic Construct
source                 1..9
                       mol_type = protein
                       organism = synthetic construct
SEQUENCE: 219
QNDYSYPLT                                                                        9

SEQ ID NO: 220         moltype = AA  length = 9
FEATURE                Location/Qualifiers
REGION                 1..9
                       note = Synthetic Construct
source                 1..9
                       mol_type = protein
                       organism = synthetic construct
SEQUENCE: 220
FQGSHLPYT                                                                        9

SEQ ID NO: 221         moltype = AA  length = 9
FEATURE                Location/Qualifiers
REGION                 1..9
                       note = Synthetic Construct
source                 1..9
                       mol_type = protein
                       organism = synthetic construct
SEQUENCE: 221
QQYHSYPPT                                                                        9

SEQ ID NO: 222         moltype = AA  length = 9
FEATURE                Location/Qualifiers
REGION                 1..9
                       note = Synthetic Construct
source                 1..9
                       mol_type = protein
                       organism = synthetic construct
SEQUENCE: 222
QQGSTLMYT                                                                        9

SEQ ID NO: 223         moltype = AA  length = 8
FEATURE                Location/Qualifiers
REGION                 1..8
                       note = Synthetic Construct
source                 1..8
                       mol_type = protein
                       organism = synthetic construct
SEQUENCE: 223
KQSYNLLT                                                                         8

SEQ ID NO: 224         moltype = AA  length = 9
FEATURE                Location/Qualifiers
REGION                 1..9
                       note = Synthetic Construct
source                 1..9
                       mol_type = protein
                       organism = synthetic construct
SEQUENCE: 224
FQGSGYPLT                                                                        9

SEQ ID NO: 225         moltype = AA  length = 122
FEATURE                Location/Qualifiers
REGION                 1..122
                       note = Synthetic Construct
source                 1..122
                       mol_type = protein
                       organism = synthetic construct
SEQUENCE: 225
QVQLQQSGAE LVRPGTSVKV SCKASGYAFT NYLIEWVKQR PGQGLEWIGV INPGSGGTKY   60
NEKLKGKATL TADKSSSTAY MQLSSLTSVD SAVYFCARRG YTIYDFYAMD YWGQGTSVTV  120
SS                                                                122

SEQ ID NO: 226         moltype = AA  length = 112
FEATURE                Location/Qualifiers
REGION                 1..112
                       note = Synthetic Construct
```

```
                        source           1..112
                                         mol_type = protein
                                         organism = synthetic construct
SEQUENCE: 226
HIQLVQSGPE LKKPGETVKI SCKASGYTFT EYPMHWVKQA PGKGFRWMGM IYTNTGEPTY      60
AAEFKGRFAF SLETSASTGY LQINNLKNED SATYFCVTAG YWGQGTLVTV SA             112

SEQ ID NO: 227          moltype = AA   length = 119
FEATURE                 Location/Qualifiers
REGION                  1..119
                        note = Synthetic Construct
source                  1..119
                        mol_type = protein
                        organism = synthetic construct
SEQUENCE: 227
QVTLKESGPG IVQPSQTLSL TCSFSGFSLN TLGRGVGWIR QPSGKGLEWL AKIWWNDDKF      60
YYPALKSRLT ISKDTSKNQI FLKIANVDTA DSATYYCARI AGGTGAAYWG QGTTLTVSS     119

SEQ ID NO: 228          moltype = AA   length = 119
FEATURE                 Location/Qualifiers
REGION                  1..119
                        note = Synthetic Construct
source                  1..119
                        mol_type = protein
                        organism = synthetic construct
SEQUENCE: 228
EVQVQQSGPV LVKPGASVKM SCKASGYTFT DYYMNWVKQS HGKNLEWIGV INPYNGGTSY      60
HQKFKGKATL TVDKSSSTAY MELNSLTSED SAVYYCARAA TVVAGFDYWG QGTTLTVSS     119

SEQ ID NO: 229          moltype = AA   length = 118
FEATURE                 Location/Qualifiers
REGION                  1..118
                        note = Synthetic Construct
source                  1..118
                        mol_type = protein
                        organism = synthetic construct
SEQUENCE: 229
QVQLQQSGTE LARPGASVKV SCKASGYIFT TYGITWVKQR GGQGLEWIGE IYPRSDNTYY      60
NEKFKDKATL TADKSSSTAY MELRSLTSED SAVYFCARSK GSGTGDYWGQ GTTVTVSS      118

SEQ ID NO: 230          moltype = AA   length = 120
FEATURE                 Location/Qualifiers
REGION                  1..120
                        note = Synthetic Construct
source                  1..120
                        mol_type = protein
                        organism = synthetic construct
SEQUENCE: 230
QVQLQQSGAE LVKPGASVKL SCKASGYTFT EYTIHWVKQR SGQGLEWIGW FYPGSTYIDY      60
NEKFKDKATL TADKSSSTVY LELSRLTSED SAVYFCARHE EDYSNWFPFW GQGTLVTVSA    120

SEQ ID NO: 231          moltype = AA   length = 118
FEATURE                 Location/Qualifiers
REGION                  1..118
                        note = Synthetic Construct
source                  1..118
                        mol_type = protein
                        organism = synthetic construct
SEQUENCE: 231
EVQLQQSGPV LVKPGPPVKI SCKASGFTFT DYYIHWVKLS HGKSLEWIGL VYPYNGDTDY      60
NQKFKGKATL TVDTSSSTAY MELNSLTSED SAVYYCARTY YANSPDYWGQ GTTVTVSS      118

SEQ ID NO: 232          moltype = AA   length = 113
FEATURE                 Location/Qualifiers
REGION                  1..113
                        note = Synthetic Construct
source                  1..113
                        mol_type = protein
                        organism = synthetic construct
SEQUENCE: 232
QIQLVQSGPE LKKPGETVKI SCKASGYTFT DYPMHWVKQA PGKGFKWMGV IYTDTGEPKY      60
AEVFKGRFAF SLETSASTAY LQINNLKNED TATYFCVRRL AYWGQGTLVT VSA           113

SEQ ID NO: 233          moltype = AA   length = 119
FEATURE                 Location/Qualifiers
REGION                  1..119
                        note = Synthetic Construct
source                  1..119
                        mol_type = protein
```

```
                        organism = synthetic construct
SEQUENCE: 233
EVQLVESGGD LVKPGGSLKL SCVASGFTFS GYGMSWVRQT PDKRLEWVAT ISSGSFYIYY    60
PDSVKGRLTV SRDNAKNTLY LQMSSLKSED TAIYYCARQN FYYGCEDYWG QGTTLTVSS    119

SEQ ID NO: 234          moltype = AA   length = 119
FEATURE                 Location/Qualifiers
REGION                  1..119
                        note = Synthetic Construct
source                  1..119
                        mol_type = protein
                        organism = synthetic construct
SEQUENCE: 234
QVQLQQSGAE LVKPGASVKI SCKGSGYAFS SYWMNWVKQR PGKGLEWIGQ IYPGDGDTNY    60
NGKFKGKATL TADKSSTTAY IHLSSLTSED SAVYFCARWG HYDEAMDDWG QGTSVTVSS    119

SEQ ID NO: 235          moltype = AA   length = 117
FEATURE                 Location/Qualifiers
REGION                  1..117
                        note = Synthetic Construct
source                  1..117
                        mol_type = protein
                        organism = synthetic construct
SEQUENCE: 235
QVQLKQSGPG QVQPSQSLSI TCTVSGFSLS DYGVHWVRQS PGKGLEWLGV IWNNGNTDYN    60
AAFISRLSIN KDNSKSQVFF KMTSLQADDT AIYYCVRSLR PLHFDYWGQG TTVTVSS      117

SEQ ID NO: 236          moltype = AA   length = 122
FEATURE                 Location/Qualifiers
REGION                  1..122
                        note = Synthetic Construct
source                  1..122
                        mol_type = protein
                        organism = synthetic construct
SEQUENCE: 236
EVQLQQSGAE LMRPGASVKL SCTASGFNIQ DYYMYWVKQR PEQGLEWIGR IDPEDGDAEY    60
APKFQGKATM TADTSSNTAY LQLSSLTSED TAVYYCSTRV IYDGYYRTMD CWGQGTSVTV  120
SS                                                                   122

SEQ ID NO: 237          moltype = AA   length = 117
FEATURE                 Location/Qualifiers
REGION                  1..117
                        note = Synthetic Construct
source                  1..117
                        mol_type = protein
                        organism = synthetic construct
SEQUENCE: 237
QVQLQQSGAE LVKPGASVKM SCKASGYTFT TFPIEWMKQS HGKGLEWIGN FHPYNDDTKY    60
NEKFKGKATL TVDKSSSTVY LDLSRLTSDD SAVYYCARYF YGGMDYWGQG TSVTVSS      117

SEQ ID NO: 238          moltype = AA   length = 122
FEATURE                 Location/Qualifiers
REGION                  1..122
                        note = Synthetic Construct
source                  1..122
                        mol_type = protein
                        organism = synthetic construct
SEQUENCE: 238
QVQLQQSGPE LVRPGTSVKV SCKASGYAFT NYLIEWVKQR PGQGLEWIGV INPGGGNTDY    60
SEKFKDKATL TADKSSNTAY IQLSSLTSED SAVYFCARSP YSSYVGYAVD YWGQGTSVTV  120
SS                                                                   122

SEQ ID NO: 239          moltype = AA   length = 117
FEATURE                 Location/Qualifiers
REGION                  1..117
                        note = Synthetic Construct
source                  1..117
                        mol_type = protein
                        organism = synthetic construct
SEQUENCE: 239
QVQLQQPGAE FVRPGASVKL SCKASGYTFT NYWITWVKQR PGHGLEWIGD IYPGSGNSNY    60
NESFKRKATL TVDTSSTAY MHLSSQTSED SAVYFCARKA YGGFPYWGQG TLVTVSA       117

SEQ ID NO: 240          moltype = AA   length = 115
FEATURE                 Location/Qualifiers
REGION                  1..115
                        note = Synthetic Construct
source                  1..115
                        mol_type = protein
```

-continued

```
                        organism = synthetic construct
SEQUENCE: 240
EVQLQQSGAE LVRPGASVKL SCTTSGFNIK DYYMHWVKQR TEQGLEWIGR IDPEDGETKY    60
APEFQGKATI TSDTSSNTAF LQLSSLTSED TAVYYCASSQ PFTYWGQGTL VTVSA        115

SEQ ID NO: 241          moltype = AA  length = 122
FEATURE                 Location/Qualifiers
REGION                  1..122
                        note = Synthetic Construct
source                  1..122
                        mol_type = protein
                        organism = synthetic construct
SEQUENCE: 241
QVQLQQSGAE LIRPGTSVKV SCKASGYAFT DYLIEWVKQR PGQGLEWIGV INPGSGGTNY    60
NEKFKGKAKL TADKSSSTAY MQLSSLTSED SAVYFCVRSS YGVYVAYPMD YWGQGTSVTV   120
SS                                                                  122

SEQ ID NO: 242          moltype = AA  length = 123
FEATURE                 Location/Qualifiers
REGION                  1..123
                        note = Synthetic Construct
source                  1..123
                        mol_type = protein
                        organism = synthetic construct
SEQUENCE: 242
EVRLQQSGPE LVKPGASVKI SCKTSGYTFT DYYMNWVKQS HGKSLEWIVN INPNNGDAFY    60
NQKFKGKATL TVDKSSNTAY LDLRSLTSED SAVYYCAREG QLRLRRVYAM DYWGQGTSVT   120
VSS                                                                 123

SEQ ID NO: 243          moltype = AA  length = 120
FEATURE                 Location/Qualifiers
REGION                  1..120
                        note = Synthetic Construct
source                  1..120
                        mol_type = protein
                        organism = synthetic construct
SEQUENCE: 243
DVQLQQSGAE LVRPGASVKL SCTASGFNIK DYYMYWVKQR PEQGLEWIGR IDPEDGDTEN    60
APKFRGMATM TADTSSNTAY LQLNSLTSED TAVYYCTTRI GNLYHVMDYW GHGTSVTVSS   120

SEQ ID NO: 244          moltype = AA  length = 117
FEATURE                 Location/Qualifiers
REGION                  1..117
                        note = Synthetic Construct
source                  1..117
                        mol_type = protein
                        organism = synthetic construct
SEQUENCE: 244
EVQLVESGGG LVKPGGSLKL SCAASGFTFS NYAMSWVRET PEKRLEWVAF ISDGGGYIYY    60
ADNVKDRFTI SRDNAKNNLY LQMRHLKSED TAMYYCARDG GTGFTYWGQG TLVTVSV      117

SEQ ID NO: 245          moltype = AA  length = 121
FEATURE                 Location/Qualifiers
REGION                  1..121
                        note = Synthetic Construct
source                  1..121
                        mol_type = protein
                        organism = synthetic construct
SEQUENCE: 245
QVQLQQSGPE LVKPGASVKI SCKASGYRFT SYYIHWVKQR PGQGLEWIGW IYPGNGITNY    60
NEKFKGKATL TADTSSSTAY MQLSSLTSED SAVYYCASPY YGIRNCYFDV WGTGTTVTVS   120
S                                                                   121

SEQ ID NO: 246          moltype = AA  length = 120
FEATURE                 Location/Qualifiers
REGION                  1..120
                        note = Synthetic Construct
source                  1..120
                        mol_type = protein
                        organism = synthetic construct
SEQUENCE: 246
QVQLQQSGAE LIRPGTSVKV SCKASGYAFT NYLIEWVKKR PGQGLEWIGV INPGSGITNY    60
NEKFKGKATL TADKSSSTAY MQLSSLTSED SAVYFCARSD FITTVVADYW GQGTTVTVSS   120

SEQ ID NO: 247          moltype = AA  length = 119
FEATURE                 Location/Qualifiers
REGION                  1..119
                        note = Synthetic Construct
source                  1..119
```

```
                        mol_type = protein
                        organism = synthetic construct
SEQUENCE: 247
EVQLVESGGD LVKPGGSLRL SCAASGFTFS GYGMSWIRQT PDKRLEWVAT ISSGGRYTVY    60
PDSVKGRFTM SRDNVKNTLY LQMSSLKSED TALYYCARDN FYSYAMDYWG LGTSVTVSA    119

SEQ ID NO: 248          moltype = AA   length = 120
FEATURE                 Location/Qualifiers
REGION                  1..120
                        note = Synthetic Construct
source                  1..120
                        mol_type = protein
                        organism = synthetic construct
SEQUENCE: 248
QVQLQQSGAE LVRPGTSVKV SCKASGYALT NYLIEWVKQR PGQGLEWIGV INPGSGSTKY    60
NEKFKGKATL TADKSSSTAY MQLSSLTSED SAVYFCARII YDHDWYFDVW GTGTTVTVSS    120

SEQ ID NO: 249          moltype = AA   length = 118
FEATURE                 Location/Qualifiers
REGION                  1..118
                        note = Synthetic Construct
source                  1..118
                        mol_type = protein
                        organism = synthetic construct
SEQUENCE: 249
EVQLQQSGPV LVKPGPSVKI SCMASVFTFN DYYIHWVKQS HGKSLEWIGL VYPYNGGTNY    60
NQNFKGKATL TVDTSSRTAY MELNSLTSED SAVYYCARSY FSNPIGYWGQ GTLVTVSE     118

SEQ ID NO: 250          moltype = AA   length = 117
FEATURE                 Location/Qualifiers
REGION                  1..117
                        note = Synthetic Construct
source                  1..117
                        mol_type = protein
                        organism = synthetic construct
SEQUENCE: 250
QVQLRQSGAE LVRPGASVKL SCKASGYTFT DYYINWVKQR PGQGLEWIAR IYPGSGYTYY    60
NEKFKGKATL TAEGSSNTAY MQLSSLTSED SAVYFCANHY TNPFAYWGQG TLVTVSA      117

SEQ ID NO: 251          moltype = AA   length = 117
FEATURE                 Location/Qualifiers
REGION                  1..117
                        note = Synthetic Construct
source                  1..117
                        mol_type = protein
                        organism = synthetic construct
SEQUENCE: 251
QVQLQQSGPE LVKPGASVKL SCKASDNTFT NYDVNWVRQR PGQGLEWIGW IYPRDGTTIY    60
NEKFKGRATL TVDTSSSTAY MELHSLTSED SAVFFCARTL PQAMDYWGQG TSVTVSS      117

SEQ ID NO: 252          moltype = AA   length = 122
FEATURE                 Location/Qualifiers
REGION                  1..122
                        note = Synthetic Construct
source                  1..122
                        mol_type = protein
                        organism = synthetic construct
SEQUENCE: 252
QVQLQQSGAE LAKPGASVKV SCKASGYTFI SYWMNWVKQR PGQGLEWIGY INPTSGYTRY    60
NQKFKDKATL TADKSSSTAY MQLSSLTYED SAVYYCARSP PTVVLIGYFD YWGQGTTLTV   120
SS                                                                  122

SEQ ID NO: 253          moltype = AA   length = 120
FEATURE                 Location/Qualifiers
REGION                  1..120
                        note = Synthetic Construct
source                  1..120
                        mol_type = protein
                        organism = synthetic construct
SEQUENCE: 253
EVQLQQSGAE LVRPGASVRL SCIASGFNIK DYYMYWVKQR PEQGLEWIGR IDPEDGDTEY    60
VPKFQGKATM TADTSSNTAY LQLSSLTSED IGVYYCTTRT WDLYYAVDNW GQGTSVTVSS   120

SEQ ID NO: 254          moltype = AA   length = 111
FEATURE                 Location/Qualifiers
REGION                  1..111
                        note = Synthetic Construct
source                  1..111
                        mol_type = protein
```

```
                        organism = synthetic construct
SEQUENCE: 254
EFQLQQSGPE LVKPGASVKI SCKASGYSFT DYNMNWVKQS NGKSLEWIGV INPNYGTTSY    60
NQKFKGKATL TVDQSSSTAY MQLNSLTSED SAVYYCASSY WGQGTLVTVS A            111

SEQ ID NO: 255          moltype = AA   length = 119
FEATURE                 Location/Qualifiers
REGION                  1..119
                        note = Synthetic Construct
source                  1..119
                        mol_type = protein
                        organism = synthetic construct
SEQUENCE: 255
EVQLVESGGG LVKPGGSLKL SCAASGFSFS DSGMDWVRQA PEKGLEWFAY ISSGSSTTHY    60
ADTVKGRFII SRDNAKNTLF LQMTSLRSED TAMYYCVRRD GNYWYFDVWG TGTTVTVSS    119

SEQ ID NO: 256          moltype = AA   length = 120
FEATURE                 Location/Qualifiers
REGION                  1..120
                        note = Synthetic Construct
source                  1..120
                        mol_type = protein
                        organism = synthetic construct
SEQUENCE: 256
QVQLQQSGPE LVRPGTSVKI SCKAPGYTFT RHWMQWVRQR PGQGLEWIGE ILPGSNNIYY    60
NEKVKGKATL TVDTSSSTSY MQLSSLTSED SAVYFCARSL YDYDGVFAYW GQGTLVTVSA   120

SEQ ID NO: 257          moltype = AA   length = 121
FEATURE                 Location/Qualifiers
REGION                  1..121
                        note = Synthetic Construct
source                  1..121
                        mol_type = protein
                        organism = synthetic construct
SEQUENCE: 257
QVQLQQSGAE LAKPGASVKL SCKASGYTFT SYWMHWVKQR PGQGLEWIGY VNPSSGYTKN    60
NQKFKDKVTL TADKSSSTAY MQLSSLTYED SAVYYCAREG GSISDWYFDV WGTGTTVTVS   120
S                                                                  121

SEQ ID NO: 258          moltype = AA   length = 121
FEATURE                 Location/Qualifiers
REGION                  1..121
                        note = Synthetic Construct
source                  1..121
                        mol_type = protein
                        organism = synthetic construct
SEQUENCE: 258
HVQRQQSGTE LAKPGASVKL SCKTSGYTFT DYWMHWIKQR PGQGLEWIGF INPSSGYTKY    60
NQNFKDKATL TADKSSSTAY MQLSSLTYED SAVFYCAREA GSISDWYFDV WGTGTTVTVS   120
S                                                                  121

SEQ ID NO: 259          moltype = AA   length = 116
FEATURE                 Location/Qualifiers
REGION                  1..116
                        note = Synthetic Construct
source                  1..116
                        mol_type = protein
                        organism = synthetic construct
SEQUENCE: 259
EVQLQQSGAE LVKPGASIKL SCTASGFNIK DCYMHWVKQR TEQGLEWIGR IDPEDGTTNF    60
APKFQDRATI TADTSSNTAY LQLTSLTSED TAVYYCAREW DSGAYWGQGT LVTVSA      116

SEQ ID NO: 260          moltype = AA   length = 121
FEATURE                 Location/Qualifiers
REGION                  1..121
                        note = Synthetic Construct
source                  1..121
                        mol_type = protein
                        organism = synthetic construct
SEQUENCE: 260
QVQLQQSGAE LAKPGASVKL SCKASGYTFT NYWMHWVKKR PGQGLEWIGY INPSSGYTKY    60
NQKFKDKATL TADKSSNTAY MQLSSLTYED SAVYYCTREG GSISDWYFDV WGTGTTVTVS   120
S                                                                  121

SEQ ID NO: 261          moltype = AA   length = 119
FEATURE                 Location/Qualifiers
REGION                  1..119
                        note = Synthetic Construct
source                  1..119
```

```
                         mol_type = protein
                         organism = synthetic construct
SEQUENCE: 261
EVQLVESGGG LVKPGGSLKL SCAASGFTFS DYGMHWVRQA PEKGLEWVAY ISSGSSTIYY    60
ADTVKGRFTI SRDNAKNTLF LQMTSLRSED TAMYYCARNY GSPYAMDYWG QGTSVTVSS    119

SEQ ID NO: 262           moltype = AA  length = 118
FEATURE                  Location/Qualifiers
REGION                   1..118
                         note = Synthetic Construct
source                   1..118
                         mol_type = protein
                         organism = synthetic construct
SEQUENCE: 262
QVQLQQSGAD LVKPGASVKI SCKASGYAFS SFWMNWVKLR PGKGLEWIGQ IYPGDGDTDY    60
NGKFKDKATL TADTSSNTAY MQLSRLTSED SAVYFCARGD GFSYFDYWGQ GTILTVSS     118

SEQ ID NO: 263           moltype = AA  length = 120
FEATURE                  Location/Qualifiers
REGION                   1..120
                         note = Synthetic Construct
source                   1..120
                         mol_type = protein
                         organism = synthetic construct
SEQUENCE: 263
QVQLKESGPV LVAPSQSLSI TCTVSGFSLT NYGVHWVRQP PGKGLEWLGV IWAGGNTNYN    60
SALMSRLSIS KDNSKSQVFL KMNSLQTDDT AMYYCAKEAK LLRSYAMDYW GQGTSVTVSS   120

SEQ ID NO: 264           moltype = AA  length = 117
FEATURE                  Location/Qualifiers
REGION                   1..117
                         note = Synthetic Construct
source                   1..117
                         mol_type = protein
                         organism = synthetic construct
SEQUENCE: 264
QVQLQQSGPE LVKPGASVKL SCKASGYTFT SYDINWVKQR PGQGLEWIGW IYPRDGNTQY    60
IEKLKGKATL TVDTSSSTAY MELHSLTSED SAVYFCARWI FYAMDYWGQG TSVTVSS      117

SEQ ID NO: 265           moltype = AA  length = 119
FEATURE                  Location/Qualifiers
REGION                   1..119
                         note = Synthetic Construct
source                   1..119
                         mol_type = protein
                         organism = synthetic construct
SEQUENCE: 265
QVQLQQPGAE LVRPGSSVKL SCKASGYTFT RFWMHWVKQR PIQGLEWIGN IDPSDSQTHY    60
NQKFKDKATL TVDKSSSTAY MQLSSLTSED SAVYYCARLI TVDYAMDYWG QGTSVTVSS    119

SEQ ID NO: 266           moltype = AA  length = 120
FEATURE                  Location/Qualifiers
REGION                   1..120
                         note = Synthetic Construct
source                   1..120
                         mol_type = protein
                         organism = synthetic construct
SEQUENCE: 266
QVQLKESGPV LVAPSQSLSI TCTVSGFSLT NYGVHWVRQP PGKGLEWLGV IWAGGNTNYN    60
SALMSRLSIS KDNSKSQVFL KMNSLQTDDT AMYYCAKEAK LLRSYAMDYW GQGTLVTVSA   120

SEQ ID NO: 267           moltype = AA  length = 126
FEATURE                  Location/Qualifiers
REGION                   1..126
                         note = Synthetic Construct
source                   1..126
                         mol_type = protein
                         organism = synthetic construct
SEQUENCE: 267
QVQLQQPGAE LVKPGASVKL SCKASGYTFT TYWIDWVKQR PGQGLEWIGN MFPGSSRTNY    60
NEKFKSRATL TVDTSSSTAY MQLSSLTSDD SAVYYCARKE GLWTYGYDGG AWFAYWGQGT   120
LVTVSA                                                              126

SEQ ID NO: 268           moltype = AA  length = 120
FEATURE                  Location/Qualifiers
REGION                   1..120
                         note = Synthetic Construct
source                   1..120
                         mol_type = protein
```

```
                        -continued
                        organism = synthetic construct
SEQUENCE: 268
QVQLQQPGAE LVKPGASVKL SCKASGYTFT NYWMHWVKQR PGQGLDWIGN IDPSDSETHY      60
NQKFKDKATL TVDKVSSTAY MQLSSLTSED SAVYYCARRG YYGRSPFAYW GQGTLVTVSA     120

SEQ ID NO: 269          moltype = AA  length = 112
FEATURE                 Location/Qualifiers
REGION                  1..112
                        note = Synthetic Construct
source                  1..112
                        mol_type = protein
                        organism = synthetic construct
SEQUENCE: 269
DVLMTQTPLS LPVSLGDHAS ISCRSSQSIV YNNGNTYLEW YLQKPGQSPK LLIYKVSNRF      60
SGVPDRFSGS GSGTDFTLKI SRVEAEDLGV YYCFQVSHVP FTFGSGTKLE IK             112

SEQ ID NO: 270          moltype = AA  length = 106
FEATURE                 Location/Qualifiers
REGION                  1..106
                        note = Synthetic Construct
source                  1..106
                        mol_type = protein
                        organism = synthetic construct
SEQUENCE: 270
QIVLTQSPAI LSASPGEKVT MTCRASSSVS YIHWFLQKPG SSPKPWIYAT SNLASGVPFR      60
FIGSGSGTSY SLTISGVEAE DSATYYCQQW SSNPSTFGAG TKLELK                   106

SEQ ID NO: 271          moltype = AA  length = 112
FEATURE                 Location/Qualifiers
REGION                  1..112
                        note = Synthetic Construct
source                  1..112
                        mol_type = protein
                        organism = synthetic construct
SEQUENCE: 271
DIVMTQAAFS NPVTLGTSAS ISCRSSKSLL HSNGITYLYW YLQKPGQSPQ LLISQMSSLA      60
SGVPDRFSSG GSGTDFTLRI SRVEAEDVGV FYCAQNLELP WTFGGGTKLE LK             112

SEQ ID NO: 272          moltype = AA  length = 109
FEATURE                 Location/Qualifiers
REGION                  1..109
                        note = Synthetic Construct
source                  1..109
                        mol_type = protein
                        organism = synthetic construct
SEQUENCE: 272
QAVVTQESAL TTSPGETVTL TCRSSTGAVT TSNYANWVQE KPDHLFTGLI GGTNNRAPGV      60
PARFSGSLIG DKAALTITGA QTEDEAIYFC VLWYSNHLVF GGGTKLTVL                109

SEQ ID NO: 273          moltype = AA  length = 107
FEATURE                 Location/Qualifiers
REGION                  1..107
                        note = Synthetic Construct
source                  1..107
                        mol_type = protein
                        organism = synthetic construct
SEQUENCE: 273
DIQMTQSPAS LSASVGETVT ITCRASENIY IYLAWYQQKQ GKTPQLLVYN GKMLAENVPS      60
RFSGSGSGTQ FSLKINSLQP EDFGSYYCQH HYGSPPAFGA GTKLELK                  107

SEQ ID NO: 274          moltype = AA  length = 107
FEATURE                 Location/Qualifiers
REGION                  1..107
                        note = Synthetic Construct
source                  1..107
                        mol_type = protein
                        organism = synthetic construct
SEQUENCE: 274
DIQMSQSSSY LSVSLGGRVT ITCKASDHIN NWLAWYQQKP GNAPRLLISG ATSLETGVPS      60
RFSGSGSGKD YTLSITSLQT EDVATYYCQQ YWSSPYTFGG GTKLEIK                  107

SEQ ID NO: 275          moltype = AA  length = 113
FEATURE                 Location/Qualifiers
REGION                  1..113
                        note = Synthetic Construct
source                  1..113
                        mol_type = protein
                        organism = synthetic construct
SEQUENCE: 275
```

```
DIVMTQSPSS LSVSAGEKVT MSCKSSQSLL NSGNQRNYLA WYQQKPGQPP KLLIYGASTR    60
ESGVPDRFTG SGSGTDFTLT ISNVQAEDLA VYYCQNDHSY PLTFGAGTKL ELK          113

SEQ ID NO: 276          moltype = AA  length = 107
FEATURE                 Location/Qualifiers
REGION                  1..107
                        note = Synthetic Construct
source                  1..107
                        mol_type = protein
                        organism = synthetic construct
SEQUENCE: 276
DIKMTQSPSS MYASLGERVT ITCKASQDIN SYLSWFQQKP GKSPKTLIFR ANRLVDGVPS    60
RFSGSGSGQD YSLTISSLEY EDMGIYYCLQ YDEFPLTFGA GTKLEMK                 107

SEQ ID NO: 277          moltype = AA  length = 112
FEATURE                 Location/Qualifiers
REGION                  1..112
                        note = Synthetic Construct
source                  1..112
                        mol_type = protein
                        organism = synthetic construct
SEQUENCE: 277
DIVMTQAAFS NPVTLGTSAS ISCRSSKSLL HSNGITYLYW YLQKPGQSPQ LLIYQMSNLA    60
SGVPNRFSSS GSGTDFTLRI SRVEAEDVGV YYCAQNLELP WTFGGGTKLE IK           112

SEQ ID NO: 278          moltype = AA  length = 112
FEATURE                 Location/Qualifiers
REGION                  1..112
                        note = Synthetic Construct
source                  1..112
                        mol_type = protein
                        organism = synthetic construct
SEQUENCE: 278
DVVMTQTPLS LPVSLGDQAS ISCRSSQSLV HSNGKTYLHW YVQKPGQSPK LLIYKISNRF    60
SGVPDRFSGS GSGTDFTLKI SRVEAEDLGV YFCSQITHVP WTFGGGTKLE SK           112

SEQ ID NO: 279          moltype = AA  length = 113
FEATURE                 Location/Qualifiers
REGION                  1..113
                        note = Synthetic Construct
source                  1..113
                        mol_type = protein
                        organism = synthetic construct
SEQUENCE: 279
DIVMTQSPSS LTMSVGQKVT MHCKSSQSLL NSNNLQNYLA WYQQKPGQSP TLLVYFASIR    60
ESGVPDRFIG SGSGTDFTLT ISSVQAEDLA DYFCQQHYNT PFTFGSGTKL EIR          113

SEQ ID NO: 280          moltype = AA  length = 112
FEATURE                 Location/Qualifiers
REGION                  1..112
                        note = Synthetic Construct
source                  1..112
                        mol_type = protein
                        organism = synthetic construct
SEQUENCE: 280
DVLMTQIPLS LPVSLGDQAS ISCRSSQTIV HSNGNTYLEW YLKKPGQSPK LLIDKISNRF    60
SGVPDRFSGS GSGTDFTLKI SRVEAEDLGV YYCFQGSHVP YTFGGGTKLE IK           112

SEQ ID NO: 281          moltype = AA  length = 107
FEATURE                 Location/Qualifiers
REGION                  1..107
                        note = Synthetic Construct
source                  1..107
                        mol_type = protein
                        organism = synthetic construct
SEQUENCE: 281
DIQMTQSPAS LSVSVGETVT ITCRASENIY SSLGWYQQKQ GESPQLLVFA ATNLADGVPS    60
RFSGSGSGTQ YSLKINSLQS EDFGTYYCQH LWSIPWTFGG GTRLEIK                 107

SEQ ID NO: 282          moltype = AA  length = 107
FEATURE                 Location/Qualifiers
REGION                  1..107
                        note = Synthetic Construct
source                  1..107
                        mol_type = protein
                        organism = synthetic construct
SEQUENCE: 282
DIQMTQSPSS LSASLGERVS LTCRASQDIG SNLNWLQQEP DGTIKRLIYA TSSLDSGVPK    60
RFSGSRSGSD YSLTISSLES EDFVVYYCLQ YASSPRTFGG GTRLEIK                 107
```

```
SEQ ID NO: 283          moltype = AA  length = 107
FEATURE                 Location/Qualifiers
REGION                  1..107
                        note = Synthetic Construct
source                  1..107
                        mol_type = protein
                        organism = synthetic construct
SEQUENCE: 283
DIQMTQSPAS LSVSVGETVT ITCRVSENIY NNLAWYQQKQ EKSPQLLVFA ATNLADGVPS   60
RFSGSGSGTQ FSLKINSLQS EDFGTYYCQH FWDTPFTFGS GTKLEIK                107

SEQ ID NO: 284          moltype = AA  length = 106
FEATURE                 Location/Qualifiers
REGION                  1..106
                        note = Synthetic Construct
source                  1..106
                        mol_type = protein
                        organism = synthetic construct
SEQUENCE: 284
QIVLTQSPAI MSASPGEKLT MTCSASSSLN YMYWYQQKPG SSPRLLIYDT SNLASGVPVR   60
FSGSGSGTSY SLTISRMEAE DGATYYCQQW TSFPPTFGAG TKLELK                 106

SEQ ID NO: 285          moltype = AA  length = 107
FEATURE                 Location/Qualifiers
REGION                  1..107
                        note = Synthetic Construct
source                  1..107
                        mol_type = protein
                        organism = synthetic construct
SEQUENCE: 285
DIQMTQSPSS LSASLGERVS LTCRASQDIG SNLNWLQQEP DGTIKRLIYA TSSLDSGVPK   60
RFSGSRSGSD YSLTISSLES EDFVDYYCLQ YASSPRTFGG GTKLEIK                107

SEQ ID NO: 286          moltype = AA  length = 111
FEATURE                 Location/Qualifiers
REGION                  1..111
                        note = Synthetic Construct
source                  1..111
                        mol_type = protein
                        organism = synthetic construct
SEQUENCE: 286
DIVLAQSPAS LAVSLGQRAT ISCRASKSVS ISVYTYVHWY QQKPGQPPKL LIYLASNLES   60
GVPARFSGSG SGTDFTLNIH PVEEEDAATY YCQHSRELPY TFGGGTKLEI K            111

SEQ ID NO: 287          moltype = AA  length = 112
FEATURE                 Location/Qualifiers
REGION                  1..112
                        note = Synthetic Construct
source                  1..112
                        mol_type = protein
                        organism = synthetic construct
SEQUENCE: 287
DVLMTQTPLS LPVSLGDQAS ISCRSSQSIV HSNGNTYLEW YLQKPGQAPK LLIDKVFNRF   60
SGVPDRFSGS GSGTDFTLKI SRVEAEDLGV YYCFQGSHVP FTFGSGTKLE IK           112

SEQ ID NO: 288          moltype = AA  length = 106
FEATURE                 Location/Qualifiers
REGION                  1..106
                        note = Synthetic Construct
source                  1..106
                        mol_type = protein
                        organism = synthetic construct
SEQUENCE: 288
QIVLTQSPAI MSASPGEKLT MTCSASSSLN YMYWYQQKPG SSPRLLIYDT SNLASGVPVR   60
FRGSGSGTSY SLTISRMEAE DGATYYCQQW TSFPPTFGAG TKLELK                 106

SEQ ID NO: 289          moltype = AA  length = 112
FEATURE                 Location/Qualifiers
REGION                  1..112
                        note = Synthetic Construct
source                  1..112
                        mol_type = protein
                        organism = synthetic construct
SEQUENCE: 289
DIVMTQAAFS NPVTLGTSAS ISCRSSKSLL HSNGITYLFW YLQKPGQSPQ LLIYQMSNLA   60
SGVPDRFSSS GSGTDFTLRI SRVEAEDVGV YYCVQNLELP YTFGGGTKLE IK           112

SEQ ID NO: 290          moltype = AA  length = 112
```

```
FEATURE                 Location/Qualifiers
REGION                  1..112
                        note = Synthetic Construct
source                  1..112
                        mol_type = protein
                        organism = synthetic construct
SEQUENCE: 290
DVLMTQTPLS LPVSLGDHAS ISCRSGQSIV HSNGNTYLEW YLQKPGQSPK LLIYKVSNRF      60
SGVPDRFSGS GSGTDFTLKI SRVEAEDLGI YYCFQGSHVP WTFGGGTKLE IK              112

SEQ ID NO: 291          moltype = AA  length = 112
FEATURE                 Location/Qualifiers
REGION                  1..112
                        note = Synthetic Construct
source                  1..112
                        mol_type = protein
                        organism = synthetic construct
SEQUENCE: 291
DIVVTQTPLS LPVSFGDQVS ISCRSSQSLT NYYGNTYLSW YLHKPGQSPQ LLIYGISNRF      60
SGVPDRFSGS GSGTDFTLKI STIKPEDLGM YYCLQGTHQP RTFGGGTKLE IK              112

SEQ ID NO: 292          moltype = AA  length = 113
FEATURE                 Location/Qualifiers
REGION                  1..113
                        note = Synthetic Construct
source                  1..113
                        mol_type = protein
                        organism = synthetic construct
SEQUENCE: 292
DIVMTQSPSS LTMSVGQKVT MNCKSSQSLL NSNNQQNYLA WYQQKPGQSP KLLVYFASIR      60
ESGVPDRFIG SGSGTDFTLT INSVQAEDLA DYFCQQHYST PFTFGSGTKL EIR             113

SEQ ID NO: 293          moltype = AA  length = 111
FEATURE                 Location/Qualifiers
REGION                  1..111
                        note = Synthetic Construct
source                  1..111
                        mol_type = protein
                        organism = synthetic construct
SEQUENCE: 293
DIVMTQAAFS NPVTLGTSAS ISCRSSKSLL HSNGITYLFW YLQKPGQSPQ LLIYQMSNLA      60
SGVPDRFSSS GSGTDFTLRI SRVEAEDVGV YYCAQNLELW TFGGGTKLEI K               111

SEQ ID NO: 294          moltype = AA  length = 106
FEATURE                 Location/Qualifiers
REGION                  1..106
                        note = Synthetic Construct
source                  1..106
                        mol_type = protein
                        organism = synthetic construct
SEQUENCE: 294
QIVLTQSPAI MSASPGEKVT ISCSASSSIS YMYWYQQKPG SSPKPWIYRT STLASGVPAR      60
FSGSGSGTSY SLTISSMEAE DAATYYCQQY HSYPRTFGGG TKLEIK                     106

SEQ ID NO: 295          moltype = AA  length = 113
FEATURE                 Location/Qualifiers
REGION                  1..113
                        note = Synthetic Construct
source                  1..113
                        mol_type = protein
                        organism = synthetic construct
SEQUENCE: 295
DIVMTQSPSS LSVSVGEKVT VSCKSSQSLL NSGNQKNYLA WYQQKPGQPP KLLIYGASTR      60
ESGVPDRFTG SGSGTDFTLT ISSVQAEDLA VYYCQNDHSY PLTFGAGTKL ELK             113

SEQ ID NO: 296          moltype = AA  length = 112
FEATURE                 Location/Qualifiers
REGION                  1..112
                        note = Synthetic Construct
source                  1..112
                        mol_type = protein
                        organism = synthetic construct
SEQUENCE: 296
DIVMTQAAFS NPVTLGTSAS ISCRSSKSLL HYNGITYLYW YLQKPGQSPQ LLIYQMSNLA      60
SGVPDRFSSS GSGTDFTLRI SRVEAEDVGV YYCAQNLELP YTFGGGTKLE IK              112

SEQ ID NO: 297          moltype = AA  length = 112
FEATURE                 Location/Qualifiers
REGION                  1..112
```

```
                        note = Synthetic Construct
source                  1..112
                        mol_type = protein
                        organism = synthetic construct
SEQUENCE: 297
DVLMTQSPLS LPVSLGDQVS ISCRSSQTIV HRNGNTYLEW YLQKPGQSPK LLIYKVSNRF    60
SGVPDRFSGS GSGTDFTLKI SRVEAEDLGV YYCFQGSHLP WTFGGGTKLE IK           112

SEQ ID NO: 298          moltype = AA   length = 107
FEATURE                 Location/Qualifiers
REGION                  1..107
                        note = Synthetic Construct
source                  1..107
                        mol_type = protein
                        organism = synthetic construct
SEQUENCE: 298
DIKMTQSPSS MYASLGERVT FTCKASQDIN SYLSWFQQKP GKSPKTLIYR GNGLVDGVPS    60
RFSGSGSGQD YSLTISSLEY EDMGIYYCLQ YDEFPFTFAS GTKLEIK                 107

SEQ ID NO: 299          moltype = AA   length = 112
FEATURE                 Location/Qualifiers
REGION                  1..112
                        note = Synthetic Construct
source                  1..112
                        mol_type = protein
                        organism = synthetic construct
SEQUENCE: 299
DVLMTQTPLS LPVSLGDQAS ISCRSSQNIV HSNGNTYLEW YLQKPGQSPK LLIDKVSNRF    60
SGVPDRFSGS GSGTDFTLKI SRVEAEDLGI YYCFQGSHVP FTFGSGTKLE IK           112

SEQ ID NO: 300          moltype = AA   length = 107
FEATURE                 Location/Qualifiers
REGION                  1..107
                        note = Synthetic Construct
source                  1..107
                        mol_type = protein
                        organism = synthetic construct
SEQUENCE: 300
DIVMTQSQKF MSTTVGDRVS ITCKASQNVG TAVAWYQQKP GQSPKLLIYS ASNRYTGVPD    60
RFTGSGSGTD FTLTISNMQS EDLADYFCQQ YSSYPYTFGG GTKLEIK                 107

SEQ ID NO: 301          moltype = AA   length = 106
FEATURE                 Location/Qualifiers
REGION                  1..106
                        note = Synthetic Construct
source                  1..106
                        mol_type = protein
                        organism = synthetic construct
SEQUENCE: 301
QIVLSQSPVI LSASPGEKVT MTCRATSSVT YMHWYQLKPG SSPKPWIYAT SNLASGVPAR    60
FSGSGSGTSY SLTISRVEAE DAATYYCQQW SSNPYTFGGG TKLEIK                  106

SEQ ID NO: 302          moltype = AA   length = 112
FEATURE                 Location/Qualifiers
REGION                  1..112
                        note = Synthetic Construct
source                  1..112
                        mol_type = protein
                        organism = synthetic construct
SEQUENCE: 302
DVLMTQIPLS LPVSLGDQAS ISCRSSQSIV HRNGNTYLEW YLQKPGQSPK LLIYKVSNRF    60
SGVPDRFSGS GSGTDFTLKI SRVEAEDLGV YYCFQGSHVP YTFGGGTKLE IK           112

SEQ ID NO: 303          moltype = AA   length = 112
FEATURE                 Location/Qualifiers
REGION                  1..112
                        note = Synthetic Construct
source                  1..112
                        mol_type = protein
                        organism = synthetic construct
SEQUENCE: 303
DIVMTQAAPS VPVTPGESVS ISCRSSKSLL HSNGNTYSYW FLQRPGQSPQ LLIYRMSNLA    60
SGVPDRFSGS GSGTAFTLRI SRVEAEDVGV YYCMQHLEYP YTFGGGTKLE IK           112

SEQ ID NO: 304          moltype = AA   length = 112
FEATURE                 Location/Qualifiers
REGION                  1..112
                        note = Synthetic Construct
source                  1..112
```

```
                        mol_type = protein
                        organism = synthetic construct
SEQUENCE: 304
DIVMTQAAPS IPVTPGESVS ISCRSSKTLL NSNGNTYLYW FLQRPGQPPQ LLIYRMSNLA      60
SGVPDRFSGS GSGTAFTLRI SRVEAEDVGV YYCMQHLDYP YTFGGGTQLE IK             112

SEQ ID NO: 305          moltype = AA   length = 113
FEATURE                 Location/Qualifiers
REGION                  1..113
                        note = Synthetic Construct
source                  1..113
                        mol_type = protein
                        organism = synthetic construct
SEQUENCE: 305
DIVMSQSPSS LAVSVGQKVT MSCKSSQSLL YSSNQKNYLA WYQQKPGQSP KLLIYWASTR      60
ESGVPDRFTG SGSGTDFTLT ISSVKTEDLA VYYCQQYYSY PYTFGGGTKL EIK            113

SEQ ID NO: 306          moltype = AA   length = 112
FEATURE                 Location/Qualifiers
REGION                  1..112
                        note = Synthetic Construct
source                  1..112
                        mol_type = protein
                        organism = synthetic construct
SEQUENCE: 306
DIVMTQAAPS LPVTPGESVS ISCRSSKSLL HSNGNTYLYW FLQRPGQSPQ LLIYRMSNLA      60
SGVPDRFSGS GSGTAFTLRI SRVEAEDVGV YYCMQHLEYP YTFGGGTKLE IK             112

SEQ ID NO: 307          moltype = AA   length = 112
FEATURE                 Location/Qualifiers
REGION                  1..112
                        note = Synthetic Construct
source                  1..112
                        mol_type = protein
                        organism = synthetic construct
SEQUENCE: 307
DIVMSQSPSS LAVSVGEKVT MSCKSSQSLL YSSNQKNYLA WYQQKPGQSP KLLIYWASTR      60
ESGVPDRFTG SGSGTDFTLT ISSVKAEDLA VYYCQQYYSY PTFGGGTKLE IK             112

SEQ ID NO: 308          moltype = AA   length = 106
FEATURE                 Location/Qualifiers
REGION                  1..106
                        note = Synthetic Construct
source                  1..106
                        mol_type = protein
                        organism = synthetic construct
SEQUENCE: 308
QIVLTQSPVI MSASPGERVT MTCCASSRVN YMHWYQQKSG SYPKRWIYDT SKLASGVPGR      60
FSGSGSGTSY SLTISSMEAE DAATYYCQQW SSNPPTFGGG TKLEIK                    106

SEQ ID NO: 309          moltype = AA   length = 113
FEATURE                 Location/Qualifiers
REGION                  1..113
                        note = Synthetic Construct
source                  1..113
                        mol_type = protein
                        organism = synthetic construct
SEQUENCE: 309
DIVMTQSPSS LTVTAGEKVT MSCKSSQSLL NSGNQKNYLT WYQQKPGQPP KLLIYWASTR      60
ESGVPDRFTG SGSGTDFTLT ISSVQAEDLA VYYCQNDYSY PLTFGAGTKL EIK            113

SEQ ID NO: 310          moltype = AA   length = 112
FEATURE                 Location/Qualifiers
REGION                  1..112
                        note = Synthetic Construct
source                  1..112
                        mol_type = protein
                        organism = synthetic construct
SEQUENCE: 310
DVLMTQTPLS LPVSLGNQAS ISCRSSQSIV HGNGNTYLEW YLQKPGQSPK LLIYKVSNRF      60
SGVPDRFSGS GSGTDFTLKI SRVEAEDLGV YYCFQGSHLP YTFGGGTKLE IK             112

SEQ ID NO: 311          moltype = AA   length = 106
FEATURE                 Location/Qualifiers
REGION                  1..106
                        note = Synthetic Construct
source                  1..106
                        mol_type = protein
                        organism = synthetic construct
```

```
SEQUENCE: 311
QIVLTQSPAI MSASPGEKVT ISCSASSSVS YMYWYQQKPG SSPKPWIHRT SNLASGVPVR    60
FSGSGSGTSY SLTISSMEAE DAATYYCQQY HSYPPTFGAG TKLELK                  106

SEQ ID NO: 312          moltype = AA   length = 107
FEATURE                 Location/Qualifiers
REGION                  1..107
                        note = Synthetic Construct
source                  1..107
                        mol_type = protein
                        organism = synthetic construct
SEQUENCE: 312
DVQMTQTTSS LSASLGDRVT ISCRASQDIN NYLYWYQQKP DGTVKLLIYY TSMLHSGVPS    60
RFSGSGSGTD YSLTISNLEQ EDIATYFCQQ GSTLMYTFGG GTKLEIK                 107

SEQ ID NO: 313          moltype = AA   length = 112
FEATURE                 Location/Qualifiers
REGION                  1..112
                        note = Synthetic Construct
source                  1..112
                        mol_type = protein
                        organism = synthetic construct
SEQUENCE: 313
DIVMSQSPSS LAVSVGEKVT MSCKSSQSLR NSRTRKNYLA WYQQKPGQSP KLLIYWASTR    60
ESGVPDRFTG SGSGTDFTLT ISSVQAEDLA IYYCKQSYNL LTFGAGTKLE LK           112

SEQ ID NO: 314          moltype = AA   length = 106
FEATURE                 Location/Qualifiers
REGION                  1..106
                        note = Synthetic Construct
source                  1..106
                        mol_type = protein
                        organism = synthetic construct
SEQUENCE: 314
ENVLTQSPAI MSASPGEKVT MTCSASSSVS YMHWYQQKSN TSPKLWIYDT SKLASGVPGR    60
FSGSGSGNSY SLTISSAEAE DVATYYCFQG SGYPLTFGAG TKLELK                  106

SEQ ID NO: 315          moltype = AA   length = 274
FEATURE                 Location/Qualifiers
source                  1..274
                        mol_type = protein
                        organism = Macaca fascicularis
SEQUENCE: 315
MGKSLSHLPL HSSKEDAYDG VTSENMRNGL VNSEVHNEDG RNGDVSQFPY VEFTGRDSVT    60
RPTCQGTGRI PRGQENQLVA LIPYSDQRLR PRRTKLYVMA SVFVCLLLSG LAVFFLFPRS   120
IDVKYIGVKS AYVSYDVQKR TIYLNITNTL NITNNNYYSV EVENITAQVQ FAKTVIGKAR   180
LNNITHIGPL DMKQIDYTVP TVIAEEMSYM YDFCTLISIK VHNIVLMMQV TVTTTYFGHS   240
EQISQERYQY VDCGRNTTYQ LGQSEYLNVL QPQQ                               274

SEQ ID NO: 316          moltype = AA   length = 126
FEATURE                 Location/Qualifiers
REGION                  1..126
                        note = Synthetic Construct
source                  1..126
                        mol_type = protein
                        organism = synthetic construct
SEQUENCE: 316
MDMRVPAQLL GLLLLWLRGA RCDVKYIGVK SAYVSYDVQK RTIYLNITNT LNITNNNYYS    60
VEVENITAQV QFSKTVIGKA RLNNITIIGP LDMKQIDYTV PTVIAEEMSY MSGGGGSHHH   120
HHHHHH                                                              126

SEQ ID NO: 317          moltype = AA   length = 338
FEATURE                 Location/Qualifiers
REGION                  1..338
                        note = Synthetic Construct
source                  1..338
                        mol_type = protein
                        organism = synthetic construct
SEQUENCE: 317
MDMRVPAQLL GLLLLWLRGA RCDVKYIGVK SAYVSYDVQK RTIYLNITNT LNITNNNYYS    60
VEVENITAQV QFSKTVIGKA RLNNITIIGP LDMKQIDYTV PTVIAEEMSY MDKTHTCPPC   120
PAPELLGGPS VFLFPPKPKD TLMISRTPEV TCVVVDVSHE DPEVKFNWYV DGVEVHNAKT   180
KPREEQYNST YRVVSVLTVL HQDWLNGKEY KCKVSNKALP APIEKTISKA KGQPREPQVY   240
TLPPSRDELT KNQVSLTCLV KGFYPSDIAV EWESNGQPEN NYKTTPPVLD SDGSFFLYSK   300
LTVDKSRWQQ GNVFSCSVMH EALHNHYTQK SLSLSPGK                           338

SEQ ID NO: 318          moltype = AA   length = 620
FEATURE                 Location/Qualifiers
REGION                  1..620
```

```
                        note = Synthetic Construct
source                  1..620
                        mol_type = protein
                        organism = synthetic construct
SEQUENCE: 318
MEFGLSWVFL VALLRGVQCE VRLLESGGGL VQPGGSLRLS CAASGFTFSN YAMGWVRQAP  60
GKGLEWVSAI SGSGGSTYYA DSVKGRFTTS RDDSKNALYL QMNSLRAEDT AVYYCARGGP 120
GWYAADVWGQ GTTVTVSSAK TTPPSVYPLA PGSAAQTNSM VTLGCLVKGY FPEPVTVTWN 180
SGSLSSGVHT FPAVLQSDLY TLSSSVTVPS SPRPSETVTC NVAHPASSTK VDKKIVPRDC 240
GCKPCICTVP EVSSVFIFPP KPKDVLTITL TPKVTCVVVD ISKDDPEVQF SWFVDDVEVH 300
TAQTQPREEQ FNSTFRSVSE LPIMHQDWLN GKEFKCRVNS AAFPAPIEKT ISKTKGRPKA 360
PQVYTIPPPK EQMAKDKVSL TCMITDFFPE DITVEWQWNG QPAENYKNTQ PIMNTNGSYF 420
VYSKLNVQKS NWEAGNTFTC SVLHEGLHNH HTEKSLSHSP GKSGGGGDVK YIGVKSAYVS 480
YDVQKRTIYL NITNTLNITN NNYYSVEVEN ITAQVQFSKT VIGKARLNNI TIIGPLDMKQ 540
IDYTVPTVIA EEMSYMYDFC TLISIKVHNI VLMMQVTVTT TYFGHSEQIS QERYQYVDCG 600
RNTTYQLGQS EYLNVLQPQQ                                            620

SEQ ID NO: 319          moltype = AA   length = 556
FEATURE                 Location/Qualifiers
REGION                  1..556
                        note = Synthetic Construct
source                  1..556
                        mol_type = protein
                        organism = synthetic construct
SEQUENCE: 319
MEFGLSWVFL VALLRGVQCE VRLLESGGGL VQPGGSLRLS CAASGFTFSN YAMGWVRQAP  60
GKGLEWVSAI SGSGGSTYYA DSVKGRFTTS RDDSKNALYL QMNSLRAEDT AVYYCARGGP 120
GWYAADVWGQ GTTVTVSSAK TTPPSVYPLA PGSAAQTNSM VTLGCLVKGY FPEPVTVTWN 180
SGSLSSGVHT FPAVLQSDLY TLSSSVTVPS SPRPSETVTC NVAHPASSTK VDKKIVPRDC 240
GCKPCICTVP EVSSVFIFPP KPKDVLTITL TPKVTCVVVD ISKDDPEVQF SWFVDDVEVH 300
TAQTQPREEQ FNSTFRSVSE LPIMHQDWLN GKEFKCRVNS AAFPAPIEKT ISKTKGRPKA 360
PQVYTIPPPK EQMAKDKVSL TCMITDFFPE DITVEWQWNG QPAENYKNTQ PIMNTNGSYF 420
VYSKLNVQKS NWEAGNTFTC SVLHEGLHNH HTEKSLSHSP GKSGGGGDVK YIGVKSAYVS 480
YDVQKRTIYL NITNTLNITN NNYYSVEVEN ITAQVQFSKT VIGKARLNNI TIIGPLDMKQ 540
IDYTVPTVIA EEMSYM                                                556

SEQ ID NO: 320          moltype = AA   length = 347
FEATURE                 Location/Qualifiers
REGION                  1..347
                        note = Synthetic Construct
source                  1..347
                        mol_type = protein
                        organism = synthetic construct
SEQUENCE: 320
MDMRVPAQLL GLLLLWLRGA RCMSPILGYW KIKGLVQPTR LLLEYLEEKY EEHLYERDEG  60
DKWRNKKFEL GLEFPNLPYY IDGDVKLTQS MAIIRYIADK HNMLGGCPKE RAEISMLEGA 120
VLDIRYGVSR IAYSKDFETL KVDFLSKLPE MLKMFEDRLC HKTYLNGDHV THPDFMLYDA 180
LDVVLYMDPM CLDAFPKLVC FKKRIEAIPQ IDKYLSSSKY IAWPLQGWQA TFGGGDHPPK 240
SDPREFIVTD DIEGRMDPDV KYIGVKSAYV SYDVQKRTIY LNITNLNIT NNNYYSVEVE 300
NITAQVQFSK TVIGKARLNN ITIIGPLDMK QIDYTVPTVI AEEMSYM             347

SEQ ID NO: 321          moltype = AA   length = 415
FEATURE                 Location/Qualifiers
REGION                  1..415
                        note = Synthetic Construct
source                  1..415
                        mol_type = protein
                        organism = synthetic construct
SEQUENCE: 321
MDMRVPAQLL GLLLLWLRGA RCMSPILGYW KIKGLVQPTR LLLEYLEEKY EEHLYERDEG  60
DKWRNKKFEL GLEFPNLPYY IDGDVKLTQS MAIIRYIADK HNMLGGCPKE RAEISMLEGA 120
VLDIRYGVSR IAYSKDFETL KVDFLSKLPE MLKMFEDRLC HKTYLNGDHV THPDFMLYDA 180
LDVVLYMDPM CLDAFPKLVC FKKRIEAIPQ IDKYLSSSKY IAWPLQGWQA TFGGGDHPPK 240
SDPREFIVTD DIEGRMDPPR SIDVKYIGVK SAYVSYDVQK RTIYLNITNT LNITNNNYYS 300
VEVENITAQV QFSKTVIGKA RLNNITIIGP LDMKQIDYTV PTVIAEEMSY MYDFCTLISI 360
KVHNIVLMMQ VTVTTTYFGH SEQISQERYQ YVDCGRNTTY QLGQSEYLNV LQPQQ      415

SEQ ID NO: 322          moltype = DNA   length = 19
FEATURE                 Location/Qualifiers
misc_feature            1..19
                        note = Synthetic Construct
source                  1..19
                        mol_type = other DNA
                        organism = synthetic construct
SEQUENCE: 322
agctgggaag gtgtgcaca                                              19

SEQ ID NO: 323          moltype = DNA   length = 21
FEATURE                 Location/Qualifiers
```

```
misc_feature            1..21
                        note = Synthetic Construct
source                  1..21
                        mol_type = other DNA
                        organism = synthetic construct
SEQUENCE: 323
ccatttgtc gttcactgcc a                                              21

SEQ ID NO: 324          moltype = AA  length = 15
FEATURE                 Location/Qualifiers
REGION                  1..15
                        note = Synthetic Construct
source                  1..15
                        mol_type = protein
                        organism = synthetic construct
SEQUENCE: 324
NITNNNYYSV EVENI                                                    15

SEQ ID NO: 325          moltype = AA  length = 11
FEATURE                 Location/Qualifiers
REGION                  1..11
                        note = Synthetic Construct
source                  1..11
                        mol_type = protein
                        organism = synthetic construct
SEQUENCE: 325
TIIGPLDMKQ I                                                        11

SEQ ID NO: 326          moltype = AA  length = 15
FEATURE                 Location/Qualifiers
REGION                  1..15
                        note = Synthetic Construct
source                  1..15
                        mol_type = protein
                        organism = synthetic construct
SEQUENCE: 326
VTCPTCQGTG RIPRG                                                    15

SEQ ID NO: 327          moltype = AA  length = 11
FEATURE                 Location/Qualifiers
REGION                  1..11
                        note = Synthetic Construct
source                  1..11
                        mol_type = protein
                        organism = synthetic construct
SEQUENCE: 327
ALIPYSDQRL R                                                        11

SEQ ID NO: 328          moltype = AA  length = 11
FEATURE                 Location/Qualifiers
REGION                  1..11
                        note = Synthetic Construct
source                  1..11
                        mol_type = protein
                        organism = synthetic construct
SEQUENCE: 328
KRTIYLNITN T                                                        11

SEQ ID NO: 329          moltype = AA  length = 11
FEATURE                 Location/Qualifiers
REGION                  1..11
                        note = Synthetic Construct
source                  1..11
                        mol_type = protein
                        organism = synthetic construct
SEQUENCE: 329
YQYVDCGRNT T                                                        11

SEQ ID NO: 330          moltype = AA  length = 10
FEATURE                 Location/Qualifiers
REGION                  1..10
                        note = Synthetic Construct
source                  1..10
                        mol_type = protein
                        organism = synthetic construct
SEQUENCE: 330
EDAYDGVTSE                                                          10

SEQ ID NO: 331          moltype = AA  length = 8
```

```
FEATURE              Location/Qualifiers
REGION               1..8
                     note = Synthetic Construct
source               1..8
                     mol_type = protein
                     organism = synthetic construct
SEQUENCE: 331
SEVHNEDG                                                                8

SEQ ID NO: 332       moltype = AA  length = 15
FEATURE              Location/Qualifiers
REGION               1..15
                     note = Synthetic Construct
source               1..15
                     mol_type = protein
                     organism = synthetic construct
SEQUENCE: 332
LSHLPLHSSK EDAYD                                                       15

SEQ ID NO: 333       moltype = AA  length = 11
FEATURE              Location/Qualifiers
REGION               1..11
                     note = Synthetic Construct
source               1..11
                     mol_type = protein
                     organism = synthetic construct
SEQUENCE: 333
LVNSEVHNED G                                                           11

SEQ ID NO: 334       moltype = AA  length = 6
FEATURE              Location/Qualifiers
REGION               1..6
                     note = Synthetic Construct
source               1..6
                     mol_type = protein
                     organism = synthetic construct
SEQUENCE: 334
NYYSVE                                                                  6

SEQ ID NO: 335       moltype = AA  length = 6
FEATURE              Location/Qualifiers
REGION               1..6
                     note = Synthetic Construct
source               1..6
                     mol_type = protein
                     organism = synthetic construct
SEQUENCE: 335
VIAEEM                                                                  6

SEQ ID NO: 336       moltype = AA  length = 15
FEATURE              Location/Qualifiers
REGION               1..15
                     note = Synthetic Construct
source               1..15
                     mol_type = protein
                     organism = synthetic construct
SEQUENCE: 336
IKVHNIVLMM QVTVT                                                       15

SEQ ID NO: 337       moltype = AA  length = 15
FEATURE              Location/Qualifiers
REGION               1..15
                     note = Synthetic Construct
source               1..15
                     mol_type = protein
                     organism = synthetic construct
SEQUENCE: 337
IGVKSAYVSY DVQKR                                                       15

SEQ ID NO: 338       moltype = AA  length = 15
FEATURE              Location/Qualifiers
REGION               1..15
                     note = Synthetic Construct
source               1..15
                     mol_type = protein
                     organism = synthetic construct
SEQUENCE: 338
QLGQSEYLNV LQPQQ                                                       15
```

```
SEQ ID NO: 339          moltype = AA   length = 7
FEATURE                 Location/Qualifiers
REGION                  1..7
                        note = Synthetic Construct
source                  1..7
                        mol_type = protein
                        organism = synthetic construct
SEQUENCE: 339
EVHNEDG                                                                  7

SEQ ID NO: 340          moltype = AA   length = 11
FEATURE                 Location/Qualifiers
REGION                  1..11
                        note = Synthetic Construct
source                  1..11
                        mol_type = protein
                        organism = synthetic construct
SEQUENCE: 340
VIAEEMSYMY D                                                            11

SEQ ID NO: 341          moltype = AA   length = 11
FEATURE                 Location/Qualifiers
REGION                  1..11
                        note = Synthetic Construct
source                  1..11
                        mol_type = protein
                        organism = synthetic construct
SEQUENCE: 341
NITNNNYYSV E                                                            11

SEQ ID NO: 342          moltype = AA   length = 11
FEATURE                 Location/Qualifiers
REGION                  1..11
                        note = Synthetic Construct
source                  1..11
                        mol_type = protein
                        organism = synthetic construct
SEQUENCE: 342
NIVLMMQVTV T                                                            11

SEQ ID NO: 343          moltype = AA   length = 11
FEATURE                 Location/Qualifiers
REGION                  1..11
                        note = Synthetic Construct
source                  1..11
                        mol_type = protein
                        organism = synthetic construct
SEQUENCE: 343
VTCPTCQGTG R                                                            11

SEQ ID NO: 344          moltype = AA   length = 11
FEATURE                 Location/Qualifiers
REGION                  1..11
                        note = Synthetic Construct
source                  1..11
                        mol_type = protein
                        organism = synthetic construct
SEQUENCE: 344
YLNITNTLNI T                                                            11

SEQ ID NO: 345          moltype = AA   length = 6
FEATURE                 Location/Qualifiers
REGION                  1..6
                        note = Synthetic Construct
source                  1..6
                        mol_type = protein
                        organism = synthetic construct
SEQUENCE: 345
NIVLMM                                                                   6

SEQ ID NO: 346          moltype = AA   length = 13
FEATURE                 Location/Qualifiers
REGION                  1..13
                        note = Synthetic Construct
source                  1..13
                        mol_type = protein
                        organism = synthetic construct
SEQUENCE: 346
VSYDVQKRTI YLN                                                          13
```

```
SEQ ID NO: 347          moltype = AA  length = 15
FEATURE                 Location/Qualifiers
REGION                  1..15
                        note = Synthetic Construct
source                  1..15
                        mol_type = protein
                        organism = synthetic construct
SEQUENCE: 347
TVPTVIAEEM SYMYD                                                          15

SEQ ID NO: 348          moltype = AA  length = 11
FEATURE                 Location/Qualifiers
REGION                  1..11
                        note = Synthetic Construct
source                  1..11
                        mol_type = protein
                        organism = synthetic construct
SEQUENCE: 348
EFTGRDSVTC P                                                              11

SEQ ID NO: 349          moltype = AA  length = 12
FEATURE                 Location/Qualifiers
REGION                  1..12
                        note = Synthetic Construct
source                  1..12
                        mol_type = protein
                        organism = synthetic construct
SEQUENCE: 349
CQGTGRIPRG QE                                                             12
```

US 12,319,734 B2

ANTI-TMEM106B ANTIBODIES AND METHODS OF USE THEREOF

CROSS-REFERENCE TO RELATED APPLICATIONS

This application is a divisional of U.S. application Ser. No. 16/959,081 (now U.S. Pat. No. 11,440,957, issued Sep. 13, 2022), which is a national phase entry of International Application No. PCT/US2018/067236, filed Dec. 21, 2018, which claims the benefit of U.S. Provisional Application No. 62/612,098, filed Dec. 29, 2017, each of which is hereby incorporated by reference in its entirety.

SUBMISSION OF SEQUENCE LISTING ON ASCII TEXT FILE

The content of the electronically submitted sequence listing (Name: 4503_0010002_Seqlisting_ST26.xml; Size: 445,586 bytes; Date of Creation: Aug. 10, 2022) is incorporated herein by reference in its entirety.

FIELD OF THE PRESENT DISCLOSURE

The present disclosure relates to anti-TMEM106B antibodies and therapeutic uses of such antibodies.

BACKGROUND OF THE PRESENT DISCLOSURE

Transmembrane protein 106B (TMEM106B) is a type 2 single pass transmembrane glycoprotein residing primarily within the membrane of late endosome and lysosomes. (See, e.g., Lang et al., 2012, J Biol Chem, 287:19355-19365; Chen-Plotkin et al., 2012, J Neurosci, 32:11213-11227; Brady et al., 2013, Human Molecular Genetics, 22:685-695.) TMEM106B is widely expressed in human tissue, and of particular interest expressed in neurons, glial cells, and endothelial and peri-vascular cells in the brain. TMEM106B is highly conserved in mammals, with the human protein sharing 99% sequence identity with the cynomolgus variant and 97% sequence identify with the murine ortholog.

TMEM106B has a cytoplasmic domain predicted to range from amino acid residues 1-92 (of human TMEM106B; SEQ ID NO:1), a transmembrane domain predicted to range from amino acid residues 96-117, and a lumenal domain predicted to range from amino acid residues 118-274. Five sequence motifs of post-translational N-glycosylation sites (N-X-T/S) span its lumenal domain. Simple glycans are added to three of the asparagine residues (N145, N151, and N164) and are not critical for TMEM106B localization. Complex glycans are added to the most C-terminal motifs at N183 and N256; loss of complex glycans on N183 impairs TMEM106B forward transport to endosomes/lysosomes and results in endoplasmic retention. Additionally, N256 complex glycosylation is necessary for proper TMEM106B sorting. (See, e.g., Nicholson and Rademakers, 2016, Acta Neuropathol, 132:639-651.)

The function of TMEM106B has not been fully characterized. Recent reports have indicated a role of TMEM106B in dendrite branching, morphogenesis, and maintenance by inhibiting trafficking of lysosomes along dendrites. (See, e.g., Brady et al., 2013, Human Molecular Genetics, 126: 696-698; Schwenk et al., 2014, EMBO J, 33:450-467; Clayton et al., 2018, Brain 141 (12): 3428-3442.)

TMEM106B has been shown to interact with various proteins, including without limitation progranulin protein (GRN), other TMEM106 protein family members, such as TMEM106A and TMEM106C, clathrin heavy chain (CLTC), the μl subunit of adipocyte protein 2 (AP2M1), charged multi-vesicular body protein 2b (CHMP2B), microtubule-associated protein 6 (MAP6), lysosomal-associated membrane protein 1 (LAMP1), and vacuolar-ATPase subunit accessory protein 1 (v-ATPase Ap1).

TMEM106B has been genetically linked to various disorders and diseases, in particular neurodegenerative disorders. Such disorders include, without limitation, conditions characterized by the presence of pathological TDP-43 inclusions (i.e., TDP-43 proteinopathies; transactive response DNA binding protein 43), Frontotemporal lobar degeneration (FTLD), FTLD with TDP-43 inclusions (FTLD-TDP), including FTLD-TDP caused by progranulin (GRN) or C9orf72 mutations, TDP-43 proteinopathies, Alzheimer's disease. Lewy body dementia (LBD), hippocampal sclerosis (HpScl), hippocampal sclerosis of aging (HS-Aging), hypomyelinating leukodystrophies, and cognitive impairment in various disorders, such as amyotrophic lateral sclerosis (ALS). TMEM106B has also been linked to metastasis in non-small cell lung cancer (Kundu et al., 2016; Nature Commun. 2018; 9:2731, Cancer Research, Proceedings of the 107th Annual Meeting of the American Association for Cancer Research, abstract no. 688). TMEM106B has also been linked to chronic traumatic encephalopathy (CTE)-related neuropathology and dementia in CTE patients, including changes in AT8 tau deposition, CD68 cell density and PSD-95 concentration (Cherry et al., 2018, Acta Neuropathol Commun. 6:115).

Accordingly, there is a need for therapies targeting TMEM106B, including therapeutic antibodies that specifically bind TMEM106B, and/or therapies that are capable of inhibiting the activity of TMEM106B, such as by reducing TMEM106B protein levels or function or by blocking or reducing the binding of TMEM106B to one or more of its ligands or binding partners, or otherwise modulate the effective concentration of one or more of its ligands or binding partners, in order to treat various diseases, disorders, and conditions associated with TMEM106B activity.

All references cited herein, including patent applications and publications, are hereby incorporated by reference in their entirety.

SUMMARY OF THE PRESENT DISCLOSURE

The present disclosure is generally directed to anti-TMEM106B antibodies and methods of using such antibodies. The methods provided herein find use in preventing, reducing risk, or treating an individual having a neurodegenerative disease, disorder, or condition. In some embodiments, the present invention provides a method for preventing, reducing risk, or treating an individual having a disease, disorder, or injury selected from the group consisting of a neurodegenerative disorder, a disorder characterized by the presence of TDP-43 inclusions, a TDP-43 proteinopathy, inflammatory cell debris or protein aggregates, abnormal circulating myeloid cells, unhealthy aging, frontotemporal lobar degeneration (FTLD), frontotemporal dementia (FTD), FTD with progranulin mutations, FTD with C9orf72 mutations, frontotemporal lobar degeneration with TDP-43 inclusions, hippocampal sclerosis (HpScl), hippocampal sclerosis of aging (HS-Aging), Alzheimer's disease, Lewy body dementia, cognitive impairment, age related cognitive impairment, age related brain atrophy, age-associated traits, including without limitations inflammation, neuronal loss, and cognitive deficits, such as cognitive defects in the absence of known brain disease, including cognitive deficits of the frontal cerebral cortex of older individuals, cognitive impairment in amyotrophic lateral sclerosis, cognitive impairment in chronic traumatic encephalopathy (CTE), diseases, disorders, and conditions associated with over expression or increased activity of TMEM106B, a hypomyelinating disorder, cancer, and metastasis the method comprising administering to an individual in need thereof a therapeutically effective amount of an anti-TMEM106B antibody.

Accordingly, certain aspects of the present disclosure relate to an isolated (e.g., monoclonal) anti-TMEM106B antibody, wherein the anti-TMEM106B antibody has a property selected from the group consisting of: decreasing cellular levels of TMEM106B, decreasing intracellular levels of TMEM106B, inhibiting or reducing the interaction between TMEM106B and one or more of its ligand or binding proteins, and any combination thereof.

In certain embodiments that may be combined with any of the preceding embodiments, the antibody decreases cell surface levels of TMEM106B, decreases intracellular levels of TMEM106B, decreases total levels of TMEM106B, decreases endosomal levels of TMEM106B, decreases lysosomal levels of TMEM106B, or any combination thereof. In certain embodiments that may be combined with any of the preceding embodiments, the anti-TMEM106B antibody induces TMEM106B degradation, TMWM106B cleavage, TMEM106B internalization, TMEM106B down regulation, or any combination thereof. In certain embodiments that may be combined with any of the preceding embodiments, the anti-TMEM106B antibody decreases cellular levels of TMEM106B in vivo. In certain embodiments that may be combined with any of the preceding embodiments, the anti-TMEM106B antibody decreases cellular levels of TMEM106B in brain. In certain embodiments that may be combined with any of the preceding embodiments, the anti-TMEM106B antibody decreases cellular levels of TMEM106B in one or more peripheral organs. In certain embodiments that may be combined with any of the preceding embodiments, the anti-TMEM106B antibody decreases cellular levels of TMEM106B in brain, one or more peripheral organs, or any combination thereof. In certain embodiments that may be combined with any of the preceding embodiments, the anti-TMEM106B antibody decreases cellular levels of TMEM106B in microglia. In certain embodiments that may be combined with any of the preceding embodiments, the anti-TMEM106B antibody decreases cellular levels of TMEM106B in neurons.

In certain embodiments that may be combined with any of the preceding embodiments, the anti-TMEM106B antibody inhibits or reduces one or more interactions between TMEM106B and progranulin protein, other TMEM106 protein family members, such as TMEM106B and TMEM106C, cathrin heavy chain (CLTC), the µl subunit of adipocyte protein 2 (AP2M1), CHMP2B, microtubule-associated protein 6 (MAP6), lysosomal-associated membrane protein 1 (LAMP1), vacuolar-ATPase subunit accessory protein 1, or any protein or polypeptide that modulates the function of TMEM106B.

In certain embodiments that may be combined with any of the preceding embodiments, an anti-TMEM106B antibody of the present disclosure binds a discontinuous TMEM106B epitope. In certain embodiments that may be combined with any of the preceding embodiments, the discontinuous TMEM106B epitope comprises two or more peptides, three or more peptides, four or more peptides, five or more peptides, six or more peptides, seven or more peptides, eight or more peptides, nine or more peptides, or 10 or more peptides. In certain embodiments that may be combined with any of the preceding embodiments, each of the peptides comprise five or more, six or more, seven or more, eight or more, nine or more, 10 or more, 11 or more, 12 or more, 13 or more 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, or 30 or more amino acid residues of the amino acid sequence of SEQ ID NO: 1, of the amino acid sequence of SEQ ID NO:2, or of the amino acid sequence of SEQ ID NO: 315; or five or more, six or more, seven or more, eight or more, nine or more, 10 or more, 11 or more, 12 or more, 13 or more 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, or 30 or more amino acid residues on a mammalian TMEM106B protein corresponding to the amino acid sequence of SEQ ID NO: 1, to the amino acid sequence of SEQ ID NO:2, or to the amino acid sequence of SEQ ID NO:315.

In certain embodiments that may be combined with any of the preceding embodiments, an anti-TMEM106B antibody of the present disclosure binds to a conformational epitope of TMEM106B.

In certain embodiments that may be combined with any of the preceding embodiments, an anti-TMEM106B antibody of the present disclosure competes with one or more reference anti-TMEM106B antibodies selected from the group consisting of TM-1, TM-17, TM-22, TM-23, TM-26, and TM-27, and any combination thereof for binding to TMEM106B. In certain embodiments that may be combined with any of the preceding embodiments, an anti-TMEM106B antibody of the present disclosure competes with one or more reference anti-TMEM106B antibodies selected from the group consisting of TM-2, TM-3, TM-5, TM-7, TM-9, TM-10, TM-11, TM-12, TM-13, TM-18, TM-19, TM-21, TM-25, TM-28, TM-29, TM-32, TM-35, TM-37, TM-39, TM-42, TM-45, TM-48, and TM-53, and any combination thereof for binding to TMEM106B. In certain embodiments that may be combined with any of the preceding embodiments, an anti-TMEM106B antibody of the present disclosure competes with one or more reference anti-TMEM106B antibodies selected from the group consisting of TM-4, TM-6, TM-8, TM-14, TM-15, TM-16, TM-20, TM-31, TM-33, TM-34, TM-36, TM-41, TM-44, TM-46, TM-47, TM-49, TM-50, TM-51, TM-52, and any combination thereof for binding to TMEM106B. In some embodiments, the reference anti-TMEM106B antibody comprises the $V_H$ and $V_L$ of the antibody selected from the group consisting of TM-4, TM-6, TM-8, TM-14, TM-15, TM-16, TM-20, TM-31, TM-33, TM-34, TM-36, TM-41, TM-44, TM-46, TM-47, TM-49, TM-50, TM-51, TM-52, and any combination thereof.

Other aspects of the present disclosure relate to an isolated (e.g., monoclonal) anti-TMEM106B antibody, wherein the anti-TMEM106B antibody comprises at least one, two, three, four, five, or six HVRs of an antibody selected from the group consisting of: TM-1, TM-2, TM-3, TM-4, TM-5, TM-6, TM-7, TM-8, TM-9, TM-10, TM-11, TM-12, TM-13, TM-14, TM-15, TM-16, TM-17, TM-18, TM-19, TM-20, TM-21, TM-22, TM-23, TM-24, TM-25, TM-26, TM-27, TM-28, TM-29, TM-30, TM-31, TM-32, TM-33, TM-34, TM-35, TM-36, TM-37, TM-38, TM-39, TM-40, TM-41, TM-42, TM-43, TM-44, TM-45, TM-46, TM-47, TM-48, TM-49, TM-50, TM-51, TM-52, and TM-53. In some embodiments, the anti-TMEM106B antibody comprises the six HVR (e.g., as shown in Table 4A below) of the antibody selected from the group consisting of TM-1, TM-2, TM-3, TM-4, TM-5, TM-6, TM-7, TM-8, TM-9, TM-10, TM-11, TM-12, TM-13, TM-14, TM-15, TM-16, TM-17, TM-18, TM-19, TM-20, TM-21, TM-22, TM-23, TM-24, TM-25, TM-26, TM-27, TM-28, TM-29, TM-30, TM-31, TM-32, TM-33, TM-34, TM-35, TM-36, TM-37, TM-38, TM-39, TM-40, TM-41, TM-42, TM-43, TM-44, TM-45, TM-46, TM-47, TM-48, TM-49, TM-50, TM-51, TM-52, and TM-53.

Other aspects of the present disclosure relate to an isolated (e.g., monoclonal) anti-TMEM106B antibody which binds essentially the same TMEM106B epitope as a reference anti-TMEM106B antibody comprising the six HVRs of an antibody selected from the group consisting of: TM-1, TM-2, TM-3, TM-4, TM-5, TM-6, TM-7, TM-8, TM-9, TM-10, TM-11, TM-12, TM-13, TM-14, TM-15, TM-16, TM-17, TM-18, TM-19, TM-20, TM-21, TM-22, TM-23, TM-24, TM-25, TM-26, TM-27, TM-28, TM-29, TM-30, TM-31, TM-32, TM-33, TM-34, TM-35, TM-36, TM-37, TM-38, TM-39, TM-40, TM-41, TM-42, TM-43, TM-44, TM-45, TM-46, TM-47, TM-48, TM-49, TM-50, TM-51, TM-52, and TM-53. In some embodiments, the reference anti-TMEM106B antibody comprises the $V_H$ and $V_L$ (e.g., as shown in Table 4B below) of the antibody selected from the group consisting of: TM-1, TM-2, TM-3, TM-4, TM-5, TM-6, TM-7, TM-8, TM-9, TM-10, TM-11, TM-12, TM-13, TM-14, TM-15, TM-16, TM-17, TM-18, TM-19, TM-20, TM-21, TM-22, TM-23, TM-24, TM-25, TM-26, TM-27, TM-28, TM-29, TM-30, TM-31, TM-32, TM-33, TM-34, TM-35, TM-36, TM-37, TM-38, TM-39, TM-40, TM-41, TM-42, TM-43, TM-44, TM-45, TM-46, TM-47, TM-48, TM-49, TM-50, TM-51, TM-52, and TM-53.

Other aspects of the present disclosure relate to an isolated (e.g., monoclonal) anti-TMEM106B antibody which binds to one or more amino acids within amino acid residues 59-73, 80-90, 5-19, 59-69, 52-62, 64-74, 151-165, 185-195, 139-149, 248-258, 156-161, 202-207, 219-233, 126-140, 185-195, 260-274, 202-212, 151-161, 223-233, 143-153, 223-228, 133-145, and/or 198-212 of human TMEM106B (SEQ ID NO:1).

In some embodiments of the present disclosure, an anti-TMEM106B antibody binds to one or more amino acids within amino acid residues 151-165 and/or 185-195. In some embodiments of the present disclosure, an anti-TMEM106B antibody binds to one or more amino acids within amino acid residues 59-73, 80-90, 139-149, and/or 248-258 of human TMEM106B (SEQ ID NO:1). In some embodiments, an anti-TMEM106B antibody binds to one or more amino acids within amino acid residues 5-19, 156-161, 202-207, and/or 219-233 of human TMEM106B (SEQ ID NO:1). In some embodiments, an anti-TMEM106B antibody binds to one or more amino acids within amino acid residues 126-140, 185-195, and/or 260-274 of human TMEM106B (SEQ ID NO:1). In some embodiments, an anti-TMEM106B antibody binds to one or more amino acids within amino acid residues 202-212 of human TMEM106B (SEQ ID NO:1). In some embodiments, an anti-TMEM106B antibody binds to one or more amino acids within amino acid residues 151-161 and/or 223-233 of human TMEM106B (SEQ ID NO:1). In some embodiments, an anti-TMEM106B antibody binds to one or more amino acids within amino acid residues 59-69, 143-153, and/or 223-228 of human TMEM106B (SEQ ID NO:1). In some embodiments, an anti-TMEM106B antibody binds to one or more amino acids within amino acid residues 133-145 and/or 198-212 of human TMEM106B (SEQ ID NO:1). In some embodiments, an anti-TMEM106B antibody binds to one or more amino acids within amino acid residues 52-62, 64-75, and/or 223-228 of human TMEM106B (SEQ ID NO:1).

Other aspects of the present disclosure relate to an isolated anti-TMEM106B antibody which binds to one or more amino acids within the amino acid sequence NITNNNYYSVEVENI (SEQ ID NO: 324), TIIGPLDMKQI (SEQ ID NO:325), VTCPTCQGTGRIPRG (SEQ ID NO:326), (ALIPYSDQRLR (SEQ ID NO:327), (KRTIYLNITNT (SEQ ID NO:328), YQYVDCGRNTT (SEQ ID NO: 329), (LSHLPLHSSKEDAYD (SEQ ID NO:332), (NYYSVE (SEQ ID NO:334), (VIAEEM (SEQ ID NO: 335), (IKVHNIVLMMQVTVT; SEQ ID NO:336), (IGVKSAYVSYDVQKR; SEQ ID NO:337), (QLGQSEYLNVLQPQQ (SEQ ID NO:338), (VIAEEMSYMYD (SEQ ID NO:340), (NITNNNYYSVE (SEQ ID NO:341), (NIVLMMQVTV (SEQ ID NO:342), (VTCPTCQGTGR (SEQ ID NO:343), (YLNITNTLNIT (SEQ ID NO:344), (NIVLMM (SEQ ID NO:345), (VSYDVQKRTIYLN (SEQ ID NO: 346), (TVPTVIAEEMSYMYD (SEQ ID NO:347), (EFTGRDSVTCP (SEQ ID NO:348), and/or (CQGTGRIPRGQE (SEQ ID NO:349).

In certain embodiments that may be combined with any of the preceding embodiments, the anti-TMEM106B antibody further inhibits interaction between TMEM106B and one or more of its ligands, signaling proteins or binding proteins by: a) reducing the effective levels of TMEM106B available for interacting with the one or more ligands or binding proteins; b); blocking one or more of the sites on TMEM106B required for interaction with the one or more ligands or binding proteins; c) preventing one or more posttranslational events on TMEM106B that are required for interaction with the one or more ligands or binding proteins and/or for correct processing and/or subcellular localization of TMEM106B; d) inducing degradation of TMEM106B; e) changing the conformation of TMEM106B, or both. In certain embodiments that may be combined with any of the preceding embodiments, the anti-TMEM106B antibody binds specifically to human TMEM106B, mouse TMEM106B, cyno TMEM106B, or a combination thereof. In certain embodiments that may be combined with any of the preceding embodiments, the anti-TMEM106B antibody is a human antibody, a humanized antibody, a bispecific antibody, a monoclonal antibody, a multivalent antibody, a conjugated antibody, or a chimeric antibody. In certain embodiments that may be combined with any of the preceding embodiments, the anti-TMEM106B antibody is a bispecific antibody recognizing a first antigen and a second antigen. In certain embodiments that may be combined with any of the preceding embodiments, the first antigen is TMEM106B and the second antigen is an antigen facilitating transport across the blood-brain-barrier. In certain embodiments that may be combined with any of the preceding embodiments, the second antigen is selected from the group consisting of TMEM106B, transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30 (A), a protein transduction domain, TAT, Syn-B, penetratin, a poly-arginine peptide, an angiopep peptide, basigin, Glut1, and CD98hc, and ANG1005.

In certain embodiments that may be combined with any of the preceding embodiments, an anti-TMEM106B antibody of the present disclosure increases the expression of TGF-beta.

In some embodiments that may be combined with any of the preceding embodiments, the antibody is a monoclonal antibody. In some embodiments that may be combined with any of the preceding embodiments, the antibody is of the IgG class, the IgM class, or the IgA class. In some embodiments, the antibody is of the IgG class and has an IgG1, IgG2, or IgG4 isotype. In certain embodiments that may be combined with any of the preceding embodiments, the anti-TMEM106B antibody is an antibody fragment that binds to an epitope comprising amino acid residues on human TMEM106B or a mammalian TMEM106B protein. In certain embodiments that may be combined with any of the preceding embodiments, the fragment is a Fab, Fab', Fab'-SH, F(ab')2, Fv, or scFv fragment. In some embodiments that may be combined with any of the preceding embodiments, the antibody is a humanized antibody or a chimeric antibody.

Other aspects of the present disclosure relate to an isolated nucleic acid comprising a nucleic acid sequence encoding the anti-TMEM106B antibody of any of the preceding embodiments. Other aspects of the present disclosure relate to a vector comprising the nucleic acid of any of the preceding embodiments. Other aspects of the present disclosure relate to an isolated host cell comprising the vector of any of the preceding embodiments. Other aspects of the present disclosure relate to a method of producing an anti-TMEM106B antibody, comprising culturing the host cell of any of the preceding embodiments so that the anti-TMEM106B antibody is produced. In certain embodiments, the method further comprises recovering the anti-TMEM106B antibody produced by the host cell. Other aspects of the present disclosure relate to an isolated anti-TMEM106B antibody produced by the method of any of the preceding embodiments. Other aspects of the present disclosure relate to a pharmaceutical composition comprising the anti-TMEM106B antibody of any of the preceding embodiments, and a pharmaceutically acceptable carrier.

Other aspects of the present disclosure relate to a method of preventing, reducing risk, or treating an individual having a disease, disorder, or injury selected from the group consisting of frontotemporal dementia, Alzheimer's disease, vascular dementia, seizures, retinal dystrophy, a traumatic brain injury, a spinal cord injury, long-term depression, atherosclerotic vascular diseases, undesirable symptoms of normal aging, dementia, mixed dementia, Creutzfeldt-Jakob disease, normal pressure hydrocephalus, amyotrophic lateral sclerosis, Huntington's disease, taupathy disease, stroke, acute trauma, chronic trauma, lupus, acute and chronic colitis, Crohn's disease, inflammatory bowel disease, ulcerative colitis, malaria, essential tremor, central nervous system lupus, Behcet's disease, Parkinson's disease, dementia with Lewy bodies, multiple system atrophy, degenerative disc disease, Shy-Drager syndrome, progressive supranuclear palsy, cortical basal ganglionic degeneration, acute disseminated encephalomyelitis, granulomartous disorders, Sarcoidosis, diseases of aging, age related macular degeneration, glaucoma, retinitis pigmentosa, retinal degeneration, respiratory tract infection, sepsis, eye infection, systemic infection, inflammatory disorders, arthritis, multiple sclerosis, metabolic disorder, obesity, insulin resistance, type 2 diabetes, tissue or vascular damage, an injury, inflammatory cell debris or protein aggregates, abnormal circulating myeloid cells, unhealthy aging, age-related cognitive impairment, age-related brain atrophy, age-associated traits, including without limitation inflammation, neuronal loss, and cognitive deficits, such as cognitive deficits in the absence of known brain disease, including cognitive deficits of the frontal cerebral cortex of an older individual and, one or more undesirable symptoms of normal aging, comprising administering to the individual a therapeutically effective amount of the anti-TMEM106B antibody of any of the preceding embodiments. Other aspects of the present disclosure relate to an anti-TMEM106B antibody of any of the preceding embodiments for use in preventing, reducing risk, or treating an individual having a disease, disorder, or injury selected from the group consisting of frontotemporal dementia, Alzheimer's disease, vascular dementia, seizures, retinal dystrophy, a traumatic brain injury, a spinal cord injury, long-term depression, atherosclerotic vascular diseases, undesirable symptoms of normal aging, dementia, mixed dementia, Creutzfeldt-Jakob disease, normal pressure hydrocephalus, amyotrophic lateral sclerosis, Huntington's disease, taupathy disease, stroke, acute trauma, chronic trauma, lupus, acute and chronic colitis, Crohn's disease, inflammatory bowel disease, ulcerative colitis, malaria, essential tremor, central nervous system lupus, Behcet's disease, Parkinson's disease, dementia with Lewy bodies, multiple system atrophy, degenerative disc disease, Shy-Drager syndrome, progressive supranuclear palsy, cortical basal ganglionic degeneration, acute disseminated encephalomyelitis, granulomartous disorders, Sarcoidosis, diseases of aging, age related macular degeneration, glaucoma, retinitis pigmentosa, retinal degeneration, respiratory tract infection, sepsis, eye infection, systemic infection, inflammatory disorders, arthritis, multiple sclerosis, metabolic disorder, obesity, insulin resistance, type 2 diabetes, tissue or vascular damage, an injury, inflammatory cell debris or protein aggregates, abnormal circulating myeloid cells, unhealthy aging, age-related cognitive impairment, age-related brain atrophy, age-associated traits, including without limitation inflammation, neuronal loss, and cognitive deficits, such as cognitive deficits in the absence of known brain disease, including cognitive deficits of the frontal cerebral cortex of older individual, and one or more undesirable symptoms of normal aging. Other aspects of the present disclosure relate to an anti-TMEM106B antibody of any of the preceding embodiments for use in preventing or reducing metastasis. Other aspects of the present disclosure relate to an anti-TMEM106B antibody of any of the preceding embodiments for use in preventing, reducing risk, or treating an individual having cancer.

Other aspects of the present disclosure relate to use of an anti-TMEM106B antibody of any of the preceding embodiments in the manufacture of a medicament for preventing, reducing risk, or treating an individual having a disease, disorder, or injury selected from the group consisting of frontotemporal dementia, Alzheimer's disease, vascular dementia, seizures, retinal dystrophy, a traumatic brain injury, a spinal cord injury, long-term depression, atherosclerotic vascular diseases, undesirable symptoms of normal aging, dementia, mixed dementia, Creutzfeldt-Jakob disease, normal pressure hydrocephalus, amyotrophic lateral sclerosis, Huntington's disease, taupathy disease, stroke, acute trauma, chronic trauma, lupus, acute and chronic colitis, Crohn's disease, inflammatory bowel disease, ulcerative colitis, malaria, essential tremor, central nervous system lupus, Behcet's disease, Parkinson's disease, dementia with Lewy bodies, multiple system atrophy, degenerative disc disease, Shy-Drager syndrome, progressive supranuclear palsy, cortical basal ganglionic degeneration, acute disseminated encephalomyelitis, granulomartous disorders, Sarcoidosis, diseases of aging, age related macular degeneration, glaucoma, retinitis pigmentosa, retinal degeneration, respiratory tract infection, sepsis, eye infection, systemic infection, inflammatory disorders, arthritis, multiple sclerosis, metabolic disorder, obesity, insulin resistance, type 2 diabetes, tissue or vascular damage, an injury, inflammatory cell debris or protein aggregates, abnormal circulating myeloid cells, unhealthy aging, age-related cognitive impairment, age-related brain atrophy, age-associated traits, including without limitations inflammation, neuronal loss, and cognitive deficits, such as cognitive deficits in the absence of known brain disease, including cognitive deficits of the frontal cerebral cortex of older individual and one or more undesirable symptoms of normal aging. Other aspects of the present disclosure relate to a method of preventing, reducing risk, or treating an individual having a disease, disorder, or injury selected from the group consisting of frontotemporal dementia, progressive supranuclear palsy, Alzheimer's disease, vascular dementia, seizures, retinal dystrophy, amyotrophic lateral sclerosis, traumatic brain injury, a spinal cord injury, dementia, stroke, Parkinson's disease, acute disseminated encephalomyelitis, retinal degeneration, age related macular degeneration, glaucoma, multiple sclerosis, septic shock, bacterial infection, arthritis, and osteoarthritis, comprising administering to the individual a therapeutically effective amount of the anti-TMEM106B antibody of any of the preceding embodiments. Other aspects of the present disclosure relate to an anti-TMEM106B antibody of any of the preceding embodiments for use in preventing, reducing risk, or treating an individual having a disease, disorder, or injury selected from the group consisting of frontotemporal dementia, progressive supranuclear palsy, Alzheimer's disease, vascular dementia, seizures, retinal dystrophy, amyotrophic lateral sclerosis, traumatic brain injury, a spinal cord injury, dementia, stroke, Parkinson's disease, acute disseminated encephalomyelitis, retinal degeneration, age related macular degeneration, glaucoma, multiple sclerosis, septic shock, bacterial infection, arthritis, and osteoarthritis. Other aspects of the present disclosure relate to use of an anti-TMEM106B antibody of any of the preceding embodiments in the manufacture of a medicament for preventing, reducing risk, or treating an individual having a disease, disorder, or injury selected from the group consisting of frontotemporal dementia, progressive supranuclear palsy, Alzheimer's disease, vascular dementia, seizures, retinal dystrophy, amyotrophic lateral sclerosis, traumatic brain injury, a spinal cord injury, dementia, stroke, Parkinson's disease, acute disseminated encephalomyelitis, retinal degeneration, age related macular degeneration, glaucoma, multiple sclerosis, septic shock, bacterial infection, arthritis, and osteoarthritis.

In certain embodiments that may be combined with any of the preceding embodiments, the anti-TMEM106B antibody comprises two or more anti-TMEM106B antibodies.

It is to be understood that one, some, or all of the properties of the various embodiments described herein may be combined to form other embodiments of the present invention. These and other aspects of the invention will become apparent to one of skill in the art. These and other embodiments of the invention are further described by the detailed description that follows.

DETAILED DESCRIPTION OF THE PRESENT DISCLOSURE

Figure 1:
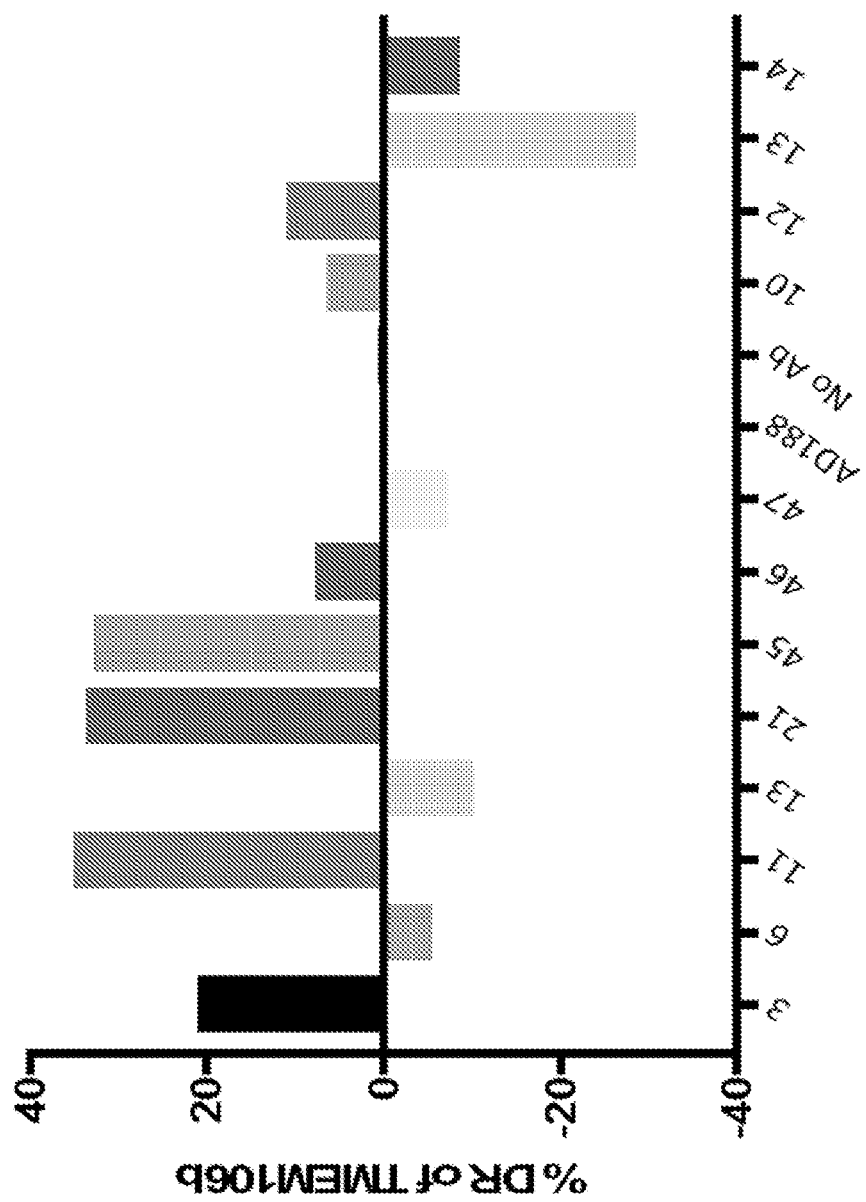
FIG. 1 sets forth data showing percent down regulation (DR) of TMEM106B in A549 cells following addition of various anti-TMEM106B antibodies of the present disclosure.

The present disclosure relates to anti-TMEM106B antibodies (e.g., monoclonal antibodies); methods of making and using such antibodies; pharmaceutical compositions comprising such antibodies; nucleic acids encoding such antibodies; and host cells comprising nucleic acids encoding such antibodies.

The techniques and procedures described or referenced herein are generally well understood and commonly employed using conventional methodology by those skilled in the art, such as, for example, the widely utilized methodologies such as those described in Sambrook et al. *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003); *Monoclonal Antibodies: A Practical Approach* (P. Shepherd and C. Dean, eds., Oxford University Press, 2000).

I. Definitions

The terms "TMEM106B" or "TMEM106B polypeptide" are used interchangeably herein refer herein to any native TMEM106B from any vertebrate source, including mammals such as primates (e.g., humans and cynos) and rodents (e.g., mice and rats), unless otherwise indicated. In some embodiments, the term encompasses both wild-type sequences and naturally occurring variant sequences, e.g., splice variants or allelic variants. In some embodiments, the term encompasses "full-length," unprocessed TMEM106B as well as any form of TMEM106B that results from processing in the cell. In some embodiments, the TMEM106B is human TMEM106B. In some embodiments, the amino acid sequence of an exemplary TMEM106B is Uniprot Accession No: Q9NUM4 as of Jun. 27, 2006. In some embodiments, the amino acid sequence of an exemplary human TMEM106B is SEQ ID NO: 1.

The terms "anti-TMEM106B antibody," an "antibody that binds to TMEM106B," and "antibody that specifically binds TMEM106B" refer to an antibody that is capable of binding TMEM106B with sufficient affinity such that the antibody is useful as a diagnostic and/or therapeutic agent in targeting TMEM106B. In one embodiment, the extent of binding of an anti-TMEM106B antibody to an unrelated, non-TMEM106B polypeptide is less than about 10% of the binding of the antibody to TMEM106B as measured, e.g., by a radioimmunoassay (RIA). In certain embodiments, an antibody that binds to TMEM106B has a dissociation constant (KD) of <1 µM, <100 nM, <10 nM, <1 nM, <0.1 nM, <0.01 nM, or <0.001 nM (e.g., $10^{-8}$ M or less, e.g. from $10^{-8}$ M to $10^{-13}$ M, e.g., from $10^{-9}$ M to $10^{-13}$ M). In certain embodiments, an anti-TMEM106B antibody binds to an epitope of TMEM106B that is conserved among TMEM106B from different species.

With regard to the binding of an antibody to a target molecule, the term "specific binding" or "specifically binds" or is "specific for" a particular polypeptide or an epitope on a particular polypeptide target means binding that is measurably different from a non-specific interaction. Specific binding can be measured, for example, by determining binding of a molecule compared to binding of a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a KD for the target of about any of $10^{-4}$ M or lower, $10^{-5}$ M or lower, 106 M or lower, $10^{-7}$ M or lower, $10^{-8}$ M or lower, $10^{-9}$ M or lower, $10^{-10}$ M or lower, $10^{-11}$ M or lower, $10^{-12}$ M or lower or a KD in the range of $10^{-4}$ M to $10^{-6}$ M or 106 M to $10^{-10}$ M or $10^{-7}$ M to $10^{-9}$ M. As will be appreciated by the skilled artisan, affinity and KD values are inversely related. A high affinity for an antigen is measured by a low KD value. In one embodiment, the term "specific binding" refers to binding where a molecule binds to a particular polypeptide or epitope on a particular polypeptide without substantially binding to any other polypeptide or polypeptide epitope.

The term "immunoglobulin" (Ig) is used interchangeably with "antibody" herein. The term "antibody" herein is used in the broadest sense and specially covers monoclonal antibodies, polyclonal antibodies, multispecific antibodies (e.g., bispecific antibodies) including those formed from at least two intact antibodies, and antibody fragments so long as they exhibit the desired biological activity.

"Native antibodies" are usually heterotetrameric glycoproteins of about 150,000 Daltons, composed of two identical Light ("L") chains and two identical heavy ("H") chains. Each light chain is linked to a heavy chain by one covalent disulfide bond, while the number of disulfide linkages varies among the heavy chains of different immunoglobulin isotypes. Each heavy and light chain also has regularly spaced intra-chain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

For the structure and properties of the different classes of antibodies, see, e.g., Basic and Clinical Immunology, 8th Ed., Daniel P. Stites, Abba I. Terr and Tristram G. Parslow (eds.), Appleton & Lange, Norwalk, CT, 1994, page 71 and Chapter 6.

The light chain from any vertebrate species can be assigned to one of two clearly distinct types, called kappa ("κ") and lambda ("λ"), based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated alpha ("α"), delta ("δ"), epsilon ("ε"), gamma ("γ"), and mu ("∪"), respectively. The γ and α classes are further divided into subclasses (isotypes) on the basis of relatively minor differences in the CH sequence and function, e.g., humans express the following subclasses: IgG1, IgG2, IgG3, IgG4, IgA1, and IgA2. The subunit structures and three-dimensional configurations of different classes of immunoglobulins are well known and described generally in, for example, Abbas et al., Cellular and Molecular Immunology, $4^{th}$ ed. (W.B. Saunders Co., 2000).

The "variable region" or "variable domain" of an antibody, such as an anti-TMEM106B antibody of the present disclosure, refers to the amino-terminal domains of the heavy or light chain of the antibody. The variable domains of the heavy chain and light chain may be referred to as "$V_H$" and "$V_L$", respectively. These domains are generally the most variable parts of the antibody (relative to other antibodies of the same class) and contain the antigen binding sites.

The term "variable" refers to the fact that certain segments of the variable domains differ extensively in sequence among antibodies, such as anti-TMEM106B antibodies of the present disclosure. The variable domain mediates antigen binding and defines the specificity of a particular antibody for its particular antigen. However, the variability is not evenly distributed across the entire span of the variable domains. Instead, it is concentrated in three segments called hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., *Sequences of Immunological Interest*, Fifth Edition, National Institute of Health, Bethesda, MD (1991)). The constant domains are not involved directly in the binding of antibody to an antigen, but exhibit various effector functions, such as participation of the antibody in antibody-dependent-cellular toxicity.

The term "monoclonal antibody" as used herein refers to an antibody, such as a monoclonal anti-TMEM106B antibody of the present disclosure, obtained from a population of substantially homogeneous antibodies, i.e., the individual antibodies comprising the population are identical except for possible naturally occurring mutations and/or post-translation modifications (e.g., isomerizations, amidations, etc.) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method, recombinant DNA methods, and technologies for producing human or human-like antibodies in animals that have parts or all of the human immunoglobulin loci or genes encoding human immunoglobulin sequences.

The terms "full-length antibody," "intact antibody" or "whole antibody" are used interchangeably to refer to an antibody, such as an anti-TMEM106B antibody of the present disclosure, in its substantially intact form, as opposed to an antibody fragment. Specifically, whole antibodies include those with heavy and light chains including an Fc region. The constant domains may be native sequence constant domains (e.g., human native sequence constant domains) or amino acid sequence variants thereof. In some cases, the intact antibody may have one or more effector functions.

An "antibody fragment" refers to a molecule other than an intact antibody that comprises a portion of an intact antibody that binds the antigen to which the intact antibody binds. Examples of antibody fragments include Fab, Fab', F(ab')$_2$ and Fv fragments; diabodies; linear antibodies (see U.S. Pat. No. 5,641,870, Example 2; Zapata et al., *Protein Eng.* 8 (10): 1057-1062 (1995)); single-chain antibody molecules and multispecific antibodies formed from antibody fragments.

Papain digestion of antibodies, such as anti-TMEM106B antibodies of the present disclosure, produces two identical antigen-binding fragments, called "Fab" fragments, and a residual "Fc" fragment, a designation reflecting the ability to crystallize readily. The Fab fragment consists of an entire light chain along with the variable region domain of the heavy chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both heavy chains held together by disulfides. The effector functions of antibodies are determined by sequences in the Fc region, the region which is also recognized by Fc receptors (FcR) found on certain types of cells.

"Functional fragments" of antibodies, such as anti-TMEM106B antibodies of the present disclosure, comprise a portion of an intact antibody, generally including the antigen binding or variable region of the intact antibody or the Fc region of an antibody which retains or has modified FcR binding capability. Examples of antibody fragments include linear antibody, single-chain antibody molecules and multispecific antibodies formed from antibody fragments.

The term "diabodies" refers to small antibody fragments prepared by constructing sFv fragments (see preceding paragraph) with short linkers (about 5-10) residues) between the $V_H$ and $V_L$ domains such that inter-chain but not intra-chain pairing of the variable domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains.

As used herein, a "chimeric antibody" refers to an antibody (immunoglobulin), such as a chimeric anti-TMEM106B antibody of the present disclosure, in which a portion of the heavy and/or light chain is identical with or homologous to corresponding sequences in antibodies derived from a particular species or belonging to a particular antibody class or subclass, while the remainder of the chain(s) is (are) identical with or homologous to corresponding sequences in antibodies derived from another species or belonging to another antibody class or subclass, as well as fragments of such antibodies, so long as they exhibit the desired biological activity. Chimeric antibodies of interest herein include PRIMATIZED® antibodies wherein the antigen-binding region of the antibody is derived from an antibody produced by, e.g., immunizing macaque monkeys with an antigen of interest. As used herein, "humanized antibody" is used a subset of "chimeric antibodies."

"Humanized" forms of non-human (e.g., murine) antibodies, such as humanized forms of anti-TMEM106B antibodies of the present disclosure, are chimeric antibodies comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

A "human antibody" is one that possesses an amino-acid sequence corresponding to that of an antibody, such as an anti-TMEM106B antibody of the present disclosure, produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries and yeast-display libraries. Human antibodies can be prepared by administering the antigen to a transgenic animal that has been modified to produce such antibodies in response to antigenic challenge, but whose endogenous loci have been disabled, e.g., immunized xenomice as well as generated via a human B-cell hybridoma technology.

The term "hypervariable region," "HVR," or "HV," when used herein refers to the regions of an antibody-variable domain, such as that of an anti-TMEM106B antibody of the present disclosure, that are hypervariable in sequence and/or form structurally defined loops. Generally, antibodies comprise six HVRs; three in the $V_H$ (H1, H2, H3), and three in the $V_L$ (L1, L2, L3). In native antibodies, H3 and L3 display the most diversity of the six HVRs, and H3 in particular is believed to play a unique role in conferring fine specificity to antibodies. Naturally occurring camelid antibodies consisting of a heavy chain only are functional and stable in the absence of light chain.

A number of HVR delineations are in use and are encompassed herein. In some embodiments, the HVRs may be Kabat complementarity-determining regions (CDRs) based on sequence variability and are the most commonly used (Kabat et al., supra). In some embodiments, the HVRs may be Chothia CDRs. Chothia refers instead to the location of the structural loops (Chothia and Lesk *J. Mol. Biol.* 196: 901-917 (1987)). In some embodiments, the HVRs may be AbM HVRs. The AbM HVRs represent a compromise between the Kabat CDRs and Chothia structural loops, and are used by Oxford Molecular's AbM antibody-modeling software. In some embodiments, the HVRs may be "contact" HVRs. The "contact" HVRs are based on an analysis of the available complex crystal structures. The residues from each of these HVRs are noted below.

| Loop | Kabat | AbM | Chothia | Contact |
|------|-------|-----|---------|---------|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat numbering) |
| H1 | H31-H35 | H26-H35 | H26-H32 | H30-H35 (Chothia numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2), and 89-97 or 89-96 (L3) in the VL, and 26-35 (H1), 50-65 or 49-65 (a preferred embodiment) (H2), and 93-102, 94-102, or 95-102 (H3) in the VH. The variable-domain residues are numbered according to Kabat et al., supra, for each of these extended-HVR definitions.

"Framework" or "FR" residues are those variable-domain residues other than the HVR residues as herein defined.

An "acceptor human framework" as used herein is a framework comprising the amino acid sequence of a $V_L$ or $V_H$ framework derived from a human immunoglobulin framework or a human consensus framework. An acceptor human framework "derived from" a human immunoglobulin framework or a human consensus framework may comprise the same amino acid sequence thereof, or it may comprise pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less. Where pre-existing amino acid changes are present in a VH, preferable those changes occur at only three, two, or one of positions 71H, 73H and 78H; for instance, the amino acid residues at those positions may by 71A, 73T and/or 78A. In one embodiment, the VL acceptor human framework is identical in sequence to the $V_L$ human immunoglobulin framework sequence or human consensus framework sequence.

A "human consensus framework" is a framework that represents the most commonly occurring amino acid residues in a selection of human immunoglobulin $V_L$ or $V_H$ framework sequences. Generally, the selection of human immunoglobulin $V_L$ or $V_H$ sequences is from a subgroup of variable domain sequences. Generally, the subgroup of sequences is a subgroup as in Kabat et al., *Sequences of Proteins of Immunological Interest,* 5th Ed. Public Health Service, National Institutes of Health, Bethesda, MD (1991). Examples include for the $V_L$, the subgroup may be subgroup kappa I, kappa II, kappa III or kappa IV as in Kabat et al., supra. Additionally, for the $V_H$, the subgroup may be subgroup I, subgroup II, or subgroup III as in Kabat et al., supra.

An "amino-acid modification" at a specified position, e.g., of an anti-TMEM106B antibody of the present disclosure, refers to the substitution or deletion of the specified residue, or the insertion of at least one amino acid residue adjacent the specified residue. Insertion "adjacent" to a specified residue means insertion within one to two residues thereof. The insertion may be N-terminal or C-terminal to the specified residue. The preferred amino acid modification herein is a substitution.

An "affinity-matured" antibody, such as an affinity matured anti-TMEM106B antibody of the present disclosure, is one with one or more alterations in one or more HVRs thereof that result in an improvement in the affinity of the antibody for antigen, compared to a parent antibody that does not possess those alteration(s). In one embodiment, an affinity-matured antibody has nanomolar or even picomolar affinities for the target antigen. Affinity-matured antibodies are produced by procedures known in the art. For example, Marks et al. *Bio/Technology* 10:779-783 (1992) describes affinity maturation by $V_H$- and $V_L$-domain shuffling. Random mutagenesis of HVR and/or framework residues is described by, for example: Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al. *J. Immunol.* 154 (7): 3310-9 (1995); and Hawkins et al., *J. Mol. Biol.* 226:889-896 (1992).

"Fv" is the minimum antibody fragment which comprises a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the $V_H$ and $V_L$ domains, which enables the sFv to form the desired structure for antigen binding.

Antibody "effector functions" refer to those biological activities attributable to the Fc region (a native sequence Fc region or amino acid sequence variant Fc region) of an antibody, and vary with the antibody isotype.

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies of the present disclosure include human IgG1, IgG2, IgG3 and IgG4.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif ("ITAM") in its cytoplasmic domain. Inhibiting receptor FcγRIIB contains an immunoreceptor tyrosine-based inhibition motif ("ITIM") in its cytoplasmic domain. Other FcRs, including those to be identified in the future, are encompassed by the term "FcR" herein. FcRs can also increase the serum half-life of antibodies.

As used herein, "percent (%) amino acid sequence identity" and "homology" with respect to a peptide, polypeptide or antibody sequence refers to the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms known in the art needed to achieve maximal alignment over the full-length of the sequences being compared.

The term "compete" when used in the context of antibodies (e.g., neutralizing antibodies) that compete for the same epitope means competition between antibody as determined by an assay in which the antibody being tested prevents or inhibits (e.g., reduces) specific binding of a reference molecule (e.g., a ligand, or a reference antibody) to a common antigen (e.g., TMEM106B or a fragment thereof). Numerous types of competitive binding assays can be used to determine if antibody competes with another, for example: solid phase direct or indirect radioimmunoassay (RIA), solid phase direct or indirect enzyme immunoassay (EIA), sandwich competition assay (see, e.g., Stahli et al., 1983, Methods in Enzymology 9:242-253); solid phase direct biotin-avidin EIA (see, e.g., Kirkland et al., 1986, J. Immunol. 137:3614-3619) solid phase direct labeled assay, solid phase direct labeled sandwich assay (see, e.g., Harlow and Lane, 1988, Antibodies, A Laboratory Manual, Cold Spring Harbor Press); solid phase direct label RIA using 1-125 label (see, e.g., Morel et al., 1988, Molec. Immunol. 25:7-15); solid phase direct biotin-avidin EIA (see, e.g., Cheung, et al., 1990, Virology 176:546-552); and direct labeled RIA (Moldenhauer et al., 1990, Scand. J. Immunol. 32:77-82). Typically, such an assay involves the use of purified antigen bound to a solid surface or cells bearing either of these, an unlabelled test antibody and a labeled reference antibody. Competitive inhibition is measured by determining the amount of label bound to the solid surface or cells in the presence of the test antibody. Usually the test antibody is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Additional details regarding methods for determining competitive binding are provided below and, in the examples, herein. Usually, when a competing antibody is present in excess, it will inhibit (e.g., reduce) specific binding of a reference antibody to a common antigen by at least 20%, 30%, 40%, 50%, 60%, 70%, 80%, 85%, 90%, 95%, 97.5%, and/or near 100%.

As used herein, an "interaction" between a TMEM106B polypeptide and a second polypeptide encompasses, without limitation, protein-protein interaction, a physical interaction, a chemical interaction, binding, covalent binding, and ionic binding. As used herein, an antibody "inhibits interaction" between two polypeptides when the antibody disrupts, reduces, or completely eliminates an interaction between the two polypeptides. An antibody of the present disclosure, thereof, "inhibits interaction" between two polypeptides when the antibody thereof binds to one of the two polypeptides. In some embodiments, the interaction can be inhibited by at least about any of 20%, 30%, 40%, 50%, 60%, 70%, 80%, 85%, 90%, 95%, 97.5%, and/or near 100%.

The term "epitope" includes any determinant capable of being bound by an antibody. An epitope is a region of an antigen that is bound by an antibody that targets that antigen, and when the antigen is a polypeptide, includes specific amino acids that directly contact the antibody. Most often, epitopes reside on polypeptides, but in some instances, can reside on other kinds of molecules, such as nucleic acids. Epitope determinants can include chemically active surface groupings of molecules such as amino acids, sugar side chains, phosphoryl or sulfonyl groups, and can have specific three-dimensional structural characteristics, and/or specific charge characteristics. Generally, antibodies specific for a particular target antigen will preferentially recognize an epitope on the target antigen in a complex mixture of polypeptides and/or macromolecules.

An "agonist" antibody or an "activating" antibody is an antibody that induces (e.g., increases) one or more activities or functions of the antigen after the antibody binds the antigen.

An "antagonist" antibody or a "blocking" antibody or an "inhibitory" antibody is an antibody that reduces, inhibits, and/or eliminates (e.g., decreases) antigen binding to one or more ligand after the antibody binds the antigen, and/or that reduces, inhibits, and/or eliminates (e.g., decreases) one or more activities or functions of the antigen after the antibody binds the antigen. In some embodiments, antagonist antibodies, or blocking antibodies, or inhibitory antibodies substantially or completely inhibit antigen binding to one or more ligand and/or one or more activities or functions of the antigen.

An "isolated" antibody, such as an isolated anti-TMEM106B antibody of the present disclosure, is one that has been identified, separated and/or recovered from a component of its production environment (e.g., naturally or recombinantly). Preferably, the isolated antibody is free of association with all other contaminant components from its production environment. Contaminant components from its production environment, such as those resulting from recombinant transfected cells, are materials that would typically interfere with research, diagnostic or therapeutic uses for the antibody, and may include enzymes, hormones, and other proteinaceous or non-proteinaceous solutes. In preferred embodiments, the antibody will be purified: (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or, preferably, silver stain. Isolated antibody includes the antibody in situ within recombinant T-cells since at least one component of the antibody's natural environment will not be present. Ordinarily, however, an isolated polypeptide or antibody will be prepared by at least one purification step.

An "isolated" nucleic acid molecule encoding an antibody, such as an anti-TMEM106B antibody of the present disclosure, is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies herein is in a form other than in the form or setting in which it is found in nature. Isolated nucleic acid molecules therefore are distinguished from nucleic acid encoding the polypeptides and antibodies herein existing naturally in cells.

The term "vector," as used herein, is intended to refer to a nucleic acid molecule capable of transporting another nucleic acid to which it has been linked. One type of vector is a "plasmid," which refers to a circular double stranded DNA into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors," or simply, "expression vectors." In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

"Carriers" as used herein include pharmaceutically acceptable carriers, excipients, or stabilizers that are non-toxic to the cell or mammal being exposed thereto at the dosages and concentrations employed.

As used herein, the term "preventing" includes providing prophylaxis with respect to occurrence or recurrence of a particular disease, disorder, or condition in an individual. An individual may be predisposed to, susceptible to a particular disease, disorder, or condition, or at risk of developing such a disease, disorder, or condition, but has not yet been diagnosed with the disease, disorder, or condition.

As used herein, an individual "at risk" of developing a particular disease, disorder, or condition may or may not have detectable disease or symptoms of disease, and may or may not have displayed detectable disease or symptoms of disease prior to the treatment methods described herein. "At risk" denotes that an individual has one or more risk factors, which are measurable parameters that correlate with development of a particular disease, disorder, or condition, as known in the art. An individual having one or more of these risk factors has a higher probability of developing a particular disease, disorder, or condition than an individual without one or more of these risk factors.

As used herein, the term "treatment" refers to clinical intervention designed to alter the natural course of the individual being treated during the course of clinical pathology. Desirable effects of treatment include decreasing the rate of progression, ameliorating or palliating the pathological state, and remission or improved prognosis of a particular disease, disorder, or condition. An individual is successfully "treated", for example, if one or more symptoms associated with a particular disease, disorder, or condition are mitigated or eliminated.

An "effective amount" refers to at least an amount effective, at dosages and for periods of time necessary, to achieve the desired therapeutic or prophylactic result. An effective amount can be provided in one or more administrations. An effective amount herein may vary according to factors such as the disease state, age, sex, and weight of the individual, and the ability of the treatment to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. An effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

An "individual" for purposes of treatment, prevention, or reduction of risk refers to any animal classified as a mammal, including humans, domestic and farm animals, and zoo, sport, or pet animals, such as dogs, horses, rabbits, cattle, pigs, hamsters, gerbils, mice, ferrets, rats, cats, and the like. In some embodiments, the individual is human.

As used herein, administration "in conjunction" with another compound or composition includes simultaneous administration and/or administration at different times. Administration in conjunction also encompasses administration as a co-formulation or administration as separate compositions, including at different dosing frequencies or intervals, and using the same route of administration or different routes of administration. In some embodiments, administration in conjunction is administration as a part of the same treatment regimen.

The term "about" as used herein refers to the usual error range for the respective value readily known to the skilled person in this technical field. Reference to "about" a value or parameter herein includes (and describes) embodiments that are directed to that value or parameter per se.

As used herein and in the appended claims, the singular forms "a," "an," and "the" include plural reference unless the context clearly indicates otherwise. For example, reference to an "antibody" is a reference to from one to many antibodies, such as molar amounts, and includes equivalents thereof known to those skilled in the art, and so forth.

As used herein a "TMEM106B" protein of the present disclosure includes, without limitation, a mammalian TMEM106B protein, human TMEM106B protein, primate TMEM106B protein, cyno TMEM106B protein, mouse TMEM106B protein, and rat TMEM106B protein. Additionally, anti-TMEM106B antibodies of the present disclosure may bind an epitope within one or more of a mammalian TMEM106B protein, human TMEM106B protein, primate TMEM106B, cyno TMEM106B protein, mouse TMEM106B protein, and rat TMEM106B protein.

It is understood that aspect and embodiments of the present disclosure described herein include "comprising," "consisting," and "consisting essentially of" aspects and embodiments.

II. Anti-TMEM106B Antibodies

Provided herein are anti-TMEM106B antibodies. Antibodies provided are useful, e.g., for the diagnosis or treatment of TMEM106B associated disorders.

In one aspect, the present disclosure provides isolated (e.g., monoclonal) antibodies that bind to an epitope within a TMEM106B protein of the present disclosure. TMEM106B proteins of the present disclosure include, without limitation, a mammalian TMEM106B protein, human TMEM106B protein, mouse TMEM106B protein, and cyno TMEM106B protein.

Human TMEM106B is a 274-amino acid protein that encodes a type 2 membrane glycoprotein. The amino acid sequence of human TMEM106B is set forth in SEQ ID NO:1:

MGKSLSHLPLHSSKEDAYDGVTSENMRNGLVNSEVHNEDGRNGDVSQFPY

VEFTGRDSVTCPTCQGTGRIPRGQENQLVALIPYSDQRLRPRRTKLYVMA

SVFVCLLLSGLAVFFLFPRSIDVKYIGVKSAYVSYDVQKRTIYLNITNTL

-continued
NITNNNYYSVEVENITAQVQFSKTVIGKARLNNITIIGPLDMKQIDYTVP

TVIAEEMSYMYDFCTLISIKVHNIVLMMQVTVTTTYFGHSEQISQERYQY

VDCGRNTTYQLGQSEYLNVLQPQQ

Additionally, the amino acid sequence of mouse TMEM106B is set forth in SEQ ID NO:2:

GKSLSHLPLHSNKEDGYDGVTSTDNMRNGLVSSEVHNEDGRNGDVSQFPY

VEFTGRDSVTCPTCQGTGRIPRGQENQLVALIPYSDQRLRPRRTKLYVMA

SVFVCLLLSGLAVFFLFPRSIEVKYIGVKSAYVSYDAEKRTIYLNITNTL

NITNNNYYSVEVENITAQVQFSKTVIGKARLNNITNIGPLDMKQIDYTVP

TVIAEEMSYMYDFCTLLSIKVHNIVLMMQVTVTTAYFGHSEQISQERYQY

VDCGRNTTYQLAQSEYLNVLQPQQ

Additionally, the amino acid sequence of cynomolgus (cyno) TMEM106B is set forth in SEQ ID NO: 315:

MGKSLSHLPLHSSKEDAYDGVTSENMRNGLVNSEVHNEDGRNGDVSQFPY

VEFTGRDSVTRPTCQGTGRIPRGQENQLVALIPYSDQRLRPRRTKLYVMA

SVFVCLLLSGLAVFFLFPRSIDVKYIGVKSAYVSYDVQKRTIYLNITNTL

NITNNNYYSVEVENITAQVQFAKTVIGKARLNNITHIGPLDMKQIDYTVP

TVIAEEMSYMYDFCTLISIKVHNIVLMMQVTVTTTYFGHSEQISQERYQY

VDCGRNTTYQLGQSEYLNVLQPQQ

In some embodiments, TMEM106B is expressed in a cell. In some embodiments, TMEM106B is expressed in endosomes and/or lysosomes. In some embodiments, TMEM106B is expressed in late endosomes and/or late lysosomes. In some embodiments, TMEM106B is expressed on the cell surface.

TMEM106B proteins of the present disclosure include several domains, including without limitation, an N-terminal lumenal domain (predicted to range from amino acid residues 11-274 of human TMEM106B; see SEQ ID NO:1), a transmembrane domain (predicted to range from amino acid residues 96-117 of human TMEM106B)), and a C-terminal domain (predicted to range from amino acid residues 1-92 of human TMEM106B). Additionally, TMEM106B proteins of the present disclosure are expressed in a number of tissues and cells, including without limitation, the brain, neurons, glial cells, endothelial cells, perivascular cells, pericytes, etc.

TMEM106B Binding Partners

TMEM106B proteins of the present disclosure can interact with (e.g., bind to) one or more ligands or binding proteins, including, without limitation, progranulin protein (GRN), other TMEM106 protein family members, such as TMEM106B and TMEM106C, clathrin heavy chain (CLTC), the μ1 subunit of adipocyte protein 2 (AP2M1), charged multi-vesicular body protein 2b (CHMP2B), microtube-associated protein 6 (MAP6), lysosomal-associated membrane protein 1 (LAMP1), and vacuolar-ATPase accessory protein 1. Anti-TMEM106B antibodies of the present disclosure affect the interaction of TMEM106B with its various ligands and binding partners.

Progranulin

TMEM106B has been shown to colocalize with progranulin in neuronal late endo-lysosomes, and TMEM106B overexpression increases intracellular levels of progranulin (Chen-Plotkin et al, 2012, J Neurosci, 32:11213-11227).

Progranulin is variously referred to as PGRN, proepithelin, granulin-epithelin precursor, PC (prostate cancer) cell-derived growth factor (PCDGF), and acrogranin. Progranulin is a 593-amino acid protein that encodes a 68.5 kD a secreted glycoprotein that has 7.5 repeats of smaller granulin (epithelin) motifs, ranging from 6-25 kDa, which can be proteolytically cleaved from the precursor PGRN. Examples of Progranulin cleavage products include, without limitation, granulin A/Epithelins 1, granulin B Epithelins 2, granulin C, granulins D, granulin E, granulin F, granulin G and any other known peptide products derived from Progranulin.

Progranulin is widely expressed, and in non-neuronal cells has been associated with a variety of events, such as cell cycle regulation and cell motility, wound repair, inflammation, induction of growth factors such as vascular endothelial growth factor (VEGF), and tumorigenesis. Progranulin is also widely expressed in early neural development, but becomes restricted in later development to defined neuronal populations, such as cortical neurons, hippocampal pyramidal neurons, and Purkinje cells.

Accordingly, in some embodiments, an anti-TMEM106B antibody of the present disclosure inhibits (e.g., blocks) or reduces the interaction between TMEM106B and progranulin. Alternatively, in some embodiments, an anti-TMEM106B antibody of the present disclosure enhances or increases the interaction between TMEM106B and progranulin.

Other TMEM106 Family Members

TMEM106B proteins have been shown to interact with other TMEM106 protein family members. For example, the N-terminus of TMEM106B has been shown to interact with its family member TMEM106C. (See Stagi et al., 2014, Mol Cell Neurosci, 61:226-240.) TMEM106B proteins of the present disclosure bind to and modify the function and activity of TMEM106B. Additionally, TMEM106B proteins bind to and modify the function and activity of TMEM106C.

Accordingly, in some embodiments, an anti-TMEM106B antibody of the present disclosure inhibits (e.g., blocks) or reduces the interaction between TMEM106B and other TMEM106 protein family members. In some embodiments, an anti-TMEM106B antibody of the present disclosure inhibits (e.g., blocks) or reduces the interaction between TMEM106B and another TMEM106B polypeptide. In some embodiments, an anti-TMEM106B antibody of the present disclosure inhibits (e.g., blocks) or reduces the interaction between TMEM106B and TMEM106C. Alternatively, in some embodiments, an anti-TMEM106B antibody of the present disclosure enhances or increases the interaction between TMEM106B and other TMEM106 protein family members. In some embodiments, an anti-TMEM106B antibody of the present disclosure enhances or increases the interaction between TMEM106B and another TMEM106B polypeptide. In some embodiments, an anti-TMEM106B antibody of the present disclosure enhances or increases the interaction between TMEM106B and TMEM106C.

Clathrin Heavy Chain

The N-terminus of TMEM106B has been shown to interact with the endocytic adaptor protein clathrin heavy chain (CLTC). (See Stagi et al., 2014, Mol Cell Neurosci, 61:226-240.) The protein interactions together with TMEM106B's endolysosomal localization imply that the TMEM106B cytoplasmic domain may participate in the delivery of endocytic cargos to the lysosome.

Accordingly, in some embodiments, an anti-TMEM106B antibody of the present disclosure inhibits (e.g., blocks) or reduces the interaction between TMEM106B and CLTC. Alternatively, in some embodiments, an anti-TMEM106B antibody of the present disclosure enhances or increases the interaction between TMEM106B and CLTC.

µl Subunit of Adipocyte Protein 2

The N-terminus of TMEM106B has been shown to interact with the endocytic adaptor proteins µl subunit of adipocyte protein 2 (AP2M1). (See Stagi et al., 2014, Mol Cell Neurosci, 61:226-240.) The protein interactions together with TMEM106's endolysosomal localization imply that the TMEM106B cytoplasmic domain may participate in the delivery of endocytic cargos to the lysosome.

Accordingly, in some embodiments, an anti-TMEM106B antibody of the present disclosure inhibits (e.g., blocks) or reduces the interaction between TMEM106B and the µl subunit of adipocyte protein 2 (AP2M1). Alternatively, in some embodiments, an anti-TMEM106B antibody of the present disclosure enhances or increases the interaction between TMEM106B and the µl subunit of adipocyte protein 2 (AP2M1).

Charged Multi-Vesicular Body Protein 2b

TMEM106B has been shown to directly bind charged multi-vesicular body protein 2b (CHMP2B), a member of the endosomal sorting complexes required for transport III (ESCRT-III) complex that regulates endolysosomal protein trafficking and autophagic structure formation (Jun et al., 2015, Mol Brain, 8:85). Accordingly, in some embodiments, an anti-TMEM106B antibody of the present disclosure inhibits (e.g., blocks) or reduces the interaction between TMEM106B and CHMP2B. Alternatively, in some embodiments, an anti-TMEM106B antibody of the present disclosure enhances or increases the interaction between TMEM106B and CHMP2B.

Microtubule-Associated Protein 6

The C-terminus of microtubule-associated protein 6 (MAP6) directly binds the N-terminus of TMEM106B (Schwenk et al., 2014, EMBO J, 33:450-467). MAP6 overexpression inhibits dendritic branching similar to TMEM106B knockdown. MAP6 knockdown fully rescues the dendritic phenotype of TMEM106B knockdown, supporting a functional interaction between TMEM106B and MAP6. TMEM106B/MAP6 interaction was shown to be crucial for regulating dendritic trafficking of lysosomes, presumably by acting as a molecular break for retrograde transport. Lysosomal misrouting may promote neurodegeneration in patients with TMEM106B risk variants. The C-terminal repeat region of the neuron-enriched splice variant of MAP6 binds to the cytoplasmic N-terminus of TMEM106B preferentially.

Accordingly, in some embodiments, an anti-TMEM106B antibody of the present disclosure inhibits (e.g., blocks) or reduces the interaction between TMEM106B and MAP6. Alternatively, in some embodiments, an anti-TMEM106B antibody of the present disclosure enhances or increases the interaction between TMEM106B and MAP6.

Lysosomal-Associated Membrane Protein 1

TMEM106B colocalizes with LAMP1 in late-endosomal/lysosomal vesicles in the cell body and in dendrites, but not with synaptic vesicles or early or recycling endosomes. (Stagi et al., 2014, Mol Cell Neurosci, 61:226-240.) LAMP1 (lysosomal-associated membrane protein 1) is a late endosomal/lysosomal marker. Reduction of TMEM106B increases axonally-transported lysosomes (increases motility), while TMEM106B elevation inhibits such transport and yields large lysosomes. Accordingly, in some embodiments, an anti-TMEM106B antibody of the present disclosure inhibits (e.g., blocks) or reduces the interaction between TMEM106B and LAMP1. In some embodiments, an anti-TMEM106B antibody of the present disclosure increases axonally-transported lysosomes. In some embodiments, an anti-TMEM106B antibody of the present disclosure increases motility of axonally-transported lysosomes. Alternatively, in some embodiments, an anti-TMEM106B antibody of the present disclosure enhances or increases the interaction between TMEM106B and LAMP1.

Vacuolar-ATPase Subunit Accessory Protein 1

TMEM106B has also been shown to bind vacuolar-ATPase subunit accessory protein 1 (v-ATPase AP1) through its lumenal (C-terminal) domain (Klein et al., 2017, Neuron, 95:281-296). V-ATPase is responsible for lysosomal acidification; modulation of its function, such as by stabilization of the multi-unit protein complex, would affect lysosomal function. Accordingly, in some embodiments, an anti-TMEM106B antibody of the present disclosure inhibits (e.g., blocks) or reduces the interaction between TMEM106B and vacuolar-ATPase subunit accessory protein 1. Alternatively, in some embodiments, an anti-TMEM106B antibody of the present disclosure enhances or increases the interaction between TMEM106B and vacuolar-ATPase subunit accessory protein 1.

Further provided herein are methods of screening for anti-TMEM106B antibodies that bind TMEM106B, and that block the interactions between TMEM106B and one or more TMEM106B ligands or binding partners (e.g., Progranulin, other TMEM106 family members (i.e., TMEM106A, TMTM106C), Clathrin heavy chain, µl subunit of adipocyte protein 2, CHMP2B, microtubule-associated protein 6, lysosomal-associated membrane protein 1, and vacuolar-ATPase accessory protein 1). In some embodiments, a peptide library can be synthesized in which a TMEM106B protein is dissected into consecutive 15-mer and 25-mer peptides separated by one amino acid residue and subsequently spotted onto filters. Binding of a TMEM106B ligand or binding partner can then then tested for its ability to interact with the TMEM106B peptide or with peptides in the presence or absence of anti-TMEM106B antibodies by SPOT binding analysis (e.g., Frank, R and Overwin, H (1996) Methods. Mol. Biol. 66, 149-169; Reineke, U et al., (2002) J. Immunol. Methods 267, 13-26; and Andersen, O S et al., (2010) J, BIOLOGICAL CHEMISTRY 285, 12210-12222). In some embodiments, a cellulose support can be prepared as an N-modified cellulose-aminohydroxylpropyl ether membrane, and all rounds of synthesis are started with spot definition by 9-fluorenylmethoxycar-bonyalanine-pentafluoophenyl ester that creates an alanine linker between peptide and membrane. For example, an automated linear synthesis of stepwise addition of the different amino acids protected at their N-terminal by 9-fluorenyl-methoxycarbonyl and appropriate side-chain protection for the growing peptide chain. In some embodiments, the pattern of de-protection, activation, and coupling is continued until 16-mer peptides are produced, resulting in an equally distributed array of covalently anchored peptides to the cellulose support at their C-terminal ends with N-terminal free ends (Scharn, D et al., (2000) J. Comb. Chem. 2, 361-369). In some embodiments, removal of the side protection group can be performed in two steps. First, the membrane can be treated with 90% trifluoroacetic acid (in dichlormethane, containing 3% triisobutylsilane and 2% H2O); and secondly with, for example, 60% trifluoroacetic acid (in dichlormethane, containing 3% triisobutylsilane and 2% H2O). To remove trifluoroacetic acid salts, the membrane can be washed several times with H2O, ethanol, Tris-buffered saline, and ethanol, and then dried. Finally, the membrane is blocked in blocking buffer dilated in Tris-buffered saline (pH 8.0) and supplemented with 5% sac-charose for 2 h before the predefined peptide library is ready for ligand binding analysis. In some embodiments, for binding studies of cellulose-bound peptides, membrane-bound librariescan be incubated with combined S-peptide and polyhistidine-tagged ligands in the presence or absence of anti-TMEM106B antibodies, for example, in blocking buffer overnight at 4° C., followed by a second incubation with 1 mg/ml of HRP-conjugated S-protein also in blocking buffer but for 3 h at room temperature. Subsequently, the membrane can be washed, for example, three times for 10 min with Tris-buffered saline before quantitative characterization of bound ligand may be carried out using the UptiLight chemiluminescence substrate and a LumiImager instrument, providing the spot signal intensities in Boehringer light units. Alternatively, detection of bound ligand can be performed by an immunochemical assay with an antibody against a histidine tag from and a secondary HRP-conjugated anti-mouse antibody. Incubations can be performed utilizing standard Western blotting procedures and spot detection.

Further provided herein are methods of screening for anti-TMEM106B antibodies that block interactions (e.g., binding) TMEM106B and one or more TMEM106B ligands or binding partners (e.g., Progranulin, other TMEM106 family members (i.e., TMEM106A, TMEM106C), Clathrin heavy chain, µl subunit of adipocyte protein 2, CHMP2B, microtubule-associated protein 6, lysosomal-associated membrane protein 1, and vacuolar-ATPase accessory protein 1).

In some embodiments, the interaction between TMEM106B and TMEM106B ligands or binding partners (e.g., Progranulin, other TMEM106 family members (i.e., TMEM106A, TMEM106C), Clathrin heavy chain, ul subunit of adipocyte protein 2, CHMP2B, microtubule-associated protein 6, lysosomal-associated membrane protein 1, and vacuolar-ATPase accessory protein 1) may be characterized using surface Plasmon resonance analysis (e.g., Skeldal et al., 2012 J Biol Chem., 287:43798; and Andersen et al., 201, J Biol Chem, 285, 12210-12222). Determination of direct binding of TMEM106B ligand or binding partner to immobilized TMEM106B in the presence or absence of blocking anti-TMEM106B antibodies can be performed, for example, on a Biacore2000 instrument (Biacore, Sweden) using CaHBS as standard running buffer (10 mM HEPES, pH 7.4, 140 mM NaCl, 2 mM CaCl2, 1 mM EGTA, and 0.005% Tween 20). In some embodiments, a biosensor chip from Biacore (CM5) can be activated using the NHS/EDC method followed by coating with TMEM106B to a protein density of 79 fmol/mm2 and used for affinity measurements of the binding partner. Preparation of a biosensor surface with pro-TMEM106B will follow an equal procedure. Regeneration of the flow cell after each cycle of ligand binding experiment can be done by two 10-µl pulses of regeneration buffer (10 mM glycine-HCl, pH 4.0, 500 mM NaCl, 20 mM EDTA, and 0.005% Tween 20) and a single injection of 0.001% SDS. Fitting of sensorgrams for affinity estimations can be done, for example, by using BIAevaluation version 3.1. Following similar protocols, immobilization of HisS-NGFpro or HisS-BDNFpro may also done on a CM5 biosensor chip using the NHS/EDC coupling kit, giving similar surface densities of immobilized protein (~300 fmol/mm2). A biosensor chip with immobilized with a TMEM106B ligand or binding partner can also be used to examine the binding of TMEM106B in the absence or presence of competing TMEM106B antibodies.

In some embodiments, the interaction between TMEM106B and TMEM106B ligands and binding partners (e.g., Progranulin, other TMEM106 family members (i.e., TMEM106A, TMEM106C), Clathrin heavy chain, µl subunit of adipocyte protein 2, CHMP2B, microtubule-associated protein 6, lysosomal-associated membrane protein 1, and vacuolar-ATPase accessory protein 1) can be characterized using a pulldown assay (e.g., Andersen et al., 2010, J Biol Chem, 285, 12210-12222). For example, expressed intracellular or extracellular domains of TMEM106B can be incubated with tagged TMEM106B ligands or binding partners in the absence or presence of TMEM106B blocking antibodies and are precipitated using 100 µl of glutathione (GSH)-Sepharose beads (Amersham Biosciences, catalog no. 17-0756-01). The amount of applied receptor domains can be determined by precipitation using Talon beads as control. Bound proteins can be separated by SDS-PAGE analysis and visualized using anti-histidine antibody by standard Western blotting analysis.

In some embodiments, the interaction between TMEM106B and TMEM106B ligands and binding partners (e.g., Progranulin, other TMEM106 family members (i.e., TMEM106A, TMEM106C), clathrin heavy chain, µl subunit of adipocyte protein 2, CHMP2B, microtubule-associated protein 6, lysosomal-associated membrane protein 1, and vacuolar-ATPase accessory protein 1) may be characterized using cellulose-bound proteins (e.g., Andersen et al., 2010, J Biol Chem, 285, 12210-12222). For example, membrane-bound proteins can be incubated with S-peptide and polyhistidine-tagged Progranulin, other TMEM106 family members (i.e., TMEM106A, TMEM106C), clathrin heavy chain, µl subunit of adipocyte protein 2, CHMP2B, microtubule-associated protein 6, lysosomal-associated membrane protein 1, vacuolar-ATPase accessory protein 1, or another TMEM106B ligand or binding partner; in blocking buffer overnight at 4° C., followed by a second incubation with 1 µg/ml of HRP-conjugated S-protein also in blocking buffer but for 3 hours at room temperature. Subsequently, the membrane may be washed three times for 10 minutes with Tris-buffered saline before quantitative characterization of bound ligand is carried out using the UptiLight chemiluminescence substrate and a Lumilmager instrument, providing the spot signal intensities in Boehringer light units. Alternatively, detection of bound ligand can be performed by an immunochemical assay with an antibody against the histidine tag and a secondary HRP-conjugated anti-mouse antibody. Incubations can be followed by standard Western blotting analysis and spot detection.

In some embodiments, the interaction between TMEM106B and TMEM106B ligands and binding partners (e.g., Progranulin, other TMEM106 family members (i.e., TMEM106A, TMEM106C), Clathrin heavy chain, µl subunit of adipocyte protein 2, CHMP2B, microtubule-associated protein 6, lysosomal-associated membrane protein 1, and vacuolar-ATPase accessory protein 1) may be characterized using a proximity ligation assay (e.g., Gustafsen et al., 2013 The Journal of Neuroscience, 33:64-71). For example, proximity ligation assay (PLA) (DuolinkII) on cells expressing or exposed to TMEM106B and its ligand or binding partner can be performed with the primary antibodies anti-TMEM106B, and antibodies against the binding partner, followed by incubation with secondary antibodies conjugated to oligonucleotides, which hybridize to subsequently added circle-forming oligonucleotides and prime a rolling circle amplification when the antigens are located within proximity of 40 nm. The amplified DNA can be visualized by addition of complementary fluorescent-labeled oligonucleotides.

In some embodiments, the interaction between TMEM106B and TMEM106B ligands and binding partners (e.g., Progranulin, other TMEM106 family members (i.e., TMEM106A, TMEM106C), Clathrin heavy chain, µl subunit of adipocyte protein 2, CHMP2B, microtubule-associated protein 6, lysosomal-associated membrane protein 1, and vacuolar-ATPase accessory protein 1) may be characterized using alkaline phosphatase-tagged ligands in cell binding assays (e.g., Hu et al., 2005, J. Neurosci. 25, 5298-5304; Fournier et al., 2001, Nature 409, 341-346; Lauren et al., 2009, Nature 457, 1128-1132; and Hu et al., 2010, Neuron 68, 654-667). For example, alkaline phosphatase (AP)-tagged ligands can be made to assess binding to TMEM106B on transfected cells or primary neurons. To detect AP tagged ligand binding to cells expressing TMEM106B, cultures can be washed with, for example, Hanks balanced salt solution containing 20 mM sodium HEPES, pH 7.05, and 1 mg/ml bovine serum albumin (BSA) (HBH). Then, the plates can be incubated with AP tagged ligands in the presence or absence of TMEM106B blocking antibodies, for example, in HBH for 2 h at 23° C. AP bound ligand can be detected and quantified according to methods well-known in the art.

In certain embodiments that may be combined with any of the preceding embodiments, the anti-TMEM106B antibody further inhibits interaction between TMEM106B and one or more of its ligands, signaling proteins or binding proteins by: a) reducing the effective levels of TMEM106B available for interacting with the one or more ligands or binding proteins; b); blocking one or more of the sites on TMEM106B required for interaction with the one or more ligands or binding proteins; c) preventing one or more posttranslational events on TMEM106B that are required for interaction with the one or more ligands or binding proteins and/or for correct processing and/or subcellular localization of TMEM106B; d) inducing degradation of TMEM106B; e) changing the conformation of TMEM106B, or both. In certain embodiments that may be combined with any of the preceding embodiments, the anti-TMEM106B antibody binds specifically to human TMEM106B, mouse TMEM106B, cyno TMEM106B, or a combination thereof. In certain embodiments that may be combined with any of the preceding embodiments, the anti-TMEM106B antibody is a human antibody, a humanized antibody, a bispecific antibody, a monoclonal antibody, a multivalent antibody, a conjugated antibody, or a chimeric antibody. In certain embodiments that may be combined with any of the preceding embodiments, the anti-TMEM106B antibody is a bispecific antibody recognizing a first antigen and a second antigen. In certain embodiments that may be combined with any of the preceding embodiments, the first antigen is TMEM106B and the second antigen is an antigen facilitating transport across the blood-brain-barrier. In certain embodiments that may be combined with any of the preceding embodiments, the second antigen is selected from the group consisting of TMEM106B, transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30 (A), a protein transduction domain, TAT, Syn-B, penetratin, a poly-arginine peptide, an angiopep peptide, basigin, Glut1, and CD98hc, and ANG1005.

TMEM106B Proteolysis

TMEM106B undergoes intramembrane proteolysis, and is processed to an N-terminal fragment (NTF) containing the transmembrane and intracellular domains; this processing is lysosomal protease-dependent. (Brady et al., 2014, J Biol Chem, 289:19670-19680) The GxGD aspartyl protease SPPL2A (and to a lesser extent SPPL2B) have been shown to be responsible for this intramembrane cleavage event. Additionally, it has been reported that an uncharacterized lysosomal protease(s) and SPPL2A cleave TMEM106B at around the 127th and 106th amino acids from the N-terminus, respectively, to generate two NTFs of TMEM106B (Brady et al., 2014, supra); however, the precise cleavage sites have not yet been identified. Overexpression of TMEM106B resulted in the appearance of NTF17 (1-127) and NTF13 (1-106), likely mediated by caspase activity.

Accordingly, in some embodiments, an anti-TMEM106B antibody of the present disclosure inhibits proteolysis of TMEM106B. In some embodiments, an anti-TMEM106B antibody of the present disclosure inhibits intramembrane proteolysis of TMEM106B. In some embodiments, an anti-TMEM106B antibody of the present disclosure inhibits proteolysis of TMEM106B, thereby preventing cleavage of TMEM106B into N-terminal fragments. In some embodiments, an anti-TMEM106B antibody of the present disclosure inhibits GxGD aspartyl protease SPPL2A cleavage of TMEM106B. In other embodiments, an anti-TMEM106B antibody of the present disclosure inhibits GxGD aspartyl protease SPPL2B cleavage of TMEM106B. In some embodiments, an anti-TMEM106B antibody of the present disclosure inhibits caspase-mediated cleavage of TMEM106B.

TMEM106B as a Disease Target

TMEM106B has been associated with various diseases, disorders, and conditions. Frontotemporal lobar degeneration (FTLD) (or frontotemporal dementia (FTD)) is the third most common neurodegenerative disease after Alzheimer's disease and Parkinson's disease and accounts for 20% of pre-senile dementia cases. (See, e.g., Rademakers et al., 2012, Nat Rev Neurol, 8:423-434). The condition results from the progressive deterioration of the frontal lobe of the brain. Over time, the degeneration may advance to the temporal lobe. The clinical presentation is diverse and the symptoms include dementia, behavioral changes, as well as speech and language impairment. (See, e.g., Cruts & Van Broeckhoven, 2008, Trends Genet. 24:186-194; Neary et al., 1998, Neurology 51:1546-1554; Ratnavalli, et al., 2002, Neurology 58:1615-1621.) Additional symptoms of upper or lower motoneuron disease are common and indicate a partial overlap with amyotrophic lateral sclerosis (ALS). The majority of FTLD cases show neuronal cytoplasmic aggregates of the nuclear DNA/RNA-binding protein TDP-43 (Neumann et al., 2006, Science, 314:130-133) and pathogenic mutations in TARDBP, the gene coding for TDP-43 are rare and predominantly cause ALS (Sreedharan et al., 2008, Science, 319:1668-1672). Familial forms of FTLD with TDP-43 pathology are mainly caused by hexanucleotide repeat expansion in C9orf72 (DeJesus-Hernandez et al., 2011; Renton et al., 2011) and dominant loss-of-function mutations in the growth factor progranulin (GRN) (Cruts et al., 2006, Curr Alzheimer Res, 3:485-491). While identification of the mutations associated with the rare familial forms of the disease yielded insight into FTLD pathogenesis, the etiology of the more common sporadic cases is more elusive, made further complex by a variability in clinical and neuropathologcial presentation.

A substantial portion of FTD cases are inherited in an autosomal dominant fashion, but even in one family, symptoms can span a spectrum from FTD with behavioral disturbances, to Primary Progressive Aphasia, to Cortico-Basal Ganglionic Degeneration. FTD, like most neurodegenerative diseases, can be characterized by the pathological presence of specific protein aggregates in the diseased brain. Historically, the first descriptions of FTD recognized the presence of intraneuronal accumulations of hyperphosphorylated Tau protein in neurofibrillary tangles or Pick bodies. A causal role for the microtubule associated protein Tau was supported by the identification of mutations in the gene encoding the Tau protein in several families (Hutton, M., et al., Nature 393:702-705 (1998). However, the majority of FTD brains show no accumulation of hyperphosphorylated Tau but do exhibit immunoreactivity to ubiquitin (Ub) and TAR DNA binding protein 43 (TDP-43) (Neumann et al., 2007, Arch. Neurol. 64:1388-1394). A majority of those FTD cases with Ub inclusions (FTD-U) were shown to carry mutations in the Progranulin gene.

Single nucleotide polymorphisms (SNPs) identified on chromosome 7 led to the discovery of the first genetic risk factors for FTLD-TDP as SNPs in the genomic region encoding TMEM106B. (Van Deerlin et al., 2010, Nat Genetics, 42:234-239.)

The initial studies assessing TMEM106B SNPs as disease risk factors in FTLD-TDP were conducted prior to the discovery of C9orf72 repeat expansion in 2012. Since this discovery, two independent groups found TMEM106B SNPs to also associate with one's risk of developing FTLD and/or ALS caused by C9orf72 mutations. (See Gallagher et al., 2014, Acta Neuropathol, 127:407-418; van Blitterswijk et al., 2014, Acta Neuropath, 127:397-406.) In these C9orf72 mutant cohorts, the frequency of individuals carrying the minor allele of TMEM106B SNPs [rs1990622 and/or rs3173615 in LD with rs1990622 was significantly reduced, although not as markedly as in cohorts of GRN mutation carriers. Further analysis of C9orf72 repeat expansion carriers in groups based on their predominant disease presentation as either FTLD, FTLD-ALS, or ALS, it was shown that TMEM106B SNPs specifically protect against the development of FTLD but not ALS, with less TDP-43 burden in the brains of C9orf72 expansion carriers homozygous for the protective TMEM106B alleles as compared to risk allele carriers. These findings are in agreement with an earlier examination of TMEM106B SNPs in a clinical cohort of ALS patients in which TMEM106B SNPs rs1990622 and rs1020004 were not associated with disease risk, but did significantly associate with cognitive function in ALS patients, with individuals homozygous for the rs1990622 minor allele having better cognitive performance than individuals heterozygous or homozygous for the major risk alleles (Vass et al., 2011, Acta Neuropathol, 121:373-380).

Neurodegenerative disease hallmarks, such as TDP-43 aggregates, are not specific to FTLD, and are observed in other neurodegenerative diseases, including Alzheimer's disease (AD), Lewy body dementia (LBD), and hippocampal sclerosis (HpScl) (Amador-Ortiz et al., 2007, Ann Neurol, 61:435-445; Zarow et al., 2008, Curr Neurol Neurosci Rep, 8:363-370), but also even in apparently healthy individuals, albeit to a limited extent (See, e.g., Yu et al., 2015, Neurology, 84:927-934). TMEM106B risk variants have been associated with TDP-43 neuropathology in the absence of a clinical neurological diagnosis. It was similarly found to affect the pathological presentation of AD with the protective TMEM106B haplotype associated with less TDP-43 pathology among AD patients (Rutherford et al., 2012, Neurology, 79:717-718). Hippocampal sclerosis is also common pathological hallmark in elderly patients with dementia, including FTLD-TDP and AD, often co-occurring with TDP-43 pathology. TMEM106B genotype was found to be associated with primary hippocampal sclerosis (Aoki et al., 2015, Acta Neuropathol, 129:53-64) as well as with hippocampal sclerosis pathology among AD patients, making TMEM106B as the strongest genetic indicator of AD-HpScl and HpScl known to date (Murray et al., 2014, Acta Neuropathol, 128:411-421). These studies collectively suggest that TMEM106B SNPs are risk factors for the development and severity of TDP-43 proteinopathy in non-FTLD disorders such as AD and HpScl.

A genomics study across over 1500 human brain autopsied samples identified common variants at TMEM106B as the main genome-wide determinant of the rate of biological aging in human brain: the presence of 2 risk alleles at the TMEM106B gene locus making an individual appear ~12 years older based on its gene expression profile than his/her actual age (Rhinn and Abeliovich, 2017, Cell Syst, 4:404-415). This effect of TMEM106B risk alleles is seen in individuals free of known neurological disease as well as in individuals with neurodegenerative processes such as Alzheimer's. The role of TMEM106B in aging appeared highly selective, in terms of brain and life (cortex and not cerebellum, specifically over 65yo). The effect was confirmed independently in additional cohorts in which carriers of the protective TMEM106B haplotype displayed reduced age-associated cognitive decline (Rhinn and Abeliovich, 2017, supra). The effect on cognitive performance was confirmed as the TMEM106B protective haplotype was shown to be associated with better cognitive performance for a given amount of cerebral pathology (White et al., 2017, PLOS Med, 14: e1002287). Those results strengthen the pleiotropic role of TMEM106B in aging beyond neurodegenerative diseases.

Evidence suggests that TMEM106B variants increase risk for developing FTLD-TDP by increasing TMEM106B mRNA and protein expression levels. Increased TMEM106B results in a decrease in the average number of late endosomes/lysosomes per cell, loss of lysosomal acidification, and impaired lysosomal degradation.

Frontotemporal lobar degeneration with TDP-43 inclusions (FTLD-TDP) is a fatal neurogenerative disease with no available treatments. Mutations in the progranulin gene (GRN) causing impaired production or secretion of progranulin are a common cause of FTLD-TDP. As discussed above, TMEM106B has been linked by genome-wide association to FTLD-TDP with and without GRN mutations. Increasing TMEM106B expression to model disease resulted in enlargement and poor acidification of endo-lysosomes, as well as impairment of mannose-6-phosphate-receptor trafficking. Endogenous neuronal TMEM106B colocalizes with progranulin in late endo-lysosomes, and TMEM106B overexpression increases intracellular levels of progranulin. (Chen-Plotkin et al., 2012, J Neurosci, 32:11213-11227.) In some embodiments, the present disclosure provides methods for preventing, reducing risk, or treating FTLD-TDP by administering to an individual in need thereof a therapeutically effective amount of an anti-TMEM-160B antibody of the present disclosure. In some embodiments, the present disclosure provides methods for FTLD has been recognized as a disease that has a common pathologic background with amyotrophic lateral sclerosis (ALS). ALS is an incurable motor neuron degenerative disease, characterized by loss of both upper and lower motor neurons. Approximately 15% of FTLD patients develop motor neuron disease, and more than 15% of ALS patients have cognitive and behavioral impairments. An important pathological hallmark of FTLD and ALS is a cytoplasmic transactive response DNA-binding protein-43 (TDP-43) inclusion. TDP-43 is the major component of inclusions in ~50^% of FTLD patients (subtype FTLD-TDP) and the majority of ALS patients. A genome-wide associated study and cohort studies have identified three SNPs (re 1990622, rs6966915, and rs1020004) in TMEM106B gene region as genetic risk modifiers for FTLD-TDP. The risk association is more prominent in FTLD-TDP cases with GRN and C9ORF72 mutations. Overexpression of TMEM106B induces cell death, enhances oxidative stress-induced cytotoxicity, and causes the cleavage of TDP-43, using cell-based models, suggesting that up-regulation of TMEM106B increases the risk of FTLD by directly causing neurotoxicity. (Suzuki and Matsuoka, 2016, J Biol Chem, 291:21448-21460.) Additionally, TMEM106B has been implicated in the development of cognitive impairment in ALS (Vass et al., 2011, Acta Neuropathol, 121:373-380).

Hippocampal sclerosis of aging (HS-Aging) is a common, high morbidity-associated neurodegenerative condition in the elderly, and is diagnosed neuropathologically when neuron loss and astrocytosis are observed in the hippocampal formation, and are not considered attributable to Alzheimer's disease-type plaques and tangles. It has a clinical course similar to Alzheimer's disease. HS-Aging is distinguished from other hippocampal sclerosis disorders by the presence of TDP-43 pathology and the absence of severe symptoms or clinical signs of frontotemporal dementia. HS-Aging is associated with SNP rs1990622 (TMEM106b), and other SNPs, as well as polymorphisms in TMEM106b, ABCC9 (not associated with FTLD), and GRN. (Nelson et al., 2015, J Neuropathol Exp Neurol, 74:75-84.) In some embodiments, the present disclosure provides methods for preventing, reducing risk, or treating hippocampal sclerosis of aging by administering to an individual in need thereof a therapeutically effective amount of an anti-TMEM-160B antibody of the present disclosure.

A recent murine genetic knockout of TMEM106B (Klein et al. 2017, Neuron 95, 281-296) showed an effect for TMEM106B in the granulin pathway. Specifically, a genetic knock-out of the TMEM106B protein was able to rescue some of the pathogenic phenotype associated with GRN knockout in a mouse model, including a partial rescue of levels of lysosomal proteins, and rescue of behavioral changes such as hyperactivity and dis-inhibition. The TMEM106B knockout itself was well tolerated in the mice, as has been reported in other studies. In addition, this work suggested a possible mechanism of action of TMEM106B by showing a direct interaction (through co-immunoprecipitation) with the v-ATPase subunit AP1. The v-ATPase complex plays an important role in lowering the pH of lysosomes and thus initiating protein degradation and recycling. Thus, its interaction with TMEM106B may cause some of the lysosomal phenotypes associated with TMEM106B overexpression, and conversely blocking this interaction (or merely reducing the level of TMEM106B present) may be able to ameliorate this phenotype.

Chronic traumatic encephalopathy (CTE) is a progressive neurodegenerative disease that has been pathologically diagnosed in individuals with a history of repeated head impacts. TMEM106B has been shown to be an important factor in the progression of CTE and specifically in CTE-related neuropathology and dementia. Specifically, carriers of the minor (G) allele at SNP rs3173615 (T185S coding mutation) were shown to have decreased levels of neuropathology including lower AT8-positive p-tau levels, lower CD68-positive cell density, and increased levels of PSD-95, a post-synaptic marker often used to investigate synaptic loss. The G-allele was also associated with a 60% decrease in odds of ante-mortem dementia. In both cases, effects of the G allele were additive, with the GG genoptype being the most protective. TMEM106B geneotype had no effect on risk of disease; rather, the effect is seen in the severity of the disease progression.

Microglia are the primary innate immune cells of the central nervous system (CNS). Microglia exist in resting or activated states depending on the inflammatory milieu, which differs in the healthy CNS and in various disease states. TGFbeta is an important factor in microglial development and function and is required for the maintenance of the microglia-specific homeostatic gene signature. Suppression of TGFbeta signaling and of the TGFbeta pathway is a common feature of microglia isolated from neurodegenerative disease models. Additionally, TGFbeta has been described as having a critical function in preventing microglia/macrophage-mediated CNS pathology and neurodegeneration (Butovsky and Weiner, 2018, Nature, 19:622-635; Lund et al, 2018, Nature Immunol, 19:425-441). Accordingly, therapies that directly or indirectly increase TGFbeta expression, signaling, and/or function would provide benefit in the treatment of neurodegenerative diseases and disorders, including amyotrophic lateral sclerosis, Alzheimer's disease, multiple sclerosis, Parkinson's disease, autism spectrum disorder, dementia, etc. In some embodiments, anti-TMEM106B antibodies of the present disclosure are effective at increasing TGFbeta levels in cells.

Dementia is a non-specific syndrome (i.e., a set of signs and symptoms) that presents as a serious loss of global cognitive ability in a previously unimpaired person, beyond what might be expected from normal ageing. Dementia may be static as the result of a unique global brain injury. Alternatively, dementia may be progressive, resulting in long-term decline due to damage or disease in the body. While dementia is much more common in the geriatric population, it can also occur before the age of 65. Cognitive areas affected by dementia include, without limitation, memory, attention span, language, and problem solving. Generally, symptoms must be present for at least six months to before an individual is diagnosed with dementia.

Exemplary forms of dementia include, without limitation, frontotemporal dementia, Alzheimer's disease, vascular dementia, semantic dementia, and dementia with Lewy bodies.

Without wishing to be bound by theory, it is believed that administering an anti-TMEM106B antibody of the present disclosure can prevent, reduce the risk, and/or treat dementia.

Alzheimer's disease (AD) is the most common form of dementia. There is no cure for the disease, which worsens as it progresses, and eventually leads to death. Most often, AD is diagnosed in people over 65 years of age. However, the less-prevalent early-onset Alzheimer's diseases can occur much earlier.

Common symptoms of Alzheimer's disease include, behavioral symptoms, such as difficulty in remembering recent events; cognitive symptoms, confusion, irritability and aggression, mood swings, trouble with language, and long-term memory loss. As the disease progresses bodily functions are lost, ultimately leading to death. Alzheimer's disease develops for an unknown and variable amount of time before becoming fully apparent, and it can progress undiagnosed for years.

Amyotrophic lateral sclerosis (ALS) or, motor neuron disease or, Lou Gehrig's disease are used interchangeably and refer to a debilitating disease with varied etiology characterized by rapidly progressive weakness, muscle atrophy and fasciculations, muscle spasticity, difficulty speaking (dysarthria), difficulty swallowing (dysphagia), and difficulty breathing (dyspnea).

TMEM106B has also been implicated in hypomyelinating leukodystrophies. (Simons et al., 2017, Brain.) Hypomyelinating leukodystrophies are a heterogeneous group of disorders with clinical presentation that includes early-onset nystagmus, ataxia, and spasticity. Brain hypomyelination in four patients with hypomyelinating leukodystrophy showed the same dominant mutation (Aps252Asn) in TMEM106B, suggesting an association of TMEM106B in hypomyelinating disorders, possibly due to the role TMEM106B plays in lysosomal function. Accordingly, in some embodiments, the present disclosure provides a method for treating a hypomyelinating disorder in an individual in need thereof, the method comprising administering to the individual a therapeutically effective amount of an anti-TMEM106B antibody of the present disclosure. In some embodiments, the present disclosure provides a method for treating a hypomyelinating leukodystrophy in an individual in need thereof, the method comprising administering to the individual a therapeutically effective amount of an anti-TMEM106B antibody of the present disclosure.

The methods provided herein find use in preventing, reducing risk, or treating an individual having a neurodegenerative disease, disorder, or condition. In some embodiments, the present invention provides a method for preventing, reducing risk, or treating an individual having a neurodegenerative disorder, the method comprising administering to an individual in need thereof a therapeutically effective amount of an anti-TMEM106B antibody.

In some embodiments, the present invention provides a method for preventing, reducing risk, or treating an individual having a disease, disorder, condition, or injury characterized by the presence of TDP-43 inclusions, the method comprising administering to an individual in need thereof a therapeutically effective amount of an anti-TMEM106B antibody.

In some embodiments, the present invention provides a method for preventing, reducing risk, or treating an individual having a TDP-43 proteinopathy, the method comprising administering to an individual in need thereof a therapeutically effective amount of an anti-TMEM106B antibody.

In some embodiments, the present invention provides a method for preventing, reducing risk, or treating an individual having a disease, disorder, condition, or injury characterized by the presence of inflammatory cell debris or protein aggregates, the method comprising administering to an individual in need thereof a therapeutically effective amount of an anti-TMEM106B antibody.

In some embodiments, the present invention provides a method for preventing, reducing risk, or treating an individual having a disease, disorder, condition, or injury characterized by the presence of abnormal circulating myeloid cells, the method comprising administering to an individual in need thereof a therapeutically effective amount of an anti-TMEM106B antibody.

In some embodiments, the present invention provides a method for preventing, reducing risk, or treating an individual having unhealthy aging, the method comprising administering to an individual in need thereof a therapeutically effective amount of an anti-TMEM106B antibody.

In some embodiments, the present invention provides a method for preventing, reducing risk, or treating an individual having frontotemporal lobar degeneration (FTLD), the method comprising administering to an individual in need thereof a therapeutically effective amount of an anti-TMEM106B antibody.

In some embodiments, the present invention provides a method for preventing, reducing risk, or treating an individual having frontotemporal dementia (FTD), the method comprising administering to an individual in need thereof a therapeutically effective amount of an anti-TMEM106B antibody.

In some embodiments, the present invention provides a method for preventing, reducing risk, or treating an individual having frontotemporal dementia with progranulin mutations, the method comprising administering to an individual in need thereof a therapeutically effective amount of an anti-TMEM106B antibody.

In some embodiments, the present invention provides a method for preventing, reducing risk, or treating an individual having frontotemporal dementia with C90rf72 mutations, the method comprising administering to an individual in need thereof a therapeutically effective amount of an anti-TMEM106B antibody.

In some embodiments, the present invention provides a method for preventing, reducing risk, or treating an individual having frontotemporal lobar degeneration with TDP-43 inclusions, the method comprising administering to an individual in need thereof a therapeutically effective amount of an anti-TMEM106B antibody.

In some embodiments, the present invention provides a method for preventing, reducing risk, or treating an individual having hippocampal sclerosis (HpScl), the method comprising administering to an individual in need thereof a therapeutically effective amount of an anti-TMEM106B antibody.

In some embodiments, the present invention provides a method for preventing, reducing risk, or treating an individual having hippocampal sclerosis of aging (HS-Aging), the method comprising administering to an individual in need thereof a therapeutically effective amount of an anti-TMEM106B antibody.

In some embodiments, the present invention provides a method for preventing, reducing risk, or treating an individual having Alzheimer's disease, the method comprising administering to an individual in need thereof a therapeutically effective amount of an anti-TMEM106B antibody.

In some embodiments, the present invention provides a method for preventing, reducing risk, or treating an individual having Lewy body dementia, the method comprising administering to an individual in need thereof a therapeutically effective amount of an anti-TMEM106B antibody.

In some embodiments, the present invention provides a method for preventing, reducing risk, or treating an individual having cognitive impairment, the method comprising administering to an individual in need thereof a therapeutically effective amount of an anti-TMEM106B antibody.

In some embodiments, the present invention provides a method for preventing, reducing risk, or treating an individual having age related cognitive impairment, the method comprising administering to an individual in need thereof a therapeutically effective amount of an anti-TMEM106B antibody.

In some embodiments, the present invention provides a method for preventing, reducing risk, or treating an individual having CTE-related cognitive impairment, the method comprising administering to an individual in need thereof a therapeutically effective amount of an anti-TMEM106B antibody.

In some embodiments, the present invention provides a method for preventing, reducing risk, or treating an individual having age related brain atrophy, the method comprising administering to an individual in need thereof a therapeutically effective amount of an anti-TMEM106B antibody.

In some embodiments, the present invention provides a method for preventing, reducing risk, or treating an individual having age-associated traits, including without limitations inflammation, neuronal loss, and cognitive deficits, such as cognitive defects in the absence of known brain disease, including cognitive deficits of the frontal cerebral cortex of older individuals, the method comprising administering to an individual in need thereof a therapeutically effective amount of an anti-TMEM106B antibody.

In some embodiments, the present invention provides a method for preventing, reducing risk, or treating an individual having cognitive impairment associated with amyotrophic lateral sclerosis, the method comprising administering to an individual in need thereof a therapeutically effective amount of an anti-TMEM106B antibody.

In some embodiments, the present invention provides a method for preventing, reducing risk, or treating an individual having a disease, disorder, or condition associated with over expression or increased activity of TMEM106B, the method comprising administering to an individual in need thereof a therapeutically effective amount of an anti-TMEM106B antibody.

In some embodiments, the present invention provides a method for preventing, reducing risk, or treating an individual having a hypomyelinating disorder, the method comprising administering to an individual in need thereof a therapeutically effective amount of an anti-TMEM106B antibody.

In some embodiments, the present invention provides a method for reducing or inhibiting metastasis in an individual in need thereof, the method comprising administering to an individual in need thereof a therapeutically effective amount of an anti-TMEM106B antibody.

In some embodiments, the present invention provides a method for preventing, reducing risk, or treating an individual having cancer, the method comprising administering to an individual in need thereof a therapeutically effective amount of an anti-TMEM106B antibody.

A. Exemplary Antibodies and Certain Other Antibody Embodiments

In some embodiments, provided herein are anti-TMEM106B antibodies comprising at least one, two, three, four, five, or six HVRs selected from: (a) HVR-H1 comprising an amino acid sequence selected from the group consisting of SEQ ID NOs: 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, and 35, or an amino acid sequence with at least about 95% homology to an amino acid sequence selected from the group consisting of SEQ ID NOs: 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, and 35; (b) HVR-H2 comprising an amino acid sequence selected from the group consisting of SEQ ID NOs: 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, and 78, or an amino acid sequence with at least about 95% homology to an amino acid sequence selected from the group consisting of SEQ ID NOs: 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, and 78; (c) HVR-H3 comprising an amino acid sequence selected from the group consisting of SEQ ID NOs: 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, and 120, or an amino acid sequence with at least about 95% homology to an amino acid sequence selected from the group consisting of SEQ ID NOs: 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, and 120; (d) HVR-L1 comprising an amino acid sequence selected from the group consisting of SEQ ID NOs: 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, and 160, or an amino acid sequence with at least about 95% homology to an amino acid sequence selected from the group consisting of SEQ ID NOs: 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, and 160; (e) HVR-L2 comprising an amino acid sequence selected from the group consisting of SEQ ID NOs: 161, 162, 163, 164, 165, 166, 167, 168, 169, 170, 171, 172, 173, 174, 175, 176, 177, 178, 179, 180, 181, 182, 183, 184, and 185, or an amino acid sequence with at least about 95% homology to an amino acid sequence selected from the group consisting of SEQ ID NOs: 161, 162, 163, 164, 165, 166, 167, 168, 169, 170, 171, 172, 173, 174, 175, 176, 177, 178, 179, 180, 181, 182, 183, 184, and 185; and (f) HVR-L3 comprising an amino acid sequence selected from the group consisting of SEQ ID NOs: 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, and 224, or an amino acid sequence with at least about 95% homology to an amino acid sequence selected from the group consisting of SEQ ID NOs: 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, and 224.

In some embodiments, provided herein are anti-TMEM106B antibodies comprising at least one, two, three, four, five, or six HVRs selected from: (a) HVR-H1 comprising the amino acid sequence of SEQ ID NO:3; (b) HVR-H2 comprising the amino acid sequence of SEQ ID NO:36; (c) HVR-H3 comprising the amino acid sequence of SEQ ID NO:79; (d) HVR-L1 comprising the amino acid sequence of SEQ ID NO: 121; (e) HVR-L2 comprising the amino acid sequence of SEQ ID NO:161; and (f) HVR-L3 comprising the amino acid sequence of SEQ ID NO:186; (a) HVR-H1 comprising the amino acid sequence of SEQ ID NO:4; (b) HVR-H2 comprising the amino acid sequence of SEQ ID NO:37; (c) HVR-H3 comprising the amino acid sequence of SEQ ID NO:80; (d) HVR-L1 comprising the amino acid sequence of SEQ ID NO: 122; (e) HVR-L2 comprising the amino acid sequence of SEQ ID NO:162; and (f) HVR-L3 comprising the amino acid sequence of SEQ ID NO: 187; (a) HVR-H1 comprising the amino acid sequence of SEQ ID NO:5; (b) HVR-H2 comprising the amino acid sequence of SEQ ID NO:38; (c) HVR-H3 comprising the amino acid sequence of SEQ ID NO:81; (d) HVR-L1 comprising the amino acid sequence of SEQ ID NO: 123; (e) HVR-L2 comprising the amino acid sequence of SEQ ID NO: 163; and (f) HVR-L3 comprising the amino acid sequence of SEQ ID NO:188; (a) HVR-H1 comprising the amino acid sequence of SEQ ID NO:6; (b) HVR-H2 comprising the amino acid sequence of SEQ ID NO:39; (c) HVR-H3 comprising the amino acid sequence of SEQ ID NO:82; (d) HVR-L1 comprising the amino acid sequence of SEQ ID NO: 124; (e) HVR-L2 comprising the amino acid sequence of SEQ ID NO: 164; and (f) HVR-L3 comprising the amino acid sequence of SEQ ID NO: 189; (a) HVR-H1 comprising the amino acid sequence of SEQ ID NO:7; (b) HVR-H2 comprising the amino acid sequence of SEQ ID NO:40; (c) HVR-H3 comprising the amino acid sequence of SEQ ID NO:83; (d) HVR-L1 comprising the amino acid sequence of SEQ ID NO:125; (e) HVR-L2 comprising the amino acid sequence of SEQ ID NO: 165; and (f) HVR-L3 comprising the amino acid sequence of SEQ ID NO: 190; (a) HVR-H1 comprising the amino acid sequence of SEQ ID NO:8; (b) HVR-H2 comprising the amino acid sequence of SEQ ID NO:41; (c) HVR-H3 comprising the amino acid sequence of SEQ ID NO:84; (d) HVR-L1 comprising the amino acid sequence of SEQ ID NO: 126; (e) HVR-L2 comprising the amino acid sequence of SEQ ID NO: 166; and (f) HVR-L3 comprising the amino acid sequence of SEQ ID NO:191; (a) HVR-H1 comprising the amino acid sequence of SEQ ID NO:9; (b) HVR-H2 comprising the amino acid sequence of SEQ ID NO:42; (c) HVR-H3 comprising the amino acid sequence of SEQ ID NO:85; (d) HVR-L1 comprising the amino acid sequence of SEQ ID NO: 127; (e) HVR-L2 comprising the amino acid sequence of SEQ ID NO:167; and (f) HVR-L3 comprising the amino acid sequence of SEQ ID NO: 192; (a) HVR-H1 comprising the amino acid sequence of SEQ ID NO:10; (b) HVR-H2 comprising the amino acid sequence of SEQ ID NO:43; (c) HVR-H3 comprising the amino acid sequence of SEQ ID NO:86; (d) HVR-L1 comprising the amino acid sequence of SEQ ID NO:128; (e) HVR-L2 comprising the amino acid sequence of SEQ ID NO: 168; and (f) HVR-L3 comprising the amino acid sequence of SEQ ID NO: 193; (a) HVR-H1 comprising the amino acid sequence of SEQ ID NO: 11; (b) HVR-H2 comprising the amino acid sequence of SEQ ID NO: 44; (c) HVR-H3 comprising the amino acid sequence of SEQ ID NO:87; (d) HVR-L1 comprising the amino acid sequence of SEQ ID NO: 123; (e) HVR-L2 comprising the amino acid sequence of SEQ ID NO: 169; and (f) HVR-L3 comprising the amino acid sequence of SEQ ID NO:188; (a) HVR-H1 comprising the amino acid sequence of SEQ ID NO: 12; (b) HVR-H2 comprising the amino acid sequence of SEQ ID NO:45; (c) HVR-H3 comprising the amino acid sequence of SEQ ID NO:88; (d) HVR-L1 comprising the amino acid sequence of SEQ ID NO: 129; (e) HVR-L2 comprising the amino acid sequence of SEQ ID NO:170; and (f) HVR-L3 comprising the amino acid sequence of SEQ ID NO: 194; (a) HVR-H1 comprising the amino acid sequence of SEQ ID NO:13; (b) HVR-H2 comprising the amino acid sequence of SEQ ID NO:46; (c) HVR-H3 comprising the amino acid sequence of SEQ ID NO:89; (d) HVR-L1 comprising the amino acid sequence of SEQ ID NO:130; (e) HVR-L2 comprising the amino acid sequence of SEQ ID NO: 171; and (f) HVR-L3 comprising the amino acid sequence of SEQ ID NO: 195; (a) HVR-H1 comprising the amino acid sequence of SEQ ID NO:14; (b) HVR-H2 comprising the amino acid sequence of SEQ ID NO:47; (c) HVR-H3 comprising the amino acid sequence of SEQ ID NO: 90; (d) HVR-L1 comprising the amino acid sequence of SEQ ID NO:131; (e) HVR-L2 comprising the amino acid sequence of SEQ ID NO:170; and (f) HVR-L3 comprising the amino acid sequence of SEQ ID NO:196; (a) HVR-H1 comprising the amino acid sequence of SEQ ID NO:15; (b) HVR-H2 comprising the amino acid sequence of SEQ ID NO:48; (c) HVR-H3 comprising the amino acid sequence of SEQ ID NO:91; (d) HVR-L1 comprising the amino acid sequence of SEQ ID NO: 132; (e) HVR-L2 comprising the amino acid sequence of SEQ ID NO:172; and (f) HVR-L3 comprising the amino acid sequence of SEQ ID NO: 197; (a) HVR-H1 comprising the amino acid sequence of SEQ ID NO:3; (b) HVR-H2 comprising the amino acid sequence of SEQ ID NO:49; (c) HVR-H3 comprising the amino acid sequence of SEQ ID NO:92; (d) HVR-L1 comprising the amino acid sequence of SEQ ID NO: 133; (e) HVR-L2 comprising the amino acid sequence of SEQ ID NO: 173; and (f) HVR-L3 comprising the amino acid sequence of SEQ ID NO: 198; (a) HVR-H1 comprising the amino acid sequence of SEQ ID NO: 16; (b) HVR-H2 comprising the amino acid sequence of SEQ ID NO:50; (c) HVR-H3 comprising the amino acid sequence of SEQ ID NO:93; (d) HVR-L1 comprising the amino acid sequence of SEQ ID NO:134; (e) HVR-L2 comprising the amino acid sequence of SEQ ID NO: 172; and (f) HVR-L3 comprising the amino acid sequence of SEQ ID NO:199; (a) HVR-H1 comprising the amino acid sequence of SEQ ID NO: 17; (b) HVR-H2 comprising the amino acid sequence of SEQ ID NO:51; (c) HVR-H3 comprising the amino acid sequence of SEQ ID NO:94; (d) HVR-L1 comprising the amino acid sequence of SEQ ID NO: 135; (e) HVR-L2 comprising the amino acid sequence of SEQ ID NO:174; and (f) HVR-L3 comprising the amino acid sequence of SEQ ID NO:200; (a) HVR-H1 comprising the amino acid sequence of SEQ ID NO:18; (b) HVR-H2 comprising the amino acid sequence of SEQ ID NO:52; (c) HVR-H3 comprising the amino acid sequence of SEQ ID NO:95; (d) HVR-L1 comprising the amino acid sequence of SEQ ID NO: 133; (e) HVR-L2 comprising the amino acid sequence of SEQ ID NO: 173; and (f) HVR-L3 comprising the amino acid sequence of SEQ ID NO:198; (a) HVR-H1 comprising the amino acid sequence of SEQ ID NO:6; (b) HVR-H2 comprising the amino acid sequence of SEQ ID NO:53; (c) HVR-H3 comprising the amino acid sequence of SEQ ID NO:96; (d) HVR-L1 comprising the amino acid sequence of SEQ ID NO: 136; (e) HVR-L2 comprising the amino acid sequence of SEQ ID NO: 175; and (f) HVR-L3 comprising the amino acid sequence of SEQ ID NO:201; (a) HVR-H1 comprising the amino acid sequence of SEQ ID NO: 14; (b) HVR-H2 comprising the amino acid sequence of SEQ ID NO:54; (c) HVR-H3 comprising the amino acid sequence of SEQ ID NO:97; (d) HVR-L1 comprising the amino acid sequence of SEQ ID NO: 137; (e) HVR-L2 comprising the amino acid sequence of SEQ ID NO: 176; and (f) HVR-L3 comprising the amino acid sequence of SEQ ID NO:202; (a) HVR-H1 comprising the amino acid sequence of SEQ ID NO:17; (b) HVR-H2 comprising the amino acid sequence of SEQ ID NO: 51; (c) HVR-H3 comprising the amino acid sequence of SEQ ID NO:94; (d) HVR-L1 comprising the amino acid sequence of SEQ ID NO: 135; (e) HVR-L2 comprising the amino acid sequence of SEQ ID NO: 174; and (f) HVR-L3 comprising the amino acid sequence of SEQ ID NO:200; (a) HVR-H1 comprising the amino acid sequence of SEQ ID NO: 19; (b) HVR-H2 comprising the amino acid sequence of SEQ ID NO:55; (c) HVR-H3 comprising the amino acid sequence of SEQ ID NO:98; (d) HVR-L1 comprising the amino acid sequence of SEQ ID NO: 138; (e) HVR-L2 comprising the amino acid sequence of SEQ ID NO: 169; and (f) HVR-L3 comprising the amino acid sequence of SEQ ID NO:203; (a) HVR-H1 comprising the amino acid sequence of SEQ ID NO:20; (b) HVR-H2 comprising the amino acid sequence of SEQ ID NO:56; (c) HVR-H3 comprising the amino acid sequence of SEQ ID NO:99; (d) HVR-L1 comprising the amino acid sequence of SEQ ID NO: 139; (e) HVR-L2 comprising the amino acid sequence of SEQ ID NO: 161; and (f) HVR-L3 comprising the amino acid sequence of SEQ ID NO: 204; (a) HVR-H1 comprising the amino acid sequence of SEQ ID NO:3; (b) HVR-H2 comprising the amino acid sequence of SEQ ID NO:57; (c) HVR-H3 comprising the amino acid sequence of SEQ ID NO: 100; (d) HVR-L1 comprising the amino acid sequence of SEQ ID NO:140; (e) HVR-L2 comprising the amino acid sequence of SEQ ID NO:177; and (f) HVR-L3 comprising the amino acid sequence of SEQ ID NO:205; (a) HVR-H1 comprising the amino acid sequence of SEQ ID NO: 13; (b) HVR-H2 comprising the amino acid sequence of SEQ ID NO:46; (c) HVR-H3 comprising the amino acid sequence of SEQ ID NO:89; (d) HVR-L1 comprising the amino acid sequence of SEQ ID NO:141; (e) HVR-L2 comprising the amino acid sequence of SEQ ID NO:171; and (f) HVR-L3 comprising the amino acid sequence of SEQ ID NO:206; (a) HVR-H1 comprising the amino acid sequence of SEQ ID NO:11; (b) HVR-H2 comprising the amino acid sequence of SEQ ID NO:58; (c) HVR-H3 comprising the amino acid sequence of SEQ ID NO:101; (d) HVR-L1 comprising the amino acid sequence of SEQ ID NO: 138; (e) HVR-L2 comprising the amino acid sequence of SEQ ID NO: 169; and (f) HVR-L3 comprising the amino acid sequence of SEQ ID NO:207; (a) HVR-H1 comprising the amino acid sequence of SEQ ID NO:3; (b) HVR-H2 comprising the amino acid sequence of SEQ ID NO:57; (c) HVR-H3 comprising the amino acid sequence of SEQ ID NO: 100; (d) HVR-L1 comprising the amino acid sequence of SEQ ID NO:140; (e) HVR-L2 comprising the amino acid sequence of SEQ ID NO:177; and (f) HVR-L3 comprising the amino acid sequence of SEQ ID NO:205; (a) HVR-H1 comprising the amino acid sequence of SEQ ID NO: 3; (b) HVR-H2 comprising the amino acid sequence of SEQ ID NO:59; (c) HVR-H3 comprising the amino acid sequence of SEQ ID NO: 102; (d) HVR-L1 comprising the amino acid sequence of SEQ ID NO: 142; (e) HVR-L2 comprising the amino acid sequence of SEQ ID NO: 178; and (f) HVR-L3 comprising the amino acid sequence of SEQ ID NO:208; (a) HVR-H1 comprising the amino acid sequence of SEQ ID NO:9; (b) HVR-H2 comprising the amino acid sequence of SEQ ID NO:60; (c) HVR-H3 comprising the amino acid sequence of SEQ ID NO: 103; (d) HVR-L1 comprising the amino acid sequence of SEQ ID NO:143; (e) HVR-L2 comprising the amino acid sequence of SEQ ID NO: 167; and (f) HVR-L3 comprising the amino acid sequence of SEQ ID NO: 192; (a) HVR-H1 comprising the amino acid sequence of SEQ ID NO:21; (b) HVR-H2 comprising the amino acid sequence of SEQ ID NO: 61; (c) HVR-H3 comprising the amino acid sequence of SEQ ID NO: 104; (d) HVR-L1 comprising the amino acid sequence of SEQ ID NO: 144; (e) HVR-L2 comprising the amino acid sequence of SEQ ID NO: 169; and (f) HVR-L3 comprising the amino acid sequence of SEQ ID NO:209; (a) HVR-H1 comprising the amino acid sequence of SEQ ID NO:22; (b) HVR-H2 comprising the amino acid sequence of SEQ ID NO:62; (c) HVR-H3 comprising the amino acid sequence of SEQ ID NO: 105; (d) HVR-L1 comprising the amino acid sequence of SEQ ID NO:145; (e) HVR-L2 comprising the amino acid sequence of SEQ ID NO: 161; and (f) HVR-L3 comprising the amino acid sequence of SEQ ID NO:210; (a) HVR-H1 comprising the amino acid sequence of SEQ ID NO:12; (b) HVR-H2 comprising the amino acid sequence of SEQ ID NO:63; (c) HVR-H3 comprising the amino acid sequence of SEQ ID NO:106; (d) HVR-L1 comprising the amino acid sequence of SEQ ID NO:128; (e) HVR-L2 comprising the amino acid sequence of SEQ ID NO:179; and (f) HVR-L3 comprising the amino acid sequence of SEQ ID NO: 211; (a) HVR-H1 comprising the amino acid sequence of SEQ ID NO:14; (b) HVR-H2 comprising the amino acid sequence of SEQ ID NO:64; (c) HVR-H3 comprising the amino acid sequence of SEQ ID NO: 107; (d) HVR-L1 comprising the amino acid sequence of SEQ ID NO: 146; (e) HVR-L2 comprising the amino acid sequence of SEQ ID NO: 161; and (f) HVR-L3 comprising the amino acid sequence of SEQ ID NO:202; (a) HVR-H1 comprising the amino acid sequence of SEQ ID NO:23; (b) HVR-H2 comprising the amino acid sequence of SEQ ID NO:65; (c) HVR-H3 comprising the amino acid sequence of SEQ ID NO: 108; (d) HVR-L1 comprising the amino acid sequence of SEQ ID NO: 147; (e) HVR-L2 comprising the amino acid sequence of SEQ ID NO:180; and (f) HVR-L3 comprising the amino acid sequence of SEQ ID NO:212; (a) HVR-H1 comprising the amino acid sequence of SEQ ID NO:24; (b) HVR-H2 comprising the amino acid sequence of SEQ ID NO:66; (c) HVR-H3 comprising the amino acid sequence of SEQ ID NO:109; (d) HVR-L1 comprising the amino acid sequence of SEQ ID NO: 148; (e) HVR-L2 comprising the amino acid sequence of SEQ ID NO: 162; and (f) HVR-L3 comprising the amino acid sequence of SEQ ID NO:213; (a) HVR-H1 comprising the amino acid sequence of SEQ ID NO:25; (b) HVR-H2 comprising the amino acid sequence of SEQ ID NO:67; (c) HVR-H3 comprising the amino acid sequence of SEQ ID NO: 110; (d) HVR-L1 comprising the amino acid sequence of SEQ ID NO:149; (e) HVR-L2 comprising the amino acid sequence of SEQ ID NO: 161; and (f) HVR-L3 comprising the amino acid sequence of SEQ ID NO: 196; (a) HVR-H1 comprising the amino acid sequence of SEQ ID NO: 26; (b) HVR-H2 comprising the amino acid sequence of SEQ ID NO:68; (c) HVR-H3 comprising the amino acid sequence of SEQ ID NO:111; (d) HVR-L1 comprising the amino acid sequence of SEQ ID NO: 150; (e) HVR-L2 comprising the amino acid sequence of SEQ ID NO: 181; and (f) HVR-L3 comprising the amino acid sequence of SEQ ID NO:214; (a) HVR-H1 comprising the amino acid sequence of SEQ ID NO:27; (b) HVR-H2 comprising the amino acid sequence of SEQ ID NO:69; (c) HVR-H3 comprising the amino acid sequence of SEQ ID NO:112; (d) HVR-L1 comprising the amino acid sequence of SEQ ID NO: 151; (e) HVR-L2 comprising the amino acid sequence of SEQ ID NO: 181; and (f) HVR-L3 comprising the amino acid sequence of SEQ ID NO:215; (a) HVR-H1 comprising the amino acid sequence of SEQ ID NO:28; (b) HVR-H2 comprising the amino acid sequence of SEQ ID NO: 70; (c) HVR-H3 comprising the amino acid sequence of SEQ ID NO:113; (d) HVR-L1 comprising the amino acid sequence of SEQ ID NO: 152; (e) HVR-L2 comprising the amino acid sequence of SEQ ID NO: 182; and (f) HVR-L3 comprising the amino acid sequence of SEQ ID NO:216; (a) HVR-H1 comprising the amino acid sequence of SEQ ID NO:29; (b) HVR-H2 comprising the amino acid sequence of SEQ ID NO:71; (c) HVR-H3 comprising the amino acid sequence of SEQ ID NO:111; (d) HVR-L1 comprising the amino acid sequence of SEQ ID NO:153; (e) HVR-L2 comprising the amino acid sequence of SEQ ID NO: 181; and (f) HVR-L3 comprising the amino acid sequence of SEQ ID NO:214; (a) HVR-H1 comprising the amino acid sequence of SEQ ID NO:30; (b) HVR-H2 comprising the amino acid sequence of SEQ ID NO:72; (c) HVR-H3 comprising the amino acid sequence of SEQ ID NO:114; (d) HVR-L1 comprising the amino acid sequence of SEQ ID NO: 152; (e) HVR-L2 comprising the amino acid sequence of SEQ ID NO: 182; and (f) HVR-L3 comprising the amino acid sequence of SEQ ID NO: 217; (a) HVR-H1 comprising the amino acid sequence of SEQ ID NO:31; (b) HVR-H2 comprising the amino acid sequence of SEQ ID NO:73; (c) HVR-H3 comprising the amino acid sequence of SEQ ID NO: 115; (d) HVR-L1 comprising the amino acid sequence of SEQ ID NO: 154; (e) HVR-L2 comprising the amino acid sequence of SEQ ID NO: 183; and (f) HVR-L3 comprising the amino acid sequence of SEQ ID NO:218; (a) HVR-H1 comprising the amino acid sequence of SEQ ID NO:32; (b) HVR-H2 comprising the amino acid sequence of SEQ ID NO:74; (c) HVR-H3 comprising the amino acid sequence of SEQ ID NO: 116; (d) HVR-L1 comprising the amino acid sequence of SEQ ID NO: 155; (e) HVR-L2 comprising the amino acid sequence of SEQ ID NO:182; and (f) HVR-L3 comprising the amino acid sequence of SEQ ID NO:219; (a) HVR-H1 comprising the amino acid sequence of SEQ ID NO:33; (b) HVR-H2 comprising the amino acid sequence of SEQ ID NO:75; (c) HVR-H3 comprising the amino acid sequence of SEQ ID NO:117; (d) HVR-L1 comprising the amino acid sequence of SEQ ID NO: 156; (e) HVR-L2 comprising the amino acid sequence of SEQ ID NO: 161; and (f) HVR-L3 comprising the amino acid sequence of SEQ ID NO:220; (a) HVR-H1 comprising the amino acid sequence of SEQ ID NO:34; (b) HVR-H2 comprising the amino acid sequence of SEQ ID NO:76; (c) HVR-H3 comprising the amino acid sequence of SEQ ID NO:118; (d) HVR-L1 comprising the amino acid sequence of SEQ ID NO:157; (e) HVR-L2 comprising the amino acid sequence of SEQ ID NO:184; and (f) HVR-L3 comprising the amino acid sequence of SEQ ID NO:221; (a) HVR-H1 comprising the amino acid sequence of SEQ ID NO: 32; (b) HVR-H2 comprising the amino acid sequence of SEQ ID NO:74; (c) HVR-H3 comprising the amino acid sequence of SEQ ID NO: 116; (d) HVR-L1 comprising the amino acid sequence of SEQ ID NO: 158; (e) HVR-L2 comprising the amino acid sequence of SEQ ID NO:185; and (f) HVR-L3 comprising the amino acid sequence of SEQ ID NO:222; (a) HVR-H1 comprising the amino acid sequence of SEQ ID NO:35; (b) HVR-H2 comprising the amino acid sequence of SEQ ID NO:77; (c) HVR-H3 comprising the amino acid sequence of SEQ ID NO: 119; (d) HVR-L1 comprising the amino acid sequence of SEQ ID NO: 159; (e) HVR-L2 comprising the amino acid sequence of SEQ ID NO: 182; and (f) HVR-L3 comprising the amino acid sequence of SEQ ID NO:223; and (a) HVR-H1 comprising the amino acid sequence of SEQ ID NO:29; (b) HVR-H2 comprising the amino acid sequence of SEQ ID NO: 78; (c) HVR-H3 comprising the amino acid sequence of SEQ ID NO:120; (d) HVR-L1 comprising the amino acid sequence of SEQ ID NO:160; (e) HVR-L2 comprising the amino acid sequence of SEQ ID NO: 183; and (f) HVR-L3 comprising the amino acid sequence of SEQ ID NO:224.

In some embodiments, provided herein are anti-TMEM106B antibodies comprising at least one, at least two, or all three $V_H$ HVR sequences selected from (a) HVR-H1 comprising an amino acid sequence selected from the group consisting of SEQ ID NO: 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, and 35, or an amino acid sequence with at least about 95% homology to an amino acid sequence selected from the group consisting of SEQ ID NOs: 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, and 35; (b)

HVR-H2 comprising an amino acid sequence selected from the group consisting of SEQ ID NO: 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, and 78, or an amino acid sequence with at least about 95% homology to an amino acid sequence selected from the group consisting of SEQ ID NOs: 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, and 78; and (c) HVR-H3 comprising an amino acid sequence selected from the group consisting of SEQ ID NO: 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, and 120, or an amino acid sequence with at least about 95% homology to an amino acid sequence selected from the group consisting of SEQ ID NOs: 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, and 120.

In some embodiments, provided herein are anti-TMEM106B antibodies comprising at least one, at least two, or all three $V_L$ HVR sequences selected from (a) HVR-L1 comprising an amino acid sequence selected from the group consisting of SEQ ID NO: 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, and 160, or an amino acid sequence with at least about 95% homology to an amino acid sequence selected from the group consisting of SEQ ID NOs: 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, and 160; (b) HVR-L2 comprising an amino acid sequence selected from the group consisting of SEQ ID NO: 161, 162, 163, 164, 165, 166, 167, 168, 169, 170, 171, 172, 173, 174, 175, 176, 177, 178, 179, 180, 181, 182, 183, 184, and 185, or an amino acid sequence with at least about 95% homology to an amino acid sequence selected from the group consisting of SEQ ID NOs: 161, 162, 163, 164, 165, 166, 167, 168, 169, 170, 171, 172, 173, 174, 175, 176, 177, 178, 179, 180, 181, 182, 183, 184, and 185; and (c) HVR-L3 comprising an amino acid sequence selected from the group consisting of SEQ ID NO: 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, and 224, or an amino acid sequence with at least about 95% homology to an amino acid sequence selected from the group consisting of SEQ ID NOs: 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, and 224.

In some embodiments, provided herein are anti-TMEM106B antibodies comprising (a) a $V_H$ domain comprising at least one, at least two, or all three $V_H$ HVR sequences selected from (i) HVR-H1 comprising an amino acid sequence selected from the group consisting of SEQ ID NO: 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, and 35, or an amino acid sequence with at least about 95% homology to an amino acid sequence selected from the group consisting of SEQ ID NOs: 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, and 35, (ii) HVR-H2 comprising an amino acid sequence selected from the group consisting of SEQ ID NO: 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, and 78, or an amino acid sequence with at least about 95% homology to an amino acid sequence selected from the group consisting of SEQ ID NOs: 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, and 78, and (iii) HVR-H3 comprising an amino acid sequence selected from the group consisting of SEQ ID NO: 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, and 120, or an amino acid sequence with at least about 95% homology to an amino acid sequence selected from the group consisting of SEQ ID NOs: 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, and 120, and (b) a $V_L$ domain comprising at least one, at least two, or all three $V_L$ HVR sequences selected from (i) HVR-L1 comprising an amino acid sequence selected from the group consisting of SEQ ID NO: 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, and 160, or an amino acid sequence with at least about 95% homology to an amino acid sequence selected from the group consisting of SEQ ID NOs: 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, and 160, (ii) HVR-L2 comprising an amino acid sequence selected from the group consisting of SEQ ID NO: 161, 162, 163, 164, 165, 166, 167, 168, 169, 170, 171, 172, 173, 174, 175, 176, 177, 178, 179, 180, 181, 182, 183, 184, and 185, or an amino acid sequence with at least about 95% homology to an amino acid sequence selected from the group consisting of SEQ ID NOs: 161, 162, 163, 164, 165, 166, 167, 168, 169, 170, 171, 172, 173, 174, 175, 176, 177, 178, 179, 180, 181, 182, 183, 184, and 185, and (iii) HVR-L3 comprising an amino acid sequence selected from the group consisting of SEQ ID NO: 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, and 224, or an amino acid sequence with at least about 95% homology to an amino acid sequence selected from the group consisting of SEQ ID NOs: 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, and 224.

In some embodiments, provided herein are anti-TMEM106B antibodies comprising (a) a $V_H$ domain comprising (i) HVR-H1 comprising an amino acid sequence selected from the group consisting of SEQ ID NO: 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, and 35, or an amino acid sequence with at least about 95% homology to an amino acid sequence selected from the group consisting of SEQ ID NOs: 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, and 35, (ii) HVR-H2 comprising an amino acid sequence selected from the group consisting of SEQ ID NO: 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, and 78, or an amino acid sequence with at least about 95% homology to an amino acid sequence selected from the group consisting of SEQ ID NOs: 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, and 78, and (iii) HVR-H3 comprising an amino acid sequence selected from the group consisting of SEQ ID NO: 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, and 120, or an amino acid sequence with at least about 95% homology to an amino acid sequence selected from the group consisting of SEQ ID NOs: 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, and 120, and (b) a $V_L$ domain comprising (i) HVR-L1 comprising an amino acid sequence selected from the group consisting of SEQ ID NO: 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, and 160, or an amino acid sequence with at least about 95% homology to an amino acid sequence selected from the group consisting of SEQ ID NOs: 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, and 160, (ii) HVR-L2 comprising an amino acid sequence selected from the group consisting of SEQ ID NO: 161, 162, 163, 164, 165, 166, 167, 168, 169, 170, 171, 172, 173, 174, 175, 176, 177, 178, 179, 180, 181, 182, 183, 184, and 185, or an amino acid sequence with at least about 95% homology to an amino acid sequence selected from the group consisting of SEQ ID NOs: 161, 162, 163, 164, 165, 166, 167, 168, 169, 170, 171, 172, 173, 174, 175, 176, 177, 178, 179, 180, 181, 182, 183, 184, and 185, and (iii) HVR-L3 comprising an amino acid sequence selected from the group consisting of SEQ ID NO: 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, and 224, or an amino acid sequence with at least about 95% homology to an amino acid sequence selected from the group consisting of SEQ ID NOs: 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, and 224.

In another aspect, an anti-TMEM106B antibody comprises a heavy chain variable domain ($V_H$) sequence having at least 90%, 91%, 92%, 93%, 94%, 95%, 96%, 97%, 98%, 99%, or 100% sequence identity to an amino acid sequence selected from the group consisting of SEQ ID NOs: 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, and 268. In certain embodiments, a $V_H$ sequence having at least 90%, 91%, 92%, 93%, 94%, 95%, 96%, 97%, 98%, or 99% identity to an amino acid sequence selected from the group consisting of SEQ ID NOs: 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, and 268 contains substitutions (e.g., conservative substitutions), insertions, or deletions relative to the reference sequence, but an anti-TMEM106B antibody comprising that sequence retains the ability to bind to TMEM106B. In certain embodiments, a total of 1 to 10 amino acids have been substituted, inserted, and/or deleted in SEQ ID NO:225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, or 268. In certain embodiments, a total of 1 to 5 amino acids have been substituted, inserted and/or deleted in SEQ ID NO:225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, or 268. In certain embodiments, substitutions, insertions, or deletions occur in regions outside the HVRs (i.e., in the FRs). Optionally, the anti-TMEM106B antibody comprises the $V_H$ sequence of SEQ ID NO:225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, or 268, including post-translational modifications of that sequence. In a particular embodiment, the $V_H$ comprises one, two or three HVRs selected from: (a) HVR-H1 comprising an amino acid sequence selected from the group consisting of SEQ ID NOs: 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, and 35, (b) HVR-H2 comprising an amino acid sequence selected from the group consisting of SEQ ID NOs: 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, and 78, and (c) HVR-H3 comprising an amino acid sequence selected from the group consisting of SEQ ID NOs: 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, and 120.

In another aspect, an anti-TMEM106B antibody is provided, wherein the antibody comprises a light chain variable domain ($V_L$) having at least 90%, 91%, 92%, 93%, 94%, 95%, 96%, 97%, 98%, 99%, or 100% sequence identity to an amino acid sequence selected from the group consisting of SEQ ID NOs: 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, and 314. In certain embodiments, a $V_L$ sequence having at least 90%, 91%, 92%, 93%, 94%, 95%, 96%, 97%, 98%, or 99% identity to an amino acid sequence selected from the group consisting of SEQ ID NOs: 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, and 314 contains substitutions (e.g., conservative substitutions), insertions, or deletions relative to the reference sequence, but an anti-TMEM106B antibody comprising that sequence retains the ability to bind to TMEM106B. In some embodiments, a total of 1 to 10 amino acids have been substituted, inserted and/or deleted in SEQ ID NO: 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, or 314. In certain embodiments, a total of 1 to 5 amino acids have been substituted, inserted and/or deleted in SEQ ID NO: 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, or 314. In certain embodiments, the substitutions, insertions, or deletions occur in regions outside the HVRs (i.e., in the FRs). Optionally, the anti-TMEM106B antibody comprises the $V_L$ sequence of SEQ ID NO: 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, or 314, including post-translational modifications of that sequence. In a particular embodiment, the $V_L$ comprises one, two or three HVRs selected from (a) HVR-L1 comprising an amino acid sequence selected from the group consisting of SEQ ID NOs: 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, and 160, (b) HVR-L2 comprising an amino acid sequence selected from the group consisting of SEQ ID NOs: 161, 162, 163, 164, 165, 166, 167, 168, 169, 170, 171, 172, 173, 174, 175, 176, 177, 178, 179, 180, 181, 182, 183, 184, and 185, and (c) HVR-L3 comprising an amino acid sequence selected from the group consisting of SEQ ID NOs: 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, and 224.

In some embodiments, an anti-TMEM106B antibody is provided, wherein the antibody comprises a $V_H$ as in any of the embodiments provided above, and a $V_L$ as in any of the embodiments provided above. In some embodiments, provided herein are anti-TMEM106B antibodies, wherein the antibody comprises a $V_H$ as in any of the embodiments provided above, and a $V_L$ as in any of the embodiments provided above. In one embodiment, the antibody comprises the $V_H$ and $V_L$ sequences in SEQ ID NOs: 225-268 and SEQ ID NOs: 269-314, respectively, including post-translational modifications of those sequences.

In some embodiments, provided herein are anti-TMEM106B antibodies comprising a heavy chain variable domain ($V_H$) and a light chain variable domain ($V_L$), wherein the $V_H$ and $V_L$ are selected from the group consisting of: $V_H$ comprising the amino acid sequence of SEQ ID NO:225 and $V_L$ comprising the amino acid sequence of SEQ ID NO:269; $V_H$ comprising the amino acid sequence of SEQ ID NO: 226 and $V_L$ comprising the amino acid sequence of SEQ ID NO:270; $V_H$ comprising the amino acid sequence of SEQ ID NO:227 and $V_L$ comprising the amino acid sequence of SEQ ID NO:271; $V_H$ comprising the amino acid sequence of SEQ ID NO:228 and $V_L$ comprising the amino acid sequence of SEQ ID NO:272; $V_H$ comprising the amino acid sequence of SEQ ID NO:229 and $V_L$ comprising the amino acid sequence of SEQ ID NO:273; $V_H$ comprising the amino acid sequence of SEQ ID NO:230 and $V_L$ comprising the amino acid sequence of SEQ ID NO:274; $V_H$ comprising the amino acid sequence of SEQ ID NO:231 and $V_L$ comprising the amino acid sequence of SEQ ID NO:275; $V_H$ comprising the amino acid sequence of SEQ ID NO:232 and $V_L$ comprising the amino acid sequence of SEQ ID NO:276; $V_H$ comprising the amino acid sequence of SEQ ID NO:233 and $V_L$ comprising the amino acid sequence of SEQ ID NO:277; $V_H$ comprising the amino acid sequence of SEQ ID NO:234 and $V_L$ comprising the amino acid sequence of SEQ ID NO:278; $V_H$ comprising the amino acid sequence of SEQ ID NO:235 and $V_L$ comprising the amino acid sequence of SEQ ID NO:279; $V_H$ comprising the amino acid sequence of SEQ ID NO:236 and $V_L$ comprising the amino acid sequence of SEQ ID NO:280; $V_H$ comprising the amino acid sequence of SEQ ID NO:237 and $V_L$ comprising the amino acid sequence of SEQ ID NO:281; $V_H$ comprising the amino acid sequence of SEQ ID NO:238 and $V_L$ comprising the amino acid sequence of SEQ ID NO:282; $V_H$ comprising the amino acid sequence of SEQ ID NO:239 and $V_L$ comprising the amino acid sequence of SEQ ID NO:283; $V_H$ comprising the amino acid sequence of SEQ ID NO:240 and $V_L$ comprising the amino acid sequence of SEQ ID NO:284; $V_H$ comprising the amino acid sequence of SEQ ID NO:241 and $V_L$ comprising the amino acid sequence of SEQ ID NO:285; $V_H$ comprising the amino acid sequence of SEQ ID NO:242 and $V_L$ comprising the amino acid sequence of SEQ ID NO:286; $V_H$ comprising the amino acid sequence of SEQ ID NO:243 and $V_L$ comprising the amino acid sequence of SEQ ID NO:287; $V_H$ comprising the amino acid sequence of SEQ ID NO:240 and $V_L$ comprising the amino acid sequence of SEQ ID NO:288; $V_H$ comprising the amino acid sequence of SEQ ID NO:244 and $V_L$ comprising the amino acid sequence of SEQ ID NO:289; $V_H$ comprising the amino acid sequence of SEQ ID NO:245 and $V_L$ comprising the amino acid sequence of SEQ ID NO:290; $V_H$ comprising the amino acid sequence of SEQ ID NO:246 and $V_L$ comprising the amino acid sequence of SEQ ID NO:291; $V_H$ comprising the amino acid sequence of SEQ ID NO:235 and $V_L$ comprising the amino acid sequence of SEQ ID NO:292; $V_H$ comprising the amino acid sequence of SEQ ID NO:247 and $V_L$ comprising the amino acid sequence of SEQ ID NO:293; $V_H$ comprising the amino acid sequence of SEQ ID NO:248 and $V_L$ comprising the amino acid sequence of SEQ ID NO:294; $V_H$ comprising the amino acid sequence of SEQ ID NO:249 and $V_L$ comprising the amino acid sequence of SEQ ID NO:295; $V_H$ comprising the amino acid sequence of SEQ ID NO:250 and $V_L$ comprising the amino acid sequence of SEQ ID NO:296; $V_H$ comprising the amino acid sequence of SEQ ID NO:251 and $V_L$ comprising the amino acid sequence of SEQ ID NO:297; $V_H$ comprising the amino acid sequence of SEQ ID NO:252 and $V_L$ comprising the amino acid sequence of SEQ ID NO:298; $V_H$ comprising the amino acid sequence of SEQ ID NO:253 and $V_L$ comprising the amino acid sequence of SEQ ID NO:299; $V_H$ comprising the amino acid sequence of SEQ ID NO:254 and $V_L$ comprising the amino acid sequence of SEQ ID NO:300; $V_H$ comprising the amino acid sequence of SEQ ID NO:255 and $V_L$ comprising the amino acid sequence of SEQ ID NO:301; $V_H$ comprising the amino acid sequence of SEQ ID NO:256 and $V_L$ comprising the amino acid sequence of SEQ ID NO:302; $V_H$ comprising the amino acid sequence of SEQ ID NO:257 and $V_L$ comprising the amino acid sequence of SEQ ID NO:303; $V_H$ comprising the amino acid sequence of SEQ ID NO:258 and $V_L$ comprising the amino acid sequence of SEQ ID NO:304; $V_H$ comprising the amino acid sequence of SEQ ID NO:259 and $V_L$ comprising the amino acid sequence of SEQ ID NO:305; $V_H$ comprising the amino acid sequence of SEQ ID NO:260 and $V_L$ comprising the amino acid sequence of SEQ ID NO:306; $V_H$ comprising the amino acid sequence of SEQ ID NO:261 and $V_L$ comprising the amino acid sequence of SEQ ID NO:307; $V_H$ comprising the amino acid sequence of SEQ ID NO:262 and $V_L$ comprising the amino acid sequence of SEQ ID NO:308; $V_H$ comprising the amino acid sequence of SEQ ID NO:263 and $V_L$ comprising the amino acid sequence of SEQ ID NO:309; $V_H$ comprising the amino acid sequence of SEQ ID NO:264 and $V_L$ comprising the amino acid sequence of SEQ ID NO:310; $V_H$ comprising the amino acid sequence of SEQ ID NO:265 and $V_L$ comprising the amino acid sequence of SEQ ID NO:311; $V_H$ comprising the amino acid sequence of SEQ ID NO:266 and $V_L$ comprising the amino acid sequence of SEQ ID NO:312; $V_H$ comprising the amino acid sequence of SEQ ID NO:267 and $V_L$ comprising the amino acid sequence of SEQ ID NO:313; and $V_H$ comprising the amino acid sequence of SEQ ID NO:268 and $V_L$ comprising the amino acid sequence of SEQ ID NO:314.

In some embodiments, an anti-TMEM106B antibody of the present disclosure competitively inhibits binding of at least one antibody selected from TM-1, TM-2, TM-3, TM-4, TM-5, TM-6, TM-7, TM-8, TM-9, TM-10, TM-11, TM-12, TM-13, TM-14, TM-15, TM-16, TM-17, TM-18, TM-19, TM-20, TM-21, TM-22, TM-23, TM-24, TM-25, TM-26, TM-27, TM-28, TM-29, TM-30, TM-31, TM-32, TM-33, TM-34, TM-35, TM-36, TM-37, TM-38, TM-39, TM-40, TM-41, TM-42, TM-43, TM-44, TM-45, TM-46, TM-47, TM-48, TM-49, TM-50, TM-51, TM-52, and TM-53. In some embodiments, an anti-TMEM106B antibody of the present disclosure competes with one or more antibodies selected from TM-1, TM-2, TM-3, TM-4, TM-5, TM-6, TM-7, TM-8, TM-9, TM-10, TM-11, TM-12, TM-13, TM-14, TM-15, TM-16, TM-17, TM-18, TM-19, TM-20, TM-21, TM-22, TM-23, TM-24, TM-25, TM-26, TM-27, TM-28, TM-29, TM-30, TM-31, TM-32, TM-33, TM-34, TM-35, TM-36, TM-37, TM-38, TM-39, TM-40, TM-41, TM-42, TM-43, TM-44, TM-45, TM-46, TM-47, TM-48, TM-49, TM-50, TM-51, TM-52, and TM-53, and any combination thereof, for binding to TMEM106B when the anti-TMEM106B antibody reduces the binding of one or more antibodies selected from TM-1, TM-2, TM-3, TM-4, TM-5, TM-6, TM-7, TM-8, TM-9, TM-10, TM-11, TM-12, TM-13, TM-14, TM-15, TM-16, TM-17, TM-18, TM-19, TM-20, TM-21, TM-22, TM-23, TM-24, TM-25, TM-26, TM-27, TM-28, TM-29, TM-30, TM-31, TM-32, TM-33, TM-34, TM-35, TM-36, TM-37, TM-38, TM-39, TM-40, TM-41, TM-42, TM-43, TM-44, TM-45, TM-46, TM-47, TM-48, TM-49, TM-50, TM-51, TM-52, and TM-53, and any combination thereof to TMEM106B by an amount the ranges from about 50% to 100%, as compared to binding to TMEM106B in the absence of the anti-TMEM106B antibody. In some embodiments, an anti-TMEM106B antibody of the present disclosure competes with one or more antibodies selected from TM-1, TM-2, TM-3, TM-4, TM-5, TM-6, TM-7, TM-8, TM-9, TM-10, TM-11, TM-12, TM-13, TM-14, TM-15, TM-16, TM-17, TM-18, TM-19, TM-20, TM-21, TM-22, TM-23, TM-24, TM-25, TM-26, TM-27, TM-28, TM-29, TM-30, TM-31, TM-32, TM-33, TM-34, TM-35, TM-36, TM-37, TM-38, TM-39, TM-40, TM-41, TM-42, TM-43, TM-44, TM-45, TM-46, TM-47, TM-48, TM-49, TM-50, TM-51, TM-52, and TM-53, and any combination thereof for binding to TMEM106B when the anti-TMEM106B antibody reduces the binding of one or more antibodies selected from TM-1, TM-2, TM-3, TM-4, TM-5, TM-6, TM-7, TM-8, TM-9, TM-10, TM-11, TM-12, TM-13, TM-14, TM-15, TM-16, TM-17, TM-18, TM-19, TM-20, TM-21, TM-22, TM-23, TM-24, TM-25, TM-26, TM-27, TM-28, TM-29, TM-30, TM-31, TM-32, TM-33, TM-34, TM-35, TM-36, TM-37, TM-38, TM-39, TM-40, TM-41, TM-42, TM-43, TM-44, TM-45, TM-46, TM-47, TM-48, TM-49, TM-50, TM-51, TM-52, and TM-53, and any combination thereof to TMEM106B by at least 50%, at least 55%, by at least 60%, at least 65%, at least 70%, at least 75%, at least 80%, at least 85%, at least 90%, at least 95%, or 100%, as compared to binding to TMEM106B in the absence of the anti-TMEM106B antibody. In some embodiments, an anti-TMEM106B antibody of the present disclosure that reduces the binding of one or more antibodies selected from TM-1, TM-2, TM-3, TM-4, TM-5, TM-6, TM-7, TM-8, TM-9, TM-10, TM-11, TM-12, TM-13, TM-14, TM-15, TM-16, TM-17, TM-18, TM-19, TM-20, TM-21, TM-22, TM-23, TM-24, TM-25, TM-26, TM-27, TM-28, TM-29, TM-30, TM-31, TM-32, TM-33, TM-34, TM-35, TM-36, TM-37, TM-38, TM-39, TM-40, TM-41, TM-42, TM-43, TM-44, TM-45, TM-46, TM-47, TM-48, TM-49, TM-50, TM-51, TM-52, and TM-53, and any combination thereof to TMEM106B by 100% indicates that the anti-TMEM106B antibody essentially completely blocks the binding of one or more antibodies selected from TM-1, TM-2, TM-3, TM-4, TM-5, TM-6, TM-7, TM-8, TM-9, TM-10, TM-11, TM-12, TM-13, TM-14, TM-15, TM-16, TM-17, TM-18, TM-19, TM-20, TM-21, TM-22, TM-23, TM-24, TM-25, TM-26, TM-27, TM-28, TM-29, TM-30, TM-31, TM-32, TM-33, TM-34, TM-35, TM-36, TM-37, TM-38, TM-39, TM-40, TM-41, TM-42, TM-43, TM-44, TM-45, TM-46, TM-47, TM-48, TM-49, TM-50, TM-51, TM-52, and TM-53, and any combination thereof to TMEM106B. In some embodiments, the anti-TMEM106B antibody and the one or more antibodies selected from TM-1, TM-2, TM-3, TM-4, TM-5, TM-6, TM-7, TM-8, TM-9, TM-10, TM-11, TM-12, TM-13, TM-14, TM-15, TM-16, TM-17, TM-18, TM-19, TM-20, TM-21, TM-22, TM-23, TM-24, TM-25, TM-26, TM-27, TM-28, TM-29, TM-30, TM-31, TM-32, TM-33, TM-34, TM-35, TM-36, TM-37, TM-38, TM-39, TM-40, TM-41, TM-42, TM-43, TM-44, TM-45, TM-46, TM-47, TM-48, TM-49, TM-50, TM-51, TM-52, and TM-53, and any combination thereof are present in an amount that corresponds to a 10:1 ratio, 9:1 ratio, 8:1 ratio, 7:1 ratio, 6:1 ratio, 5:1 ratio, 4:1 ratio, 3:1 ratio, 2:1 ratio, 1:1 ratio, 0.75:1 ratio, 0.5:1 ratio, 0.25:1 ratio, 0.1:1 ratio, 0.075:1 ratio, 0.050:1 ratio, 0.025:1 ratio, 0.01:1 ratio, 0.0075: ratio, 0.0050:1 ratio, 0.0025:1 ratio, 0.001: ratio, 0.00075:1 ratio, 0.00050:1 ratio, 0.00025:1 ratio, 0.0001: ratio, 1:10 ratio, 1:9 ratio, 1:8 ratio, 1:7 ratio, 1:6 ratio, 1:5 ratio, 1:4 ratio, 1:3 ratio, 1:2 ratio, 1:0.75 ratio, 1:0.5 ratio, 1:0.25 ratio, 1:0.1 ratio, 1:0.075 ratio, 1:0.050 ratio, 1:0.025 ratio, 1:0.01 ratio, 1:0.0075 ratio, 1:0.0050 ratio, 1:0.0025 ratio, 1:0.001 ratio, 1:0.00075 ratio, 1:0.00050 ratio, 1:0.00025 ratio, or 1:0.0001 ratio of anti-TMEM106B antibody to one or more antibodies selected from TM-1, TM-2, TM-3, TM-4, TM-5, TM-6, TM-7, TM-8, TM-9, TM-10, TM-11, TM-12, TM-13, TM-14, TM-15, TM-16, TM-17, TM-18, TM-19, TM-20, TM-21, TM-22, TM-23, TM-24, TM-25, TM-26, TM-27, TM-28, TM-29, TM-30, TM-31, TM-32, TM-33, TM-34, TM-35, TM-36, TM-37, TM-38, TM-39, TM-40, TM-41, TM-42, TM-43, TM-44, TM-45, TM-46, TM-47, TM-48, TM-49, TM-50, TM-51, TM-52, and TM-53, and any combination thereof. In some embodiments, the anti-TMEM106B antibody is present in excess by an amount that ranges from about 1.5-fold to 100-fold, or greater than 100-fold compared to the amount of the one or more antibodies selected from TM-1, TM-2, TM-3, TM-4, TM-5, TM-6, TM-7, TM-8, TM-9, TM-10, TM-11, TM-12, TM-13, TM-14, TM-15, TM-16, TM-17, TM-18, TM-19, TM-20, TM-21, TM-22, TM-23, TM-24, TM-25, TM-26, TM-27, TM-28, TM-29, TM-30, TM-31, TM-32, TM-33, TM-34, TM-35, TM-36, TM-37, TM-38, TM-39, TM-40, TM-41, TM-42, TM-43, TM-44, TM-45, TM-46, TM-47, TM-48, TM-49, TM-50, TM-51, TM-52, and TM-53, and any combination thereof. In some embodiments, the anti-TMEM106B antibody is present in an amount that is about a 2-fold, 3-fold, 4-fold, 5-fold, 6-fold, 7-fold, 8-fold, 9-fold, 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, or 100-fold excess compared to the amount of the one or more antibodies selected from TM-1, TM-2, TM-3, TM-4, TM-5, TM-6, TM-7, TM-8, TM-9, TM-10, TM-11, TM-12, TM-13, TM-14, TM-15, TM-16, TM-17, TM-18, TM-19, TM-20, TM-21, TM-22, TM-23, TM-24, TM-25, TM-26, TM-27, TM-28, TM-29, TM-30, TM-31, TM-32, TM-33, TM-34, TM-35, TM-36, TM-37, TM-38, TM-39, TM-40, TM-41, TM-42, TM-43, TM-44, TM-45, TM-46, TM-47, TM-48, TM-49, TM-50, TM-51, TM-52, and TM-53, and any combination thereof.

In some embodiments, an anti-TMEM106B antibody of the present disclosure binds to an epitope of human TMEM106B that is the same as or overlaps with the TMEM106B epitope bound by at least one antibody selected from TM-1, TM-2, TM-3, TM-4, TM-5, TM-6, TM-7, TM-8, TM-9, TM-10, TM-11, TM-12, TM-13, TM-14, TM-15, TM-16, TM-17, TM-18, TM-19, TM-20, TM-21, TM-22, TM-23, TM-24, TM-25, TM-26, TM-27, TM-28, TM-29, TM-30, TM-31, TM-32, TM-33, TM-34, TM-35, TM-36, TM-37, TM-38, TM-39, TM-40, TM-41, TM-42, TM-43, TM-44, TM-45, TM-46, TM-47, TM-48, TM-49, TM-50, TM-51, TM-52, and TM-53. In some embodiments, an anti-TMEM106B antibody of the present disclosure binds essentially the same TMEM106B epitope bound by at least one antibody selected from TM-1, TM-2, TM-3, TM-4, TM-5, TM-6, TM-7, TM-8, TM-9, TM-10, TM-11, TM-12, TM-13, TM-14, TM-15, TM-16, TM-17, TM-18, TM-19, TM-20, TM-21, TM-22, TM-23, TM-24, TM-25, TM-26, TM-27, TM-28, TM-29, TM-30, TM-31, TM-32, TM-33, TM-34, TM-35, TM-36, TM-37, TM-38, TM-39, TM-40, TM-41, TM-42, TM-43, TM-44, TM-45, TM-46, TM-47, TM-48, TM-49, TM-50, TM-51, TM-52, and TM-53. Detailed exemplary methods for mapping an epitope to which an antibody binds are provided in Morris (1996) "Epitope Mapping Protocols," in Methods in Molecular Biology vol. 66 (Humana Press, Totowa, NJ).

In some embodiments, an anti-TMEM106B antibody of the present disclosure competes with one or more antibodies selected from TM-1, TM-17, TM-22, TM-23, TM-26, and TM-27, and any combination thereof, for binding to TMEM106B. In some embodiments, an anti-TMEM106B antibody of the present disclosure competes with one or more antibodies selected from TM-2, TM-3, TM-5, TM-7, TM-9, TM-10, TM-11, TM-12, TM-13, TM-18, TM-19, TM-21, TM-25, TM-28, TM-29, TM-32, TM-35, TM-37, TM-39, TM-42, TM-45, TM-48, and TM-53, and any combination thereof for binding to TMEM106B. In some embodiments, an anti-TMEM106B antibody of the present disclosure competes with one or more antibodies selected from TM-4, TM-6, TM-8, TM-14, TM-15, TM-16, TM-20, TM-31, TM-33, TM-34, TM-36, TM-41, TM-44, TM-46, TM-47, TM-49, TM-50, TM-51, TM-52, and any combination thereof for binding to TMEM106B. In some embodiments, an anti-TMEM106B antibody of the present disclosure competes with one or more antibodies selected from TM-1, TM-2, TM-3, TM-7, TM-12, TM-13, TM-23, TM-24, TM-29, TM-30, TM-51, and any combination thereof, for binding to TMEM106B.

In some embodiments, an anti-TMEM106B antibody of the present disclosure competitively inhibits binding of at least one antibody selected from TM-1, TM-17, TM-22, TM-23, TM-26, and TM-27, and any combination thereof, for binding to TMEM106B. In some embodiments, an anti-TMEM106B antibody of the present disclosure competitively inhibits binding of at least one antibody selected from TM-2, TM-3, TM-5, TM-7, TM-9, TM-10, TM-11, TM-12, TM-13, TM-18, TM-19, TM-21, TM-25, TM-28, TM-29, TM-32, TM-35, TM-37, TM-39, TM-42, TM-45, TM-48, and TM-53, and any combination thereof, for binding to TMEM106B. In some embodiments, an anti-TMEM106B antibody of the present disclosure competitively inhibits binding of at least one antibody selected from TM-4, TM-6, TM-8, TM-14, TM-15, TM-16, TM-20, TM-31, TM-33, TM-34, TM-36, TM-41, TM-44, TM-46, TM-47, TM-49, TM-50, TM-51, TM-52, and any combination thereof, for binding to TMEM106B. In some embodiments, an anti-TMEM106B antibody of the present disclosure competitively inhibits binding of at least one antibody selected from TM-1, TM-2, TM-3, TM-7, TM-12, TM-13, TM-23, TM-24, TM-29, TM-30, TM-51, and any combination thereof, for binding to TMEM106B.

In some embodiments, an anti-TMEM106B antibody of the present disclosure has the same or overlapping epitope on TMEM106B as at least one antibody selected from TM-1, TM-17, TM-22, TM-23, TM-26, and TM-27, and any combination thereof, for binding to TMEM106B. In some embodiments, an anti-TMEM106B antibody of the present disclosure has the same or overlapping epitope on TMEM106B as at least one antibody selected from TM-2, TM-3, TM-5, TM-7, TM-9, TM-10, TM-11, TM-12, TM-13, TM-18, TM-19, TM-21, TM-25, TM-28, TM-29, TM-32, TM-35, TM-37, TM-39, TM-42, TM-45, TM-48, and TM-53, and any combination thereof, for binding to TMEM106B. In some embodiments, an anti-TMEM106B antibody of the present disclosure has the same or overlapping epitope on TMEM106B as at least one antibody selected from TM-4, TM-6, TM-8, TM-14, TM-15, TM-16, TM-20, TM-31, TM-33, TM-34, TM-36, TM-41, TM-44, TM-46, TM-47, TM-49, TM-50, TM-51, TM-52, and any combination thereof, for binding to TMEM106B. In some embodiments, an anti-TMEM106B antibody of the present disclosure has the same or overlapping epitope on TMEM106B as at least one antibody selected from TM-1, TM-2, TM-3, TM-7, TM-12, TM-13, TM-23, TM-24, TM-29, TM-30, TM-51, and any combination thereof, for binding to TMEM106B.

Any suitable competition assay or TMEM106B binding assay known in the art, such as BIAcore analysis, ELISA assays, or flow cytometry, may be utilized to determine whether an anti-TMEM106B antibody competes with (or competitively inhibits the binding of) one or more antibodies selected from TM-1, TM-2, TM-3, TM-4, TM-5, TM-6, TM-7, TM-8, TM-9, TM-10, TM-11, TM-12, TM-13, TM-14, TM-15, TM-16, TM-17, TM-18, TM-19, TM-20, TM-21, TM-22, TM-23, TM-24, TM-25, TM-26, TM-27, TM-28, TM-29, TM-30, TM-31, TM-32, TM-33, TM-34, TM-35, TM-36, TM-37, TM-38, TM-39, TM-40, TM-41, TM-42, TM-43, TM-44, TM-45, TM-46, TM-47, TM-48, TM-49, TM-50, TM-51, TM-52, and TM-53, and any combination thereof for binding to TMEM106B. In an exemplary competition assay, immobilized TMEM106B or cells expressing TMEM106B on the cell surface are incubated in a solution comprising a first labeled antibody that binds to TMEM106B (e.g., human or non-human primate) and a second unlabeled antibody that is being tested for its ability to compete with the first antibody for binding to TMEM106B. The second antibody may be present in a hybridoma supernatant. As a control, immobilized TMEM106B or cells expressing TMEM106B is incubated in a solution comprising the first labeled antibody but not the second unlabeled antibody. After incubation under conditions permissive for binding of the first antibody to TMEM106B, excess unbound antibody is removed, and the amount of label associated with immobilized TMEM106B or cells expressing TMEM106B is measured. If the amount of label associated with immobilized TMEM106B or cells expressing TMEM106B is substantially reduced in the test sample relative to the control sample, then that indicates that the second antibody is competing with the first antibody for binding to TMEM106B. See, Harlow and Lane (1988)

*Antibodies: A Laboratory Manual* ch. 14 (Cold Spring Harbor Laboratory, Cold Spring Harbor, NY).

Further provided herein are anti-TMEM106B antibodies which competitively inhibit binding of and/or compete for binding with an anti-TMEM106B antibody comprising (a) a $V_H$ domain comprising (i) HVR-H1 comprising an amino acid sequence selected from the group consisting of SEQ ID NO: 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, and 35, (ii) HVR-H2 comprising an amino acid sequence selected from the group consisting of SEQ ID NO: 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, and 78, and (iii) HVR-H3 comprising an amino acid sequence selected from the group consisting of SEQ ID NO: 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, and 120, and (b) a $V_L$ domain comprising (i) HVR-L1 comprising an amino acid sequence selected from the group consisting of SEQ ID NO: 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, and 160, (ii) HVR-L2 comprising an amino acid sequence selected from the group consisting of SEQ ID NO: 161, 162, 163, 164, 165, 166, 167, 168, 169, 170, 171, 172, 173, 174, 175, 176, 177, 178, 179, 180, 181, 182, 183, 184, and 185, and (iii) HVR-L3 comprising an amino acid sequence selected from the group consisting of SEQ ID NO: 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, and 224 . . . . In some embodiments, the antibody comprises the $V_H$ and $V_L$ sequences in SEQ ID NOs: 225-268 and SEQ ID NOs: 269-314, respectively.

Provided herein are anti-TMEM106B antibodies which bind to an epitope of human TMEM106B that is the same as or overlaps with the epitope bound by an anti-TMEM106B antibody comprising (a) a $V_H$ domain comprising (i) HVR-H1 comprising an amino acid sequence selected from the group consisting of SEQ ID NO: 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, and 35, (ii) HVR-H2 comprising an amino acid sequence selected from the group consisting of SEQ ID NO: 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, and 78, and (iii) HVR-H3 comprising an amino acid sequence selected from the group consisting of SEQ ID NO: 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, and 120, and (b) a $V_L$ domain comprising (i) HVR-L1 comprising an amino acid sequence selected from the group consisting of SEQ ID NO: 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, and 160, (ii) HVR-L2 comprising an amino acid sequence selected from the group consisting of SEQ ID NO: 161, 162, 163, 164, 165, 166, 167, 168, 169, 170, 171, 172, 173, 174, 175, 176, 177, 178, 179, 180, 181, 182, 183, 184, and 185, and (iii) HVR-L3 comprising an amino acid sequence selected from the group consisting of SEQ ID NO: 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, and 224. In some embodiments, the antibody comprises the $V_H$ and $V_L$ sequences in SEQ ID NOs: 225-268 and SEQ ID NOs: 269-314, respectively. In some embodiments, the epitope of human TMEM106B is the same epitope as bound by an anti-TMEM106B antibody.

Anti-TMEM106B antibodies of the present disclosure may bind to various regions of TMEM106B, including various regions of human TMEM106B. Such regions of TMEM106B include the cytoplasmic domain of TMEM106B or the lumenal domain TMEM106B.

In some embodiments, an anti-TMEM106B antibody of the present disclosure binds to one or more regions or domains of TMEM106B. In some embodiments, an anti-TMEM106B antibody of the present disclosure binds to one or more regions or domains of human TMEM106B.

In some embodiments, an anti-TMEM106B antibody of the present disclosure binds to the cytoplasmic and/or lumenal domain of TMEM106B. In some embodiments, an anti-TMEM106B antibody of the present disclosure binds to one or more amino acids within amino acid residues 59-73, 80-90, 15-24, 33-40, 5-19, 30-40, 34-40, 59-69, 52-62, 64-74, 151-165, 185-195, 139-149, 248-258, 156-161, 202-207, 219-233, 126-140, 185-195, 260-274, 202-212, 151-161, 223-233, 143-153, 223-228, 133-145, and/or 198-212 of human TMEM106B (SEQ ID NO:1).

In some embodiments, an anti-TMEM106B antibody of the present disclosure binds to one or more amino acids within amino acid residues 151-165 and/or 185-195 of human TMEM106B. In some embodiments, an anti-TMEM106B antibody of the present disclosure binds to one or more amino acids within amino acid residues 151-165 (NITNNNYYSVEVENI; SEQ ID NO:324). In some embodiments, an anti-TMEM106B antibody of the present disclosure binds to one or more amino acids within amino acid residues T>S is risk allele 185-195 (TIIGPLDMKQI; SEQ ID NO:325) of human TMEM106B. In some embodiments, an anti-TMEM106B antibody of the present disclosure binds to a discontinuous epitope formed by one or more amino acids within amino acid residues 151-165 (NITNN-NYYSVEVENI; SEQ ID NO:324) and to one or more amino acids within amino acid residues 185-195 (TIIG-PLDMKQI; SEQ ID NO:325) of human TMEM106B.

In some embodiments, an anti-TMEM106B antibody of the present disclosure binds to one or more amino acids within amino acid residues 59-73, 80-90 cytoplasmic, 139-149, and/or 248-258 of human TMEM106B. In some embodiments, an anti-TMEM106B antibody of the present disclosure binds to one or more amino acids within amino acid residues 59-73 (VTCPTCQGTGRIPRG; SEQ ID NO: 326) of human TMEM106B. In some embodiments, an anti-TMEM106B antibody of the present disclosure binds to one or more amino acids within amino acid residues 80-90 (ALIPYSDQRLR; SEQ ID NO: 327) of human TMEM106B. In some embodiments, an anti-TMEM106B antibody of the present disclosure binds to one or more amino acids within amino acid residues 139-149 (KRTIYLNITNT; SEQ ID NO: 328) of human TMEM106B. In some embodiments, an anti-TMEM106B antibody of the present disclosure binds to one or more amino acids within amino acid residues 248-258 (YQYVDCGRNTT: 329) of human TMEM106B. In some embodiments, an anti-TMEM106B antibody of the present disclosure binds to one or more amino acids within amino acid residues 59-73 (VTCPTCQGTGRIPRG; SEQ ID NO: 326), to one or more amino acids within amino acid residues 80-90 (ALIPYSDQRLR; SEQ ID NO: 327), to one or more amino acids within amino acid residues 139-149 (KRTIYLNITNT; SEQ ID NO: 328), and to one or more amino acids within amino acid residues 248-258 (YQYVDCGRNTT: 329) of human TMEM106B.

In some embodiments, an anti-TMEM106B antibody of the present disclosure binds to one or more amino acids within amino acid residues 15-24 and/or 33-40 of human TMEM106B. In some embodiments, an anti-TMEM106B antibody of the present disclosure binds to one or more amino acids within amino acid residues 15-24 (EDAYDGVTSE; SEQ ID NO:330) of human TMEM106B. In some embodiments, an anti-TMEM106B antibody of the present disclosure binds to one or more amino acids within amino acid residues 33-40 (SEVHNEDG; SEQ ID NO:331) of human TMEM106B. In some embodiments, an anti-TMEM106B antibody of the present disclosure binds to one or more amino acids within amino acid residues 15-24 (EDAYDGVTSE; SEQ ID NO:330) and to one or more amino acids within amino acid residues 33-40 (SEVHNEDG; SEQ ID NO:331) of human TMEM106B.

In some embodiments, an anti-TMEM106B antibody of the present disclosure binds to one or more amino acids within amino acid residues 5-19, 30-40, 156-161, 202-207, and/or 219-233 of human TMEM106B. In some embodiments, an anti-TMEM106B antibody of the present disclosure binds to one or more amino acids within amino acid residues 5-19 (LSHLPLHSSKEDAYD; SEQ ID NO:332) of human TMEM106B. In some embodiments, an anti-TMEM106B antibody of the present disclosure binds to one or more amino acids within amino acid residues 30-40 (SEVHNEDG; SEQ ID NO:333) of human TMEM106B. In some embodiments, an anti-TMEM106B antibody of the present disclosure binds to one or more amino acids within amino acid residues 156-161 (NYYSVE; SEQ ID NO:334) of human TMEM106B. In some embodiments, an anti-TMEM106B antibody of the present disclosure binds to one or more amino acids within amino acid residues 202-207 (VIAEEM; SEQ ID NO:335) of human TMEM106B. In some embodiments, an anti-TMEM106B antibody of the present disclosure binds to one or more amino acids within amino acid residues 219-233 (IKVHNIVLMMQVTVT; SEQ ID NO: 336) of human TMEM106B. In some embodiments, an anti-TMEM106B antibody of the present disclosure binds to one or more amino acids within amino acid residues 5-19 (LSHLPLHSSKEDAYD; SEQ ID NO:332), 30-40 (SEVHNEDG; SEQ ID NO:333), 156-161 (NYYSVE; SEQ ID NO:334), 202-207 (VIAEEM; SEQ ID NO:335), and 219-233 (IKVHNIVLMMQVTVT; SEQ ID NO:336) of human TMEM106B.

In some embodiments, an anti-TMEM106B antibody of the present disclosure binds to one or more amino acids within amino acid residues 126-140, 185-195, and/or 260-274 of human TMEM106B. In some embodiments, an anti-TMEM106B antibody of the present disclosure binds to one or more amino acids within amino acid residues 126-140 (IGVKSAYVSYDVQKR; SEQ ID NO:337) of human TMEM106B. In some embodiments, an anti-TMEM106B antibody of the present disclosure binds to one or more amino acids within amino acid residues T185S risk allele 185-195 (TIIGPLDMKQI; SEQ ID NO: 325) of human TMEM106B. In some embodiments, an anti-TMEM106B antibody of the present disclosure binds to one or more amino acids within amino acid residues 260-274 (QLGQSEYLNVLQPQQ; SEQ ID NO:338) of human TMEM106B. In some embodiments, an anti-TMEM106B antibody of the present disclosure binds to one or more amino acids within amino acid residues 126-140 (IGVKSAYVSYDVQKR; SEQ ID NO:337), 185-195 (TIIGPLDMKQI; SEQ ID NO: 325), and 260-274 (QLGQSEYLNVLQPQQ; SEQ ID NO:338) of human TMEM106B.

In some embodiments, an anti-TMEM106B antibody of the present disclosure binds to one or more amino acids within amino acid residues 34-40 and/or 202-212 of human TMEM106B. In some embodiments, an anti-TMEM106B antibody of the present disclosure binds to one or more amino acids within amino acid residues sticky 34-40 (EVHNEDG; SEQ ID NO:339) of human TMEM106B. In some embodiments, an anti-TMEM106B antibody of the present disclosure binds to one or more amino acids within amino acid residues 202-212 (VIAEEMSYMYD; SEQ ID NO:340) of human TMEM106B. In some embodiments, an anti-TMEM106B antibody of the present disclosure binds to one or more amino acids within amino acid residues 34-40 (EVHNEDG; SEQ ID NO:339) and 202-212 (VIAEEMSYMYD; SEQ ID NO:340 of human TMEM106B.

In some embodiments, an anti-TMEM106B antibody of the present disclosure binds to one or more amino acids within amino acid residues 151-161 and/or 223-233 of human TMEM106B. In some embodiments, an anti-TMEM106B antibody of the present disclosure binds to one or more amino acids within amino acid residues 151-161 (NITNNNYYSVE; SEQ ID NO:341) of human TMEM106B. In some embodiments, an anti-TMEM106B antibody of the present disclosure binds to one or more amino acids within amino acid residues 223-233 (NIVLMMQVTV; SEQ ID NO:342) of human TMEM106B. In some embodiments, an anti-TMEM106B antibody of the present disclosure binds to one or more amino acids within amino acid residues 151-161 (NITNNNYYSVE; SEQ ID NO:341) and 223-233 (NIVLMMQVTV; SEQ ID NO:342) of human TMEM106B.

In some embodiments, an anti-TMEM106B antibody of the present disclosure binds to one or more amino acids within amino acid residues 59-69, 143-153, and/or 223-228 of human TMEM106B. In some embodiments, an anti-TMEM106B antibody of the present disclosure binds to one or more amino acids within amino acid residues 59-69 (VTCPTCQGTGR; SEQ ID NO:343) of human TMEM106B. In some embodiments, an anti-TMEM106B antibody of the present disclosure binds to one or more amino acids within amino acid residues 143-153 (YLNITNTLNIT; SEQ ID NO:344) of human TMEM106B. In some embodiments, an anti-TMEM106B antibody of the present disclosure binds to one or more amino acids within amino acid residues 223-228 (NIVLMM; SEQ ID NO:345) of human TMEM106B. In some embodiments, an anti-TMEM106B antibody of the present disclosure binds to one or more amino acids within amino acid residues 59-69 (VTCPTCQGTGR; SEQ ID NO:343), 143-153 (YLNITNTLNIT; SEQ ID NO: 344), and 223-228 (NIVLMM; SEQ ID NO:345) of human TMEM106B.

In some embodiments, an anti-TMEM106B antibody of the present disclosure binds to one or more amino acids within amino acid residues 133-145 and/or 198-212 of human TMEM106B. In some embodiments, an anti-TMEM106B antibody of the present disclosure binds to one or more amino acids within amino acid residues 133-145 (VSYDVQKRTIYLN; SEQ ID NO:346) of human TMEM106B. In some embodiments, an anti-TMEM106B antibody of the present disclosure binds to one or more amino acids within amino acid residues 198-212 (TVPTVIAEEMSYMYD; SEQ ID NO:347) of human TMEM106B. In some embodiments, an anti-TMEM106B antibody of the present disclosure binds to one or more amino acids within amino acid residues 133-145 (VSYDVQKRTIYLN; SEQ ID NO:346) and 198-212 (TVPTVIAEEMSYMYD; SEQ ID NO:347) of human TMEM106B.

In some embodiments, an anti-TMEM106B antibody of the present disclosure binds to one or more amino acids within amino acid residues 52-62, 64-75, and/or 223-228 of human TMEM106B. In some embodiments, an anti-TMEM106B antibody of the present disclosure binds to one or more amino acids within amino acid residues 52-62 (EFTGRDSVTCP; SEQ ID NO:348) of human TMEM106B. In some embodiments, an anti-TMEM106B antibody of the present disclosure binds to one or more amino acids within amino acid residues 64-75 (CQGTGRIPRGQE; SEQ ID NO:349) of human TMEM106B. In some embodiments, an anti-TMEM106B antibody of the present disclosure binds to one or more amino acids within amino acid residues 223-228 (NIVLMM; SEQ ID NO:345) of human TMEM106B. In some embodiments, an anti-TMEM106B antibody of the present disclosure binds to one or more amino acids within amino acid residues 52-62 (EFTGRDSVTCP; SEQ ID NO:348), 64-75 (CQGTGRIPRGQE; SEQ ID NO: 349), and 223-228 (NIVLMM; SEQ ID NO:345) of human TMEM106B.

In some embodiments, an anti-TMEM106B antibody of the present disclosure binds to one or more epitopes within human TMEM106B selected from the group consisting of amino acid residues NITNNNYYSVEVENI (SEQ ID NO:324), TIIGPLDMKQI (SEQ ID NO:325), VTCPTCQGTGRIPRG (SEQ ID NO:326), ALIPYSDQRLR (SEQ ID NO:327), KRTIYLNITNT (SEQ ID NO:328), YQYVDCGRNTT (SEQ ID NO:329), EDAYDGVTSE (SEQ ID NO:330), SEVHNEDG (SEQ ID NO: 331), LSHLPLHSSKEDAYD (SEQ ID NO:332), LVNSEVHNEDG (SEQ ID NO:333), NYYSVE (SEQ ID NO:334), VIAEEM (SEQ ID NO:335), IKVHNIVLMMQVTVT (SEQ ID NO:336), IGVKSAYVSYDVQKR (SEQ ID NO:337), QLGQSEYLNVLQPQQ (SEQ ID NO:338), EVHNEDG (SEQ ID NO:339), VIAEEMSYMYD (SEQ ID NO:340), NITNNNYYSVE (SEQ ID NO:341), NIVLMMQVTVT (SEQ ID NO:342), VTCPTCQGTGR (SEQ ID NO:343), YLNITNTLNIT (SEQ ID NO: 344), NIVLMM (SEQ ID NO:345), VSYDVQKRTIYLN (SEQ ID NO:346), TVPTVIAEEMSYMYD (SEQ ID NO:347), EFTGRDSVTCP (SEQ ID NO:348), and CQGTGRIPRGQE (SEQ ID NO:349) of human TMEM106B.

In some embodiments, the anti-TMEM106B antibody according to any of the above embodiments is a monoclonal antibody, including a humanized and/or human antibody. In some embodiments, the anti-TMEM106B antibody is an antibody fragment, e.g., a Fv, Fab, Fab', scFv, diabody, or F(ab')2 fragment. In some embodiments, the anti-TMEM106B antibody is a substantially full-length antibody, e.g., an IgG1 antibody, IgG2a antibody or other antibody class or isotype as defined herein.

In some embodiments, an anti-TMEM106B antibody according to any of the above embodiments may incorporate any of the features, singly or in combination, as described in Sections 1-7 below:

(1) Anti-TMEM106B Antibody Binding Affinity

In some embodiments of any of the antibodies provided herein, the antibody has a dissociation constant (Kd) of <1 µM, <100 nM, <10 nM, <1 nM, <0.1 nM, <0.01 nM, or <0.001 nM (e.g., $10^{-8}$ M or less, e.g., from $10^{-8}$ M to $10^{-13}$ M, e.g., from $10^{-9}$ M to $10^{-13}$ M). Dissociation constants may be determined through any analytical technique, including any biochemical or biophysical technique such as ELISA, surface plasmon resonance (SPR), bio-layer interferometry (see, e.g., Octet System by ForteBio), isothermal titration calorimetry (ITC), differential scanning calorimetry (DSC), circular dichroism (CD), stopped-flow analysis, and colorimetric or fluorescent protein melting analyses. In one embodiment, Kd is measured by a radiolabeled antigen binding assay (RIA). In some embodiment, an RIA is performed with the Fab version of an antibody of interest and its antigen, for example as described in Chen et al. *J. Mol. Biol.* 293:865-881 (1999)). In some embodiments, Kd is measured using a BIACORE surface plasmon resonance assay, for example, an assay using a BIACORE-2000 or a BIACORE-3000 (BIAcore, Inc., Piscataway, NJ) is performed at 25° C. with immobilized antigen CM5 chips at ~10 response units (RU). In some embodiments, the $K_D$ is determined using a monovalent antibody (e.g., a Fab) or a full-length antibody. In some embodiments, the $K_D$ is determined using a full-length antibody in a monovalent form.

In some embodiments, an anti-TMEM106B antibody of the present disclosure may have nanomolar or even picomolar affinities for TMEM106B. In some embodiments, the dissociation constant (Kd) of the antibody is about 0.1 nM to about 500 nM. For example, the Kd of the antibody is any of about 500 nM, about 400 nM, about 300 nM, about 200 nM, about 100 nM, about 75 nM, about 50 nM, about 25 nM, about 10 nM, about 9 nM, about 8 nM, about 7 nM, about 6 nM, about 5 nM, about 4 nM, about 3 nM, about 2 nM, about 1 nM, or about 1 nM to about 0.1 nM for binding to human TMEM106B.

(2) Antibody Fragments

In some embodiments of any of the antibodies provided herein, the antibody antibodies is an antibody fragment. Antibody fragments include, but are not limited to, Fab, Fab', Fab'-SH, F(ab')2, Fv, and scFv fragments, and other fragments described below. For a review of certain antibody fragments, see Hudson et al. *Nat. Med.* 9:129-134 (2003). For a review of scFv fragments, see, e.g., WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP404097; WO 1993/01161; Hudson et al. *Nat. Med.* 9:129-134 (2003). Triabodies and tetrabodies are also described in Hudson et al. *Nat. Med.* 9:129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (see, e.g., U.S. Pat. No. 6,248,516).

Antibody fragments can be made by various techniques, including but not limited to proteolytic digestion of an intact antibody as well as production by recombinant host cells (e.g., *E. coli* or phage), as described herein.

(3) Chimeric and Humanized Antibodies

In some embodiments of any of the antibodies provided herein, the antibody is a chimeric antibody. Certain chimeric antibodies are described, e.g., in U.S. Pat. No. 4,816,567. In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In some embodiments of any of the antibodies provided herein, the antibody is a humanized antibody. Typically, a non-human antibody is humanized to reduce immunogenicity to humans, while retaining the specificity and affinity of the parental non-human antibody. In certain embodiments, a humanized antibody is substantially non-immunogenic in humans. In certain embodiments, a humanized antibody has substantially the same affinity for a target as an antibody from another species from which the humanized antibody is derived. See, e.g., U.S. Pat. Nos. 5,530,101, 5,693,761; 5,693,762; and 5,585,089. In certain embodiments, amino acids of an antibody variable domain that can be modified without diminishing the native affinity of the antigen binding domain while reducing its immunogenicity are identified. See, e.g., U.S. Pat. Nos. 5,766,886 and 5,869,619. Generally, a humanized antibody comprises one or more variable domains in which HVRs (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), for example, to restore or improve antibody specificity or affinity.

Humanized antibodies and methods of making them are reviewed, for example, in Almagro et al. *Front. Biosci.* 13:161 9-1633 (2008), and are further described, e.g., in U.S. Pat. Nos. 5,821,337, 7,527,791, 6,982,321, and 7,087, 409. Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA* 89:4285 (1992); and Presta et al., *J. Immunol.* 151:2623 (1993)); human mature (somatically mutated) framework regions or human germline framework regions (see, e.g., Almagro and Fransson *Front. Biosci.* 13:1619-1633 (2008)); and framework regions derived from screening FR libraries (see, e.g., Baca et al. *J. Biol. Chem.* 272:10678-10684 (1997) and Rosok et al. *J. Biol. Chem.* 271:22611-22618 (1996)).

(4) Human Antibodies

In some embodiments of any of the antibodies provided herein, the antibody is a human antibody. Human antibodies can be produced using various techniques known in the art. Human antibodies are described generally in van Dijk et al. *Curr. Opin. Pharmacol.* 5:368-74 (2001) and Lonberg *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. One can engineer mouse strains deficient in mouse antibody production with large fragments of the human Ig loci in anticipation that such mice would produce human antibodies in the absence of mouse antibodies. Large human Ig fragments can preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains can yield high affinity fully human antibodies against any antigen of interest, including human antigens. Using the hybridoma technology, antigen-specific human monoclonal antibodies with the desired specificity can be produced and selected. Certain exemplary methods are described in U.S. Pat. No. 5,545,807, EP 546073, and EP 546073. See also, for example, U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCI-MOUSE® technology. Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.* 133:3001 (1984) and Boerner et al. *J. Immunol.* 147:86 (1991)). Human antibodies generated via human B-cell hybridoma technology are also described in Li et al. *Proc. Natl. Acad. Sci. USA,* 1 03:3557-3562 (2006). Additional methods include those described, for example, in U.S. Pat. No. 7,189,826 (describing production of monoclonal human IgM antibodies from hybridoma cell lines). Human hybridoma technology (Trioma technology) is also described in Vollmers et al. *Histology and Histopathology* 20 (3): 927-937 (2005) and Vollmers et al. *Methods and Findings in Experimental and Clinical Pharmacology* 27 (3): 185-91 (2005). Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

In some embodiments of any of the antibodies provided herein, the antibody is a human antibody isolated by in vitro methods and/or screening combinatorial libraries for antibodies with the desired activity or activities. Suitable examples include but are not limited to phage display (CAT, Morphosys, Dyax, Biosite/Medarex, Xoma, Symphogen, Alexion (formerly Proliferon), Affimed) ribosome display (CAT), yeast display (Adimab), and the like. In certain phage display methods, repertoires of VH and VL genes are separately cloned by polymerase chain reaction (PCR) and recombined randomly in phage libraries, which can then be screened for antigen-binding phage as described in Winter et al. *Ann. Rev. Immunol.* 12:433-455 (1994). For example, a variety of methods are known in the art for generating phage display libraries and screening such libraries for antibodies possessing the desired binding characteristics. See also Sidhu et al. *J. Mol. Biol.* 338 (2): 299-310, 2004; Lee et al. *J. Mol. Biol.* 340 (5): 1073-1093, 2004; Fellouse *Proc. Natl. Acad. Sci. USA* 101 (34): 12467-12472 (2004); and Lee et al. *J. Immunol. Methods* 284 (–2): 1 19-132 (2004). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths et al.

EMBO J. 12:725-734 (1993). Finally, naive libraries can also be made synthetically by cloning unrearranged V-gene segments from stem cells, and using PCR primers comprising random sequence to encode the highly variable HVR3 regions and to accomplish rearrangement in vitro, as described by Hoogenboom et al. *J. Mol. Biol.*, 227:381-388, 1992. Patent publications describing human antibody phage libraries include, for example: U.S. Pat. No. 5,750,373, and US Patent Publication Nos. 2007/0292936 and 2009/0002360. Antibodies isolated from human antibody libraries are considered human antibodies or human antibody fragments herein.

(5) Constant Regions Including Fc Regions

In some embodiments of any of the antibodies provided herein, the antibody comprises an Fc. In some embodiments, the Fc is a human IgG1, IgG2, IgG3, and/or IgG4 isotype. In some embodiments, the antibody is of the IgG class, the IgM class, or the IgA class.

In certain embodiments of any of the antibodies provided herein, the antibody has an IgG2 isotype. In some embodiments, the antibody contains a human IgG2 constant region. In some embodiments, the human IgG2 constant region includes an Fc region. In some embodiments, the antibody induces the one or more TMEM106B activities or independently of binding to an Fc receptor. In some embodiments, the antibody binds an inhibitory Fc receptor. In certain embodiments, the inhibitory Fc receptor is inhibitory Fc-gamma receptor IIB (FcγIIB).

In certain embodiments of any of the antibodies provided herein, the antibody has an IgG1 isotype. In some embodiments, the antibody contains a mouse IgG1 constant region. In some embodiments, the antibody contains a human IgG1 constant region. In some embodiments, the human IgG1 constant region includes an Fc region. In some embodiments, the antibody binds an inhibitory Fc receptor. In certain embodiments, the inhibitory Fc receptor is inhibitory Fc-gamma receptor IIB (FcγIIB).

In certain embodiments of any of the antibodies provided herein, the antibody has an IgG4 isotype. In some embodiments, the antibody contains a human IgG4 constant region. In some embodiments, the human IgG4 constant region includes an Fc region. In some embodiments, the antibody binds an inhibitory Fc receptor. In certain embodiments, the inhibitory Fc receptor is inhibitory Fc-gamma receptor IIB (FcγIIB).

In certain embodiments of any of the antibodies provided herein, the antibody has a hybrid IgG2/4 isotype. In some embodiments, the antibody includes an amino acid sequence comprising amino acids 118 to 260 according to EU numbering of human IgG2 and amino acids 261-447 according to EU numbering of human IgG4 (WO 1997/11971; WO 2007/106585).

In some embodiments, the Fc region increases clustering without activating complement as compared to a corresponding antibody comprising an Fc region that does not comprise the amino acid substitutions. In some embodiments, the antibody induces one or more activities of a target specifically bound by the antibody. In some embodiments, the antibody binds to TMEM106B.

It may also be desirable to modify an anti-TMEM106B antibody of the present disclosure to modify effector function and/or to increase serum half-life of the antibody. For example, the Fc receptor binding site on the constant region may be modified or mutated to remove or reduce binding affinity to certain Fc receptors, such as FcγRI, FcγRII, and/or FcγRIII to reduce Antibody-dependent cell-mediated cytotoxicity. In some embodiments, the effector function is impaired by removing N-glycosylation of the Fc region (e.g., in the CH2 domain of IgG) of the antibody. In some embodiments, the effector function is impaired by modifying regions such as 233-236, 297, and/or 327-331 of human IgG as described in WO 99/58572 and Armour et al. *Molecular Immunology* 40:585-593 (2003); Reddy et al. *J. Immunology* 164:1925-1933 (2000). In other embodiments, it may also be desirable to modify an anti-TMEM106B antibody of the present disclosure to modify effector function to increase finding selectivity toward the ITIM-containing FcgRIIb (CD32b) to increase clustering of TMEM106B antibodies on adjacent cells without activating humoral responses including Antibody-dependent cell-mediated cytotoxicity and antibody-dependent cellular phagocytosis.

To increase the serum half-life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule. Other amino acid sequence modifications.

(6) Multispecific Antibodies

Multispecific antibodies are antibodies that have binding specificities for at least two different epitopes, including those on the same or another polypeptide (e.g., one or more TMEM106B polypeptides of the present disclosure). In some embodiments, the multispecific antibody can be a bispecific antibody. In some embodiments, the multispecific antibody can be a trispecific antibody. In some embodiments, the multispecific antibody can be a tetraspecific antibody. Such antibodies can be derived from full-length antibodies or antibody fragments (e.g., F(ab')$_2$ bispecific antibodies). In some embodiments, the multispecific antibody comprises a first antigen binding region which binds to first site on TMEM106B and comprises a second antigen binding region which binds to a second site on TMEM106B. In some embodiment, the multispecific antibodies comprises a first antigen binding region which binds to TMEM106B and a second antigen binding region that binds to a second polypeptide.

Provided herein are multispecific antibodies comprises a first antigen binding region, wherein the first antigen binding region comprises the six HVRs of an antibody described herein, which binds to TMEM106B and a second antigen binding region that binds to a second polypeptide. In some embodiments, the first antigen binding region comprises the $V_H$ or $V_L$ of an antibody described herein.

In some embodiments of any of the multispecific antibodies, the second polypeptide is a) an antigen facilitating transport across the blood-brain-barrier; (b) an antigen facilitating transport across the blood-brain-barrier selected from transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30 (A), a protein transduction domain, TAT, Syn-B, penetratin, a poly-arginine peptide, an angiopep peptide, and ANG1005; (c) a disease-causing protein selected from amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides; (d) ligands and/or proteins expressed on immune cells, wherein the ligands and/or proteins selected from CD40, OX40, ICOS, CD28, CD137/4-1BB, CD27, GITR, PD-L1, CTLA-4, PD-L2, PD-1, B7-H3, B7-H4, HVEM, BTLA, KIR, GAL9, TIM3, A2AR, LAG-3, and phosphatidylserine; and/or (e) a protein, lipid, polysaccharide, or glycolipid expressed on one or more tumor cells and any combination thereof.

Numerous antigens are known in the art that facilitate transport across the blood-brain barrier (see, e.g., Gabathuler R. *Neurobiol. Dis.* 37:48-57 (2010)). Such second antigens include, without limitation, transferrin receptor (TR), insulin receptor (HIR), Insulin-like growth factor receptor (IGFR), low-density lipoprotein receptor related proteins 1 and 2 (LPR-1 and 2), diphtheria toxin receptor, including CRM197 (a non-toxic mutant of diphtheria toxin), llama single domain antibodies such as TMEM 30 (A) (Flippase), protein transduction domains such as TAT, Syn-B, or penetratin, poly-arginine or generally positively charged peptides, Angiopep peptides such as ANG1005 (see, e.g., Gabathuler, 2010), and other cell surface proteins that are enriched on blood-brain barrier endothelial cells (see, e.g., Daneman et al. *PLOS One* 5 (10): e13741 (2010)).

The multivalent antibodies may recognize the TMEM106B antigen as well as without limitation additional antigens Aβ peptide, antigen or an α-synuclein protein antigen or, Tau protein antigen or, TDP-43 protein antigen or, prion protein antigen or, huntingtin protein antigen, or RAN, translation Products antigen, including the DiPeptide Repeats, (DPRs peptides) composed of glycine-alanine (GA), glycine-proline (GP), glycine-arginine (GR), proline-alanine (PA), or proline-arginine (PR), Insulin receptor, insulin like growth factor receptor. Transferrin receptor or any other antigen that facilitate antibody transfer across the blood brain barrier. In some embodiments, the second polypeptide is transferrin. In some embodiments, the second polypeptide is Tau. In some embodiments, the second polypeptide is Aβ. In some embodiments, the second polypeptide is TREM2. In some embodiments, the second polypeptide is α-synuclein.

The multivalent antibody contains at least one polypeptide chain (and preferably two polypeptide chains), wherein the polypeptide chain or chains comprise two or more variable domains. For instance, the polypeptide chain or chains may comprise VD1-(X1)$_n$-VD2-(X2)$_n$-Fc, wherein VD1 is a first variable domain, VD2 is a second variable domain, Fc is one polypeptide chain of an Fc region, X1 and X2 represent an amino acid or polypeptide, and n is 0 or 1. Similarly, the polypeptide chain or chains may comprise $V_H$-$C_H$1-flexible linker-$V_H$-$C_H$1-Fc region chain; or $V_H$-$C_H$1-$V_H$-$C_H$1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

Techniques for making multispecific antibodies include, but are not limited to, recombinant co-expression of two immunoglobulin heavy chain-light chain pairs having different specificities (see Milstein and Cuello *Nature* 305:537 (1983), WO 93/08829, and Traunecker et al. *EMBO J.* 10:3655 (1991)), and "knob-in-hole" engineering (see, e.g., U.S. Pat. No. 5,731,168). See also WO 2013/026833 (CrossMab). Multi-specific antibodies may also be made by engineering electrostatic steering effects for making antibody Fc-heterodimeric molecules (WO 2009/089004A1); cross-linking two or more antibodies (see, e.g., U.S. Pat. No. 4,676,980); using leucine; using "diabody" technology for making bispecific antibody fragments (see, e.g., Hollinger et al. *Proc. Natl. Acad. Sci. USA* 90:6444-6448 (1993)); and using single-chain Fv (scFv) dimers (see, e.g., Gruber et al. *J. Immunol.* 152:5368 (1994)); and preparing trispecific antibodies as described, e.g., in Tutt et al. *J. Immunol.* 147:60 (1991).

Engineered antibodies with three or more functional antigen binding sites, including "Octopus antibodies," are also included herein (see, e.g., US 2006/0025576). The antibody herein also includes a "Dual Acting FAb" or "DAF" comprising an antigen binding site that binds to multiple TMEM106B (see, US 2008/0069820, for example).

(7) Antibody Variants

In some embodiments of any of the antibodies provided herein, amino acid sequence variants of the antibodies are contemplated. For example, it may be desirable to improve the binding affinity and/or other biological properties of the antibody.

(i) Substitution, Insertion, and Deletion Variants

In some embodiments of any of the antibodies provided herein, antibody variants having one or more amino acid substitutions are provided. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody.

TABLE A

Amino Acid Substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Tyr |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro; and
(6) aromatic: Trp, Tyr, Phe.

For example, non-conservative substitutions can involve the exchange of a member of one of these classes for a member from another class. Such substituted residues can be introduced, for example, into regions of a human antibody that are homologous with non-human antibodies, or into the non-homologous regions of the molecule.

In making changes to the polypeptide or antibody described herein, according to certain embodiments, the hydropathic index of amino acids can be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al. *J. Mol. Biol.*, 157:105-131 (1982). It is known that certain amino acids can be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those which are within ±1 are included, and in certain embodiments, those within ±0.5 are included.

It is also understood in the art that the substitution of like amino acids can be made effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0±1); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those which are within ±1 are included, and in certain embodiments, those within ±0.5 are included. One can also identify epitopes from primary amino acid sequences on the basis of hydrophilicity. These regions are also referred to as "epitopic core regions".

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

Amino acid sequence insertions include amino- and/or carboxyl-terminal fusions ranging in length from one residue to polypeptides comprising a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment, such as an Fv fragment).

(ii) Glycosylation Variants

In some embodiments of any of the antibodies provided herein, the antibody is altered to increase or decrease the extent to which the antibody is glycosylated. Addition or deletion of glycosylation sites to an antibody may be conveniently accomplished by altering the amino acid sequence such that one or more glycosylation sites is created or removed.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Where the antibody comprises an Fc region, the carbohydrate attached thereto may be altered. Native antibodies produced by mammalian cells typically comprise a branched, biantennary oligosaccharide that is generally attached by an N-linkage to Asn297 according to Kabat numbering of the CH2 domain of the Fc region. The oligosaccharide may include various carbohydrates, for example, mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. See, e.g., US Patent Publication Nos. 2003/0157108 and 2004/0093621. Examples of publications related to "defucosylated" or "fucose-deficient" antibody variants include: US 2003/0157108; US 2003/0115614; US 2002/0164328; US 2004/0093621; US 2004/0132140; US 2004/0110704; US 2004/0110282; US 2004/0109865; Okazaki et al. *J. Mol. Biol.* 336:1239-1249 (2004); Yamane-Ohnuki et al. *Biotech. Bioeng.* 87:614 (2004). Examples of cell lines capable of producing defucosylated antibodies include Led 3 CHO cells deficient in protein fucosylation (Ripka et al. *Arch. Biochem. Biophys.* 249:533-545 (1986); US 2003/0157108), and knockout cell lines, such as alpha-1,6-fucosyltransferase gene, FUT8, knockout CHO cells (see, e.g., Yamane-Ohnuki et al. *Biotech. Bioeng.* 87:614 (2004) and Kanda et al. *Biotechnol. Bioeng.* 94 (4): 680-688 (2006)).

(iii) Modified Constant Regions

In some embodiments of any of the antibodies provided herein, the antibody Fc is an antibody Fc isotypes and/or modifications. In some embodiments, the antibody Fc isotype and/or modification is capable of binding to Fc gamma receptor.

In some embodiments of any of the antibodies provided herein, the modified antibody Fc is an IgG1 modified Fc. In some embodiments, the IgG1 modified Fc comprises one or more modifications. For example, in some embodiments, the IgG1 modified Fc comprises one or more amino acid substitutions (e.g., relative to a wild-type Fc region of the same isotype). In some embodiments, the one or more amino acid substitutions are selected from N297A (Bolt S et al. (1993) *Eur J Immunol* 23:403-411), D265A (Shields et al. (2001) *R. J. Biol. Chem.* 276, 6591-6604), L234A, L235A (Hutchins et al. (1995) *Proc Natl Acad Sci USA,* 92:11980-11984; Alegre et al., (1994) *Transplantation* 57:1537-1543. 31; Xu et al., (2000) *Cell Immunol,* 200:16-26), G237A (Alegre et al. (1994) *Transplantation* 57:1537-1543. 31; Xu et al. (2000) *Cell Immunol,* 200:16-26), C226S, C229S, E233P, L234V, L234F, L235E (McEarchern et al., (2007) *Blood,* 109:1185-1192), P331S (Sazinsky et al., (2008) *Proc Natl Acad Sci USA* 2008, 105:20167-20172), S267E, L328F, A330L, M252Y, S254T, and/or T256E, where the amino acid position is according to the EU numbering convention.

In some embodiments of any of the IgG1 modified Fc, the Fc comprises N297A mutation according to EU numbering. In some embodiments of any of the IgG1 modified Fc, the Fc comprises D265A and N297A mutations according to EU numbering. In some embodiments of any of the IgG1 modified Fc, the Fc comprises D270A mutations according to EU numbering. In some embodiments, the IgG1 modified Fc comprises L234A and L235A mutations according to EU numbering. In some embodiments of any of the IgG1 modified Fc, the Fc comprises L234A and G237A mutations according to EU numbering. In some embodiments of any of the IgG1 modified Fc, the Fc comprises L234A, L235A and G237A mutations according to EU numbering. In some embodiments of any of the IgG1 modified Fc, the Fc comprises one or more (including all) of P238D, L328E, E233, G237D, H268D, P271G and A330R mutations according to EU numbering. In some embodiments of any of the IgG1 modified Fc, the Fc comprises one or more of S267E/L328F mutations according to EU numbering. In some embodiments of any of the IgG1 modified Fc, the Fc comprises P238D, L328E, E233D, G237D, H268D, P271G and A330R mutations according to EU numbering. In some embodiments of any of the IgG1 modified Fc, the Fc comprises P238D, L328E, G237D, H268D, P271G and A330R mutations according to EU numbering. In some embodiments of any of the IgG1 modified Fc, the Fc comprises P238D, S267E, L328E, E233D, G237D, H268D, P271G and A330R mutations according to EU numbering. In some embodiments of any of the IgG1 modified Fc, the Fc comprises P238D, S267E, L328E, G237D, H268D, P271G and A330R mutations according to EU numbering. In some embodiments of any of the IgG1 modified Fc, the Fc comprises C226S, C229S, E233P, L234V, and L235A mutations according to EU numbering. In some embodiments of any of the IgG1 modified Fc, the Fc comprises L234F, L235E, and P331S mutations according to EU numbering. In some embodiments of any of the IgG1 modified Fc, the Fc comprises S267E and L328F mutations according to EU numbering. In some embodiments of any of the IgG1 modified Fc, the Fc comprises S267E mutations according to EU numbering. In some embodiments of any of the IgG1 modified Fc, the Fc comprises a substitute of the constant heavy 1 (CH1) and hinge region of IgG1 with CH1 and hinge region of IgG2 (amino acids 118-230 of IgG2 according to EU numbering) with a Kappa light chain.

In some embodiments of any of the IgG1 modified Fc, the Fc includes two or more amino acid substitutions that increase antibody clustering without activating complement as compared to a corresponding antibody having an Fc region that does not include the two or more amino acid substitutions. Accordingly, in some embodiments of any of the IgG1 modified Fc, the IgG1 modified Fc is an antibody comprising an Fc region, where the antibody comprises an amino acid substitution at position E430G and one or more amino acid substitutions in the Fc region at a residue position selected from: L234F, L235A, L235E, S267E, K322A, L328F, A330S, P331S, and any combination thereof according to EU numbering. In some embodiments, the IgG1 modified Fc comprises an amino acid substitution at positions E430G, L243A, L235A, and P331S according to EU numbering. In some embodiments, the IgG1 modified Fc comprises an amino acid substitution at positions E430G and P331S according to EU numbering. In some embodiments, the IgG1 modified Fc comprises an amino acid substitution at positions E430G and K322A according to EU numbering. In some embodiments, the IgG1 modified Fc comprises an amino acid substitution at positions E430G, A330S, and P331S according to EU numbering. In some embodiments, the IgG1 modified Fc comprises an amino acid substitution at positions E430G, K322A, A330S, and P331S according to EU numbering. In some embodiments, the IgG1 modified Fc comprises an amino acid substitution at positions E430G, K322A, and A330S according to EU numbering. In some embodiments, the IgG1 modified Fc comprises an amino acid substitution at positions E430G, K322A, and P331S according to EU numbering.

In some embodiments of any of the IgG1 modified Fc, the IgG1 modified Fc may further comprise herein may be combined with an A330L mutation (Lazar et al. *Proc Natl Acad Sci USA,* 103:4005-4010 (2006)), or one or more of L234F, L235E, and/or P331S mutations (Sazinsky et al. *Proc Natl Acad Sci USA,* 105:20167-20172 (2008)), according to the EU numbering convention, to eliminate complement activation. In some embodiments of any of the IgG1 modified Fc, the IgG1 modified Fc may further comprise one or more of A330L, A330S, L234F, L235E, and/or P331S according to EU numbering. In some embodiments of any of the IgG1 modified Fc, the IgG1 modified Fc may further comprise one or more mutations to enhance the antibody half-life in human serum (e.g., one or more (including all) of M252Y, S254T, and T256E mutations according to the EU numbering convention). In some embodiments of any of the IgG1 modified Fc, the IgG1 modified Fc may further comprise one or more of E430G, E430S, E430F, E430T, E345K, E345Q, E345R, E345Y, S440Y, and/or S440W according to EU numbering.

Other aspects of the present disclosure relate to antibodies having modified constant regions (i.e., Fc regions). An antibody dependent on binding to FcgR receptor to activate targeted receptors may lose its agonist activity if engineered to eliminate FcgR binding (see, e.g., Wilson et al. *Cancer Cell* 19:101-113 (2011); Armour at al. *Immunology* 40:585-593 (2003); and White et al. *Cancer Cell* 27:138-148 (2015)). As such, it is thought that an anti-TMEM106B antibody of the present disclosure with the correct epitope specificity can activate the target antigen, with minimal adverse effects, when the antibody has an Fc domain from a human IgG2 isotype (CH1 and hinge region) or another type of Fc domain that is capable of preferentially binding the inhibitory FcgRIIB r receptors, or a variation thereof.

In some embodiments of any of the antibodies provided herein, the modified antibody Fc is an IgG2 modified Fc. In some embodiments, the IgG2 modified Fc comprises one or more modifications. For example, in some embodiments, the IgG2 modified Fc comprises one or more amino acid substitutions (e.g., relative to a wild-type Fc region of the same isotype). In some embodiments of any of the IgG2 modified Fc, the one or more amino acid substitutions are selected from V234A (Alegre et al. *Transplantation* 57:1537-1543 (1994); Xu et al. *Cell Immunol,* 200:16-26 (2000)); G237A (Cole et al. *Transplantation,* 68:563-571 (1999)); H268Q, V309L, A330S, P331S (US 2007/0148167; Armour et al. *Eur J Immunol* 29:2613-2624 (1999); Armour et al. *The Haematology Journal* 1 (Suppl.1): 27 (2000); Armour et al. *The Haematology Journal* 1 (Suppl.1): 27 (2000)), C219S, and/or C220S (White et al. *Cancer Cell* 27, 138-148 (2015)); S267E, L328F (Chu et al. *Mol Immunol,* 45:3926-3933 (2008)); and M252Y, S254T, and/or T256E according to the EU numbering convention. In some embodiments of any of the IgG2 modified Fc, the Fc comprises an amino acid substitution at positions V234A and G237A according to EU numbering. In some embodiments of any of the IgG2 modified Fc, the Fc comprises an amino acid substitution at positions C219S or C220S according to EU numbering. In some embodiments of any of the IgG2 modified Fc, the Fc comprises an amino acid substitution at positions A330S and P331S according to EU numbering. In some embodiments of any of the IgG2 modified Fc, the Fc comprises an amino acid substitution at positions S267E and L328F according to EU numbering.

In some embodiments of any of the IgG2 modified Fc, the Fc comprises a C127S amino acid substitution according to the EU numbering convention (White et al., (2015) *Cancer Cell* 27, 138-148; Lightle et al. *Protein Sci.* 19:753-762 (2010); and WO 2008/079246). In some embodiments of any of the IgG2 modified Fc, the antibody has an IgG2 isotype with a Kappa light chain constant domain that comprises a C214S amino acid substitution according to the EU numbering convention (White et al. *Cancer Cell* 27:138-148 (2015); Lightle et al. *Protein Sci.* 19:753-762 (2010); and WO 2008/079246).

In some embodiments of any of the IgG2 modified Fc, the Fc comprises a C220S amino acid substitution according to the EU numbering convention. In some embodiments of any of the IgG2 modified Fc, the antibody has an IgG2 isotype with a Kappa light chain constant domain that comprises a C214S amino acid substitution according to the EU numbering convention.

In some embodiments of any of the IgG2 modified Fc, the Fc comprises a C219S amino acid substitution according to the EU numbering convention. In some embodiments of any of the IgG2 modified Fc, the antibody has an IgG2 isotype with a Kappa light chain constant domain that comprises a C214S amino acid substitution according to the EU numbering convention.

In some embodiments of any of the IgG2 modified Fc, the Fc includes an IgG2 isotype heavy chain constant domain 1 (CH1) and hinge region (White et al. *Cancer Cell* 27:138-148 (2015)). In certain embodiments of any of the IgG2 modified Fc, the IgG2 isotype CH1 and hinge region comprise the amino acid sequence of 118-230 according to EU numbering. In some embodiments of any of the IgG2 modified Fc, the antibody Fc region comprises a S267E amino acid substitution, a L328F amino acid substitution, or both, and/or a N297A or N297Q amino acid substitution according to the EU numbering convention.

In some embodiments of any of the IgG2 modified Fc, the Fc further comprises one or more amino acid substitution at positions E430G, E430S, E430F, E430T, E345K, E345Q, E345R, E345Y, S440Y, and S440W according to EU numbering. In some embodiments of any of the IgG2 modified Fc, the Fc may further comprise one or more mutations to enhance the antibody half-life in human serum (e.g., one or more (including all) of M252Y, S254T, and T256E mutations according to the EU numbering convention). In some embodiments of any of the IgG2 modified Fc, the Fc may further comprise A330S and P331S.

In some embodiments of any of the IgG2 modified Fc, the Fc is an IgG2/4 hybrid Fc. In some embodiments, the IgG2/4 hybrid Fc comprises IgG2 aa 118 to 260 and IgG4 aa 261 to 447. In some embodiments of any IgG2 modified Fc, the Fc comprises one or more amino acid substitutions at positions H268Q, V309L, A330S, and P331S according to EU numbering.

In some embodiments of any of the IgG1 and/or IgG2 modified Fc, the Fc comprises one or more additional amino acid substitutions selected from A330L, L234F; L235E, or P331S according to EU numbering; and any combination thereof.

In certain embodiments of any of the IgG1 and/or IgG2 modified Fc, the Fc comprises one or more amino acid substitutions at a residue position selected from C127S, L234A, L234F, L235A, L235E, S267E, K322A, L328F, A330S, P331S, E345R, E430G, S440Y, and any combination thereof according to EU numbering. In some embodiments of any of the IgG1 and/or IgG2 modified Fc, the Fc comprises an amino acid substitution at positions E430G, L243A, L235A, and P331S according to EU numbering. In some embodiments of any of the IgG1 and/or IgG2 modified Fc, the Fc comprises an amino acid substitution at positions E430G and P331S according to EU numbering. In some embodiments of any of the IgG1 and/or IgG2 modified Fc, the Fc comprises an amino acid substitution at positions E430G and K322A according to EU numbering. In some embodiments of any of the IgG1 and/or IgG2 modified Fc, the Fc comprises an amino acid substitution at positions E430G, A330S, and P331S according to EU numbering. In some embodiments of any of the IgG1 and/or IgG2 modified Fc, the Fc comprises an amino acid substitution at positions E430G, K322A, A330S, and P331S according to EU numbering. In some embodiments of any of the IgG1 and/or IgG2 modified Fc, the Fc comprises an amino acid substitution at positions E430G, K322A, and A330S according to EU numbering. In some embodiments of any of the IgG1 and/or IgG2 modified Fc, the Fc comprises an amino acid substitution at positions E430G, K322A, and P331S according to EU numbering. In some embodiments of any of the IgG1 and/or IgG2 modified Fc, the Fc comprises an amino acid substitution at positions S267E and L328F according to EU numbering. In some embodiments of any of the IgG1 and/or IgG2 modified Fc, the Fc comprises an amino acid substitution at position C127S according to EU numbering. In some embodiments of any of the IgG1 and/or IgG2 modified Fc, the Fc comprises an amino acid substitution at positions E345R, E430G and S440Y according to EU numbering.

In some embodiments of any of the antibodies provided herein, the modified antibody Fc is an IgG4 modified Fc. In some embodiments, the IgG4 modified Fc comprises one or more modifications. For example, in some embodiments, the IgG4 modified Fc comprises one or more amino acid substitutions (e.g., relative to a wild-type Fc region of the same isotype). In some embodiments of any of the IgG4 modified Fc, the one or more amino acid substitutions are selected from L235A, G237A, S229P, L236E (Reddy et al. *J Immunol* 164:1925-1933 (2000)), S267E, E318A, L328F, M252Y, S254T, and/or T256E according to the EU numbering convention. In some embodiments of any of the IgG4 modified Fc, the Fc may further comprise L235A, G237A, and E318A according to the EU numbering convention. In some embodiments of any of the IgG4 modified Fc, the Fc may further comprise S228P and L235E according to the EU numbering convention. In some embodiments of any of the IgG4 modified Fc, the IgG4 modified Fc may further comprise S267E and L328F according to the EU numbering convention.

In some embodiments of any of the IgG4 modified Fc, the IgG4 modified Fc comprises may be combined with an S228P mutation according to the EU numbering convention (Angal et al. *Mol Immunol.* 30:105-108 (1993)) and/or with one or more mutations described in (Peters et al. *J Biol Chem.* 287 (29): 24525-33 (2012)) to enhance antibody stabilization.

In some embodiments of any of the IgG4 modified Fc, the IgG4 modified Fc may further comprise one or more mutations to enhance the antibody half-life in human serum (e.g., one or more (including all) of M252Y, S254T, and T256E mutations according to the EU numbering convention).

In some embodiments of any of the IgG4 modified Fc, the Fc comprises L235E according to EU numbering. In certain embodiments of any of the IgG4 modified Fc, the Fc comprises one or more amino acid substitutions at a residue position selected from C127S, F234A, L235A, L235E, S267E, K322A, L328F, E345R, E430G, S440Y, and any combination thereof, according to EU numbering. In some embodiments of any of the IgG4 modified Fc, the Fc comprises an amino acid substitution at positions E430G, L243A, L235A, and P331S according to EU numbering. In some embodiments of any of the IgG4 modified Fc, the Fc comprises an amino acid substitution at positions E430G and P331S according to EU numbering. In some embodiments of any of the IgG4 modified Fc, the Fc comprises an amino acid substitution at positions E430G and K322A according to EU numbering. In some embodiments of any of the IgG4 modified Fc, the Fc comprises an amino acid substitution at position E430 according to EU numbering. In some embodiments of any of the IgG4 modified Fc, the Fc region comprises an amino acid substitution at positions E430G and K322A according to EU numbering. In some embodiments of any of the IgG4 modified Fc, the Fc comprises an amino acid substitution at positions S267E and L328F according to EU numbering. In some embodiments of any of the IgG4 modified Fc, the Fc comprises an amino acid substitution at position C127S according to EU numbering. In some embodiments of any of the IgG4 modified Fc, the Fc comprises an amino acid substitution at positions E345R, E430G and S440Y according to EU numbering.

(8) Other Antibody Modifications

In some embodiments of any of the antibodies, the antibody is a derivative. The term "derivative" refers to a molecule that includes a chemical modification other than an insertion, deletion, or substitution of amino acids (or nucleic acids). In certain embodiments, derivatives comprise covalent modifications, including, but not limited to, chemical bonding with polymers, lipids, or other organic or inorganic moieties. In certain embodiments, a chemically modified antigen binding protein can have a greater circulating half-life than an antigen binding protein that is not chemically modified. In certain embodiments, a chemically modified antigen binding protein can have improved targeting capacity for desired cells, tissues, and/or organs. In some embodiments, a derivative antigen binding protein is covalently modified to include one or more water soluble polymer attachments, including, but not limited to, polyethylene glycol, polyoxyethylene glycol, or polypropylene glycol. See, e.g., U.S. Pat. Nos. 4,640,835, 4,496,689, 4,301,144, 4,670,417, 4,791,192 and 4,179,337. In certain embodiments, a derivative antigen binding protein comprises one or more polymer, including, but not limited to, monomethoxy-polyethylene glycol, dextran, cellulose, copolymers of ethylene glycol/propylene glycol, carboxymethylcellulose, polyvinyl pyrrolidone, poly-1,3-dioxolane, poly-1,3,6-trioxane, ethylene/maleic anhydride copolymer, polyaminoacids (either homopolymers or random copolymers), poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of such polymers.

In certain embodiments, a derivative is covalently modified with polyethylene glycol (PEG) subunits. In certain embodiments, one or more water-soluble polymer is bonded at one or more specific position, for example at the amino terminus, of a derivative. In certain embodiments, one or more water-soluble polymer is randomly attached to one or more side chains of a derivative. In certain embodiments, PEG is used to improve the therapeutic capacity for an antigen binding protein. In certain embodiments, PEG is used to improve the therapeutic capacity for a humanized antibody. Certain such methods are discussed, for example, in U.S. Pat. No. 6,133,426, which is hereby incorporated by reference for any purpose.

Peptide analogs are commonly used in the pharmaceutical industry as non-peptide drugs with properties analogous to those of the template peptide. These types of non-peptide compound are termed "peptide mimetics" or "peptidomimetics." Fauchere, *J. Adv. Drug Res.,* 15:29 (1986); and Evans et al. *J. Med. Chem.,* 30:1229 (1987), which are incorporated herein by reference for any purpose. Such compounds are often developed with the aid of computerized molecular modeling. Peptide mimetics that are structurally similar to therapeutically useful peptides can be used to produce a similar therapeutic or prophylactic effect.

Generally, peptidomimetics are structurally similar to a paradigm polypeptide (i.e., a polypeptide that has a biochemical property or pharmacological activity), such as human antibody, but have one or more peptide linkages optionally replaced by a linkage selected from: —CH$_2$NH—, —CH$_2$S—, —CH$_2$—CH$_2$—, —CH═CH- (cis and trans), —COCH$_2$—, —CH(OH)CH$_2$—, and —CH$_2$SO—, by methods well known in the art. Systematic substitution of one or more amino acids of a consensus sequence with a D-amino acid of the same type (e.g., D-lysine in place of L-lysine) can be used in certain embodiments to generate more stable peptides. In addition, constrained peptides comprising a consensus sequence or a substantially identical consensus sequence variation can be generated by methods known in the art (Rizo and Gierasch *Ann. Rev. Biochem.*, 61:387 (1992), incorporated herein by reference for any purpose); for example, by adding internal cysteine residues capable of forming intramolecular disulfide bridges which cyclize the peptide.

Drug conjugation involves coupling of a biological active cytotoxic (anticancer) payload or drug to an antibody that specifically targets a certain tumor marker (e.g. a polypeptide that, ideally, is only to be found in or on tumor cells). Antibodies track these proteins down in the body and attach themselves to the surface of cancer cells. The biochemical reaction between the antibody and the target protein (antigen) triggers a signal in the tumor cell, which then absorbs or internalizes the antibody together with the cytotoxin. After the ADC is interalized, the cytotoxic drug is released and kills the cancer. Due to this targeting, ideally the drug has lower side effects and gives a wider therapeutic window than other chemotherapeutic agents. Technics to conjugate antibodies are disclosed are known in the art (see, e.g., Jane de Lartigue OncLive Jul. 5, 2012; ADC Review on antibody-drug conjugates; and Ducry et al. *Bioconjugate Chemistry* 21 (1): 5-13 (2010).

III. Nucleic Acids, Vectors, and Host Cells

Anti-TMEM106B antibodies of the present disclosure may be produced using recombinant methods and compositions, e.g., as described in U.S. Pat. No. 4,816,567. In some embodiments, isolated nucleic acids having a nucleotide sequence encoding any of the anti-TMEM106B antibodies of the present disclosure are provided. Such nucleic acids may encode an amino acid sequence comprising the V$_L$ and/or an amino acid sequence comprising the V$_H$ of the anti-TMEM106B antibody (e.g., the light and/or heavy chains of the antibody). In some embodiments, one or more vectors (e.g., expression vectors) comprising such nucleic acids are provided. In some embodiments, a host cell comprising such nucleic acid is also provided. In some embodiments, the host cell comprises (e.g., has been transduced with): (1) a vector comprising a nucleic acid that encodes an amino acid sequence comprising the V$_L$ of the antibody and an amino acid sequence comprising the V$_H$ of the antibody, or (2) a first vector comprising a nucleic acid that encodes an amino acid sequence comprising the V$_L$ of the antibody and a second vector comprising a nucleic acid that encodes an amino acid sequence comprising the V$_H$ of the antibody. In some embodiments, the host cell is eukaryotic, e.g., a Chinese Hamster Ovary (CHO) cell or lymphoid cell (e.g., Y0, NS0, Sp20 cell). Host cells of the present disclosure also include, without limitation, isolated cells, in vitro cultured cells, and ex vivo cultured cells.

Methods of making an anti-TMEM106B antibody of the present disclosure are provided. In some embodiments, the method includes culturing a host cell of the present disclosure comprising a nucleic acid encoding the anti-TMEM106B antibody, under conditions suitable for expression of the antibody. In some embodiments, the antibody is subsequently recovered from the host cell (or host cell culture medium).

For recombinant production of an anti-TMEM106B antibody of the present disclosure, a nucleic acid encoding the anti-TMEM106B antibody is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable vectors comprising a nucleic acid sequence encoding any of the anti-TMEM106B antibodies of the present disclosure, or cell-surface expressed fragments or polypeptides thereof polypeptides (including antibodies) described herein include, without limitation, cloning vectors and expression vectors. Suitable cloning vectors can be constructed according to standard techniques, or may be selected from a large number of cloning vectors available in the art. While the cloning vector selected may vary according to the host cell intended to be used, useful cloning vectors generally have the ability to self-replicate, may possess a single target for a particular restriction endonuclease, and/or may carry genes for a marker that can be used in selecting clones comprising the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Suitable host cells for cloning or expression of antibody-encoding vectors include prokaryotic or eukaryotic cells. For example, anti-TMEM106B antibodies of the present disclosure may be produced in bacteria, in particular when glycosylation and Fc effector function are not needed. For expression of antibody fragments and polypeptides in bacteria (e.g., U.S. Pat. Nos. 5,648,237, 5,789,199, and 5,840,523. After expression, the antibody may be isolated from the bacterial cell paste in a soluble fraction and can be further purified.

In addition to prokaryotes, eukaryotic microorganisms, such as filamentous fungi or yeast, are also suitable cloning or expression hosts for antibody-encoding vectors, including fungi and yeast strains whose glycosylation pathways have been "humanized," resulting in the production of an antibody with a partially or fully human glycosylation pattern (e.g., Gerngross *Nat. Biotech.* 22:1409-1414 (2004); and Li et al. *Nat. Biotech.* 24:210-215 (2006)).

Suitable host cells for the expression of glycosylated antibody can also be derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts (e.g., U.S. Pat. Nos. 5,959,177, 6,040,498, 6,420,548, 7,125,978, and 6,417,429, describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al. *J. Gen Virol.* 36:59 (1977)); baby hamster kidney cells (BHK); mouse sertoli cells (TM4 cells as described, e.g., in *Mather, Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al. *Annals N.Y. Acad. Sci.* 383:44-68 (1982); MRC 5 cells; and FS4 cells. Other useful mammalian host cell lines include Chinese hamster ovary (CHO) cells, including DHFR-CHO cells (Urlaub et al. *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, NJ), pp. 255-268 (2003).

IV. Pharmaceutical Compositions/Formulations

Provided herein are pharmaceutical compositions and/or pharmaceutical formulations comprising the anti-TMEM106B antibodies of the present disclosure and a pharmaceutically acceptable carrier.

In some embodiments, pharmaceutically acceptable carriers preferably are nontoxic to recipients at the dosages and concentrations employed. The antibodies described herein may be formulated into preparations in solid, semi-solid, liquid or gaseous forms. Examples of such formulations include, without limitation, tablets, capsules, powders, granules, ointments, solutions, suppositories, injections, inhalants, gels, microspheres, and aerosols. Pharmaceutically acceptable carriers can include, depending on the formulation desired, pharmaceutically-acceptable, non-toxic carriers of diluents, which are vehicles commonly used to formulate pharmaceutical compositions for animal or human administration. In certain embodiments, the pharmaceutical composition can comprise formulation materials for modifying, maintaining or preserving, for example, the pH, osmolarity, viscosity, clarity, color, isotonicity, odor, sterility, stability, rate of dissolution or release, adsorption or penetration of the composition.

In certain embodiments, pharmaceutically acceptable carriers include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. Further examples of formulations that are suitable for various types of administration can be found in *Remington: The Science and Practice of Pharmacy*, Pharmaceutical Press 22nd ed. (2013). For a brief review of methods for drug delivery, see, Langer, Science 249:1527-1533 (1990).

Formulations suitable for parenteral administration include aqueous and non-aqueous, isotonic sterile injection solutions, which can comprise antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Formulations may be optimized for retention and stabilization in the brain or central nervous system. When the agent is administered into the cranial compartment, it is desirable for the agent to be retained in the compartment, and not to diffuse or otherwise cross the blood brain barrier. Stabilization techniques include cross-linking, multimerizing, or linking to groups such as polyethylene glycol, polyacrylamide, neutral protein carriers, etc. in order to achieve an increase in molecular weight.

Other strategies for increasing retention include the entrapment of the antibody, such as an anti-TMEM106B antibody of the present disclosure, in a biodegradable or bioerodible implant. The rate of release of the therapeutically active agent is controlled by the rate of transport through the polymeric matrix, and the biodegradation of the implant. Implants may be particles, sheets, patches, plaques, fibers, microcapsules and the like and may be of any size or shape compatible with the selected site of insertion. Biodegradable polymeric compositions which may be employed may be organic esters or ethers, which when degraded result in physiologically acceptable degradation products, including the monomers. Anhydrides, amides, orthoesters or the like, by themselves or in combination with other monomers, may find use. The polymers will be condensation polymers. The polymers may be cross-linked or non-cross-linked. Of particular interest are polymers of hydroxyaliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. Among the polysaccharides of interest are calcium alginate, and functionalized celluloses, particularly carboxymethylcellulose esters characterized by being water insoluble, a molecular weight of about 5 kD to 500 kD, etc. Biodegradable hydrogels may also be employed in the implants of the subject invention. Hydrogels are typically a copolymer material, characterized by the ability to imbibe a liquid.

V. Therapeutic Uses

As disclosed herein, anti-TMEM106B antibodies of the present disclosure may be used for preventing, reducing risk, or treating various diseases, disorders, and conditions. In some embodiments, an anti-TMEM106B antibody of the present disclosure is effective at preventing, reducing risk, or treating frontotemporal lobar degeneration, frontotemporal dementia, frontotemporal dementia with progranulin mutations, frontotemporal dementia with C9orf72 mutations, frontotemporal lobar degeneration with TDP-43 inclusions, TDP-43 proteinopathy, hippocampal sclerosis (HpScl), hippocampal sclerosis of aging (HS-Aging), cognitive impairments associated with various disorders (including without limitation cognitive impairment in amyotrophic lateral sclerosis), cognitive impairments associated with chronic traumatic encephalopathy, and hypomyelinating disorders (including without limitation hypomyelinating leukodystrophy).

Other aspects of the present disclosure relate to a method of preventing, reducing risk, or treating an individual having a disease, disorder, or injury selected from the group consisting of frontotemporal dementia, Alzheimer's disease, vascular dementia, seizures, retinal dystrophy, a traumatic brain injury, a spinal cord injury, long-term depression, atherosclerotic vascular diseases, undesirable symptoms of normal aging, dementia, mixed dementia, Creutzfeldt-Jakob disease, normal pressure hydrocephalus, amyotrophic lateral sclerosis, Huntington's disease, taupathy disease, stroke, acute trauma, chronic trauma, lupus, acute and chronic colitis, Crohn's disease, inflammatory bowel disease, ulcerative colitis, malaria, essential tremor, central nervous system lupus, Behcet's disease, Parkinson's disease, dementia with Lewy bodies, multiple system atrophy, degenerative disc disease, Shy-Drager syndrome, progressive supranuclear palsy, cortical basal ganglionic degeneration, acute disseminated encephalomyelitis, granulomartous disorders, Sarcoidosis, diseases of aging, age related macular degeneration, glaucoma, retinitis pigmentosa, retinal degeneration, respiratory tract infection, sepsis, eye infection, systemic infection, inflammatory disorders, arthritis, multiple sclerosis, metabolic disorder, obesity, insulin resistance, type 2 diabetes, tissue or vascular damage, an injury, and one or more undesirable symptoms of normal aging, comprising administering to the individual a therapeutically effective amount of the anti-TMEM106B antibody of any of the preceding embodiments.

In some embodiments, an anti-TMEM106B antibody of the present disclosure may reduce TDP-43 inclusions in brain, reduce decline in cognitive and behavioral function, and improve cognitive and behavioral function.

In some embodiments, a subject or individual is a mammal. Mammals include, without limitation, domesticated animals (e.g., cows, sheep, cats, dogs, and horses), primates (e.g., humans and non-human primates such as monkeys), rabbits, and rodents (e.g., mice and rats). In some embodiments, the subject or individual is a human.

An antibody provided herein (and any additional therapeutic agent) can be administered by any suitable means, including parenteral, intrapulmonary, intranasal, intralesional administration, intracerobrospinal, intracranial, intraspinal, intrasynovial, intrathecal, oral, topical, or inhalation routes. Parenteral infusions include intramuscular, intravenous administration as a bolus or by continuous infusion over a period of time, intraarterial, intra-articular, intraperitoneal, or subcutaneous administration. In some embodiments, the administration is intravenous administration. In some embodiments, the administration is subcutaneous. Dosing can be by any suitable route, e.g. by injections, such as intravenous or subcutaneous injections, depending in part on whether the administration is brief or chronic. Various dosing schedules including but not limited to single or multiple administrations over various timepoints, bolus administration, and pulse infusion are contemplated herein.

Antibodies provided herein would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

Depending on the type and severity of the disease, about 1 µg/kg to 15 mg/kg (e.g., 0.1 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g., every week or every three weeks (e.g., such that the patient receives from about two to about twenty, or e.g., about six doses of the antibody). In certain embodiments, dosing frequency is three times per day, twice per day, once per day, once every other day, once weekly, once every two weeks, once every four weeks, once every five weeks, once every six weeks, once every seven weeks, once every eight weeks, once every nine weeks, once every ten weeks, or once monthly, once every two months, once every three months, or longer. An initial higher loading dose, followed by one or more lower doses may be administered. However, other dosage regimens may be useful. The progress of this therapy is easily monitored by conventional techniques and assays.

VI. Diagnostic Uses

In some embodiments of any of the antibodies, any of the anti-TMEM106B antibodies provided herein is useful for detecting the presence of TMEM106B in a sample or an individual. The term "detecting" as used herein encompasses quantitative or qualitative detection. Provided herein are methods of using the antibodies of this disclosure for diagnostic purposes, such as the detection of TMEM106B in an individual or in tissue samples derived from an individual. In some embodiments, the individual is a human. In some embodiments, the tissue sample is blood, brain, spinal fluid, etc.

The detection method may involve quantification of the antigen-bound antibody. Antibody detection in biological samples may occur with any method known in the art, including immunofluorescence microscopy, immunocytochemistry, immunohistochemistry, ELISA, FACS analysis, immunoprecipitation, or micro-positron emission tomography. In certain embodiments, the antibody is radiolabeled, for example with 18F and subsequently detected utilizing micro-positron emission tomography analysis. Antibody-binding may also be quantified in a patient by non-invasive techniques such as positron emission tomography (PET), X-ray computed tomography, single-photon emission computed tomography (SPECT), computed tomography (CT), and computed axial tomography (CAT).

VII. Articles of Manufacture

Provided herein are articles of manufacture (e.g., kit) comprising an anti-TMEM106B antibody described herein. Article of manufacture may include one or more containers comprising an antibody described herein. Containers may be any suitable packaging including, but is not limited to, vials, bottles, jars, flexible packaging (e.g., sealed Mylar or plastic bags), and the like. The containers may be unit doses, bulk packages (e.g., multi-dose packages) or sub-unit doses.

In some embodiments, the kits may further include a second agent. In some embodiments, the second agent is a pharmaceutically-acceptable buffer or diluting agent including, but not limited to, such as bacteriostatic water for injection (BWFI), phosphate-buffered saline, Ringer's solution and dextrose solution. In some embodiments, the second agent is a pharmaceutically active agent.

In some embodiments of any of the articles of manufacture, the article of manufactures further include instructions for use in accordance with the methods of this disclosure. The instructions generally include information as to dosage, dosing schedule, and route of administration for the intended treatment. In some embodiments, these instructions comprise a description of administration of the isolated antibody of the present disclosure (e.g., an anti-TMEM106B antibody described herein) to prevent, reduce risk, or treat an individual having a disease, disorder, or injury selected from frontotemporal lobar degeneration, frontotemporal dementia, frontotemporal dementia with progranulin mutations, frontotemporal dementia with C9orf72 mutations, frontotemporal lobar degeneration with TDP-43 inclusions, TDP-43 proteinopathy, hippocampal sclerosis (HpScl), hippocampal sclerosis of aging (HS-Aging), cognitive impairments associated with various disorders (including without limitation cognitive impairment in amyotrophic lateral sclerosis), and hypomyelinating disorder (including without limitation hypomyelinating leukodystrophy), according to any methods of this disclosure. In some embodiments, the instructions include instructions for use of the anti-TMEM106B antibody and the second agent (e.g., second pharmaceutically active agent).

The present disclosure will be more fully understood by reference to the following Examples. They should not, however, be construed as limiting the scope of the present disclosure. All citations throughout the disclosure are hereby expressly incorporated by reference.

EXAMPLES

Example 1: TMEM106B is a Risk Factor in Various Neurodegenerative Disorders

In an attempt to find genetic risk factors for FTLD, a genome-wide association study (GWAS) was performed in 2509 control subjects and 515 subjects with pathologically confirmed FTLD-TDP, some of which contained a GRN mutation (van Deerlin et al., 2010, Nat Genetics, 42:234-239). This GWAS led to the discovery of 3 SNPs within a 68 kb region on chromosome 7p21.3 that associated with the occurrence of FTLD-TDP with genome-wide significance (rs6966915, rs102004, and top marker SNP rs1990622; p value range=5.00×10-11 to 1.08×10-11). The three significantly associated SNPs were in the same linkage disequilibrium (LD) block as nine other SNPs of nominal association, and all spanned the TMEM106B gene locus. In this case control cohort, the minor allele of each significant SNP was greatly underrepresented in FTLD-TDP patients (32.1 versus 43.6% in controls for rs1990622 minor C-allele; p value=1.08×10-11), suggesting that individuals expressing the minor TMEM106B alleles are less likely to develop disease [odds ratio (OR)=0.61 for the rs1990622 minor allele]. Upon stratification of the initial GWAS cohort by GRN mutation status, the association of the top three SNPs remained significant in both groups, but was greatest in people with GRN-related FTLD-TDP (rs1990622 p value=1.34×10-9; OR 0.34) in GRN carriers versus in non-GRN carriers (rs1990622 p value=6.90×10-7; OR 0.68). These SNPs conferred the strongest risk in patients also carrying a GRN mutation suggesting a functional interaction between TMEM106B and GRN. The genetic association of TMEM106B variants with FTLD-TDP was replicated with high confidence (Cruchaga et al., 2011; Finch et al., 2011; Van der Zee et al., 2011). In addition to increasing the risk of FTLD, the major allele at rs1990622, also reduces the age of FTLD onset. (See, e.g., Finch et al., 2011, Neurology, 76:467-474; Cruchaga et al., 2011, Arch Neurol.)

The initial studies assessing TMEM106B SNPs as disease risk factors in FTLD-TDP were conducted prior to the discovery of C9orf72 repeat expansion in 2012. Two independent groups found TMEM106B SNPs to also associate with the risk of developing FTLD and/or ALS caused by C9orf72 mutations. (See Gallagher et al., 2014, Acta Neuropathol, 127:407-418; van Blitterswijk et al., 2014, Acta Neuropath, 127:397-406.) In these C9orf72 mutant cohorts, the frequency of individuals carrying the minor allele of TMEM106B SNPs [rs1990622 and/or rs3173615 in LD with rs1990622 was significantly reduced, although not as markedly as in cohorts of GRN mutation carriers. Interestingly. analysis of the C9orf72 repeat expansion carriers in groups based on their predominant disease presentation as either FTLD, FTLD-ALS, or ALS showed that TMEM106B SNPs specifically protect against the development of FTLD but not ALS, with less TDP-43 burden in the brains of C9orf72 expansion carriers homozygous for the protective TMEM106B alleles as compared to risk allele carriers. These findings are in agreement with an earlier examination of TMEM106B SNPs in a clinical cohort of ALS patients in which TMEM106B SNPs rs1990622 and rs1020004 were not associated with disease risk, but did significantly associate with cognitive function in ALS patients, with individuals homozygous for the rs1990622 minor allele having better cognitive performance than individuals heterozygous or homozygous for the major risk alleles (Vass et al., 2011, Acta Neuropathol, 121:373-380).

Neurodegenerative disease hallmarks, such as TDP-43 aggregates, are not specific to FTLD, and are observed in other neurodegenerative diseases, including Alzheimer's disease (AD), Lewy body dementia (LBD), and hippocampal sclerosis (HpScl) (Amador-Ortiz et al., 2007, Ann Neurol, 61:435-445; Zarow et al., 2008, Curr Neurol Neurosci Rep, 8:363-370), but also even in apparently healthy individuals, albeit to a limited extent (See, e.g., Yu et al., 2015, Neurology, 84:927-934). TMEM106B risk variants have been associated with TDP-43 neuropathology in the absence of a clinical neurological diagnosis. It was similarly found to affect the pathological presentation of AD with the protective TMEM106B haplotype associated with less TDP-43 pathology among AD patients (Rutherford et al., 2012, Neurology, 79:717-718). Hippocampal sclerosis is also common pathological hallmark in elderly patients with dementia, including FTLD-TDP and AD, often co-occurring with TDP-43 pathology. TMEM106B genotype was found to be associated with primary hippocampal sclerosis (Aoki et al., 2015, Acta Neuropathol, 129:53-64) as well as with hippocampal sclerosis pathology among AD patients, making TMEM106B as the strongest genetic indicator of AD-HpScl and HpScl known to date (Murray et al., 2014, Acta Neuropathol, 128:411-421). These studies collectively suggest that TMEM106B SNPs are risk factors for the development and severity of TDP-43 proteinopathy in non-FTLD disorders such as AD and HpScl.

A genomics study across over 1500 human brain autopsied samples identified common variants at TMEM106B as the main genome-wide determinant of the rate of biological aging in human brain: the presence of 2 risk alleles at the TMEM106B gene locus making an individual appear ~12 years older based on its gene expression profile than his/her actual age (Rhinn and Abeliovich, 2017, Cell Syst, 4:404-415). This effect of TMEM106B risk alleles is seen in individuals free of known neurological disease as well as in individuals with neurodegenerative processes such as Alzheimer's. The role of TMEM106B in aging appeared highly selective, in terms of brain and life (cortex and not cerebellum, specifically over 65yo). The effect was confirmed independently in additional cohorts in which carriers of the protective TMEM106B haplotype displayed reduced age-associated cognitive decline (Rhinn and Abeliovich, 2017, supra). The effect on cognitive performance was confirmed as the TMEM106B protective haplotype was shown to be associated with better cognitive performance for a given amount of cerebral pathology (White et al., 2017, PLOS Med, 14: e1002287). Those results strengthen the pleiotropic role of TMEM106B in aging beyond neurodegenerative diseases.

TMEM106B variants may increase risk for developing FTLD-TDP by increasing TMEM106B mRNA and protein expression levels. Increased TMEM106B results in a decrease in the average number of late endosomes/lysosomes per cell, loss of lysosomal acidification, and impaired lysosomal degradation.

A murine genetic knockout of TMEM106B (Klein et al. 2017, *Neuron* 95, 281-296) showed an effect for TMEM106b in the granulin pathway. Specifically, a genetic knock-out of the TMEM106B protein was able to rescue some of the pathogenic phenotype associated with GRN knockout in a mouse model, including a partial rescue of levels of lysosomal proteins, and rescue of behavioral changes such as hyperactivity and dis-inhibition. The TMEM106B knockout itself was well tolerated in the mice, and TMEM106B may work through the direct interaction (as evidenced by co-immunoprecipitation) with the V-ATPase subunit AP1. The v-ATPase complex plays an important role in lowering the pH of lysosomes and thus initiating protein degradation and recycling. Thus, its interaction with TMEM106B may cause some of the lysosomal phenotypes associated with TMEM106B overexpression, and conversely blocking this interaction (or merely reducing the level of TMEM106B present) may be able to ameliorate this phenotype.

The above and additional analyses identify an association TMEM106B and various diseases, disorders, and conditions, such as without limitation, frontotemporal lobar degeneration, frontotemporal dementia, frontotemporal dementia with progranulin mutations, frontotemporal dementia with C9orf72 mutations, frontotemporal lobar degeneration with TDP-43 inclusions, TDP-43 proteinopathy, hippocampal sclerosis, hippocampal sclerosis of aging, cognitive impairments associated with various disorders (including without limitation cognitive impairment in amyotrophic lateral sclerosis and chronic traumatic encephalopathy), and hypomyelinating disorder (including without limitation hypomyelinating leukodystrophy). Accordingly, the present disclosure provides therapies targeting TMEM106B, including anti-TMEM106B antibodies that specifically bind TMEM106B and affect its function.

Example 2: Production of GST and Murine-Fc-Conjugated Human TMEM106B

Various human TMEM106B polypeptides and TMEM106B polypeptide fusion proteins were generated as follows. Mammalian recombinant expression of various TMEM106B polypeptides was performed by cloning synthetic genes based on TMEM106B cDNA into mammalian expression vectors, followed by transient transfection and expression in HEK293T cells. Each TMEM106B expression construct included a heterologous signal peptide, and either a His-tag, a human IgG1 Fc, Glutathione-S-transferase, or murine IgG1 Fc for fusion constructs. Some TMEM106B expression constructs included the C-terminal region of TMEM106B (the putative extracellular domain (ECD) (amino acid residues 122-274 of SEQ ID NO: 1). Other TMEM106B expression constructs included a truncated version of the ECD (amino acid residues 122-210 of SEQ ID NO:1) in order to avoid expression of a hydrophobic patch within the TMEM106B protein (located at approximately amino acid residues 210-240), thought to possibly impair folding of the soluble TMEM106B protein product.

The amino acid sequences of each TMEM106B polypeptide used in the expression constructs are provided below:

```
Human TMEM106B truncated
ECD poly His
                                    (SEQ ID NO: 316)
     1        MDMRVPAQLL GLLLLWLRGA RCDVKYIGVK
              SAYVSYDVQK RTIYLNITNT

51        LNITNNNYYS VEVENITAQV QFSKTVIGKA
              RLNNITIIGP LDMKQIDYTV

101        PTVIAEEMSY MSGGGGSHHH HHHHHH**

Human IgG1 Fc - TMEM106B
ECD Truncated fusion
                                    (SEQ ID NO: 317)
     1        MDMRVPAQLL GLLLLWLRGA RCDVKYIGVK
              SAYVSYDVQK RTIYLNITNT

51        LNITNNNYYS VEVENITAQV QFSKTVIGKA
              RLNNITIIGP LDMKQIDYTV

101        PTVIAEEMSY MDKTHTCPPC PAPELLGGPS
              VFLFPPKPKD TLMISRTPEV

151        TCVVVDVSHE DPEVKFNWYV DGVEVHNAKT
              KPREEQYNST YRVVSVLTVL

201        HQDWLNGKEY KCKVSNKALP APIEKTISKA
              KGQPREPQVY TLPPSRDELT

251        KNQVSLTCLV KGFYPSDIAV EWESNGQPEN
              NYKTTPPVLD SDGSFFLYSK

301        LTVDKSRWQQ GNVFSCSVMH EALHNHYTQK
              SLSLSPGK**
```

Murine IgG1-TMEM106B human
ECD fusion (SEQ ID NO: 318)

```
  1   MEFGLSWVFL VALLRGVQCE VRLLESGGGL
      VQPGGSLRLS CAASGFTFSN
 51   YAMGWVRQAP GKGLEWVSAI SGSGGSTYYA
      DSVKGRFTTS RDDSKNALYL
101   QMNSLRAEDT AVYYCARGGP GWYAADVWGQ
      GTTVTVSSAK TTPPSVYPLA
151   PGSAAQTNSM VTLGCLVKGY FPEPVTVTWN
      SGSLSSGVHT FPAVLQSDLY
201   TLSSSVTVPS SPRPSETVTC NVAHPASSTK
      VDKKIVPRDC GCKPCICTVP
251   EVSSVFIFPP KPKDVLTITL TPKVTCVVVD
      ISKDDPEVQF SWFVDDVEVH
301   TAQTQPREEQ FNSTFRSVSE LPIMHQDWLN
      GKEFKCRVNS AAFPAPIEKT
351   ISKTKGRPKA PQVYTIPPPK EQMAKDKVSL
      TCMITDFFPE DITVEWQWNG
401   QPAENYKNTQ PIMNTNGSYF VYSKLNVQKS
      NWEAGNTFTC SVLHEGLHNH
451   HTEKSLSHSP GKSGGGGDVK YIGVKSAYVS
      YDVQKRTIYL NITNTLNITN
501   NNYYSVEVEN ITAQVQFSKT VIGKARLNNI
      TIIGPLDMKQ IDYTVPTVIA
551   EEMSYMYDFC TLISIKVHNI VLMMQVTVTT
      TYFGHSEQIS QERYQYVDCG
601   RNTTYQLGQS EYLNVLQPQQ
```

Murine IgG1-TMEM106B human
truncated ECD fusion (SEQ ID NO: 319)

```
  1   MEFGLSWVFL VALLRGVQCE VRLLESGGGL
      VQPGGSLRLS CAASGFTFSN
 51   YAMGWVRQAP GKGLEWVSAI SGSGGSTYYA
      DSVKGRFTTS RDDSKNALYL
101   QMNSLRAEDT AVYYCARGGP GWYAADVWGQ
      GTTVTVSSAK TTPPSVYPLA
151   PGSAAQTNSM VTLGCLVKGY FPEPVTVTWN
      SGSLSSGVHT FPAVLQSDLY
201   TLSSSVTVPS SPRPSETVTC NVAHPASSTK
      VDKKIVPRDC GCKPCICTVP
251   EVSSVFIFPP KPKDVLTITL TPKVTCVVVD
      ISKDDPEVQF SWFVDDVEVH
301   TAQTQPREEQ FNSTFRSVSE LPIMHQDWLN
      GKEFKCRVNS AAFPAPIEKT
351   ISKTKGRPKA PQVYTIPPPK EQMAKDKVSL
      TCMITDFFPE DITVEWQWNG
401   QPAENYKNTQ PIMNTNGSYF VYSKLNVQKS
      NWEAGNTFTC SVLHEGLHNH
451   HTEKSLSHSP GKSGGGGDVK YIGVKSAYVS
      YDVQKRTIYL NITNTLNITN
501   NNYYSVEVEN ITAQVQFSKT VIGKARLNNI
      TIIGPLDMKQ IDYTVPTVIA
551   EEMSYM**
```

GST Fusion human TMEM106B
ECD (Truncated)

(SEQ ID NO: 320)

```
  1   MDMRVPAQLL GLLLLWLRGA RCMSPILGYW
      KIKGLVQPTR LLLEYLEEKY
 51   EEHLYERDEG DKWRNKKFEL GLEFPNLPYY
      IDGDVKLTQS MAIIRYIADK
101   HNMLGGCPKE RAEISMLEGA VLDIRYGVSR
      IAYSKDFETL KVDFLSKLPE
151   MLKMFEDRLC HKTYLNGDHV THPDFMLYDA
      LDVVLYMDPM CLDAFPKLVC
201   FKKRIEAIPQ IDKYLKSSKY IAWPLQGWQA
      TFGGGDHPPK SDPREFIVTD
251   DIEGRMDPDV KYIGVKSAYV SYDVQKRTIY
      LNITNTLNIT NNNYYSVEVE
301   NITAQVQFSK TVIGKARLNN ITIIGPLDMK
      QIDYTVPTVI AEEMSYM**
```

GST Fusion human TMEM106B
ECD (SEQ ID NO: 321)

```
  1   MDMRVPAQLL GLLLLWLRGA RCMSPILGYW
      KIKGLVQPTR LLLEYLEEKY
 51   EEHLYERDEG DKWRNKKFEL GLEFPNLPYY
      IDGDVKLTQS MAIIRYIADK
101   HNMLGGCPKE RAEISMLEGA VLDIRYGVSR
      IAYSKDFETL KVDFLSKLPE
151   MLKMFEDRLC HKTYLNGDHV THPDFMLYDA
      LDVVLYMDPM CLDAFPKLVC
201   FKKRIEAIPQ IDKYLKSSKY IAWPLQGWQA
      TFGGGDHPPK SDPREFIVTD
251   DIEGRMDPPR SIDVKYIGVK SAYVSYDVQK
      RTIYLNITNT LNITNNNYYS
301   VEVENITAQV QFSKTVIGKA RLNNITIIGP
      LDMKQIDYTV PTVIAEEMSY
351   MYDFCTLISI KVHNIVLMMQ VTVTTTYFGH
      SEQISQERYQ YVDCGRNTTY
401   QLGQSEYLNV LQPQQ**
```

Transfection of the TMEM106B expression constructs was carried out using Expifectamine-293 system according to the manufacturer's protocol (ThermoFischerScientific Cat #A14524). Briefly, for each 30 mL of Expi293 cells, 30 μg of plasmid DNA were diluted into 1.5 mL OptiMEM (ThermoFischerScientific Cat #31985070), to which was added 80 μL of Expifectamine reagent. The resulting solution was mixed and incubated at room temperature for 30 min prior to addition to 30 mL of Expi293 cells (ThemoFischerScientificA14527) cultured in Expi293 expression media (ThermoFischerScientific Cat #A1435101) in 125 mL flasks (Fischer Scientific FIS #PBV12-5) to approximately 3×10^6 cells/ml prior to transfection. Culture Expi293 cells were cultured at 370C and 8% CO2 with orbital shaking at 125 rpm. 16-24 hrs after transfection 150 μL of ExpiFectamine™ 293 Transfection Enhancer 1 and 1.5 mL of ExpiFectamine™ 293 Transfection Enhancer 2 were added to each flask to enhance protein yield. For some of the TMEM106B protein expression experiments, larger volume cultures were used, with all reagents being scaled accordingly (i.e., for 120 mL culture all reagents multiplied by 4×, etc). Cell culture supernatants were harvested 5-7 days after transfection, filtered (0.2 micron), and the TMEM106B polypeptides purified via Protein A, Ni-NTA, or glutathione chromatography.

Protein yields from transient expression of each of the TMEM106B expression constructs described above (SEQ ID Nos: 316-321) were determined. The GST-fusion human TMEM106B truncated (SEQ ID No:320) was expressed in sufficient yield and provided sufficient purity for use in further experiments, such as ELISA and surface plasmon resonance (SPR) binding assays and SPR-based binning assays as described below.

The quantities of TMEM106B polypeptides obtained using the other TMEM106B expression constructs described above were insufficient for use in immunizations for antibody generation. Accordingly, initial immunizations for anti-TMEM106B antibody generation were carried out using plasmid DNA constructs as described herein.

Example 3: Construction of TMEM106B Expression Plasmids for DNA Immunization A DNA immunization approach was used for developing antibodies directed against TMEM106B. cDNA sequences encoding human TMEM106B, mouse TMEM106B, and cyno TMEM106B (SEQ ID NOs: 1, 2 and 315, respectively) were cloned into the pCAGGS mammalian expression vector (KeraFAST EH1017) for DNA immunization. Expression of each TMEM106B polypeptide was confirmed by transient transfection of the expression constructs into HEK293T cells, followed by Western blot and intracellular and extracellular FACS analysis using commercial-available anti-TMEM106B antibodies (EMD Millipore MAB-N473, Thermo-Fischer PA5-6338, Abcam ab140185, Abcam ab116023, Protein Tech 20995-1-AP, LifeSpan Biosciences LS-C145601, Abgent Al12796, MyBioSource MBS9412982, Sigma SAB2106773, Bethyl Labs A303-439A). The expression constructs where then used for DNA immunization in mice as described below.

Example 4: Generation of Anti-TMEM106B Hybridoma Antibodies

In order to obtain antibodies against TMEM106B, the following procedures were used to generate hybridomas. NZB/W mice (JAX100008, Jackson Laboratory, Bar Harbor, ME), SJL mice (JAX000686, Jackson Laboratory), or TMEM106B.knockout mice (Taconic, Rensselaer, NY) were co-immunized weekly with 50 µg each of plasmid DNA encoding full-length human, cyno, or mouse TMEM106B (SEQ ID Nos: 1, 2, and 315) with or without mFlt3 ligand (DNA) and mGM-CSF (DNA) (Invitrogen, San Diego, CA) diluted in lactated Ringer's solution. A total of 5-7 injections of the TMEM106B expression plasmids for DNA immunizations were performed per mouse. Spleens were harvested from the mice three days following the final DNA immunization. Sera from the mice were analyzed for reactivity to TMEM106B by FACS analyses using HEK293 cells overexpressing human, cyno, and/or mouse TMEM106B. Splenocytes from mice whose sera demonstrated strong binding to HEK293 cells overexpressing human, cyno, and/or mouse TMEM106B were fused with P3X63Ag8.653 mouse myeloma cells (CRL-1580, American Type Culture Collection, Rockville, MD) via electrofusion (ECM 2001, BTX, Holliston, MA) and incubated at 37° C./5% CO2 overnight in Clonacell-HY Medium C (StemCell Technologies, Vancouver, BC, Canada). Three rounds of fusions were performed: Fusion A, using splenocytes obtained from immunized TMEM106B.knockout mice; Fusion B, using splenocytes obtained from immunized SJL mice; and Fusion C, using splenocytes obtained from immunized NZB/W mice.

The following day, the fused cells were centrifuged and resuspended in 10 mls of ClonaCell-HY Medium C with anti-mouse IgG Fc-FITC (Jackson Immunoresearch, West Grove, PA) and then gently mixed with 90 mls of methylcellulose-based ClonaCell-HY Medium D (Stemcell Technologies) containing HAT components. The cells were plated into Nunc OmniTrays (Thermo Fisher Scientific, Rochester, NY) and allowed to grow at 37° C./5% CO2 for seven days. Fluorescent colonies were selected and transferred into 96-well plates containing Clonacell-HY Medium E (StemCell Technologies) using a Clonepix 2 (Molecular Devices, Sunnyvale, CA) and screened for TMEM106B reactivity 5 days later. 1205 hybridomas were obtained.

Example 5: Primary Screening of Anti-TMEM106B Hybridomas

Initial screening of the anti-TMEM106B hybridomas was performed as follows. Tissue culture supernatants from 1205 hybridomas obtained were initially screened for their ability to differentially bind human TMEM106B transiently-transfected HEK293 cells by comparing the extent of binding to parental (non-transfected) HEK293 cells compared to transfected cells. TMEM106B over-expressing cells were produced via transient transfection of HEK293 cells using the lipofectamine system, according to the manufacturer's protocol with modifications as described above in Example 1. To ensure reproducibility across screening experiments, a large bank of transfected cells (~1×109) was prepared in a single round of transient transfection, and aliquoted and frozen for all further screening experiments.

For screening of the hybridoma cell culture supernatants, humanTMEM106B-transfected HEK293 cells were aliquoted in 96-well round bottom plates (2×105 cells per well) and incubated with 50 µL of hybridoma cell culture supernatant on ice for 30 minutes. After this primary incubation, the supernatant was removed via centrifugation, the cells were washed twice with 175 µL of ice-cold FACS buffer (PBS+1% FBS+2 mM EDTA), and then further incubated on ice for 20 minutes with anti-mouse IgG Fc-APC (Jackson Labs, Cat #115-136-071) (diluted 1:500). Following this secondary incubation, the cells were again washed twice with ice-cold FACS buffer and resuspended in a final volume of 30 µL of FACS buffer+0.25 µl/well propidium iodide (BD Biosciences Cat #556463). Cell sorting was performed on a FACS Canto system (BD Biosciences) or iQue (Intellicyt), with sort gates drawn to exclude dead (i.e., propidium iodide-positive) cells. Median fluorescence intensity (MFI) of anti-mouse-APC MFI on TMEM106B+HEK293 cells was calculated for each clone, and those displaying a signal of at least 2-fold over background compared to a secondary-antibody only well were taken forward for further analysis and characterization.

The 1205 hybridoma clones identified above were tested across 3 rounds of fusions. A total of 53 clones were identified that displayed greater than 2-fold difference in binding to TMEM106B-transiently transfected HEK293 cells compared to negative controls (e.g., using non-specific supernatants, media-only, secondary-antibody only). Of these 53 hybridoma clones, 32 were obtained from Fusion A, 18 were obtained from Fusion B, and 3 were obtained from Fusion C. These clones were named as anti-TMEM106B antibodies TM-1 to TM-53 and further characterized as described below.

Example 6: Anti-TMEM106B Antibody Cross-Reactivity Screen

Anti-human TMEM106B antibody positive clones obtained from the initial rounds of sorting as described above were screened for cross-reactivity to mouse TMEM106B and cynomolgus (cyno) TMEM106B using a method similar to that used in the initial screen, but using HEK293 cells overexpressing either murine TMEM106B or cynomolgus TMEM106B, as well as parental HEK293 cells as a negative control. The anti-TMEM106B antibodies from the hybridoma clones were binned as human/mouse/cyno cross-reactive, human-only, human/mouse cross-reactive, and human/cyno cross-reactive based on the results of this screen. Results of this cross-reactivity screen are shown below in Table 1; the data is presented as fold-change in binding to HEK293 cells transiently transfected with either human TMEM106B (hu), cyno TMEM106B, or mouse TMEM106B (mo) over binding to the parental HEK293 cells.

TABLE 1

| | huTMEM106B | cynoTMEM106B | moTMEM106B |
|---|---|---|---|
| TM-1 | 4.72 | 11.73 | 4.61 |
| TM-2 | 9.84 | 32.30 | 17.47 |
| TM-3 | 24.38 | 40.46 | 29.24 |
| TM-4 | 1.13 | 2.08 | 1.97 |
| TM-5 | 11.39 | 37.05 | 26.61 |
| TM-6 | 4.13 | 1.25 | 1.25 |
| TM-7 | 17.51 | 47.49 | 15.54 |
| TM-8 | 2.10 | 2.62 | 1.63 |
| TM-9 | 10.71 | 22.28 | 8.52 |
| TM-10 | 37.15 | 65.93 | 45.91 |
| TM-11 | 9.96 | 23.66 | 18.29 |
| TM-12 | 25.86 | 44.12 | 32.69 |
| TM-13 | 36.69 | 55.54 | 52.72 |
| TM-14 | 3.96 | 4.56 | 1.77 |
| TM-15 | 31.35 | 57.70 | 46.80 |
| TM-16 | 8.30 | 17.57 | 1.42 |
| TM-17 | 12.64 | 14.34 | 6.42 |
| TM-18 | 18.75 | 38.82 | 28.98 |
| TM-19 | 13.85 | 34.90 | 35.96 |
| TM-20 | 8.05 | 26.54 | 2.34 |
| TM-21 | 29.78 | 48.85 | 46.47 |
| TM-22 | 4.17 | 9.72 | 3.61 |
| TM-23 | 7.09 | 12.21 | 4.46 |
| TM-24 | | Not determined | |
| TM-25 | 13.01 | 21.40 | 2.87 |
| TM-26 | 11.80 | 18.01 | 6.54 |
| TM-27 | 7.62 | 13.54 | 3.32 |
| TM-28 | 19.71 | 33.66 | 22.14 |
| TM-29 | 35.10 | 65.97 | 44.64 |
| TM-30 | | Not determined | |
| TM-31 | 22.13 | 64.72 | 68.73 |
| TM-32 | | Not determined | |
| TM-33 | 10.22 | 7.74 | 45.84 |
| TM-34 | 11.74 | 11.91 | 0.70 |
| TM-35 | 11.54 | 14.67 | 1.04 |
| TM-36 | 10.50 | 10.08 | 1.29 |
| TM-37 | 12.92 | 15.97 | 0.61 |
| TM-38 | 12.58 | 14.38 | 0.65 |
| TM-39 | | Not determined | |
| TM-40 | 7.59 | 5.16 | 0.73 |
| TM 41 | 3.03 | 2.05 | 2.05 |
| TM-42 | 15.60 | 16.83 | 0.60 |
| TM-43 | 7.11 | 6.71 | 1.12 |
| TM-44 | 4.35 | 3.74 | 0.57 |
| TM-45 | 10.40 | 10.59 | 0.55 |
| TM-46 | 19.43 | 18.92 | 41.12 |
| TM-47 | 22.27 | 18.62 | 57.80 |
| TM-48 | 16.67 | 16.44 | 28.47 |
| TM-49 | 15.59 | 13.76 | 21.32 |
| TM-50 | 16.02 | 17.77 | 17.51 |
| TM-51 | 11.74 | 11.36 | 11.87 |
| TM-52 | 17.29 | 22.59 | 0.67 |
| TM-53 | | Not determined | |

These results indicated that the isolated anti-TMEM106B antibodies obtained are specific for the TMEM106B protein and are generally cross-reactive to TMEM106B proteins of human, mouse, and cyno origin. In general, the anti-TMEM106B antibodies displayed a high-degree of human and cyno cross-reactivity, as predicted based on the very high homology of these proteins. Cross-reactivity to mouse TMEM106B protein was also high (24/31 clones) from the clones obtained from Fusion A (TM1-TM32) in which TMEM106B knockout mice were used for immunizations. Clones from Fusion B (TM33-TM49) and Fusion C (TM50-TM52), in which wildtype (TMEM106B+/+) mice were used for immunizations, had a much lower percentage of clones (8/20) showing strong mouse cross-reactivity.

Example 7: Anti-TMEM106B ELISA Screen

Anti-TMEM106B hybridoma supernatants were tested for binding to recombinantly produced GST-TMEM106B-truncated protein (SEQ ID NO:321) protein using an enzyme-linked immunosorbent assay (ELISA). Briefly, 96-well polystyrene plates were coated with 1-10 µg/ml of recombinant GST-TMEM106B-truncated protein or GST (Pierce) in PBS either at 370C for 1-4 hours or overnight at 40C. Coated plates were then blocked with 5% BSA for 1-hour, washed 3×150 µL in TBST (Tris-buffered saline+ 0.1% Tween20), and then the antibodies were added at various dilutions (100-1000×) in PBS. After 1-hour incubation (room temperature, with shaking), the plates were washed 3×150 µL in TBST. A secondary anti-mouse HRP antibody (Jackson Immunoresearch Cat #115-035-003) added at a 1:1000 dilution in TBST (100 µl/well) and incubated for 30 minutes at room temperature with shaking. After a final set of washes (3×150 µL in TBST), 100 µL of peroxidase substrate was added for 1 minute; the reaction was then quenched with 2N sulfuric acid (100 µL). The quenched reaction wells were detected for absorbance at 650 nm with a BioTek Synergy Microplate Reader using GEN5 2.04 software.

Of the 53 anti-TMEM106B positive hybridoma clones identified, supernatants from 29 hybridoma clones displayed strong binding to the GST-TMEM106B truncated protein (i.e., the extent of binding was the same at 100× and 1000× diluted supernatant); supernatants from 2 hybridoma clones displayed low binding; and supernatants from 18 hybridoma clones did not bind to the GST-TMEM106B-truncated protein. Binding data for supernatants from 4 hybridoma clones was not determined. These binding results were not unexpected, as the truncated version of TMEM106B used in this screen does not contain the last 64 amino acid residues of the C-terminal portion of the human TMEM106B protein; accordingly, the binding sites of the 18 non-binders may not have been present on this particular TMEM106B-truncated protein. None of the anti-TMEM106B hybridoma supernatants tested bound GST at any concentration. The results of the ELISA binding experiments are shown below in Table 2.

TABLE 2

| Strong binding | Low binding | No binding detected | Not determined |
|---|---|---|---|
| TM-1, TM-2, TM-3, TM-5, TM-7, TM-9, TM-10, TM-11, TM-12, TM-13, TM-17, TM-18, TM-19, TM-21, TM-22, TM-23, TM-25, TM-26, TM-27, TM-28, TM-29, TM-32, TM-35, TM-37, TM-39, TM-40, TM-42, TM-46, TM-48 | TM-16, TM-20 | TM-4, TM-6, TM-8, TM-14, TM-15, TM-31, TM-33, TM-34, TM-36, TM-41, TM-44, TM-45, TM-47, TM-49, TM-50, TM-51, TM-52, TM-53 | TM-24, TM-30, TM-38, TM-43, |

Example 8: Anti-TMEM106B Screen on TMEM106B Natively-Expressing Cell Lines

Anti-human TMEM106B antibody hybridoma clones identified from the initial rounds of sorting were also screened for their ability to bind TMEM106B natively-expressed on human-derived cell lines. The following human-derived cell lines were used for these studies: human adenocarcinoma line HeLa (ATCC CTL-2), human glioblastoma cell line U251 (Sigma 09063001), mouse Neuroblastoma cell line Neuro2a (ATCC CCL-131), and A549 human lung carcinoma line (ATCC CCL-185).

HeLa cells, U251 cells, and Neuro2a cells were cultured in Eagle's Minimum Essential Media (EMEM, ATCC #30-2003)+10% FBS (fetal bovine serum); A549 cells were cultured in DMEM+10% FBS. All cells were cultured in either T75 or T150 flasks. When the cells reached >80% confluence, they were detached from the flasks using trypsin-EDTA (ThermoFischerScientific Cat #25200056) at 37° C. for 10 minutes. The enzyme was quenched by addition of fresh media, and the cells were then distributed into 96-well plates for FACS analysis.

FACS analysis was performed as follows. Each cell type was aliquoted in 96-well round bottom plates (2×105 cells per well), washed once with FACS buffer (PBS+2% FBS+1 mM EDTA), and incubated with 50 μL of hybridoma supernatant or purified antibody (10 μg/ml in FACS buffer) on ice for 1 hour. After this primary incubation, the supernatant was removed via centrifugation, the cells were washed 2× with 150 μL of ice-cold FACS buffer, and then incubated on ice for 30 minutes with anti-mouse APC (Jackson Labs #115-136-071), diluted 1:200. Following this secondary incubation, the cells were again washed 2× with ice-cold FACS buffer and resuspended in a final volume of 50 μL of FACS buffer+0.25 μl/well propidium iodide (Fisher Scientific #BDB556463). Analysis was performed on a FACSCanto system (BD Biosciences) or iQue (Intellicyt), with sort gates drawn to exclude dead (i.e., propidium iodide positive) cells.

The results of the FACS analysis of the anti-TMEM106B antibodies binding to HeLa cells, U251 cells, Neuro2a cells, and A549 cells which natively express human TMEM106B is shown below in Table 3. Data is presented as mean fluorescence intensity (MFI).

TABLE 3

| Clone name | HeLa MFI | U251 MFI | Neuro2a MFI | A549 MFI |
|---|---|---|---|---|
| TM-1 | 253 | 244 | 253 | 1456.5 |
| TM-2 | 2533 | 1406.5 | 2899 | 1887 |
| TM-3 | 2688 | 1079 | 1980.5 | 1797 |
| TM-4 | 323 | 349 | 325 | 916 |
| TM-5 | 1737 | 866 | 1612 | 1174 |
| TM-6 | 520 | 304 | 371 | 1095 |
| TM-7 | 1066 | 442 | 1205 | 647 |
| TM-8 | 568.5 | 304 | 370 | 554 |
| TM-9 | 2535 | 1544 | 2710 | 1994 |
| TM-10 | 596 | 328 | 604 | 823 |
| TM-11 | 1872 | 866 | 1045 | 1342 |
| TM-12 | 2665 | 1331 | 3037 | 1938 |
| TM-13 | 1376 | 787 | 927 | 1265 |
| TM-14 | 307 | 270 | 300 | 896 |
| TM-15 | 659.5 | 382 | 470 | 938 |
| TM-16 | 548 | 292 | 392 | 605 |
| TM-17 | 437 | 305 | 385 | 953 |
| TM-18 | 1919 | 874 | 1933.5 | 1489 |
| TM-19 | 2429 | 878 | 2145 | 1817 |
| TM-20 | 302 | 250 | 358 | 1603 |
| TM-21 | 1197.5 | 671.5 | 706 | 1026 |
| TM-22 | 408 | 313 | 400 | 1566 |
| TM-23 | 308 | 278 | 333 | 1089 |
| TM-24 | Not determined | | | |
| TM-25 | 2559.5 | 1108 | 354 | 1704 |
| TM-26 | 384 | 300 | 324 | 952.5 |
| TM-27 | 2958.5 | 1315 | 1584 | 1934 |
| TM-28 | 2793 | 998 | 2738 | 2001.5 |
| TM-29 | 1649 | 730 | 1483 | 1414 |
| TM-30 | Not determined | | | |
| TM-31 | 799 | 352 | 325 | |
| TM-32 | Not determined | | | |
| TM-33 | 148.5 | 202 | 233 | 298 |
| TM-34 | 225 | 393 | 202 | 856 |
| TM-35 | 241 | 370 | 181 | 982.5 |
| TM-36 | 256 | 336 | 206 | 1025.5 |
| TM-37 | 254 | 408 | 208 | 1041 |
| TM-38 | 542 | 657 | 214 | 1193.5 |
| TM-39 | Not determined | | | |
| TM-40 | 174 | 279 | 203 | 328 |
| TM-41 | 151 | 183 | 225 | 284 |
| TM-42 | 215 | 326 | 237 | 947 |
| TM-43 | 162 | 273 | 220 | 698 |
| TM-44 | 168 | 521.5 | 202 | 392 |
| TM-45 | 191 | 517 | 187 | 819 |
| TM-46 | 219 | 313 | 256 | 606 |
| TM-47 | 189 | 366 | 328 | 646 |
| TM-48 | 219 | 346 | 292 | 677 |
| TM-49 | 187 | 434 | 291 | 923.5 |
| TM-50 | 159 | 260 | 257 | 580 |
| TM-51 | 137 | 280 | 232 | 668 |
| TM-52 | 227 | 341 | 210.5 | 987 |
| Media-only | 149 | 165 | 220.5 | 154 |
| Negative ctrl #1 | 152 | 165 | 220 | 148 |
| Negative ctrl #2 | 149 | 165 | 235 | 162 |
| Negative ctrl #3 | 143 | 164 | 216 | 95 |
| secondary only | 148 | 182 | 239 | 178 |

Binding data using these cell lines which natively express TMEM106B confirmed the anti-TMEM106B antibody binding specificity. All TMEM106B-specific antibodies displayed increased binding on at least one of the above cell lines as compared to the binding observed using negative control antibodies which consistently showed low binding.

Binding to U251 cells (human) and Neuro2a cells (mouse) was also used as a proxy for binding to TMEM106B in the brain, as both of these cell lines derive from the brain: U251 cells derive from human astrocytoma, and Neuro2A cells derive from a neuronal lineage.

Example 9: Molecular Cloning of Anti-TMEM106B Hybridoma Antibodies

Anti-TMEM106B antibodies obtained from the hybridomas were subcloned as follows. 5×105 hybridoma cells were resuspended in 0.5 ml Trizol solution (Thermo Fisher Scientific, cat #15596026). Total RNA was extracted from the cells by chloroform extraction and ethanol precipitation. cDNA was generated by using Clontech's SMARTer® RACE 5'/3' Kit (Takara Bio USA Inc, Cat. No. 634859) following the manufacturer's protocol. Variable heavy and light immunoglobulin regions were cloned separately by touchdown PCR using the 5' UPM primer provided in the RACE kit and heavy chain constant region primer (5'-AGCTGGGAAGGTGTGCACA-3') [SEQ ID NO:322] and light constant region primer (5'-CCATTTTGTCGTT-CACTGCCA-3') [SEQ ID NO:323]. PCR products were purified by QIAquick PCR Purification Kit (QIAGEN, Cat No. 28106) and ligated into a pCR2.1®-TOPOR cloning vector (TOPOR TA cloning Kit, Invitrogen) and transformed into ONESHOT® TOP10 Competent cells. Transformed *Escherichia coli* (*E. coli*) colonies were isolated and the variable heavy chain (VH) and variable light chain (VL) nucleic acids were sequenced for each corresponding hybridoma cell line. Following the sequence determination, variable heavy chain regions and variable light chain regions were amplified by PCR using primers containing endonuclease restriction sites (BsrGI and BstEII for HV and BssHII and BsiWI for LV) and subcloned into pJG mammalian expression vector (Alector Inc.) encoding human IgG1 and IgGK, respectively.

Example 10: Production of Recombinant Anti-TMEM106B Antibodies

Purified hybridoma-derived anti-TMEM106B antibodies were purified using Protein A from hybridoma supernatants after culturing the hybridomas in low-IgG or chemically defined media. Some of the anti-TMEM106B antibodies were also produced via direct cloning of the variable gene regions obtained from the hybridomas into a recombinant expression plasmid for production of chimeric antibodies containing a human Fc domain (human IgG1). The expression plasmids were transiently transfected into Expi293 cells and the resulting anti-TMEM106B antibodies purified via Protein A. Recombinant production of anti-TMEM106B antibodies was performed as follows.

Expression plasmids containing nucleic acid encoding the anti-TMEM106B antibody VH and VL chains used for recombinant antibody expression in Expi293 cells. Transfection of expression plasmids was carried out using the Expifectamine-293 system (ThermoFischerScientific Cat #A14524) according to the manufacturer's protocol. Briefly, for each anti-TMEM106B antibody, 12 μg of light chain plasmid DNA and 18 μg of heavy chain plasmid DNA was diluted into 1.5 mL OptiMEM (ThermoFischerScientific Cat #31985070), to which was added 80 μL of Expifectamine reagent. The resulting solution was mixed and incubated at room temperature for 30 minutes prior to addition to 30 mL of Expi293 cells (ThemoFischerScientific A14527) in Expi293 expression media (ThermoFischerScientific Cat #A1435101) in 125 mL flasks (Fischer Scientific FIS #PBV12-5). The cells were cultured to approximately 3×10^6 cells/ml prior to transfection. Culture conditions for Expi293 cells were 370C/8% CO2 with orbital shaking at 125 rpm. 16-24 hours after transfection, 150 μL of Expi-Fectamine™ 293 Transfection Enhancer 1 and 1.5 mL of ExpiFectamine™ 293 Transfection Enhancer 2 were added to each flask to enhance recombinant antibody yield. Culture supernatants were harvested 5-7 days after transfection, filtered (0.2 micron), and purified via Protein A chromatography.

Example 11: Antibody Heavy Chain and Light Chain Variable Domain Sequences

Sequences were determined for 48/53 of the positive hybridoma anti-TMEM106B antibodies identified in the primary screen. Using standard techniques, the amino acid sequences encoding the light chain variable regions and the heavy chain variable regions of the generated antibodies were determined. The Kabat light chain CDR sequences and heavy chain CDR sequences of the antibodies are set forth in Table 4A below. The light chain variable region and heavy chain variable region sequences of the antibodies are set forth in Table 4B below.

TABLE 4A

Antibody CDR sequences

| Clone ID | CDR-H1 | CDR-H2 | CDR-H3 | CDR-L1 | CDR-L2 | CDR-L3 |
|---|---|---|---|---|---|---|
| TM-1 | NYL1E SEQ ID NO: 3 | VINPGSGGTKYN EKLKG SEQ ID NO: 36 | RGYTIYDFYA MDY SEQ ID NO: 79 | RSSQSIVYNNG NTYLE SEQ ID NO: 121 | KVSNRFS SEQ ID NO: 161 | FQVSHVPFT SEQ ID NO: 186 |
| TM-2 | EYPMEE SEQ ID NO: 4 | MIYTNTGEPTYA AEFKG SEQ ID NO: 37 | AGY SEQ ID NO: 80 | RASSSVSYIH SEQ ID NO: 122 | ATSNLAS SEQ ID NO: 162 | QQWSSNPST SEQ ID NO: 187 |
| TM-3 | TLGRG VG SEQ ID NO: 5 | KIWWNDDKFYY PALKS SEQ ID NO: 38 | IAGGTGAAY SEQ ID NO: 81 | RSSKSLLHSNG ITYLY SEQ ID NO: 123 | QMSSLAS SEQ ID NO: 163 | AQNLELPWT SEQ ID NO: 188 |
| TM-4 | DYYMN SEQ ID NO: 6 | VINPYNGGTSYH QKFKG SEQ ID NO: 39 | AATVVAGFD Y SEQ ID NO: 82 | RSSTGAVTTSN YAN SEQ ID NO: 124 | GTNNRAP SEQ ID NO: 164 | VLWYSNHLV SEQ ID NO: 189 |

TABLE 4A-continued

Antibody CDR sequences

| Clone ID | CDR-H1 | CDR-H2 | CDR-H3 | CDR-L1 | CDR-L2 | CDR-L3 |
|---|---|---|---|---|---|---|
| TM-5 | TYGIT SEQ ID NO: 7 | EIYPRSDNTYYN EKFKD SEQ ID NO: 40 | SKGSGTGDY SEQ ID NO: 83 | RASENIYIYLA SEQ ID NO: 125 | NGKMLAE SEQ ID NO: 165 | QHHYGSPPA SEQ ID NO: 190 |
| TM-6 | EYTIH SEQ ID NO: 8 | WFYPGSTYIDYN EKFKD SEQ ID NO: 41 | HEEDYSNWF PF SEQ ID NO: 84 | KASDHINNWL A SEQ ID NO: 126 | GATSLET SEQ ID NO: 166 | QQYWSSPYT SEQ ID NO: 191 |
| TM-7 | DYYIH SEQ ID NO: 9 | LVYPYNGDTDY NQKFKG SEQ ID NO: 42 | TYYANSPDY SEQ ID NO: 85 | KSSQSLLNSGN QRNYLA SEQ ID NO: 127 | GASTRES SEQ ID NO: 167 | QNDHSYPLT SEQ ID NO: 192 |
| TM-8 | DYPMH SEQ ID NO: 10 | VIYTDTGEPKYA EVFKG SEQ ID NO: 43 | RLAY SEQ ID NO: 86 | KASQDINSYLS SEQ ID NO: 128 | RANRLVD SEQ ID NO: 168 | LQYDEFPLT SEQ ID NO: 193 |
| TM-9 | GYGMS SEQ ID NO: 11 | TISSGSFYIYYPD SVKG SEQ ID NO: 44 | QNFYYGCED Y SEQ ID NO: 87 | RSSKSLLHSNG ITYLY SEQ ID NO: 123 | QMSNLAS SEQ ID NO: 169 | AQNLELPWT SEQ ID NO: 188 |
| TM-10 | SYWMN SEQ ID NO: 12 | QIYPGDGDTNY NGKFKG SEQ ID NO: 45 | WGHYDEAM DD SEQ ID NO: 88 | RSSQSLVHSNG KTYLH SEQ ID NO: 129 | KISNRFS SEQ ID NO: 170 | SQITHVPWT SEQ ID NO: 194 |
| TM-11 | DYGVH SEQ ID NO: 13 | VIWNNGNTDYN AAFIS SEQ ID NO: 46 | SLRPLHFDY SEQ ID NO: 89 | KSSQSLLNSNN LQNYLA SEQ ID NO: 130 | FASIRES SEQ ID NO: 171 | QQHYNTPFT SEQ ID NO: 195 |
| TM-12 | DYYMY SEQ ID NO: 14 | RIDPEDGDAEYA PKFQG SEQ ID NO: 47 | RVIYDGYYRT MDC SEQ ID NO: 90 | RSSQTIVHSNG NTYLE SEQ ID NO: 131 | KISNRFS SEQ ID NO: 170 | FQGSHVPYT SEQ ID NO: 196 |
| TM-13 | TFPIE SEQ ID NO: 15 | NFHPYNDDTKY NEKFKG SEQ ID NO: 48 | YFYGGMDY SEQ ID NO: 91 | RASENIYSSLG SEQ ID NO: 132 | AATNLAD SEQ ID NO: 172 | QHLWSIPWT SEQ ID NO: 197 |
| TM-14 | NYLIE SEQ ID NO: 3 | VINPGGGNTDYS EKFKD SEQ ID NO: 49 | SPYSSYVGYA VDY SEQ ID NO: 92 | RASQDIGSNLN SEQ ID NO: 133 | ATSSLDS SEQ ID NO: 173 | LQYASSPRT SEQ ID NO: 198 |
| TM-15 | NYWIT SEQ ID NO: 16 | DIYPGSGNSNYN ESFKR SEQ ID NO: 50 | KAYGGFPY SEQ ID NO: 93 | RVSENIYNNLA SEQ ID NO: 134 | AATNLAD SEQ ID NO: 172 | QHFWDTPFT SEQ ID NO: 199 |
| TM-16 | DYYMEE SEQ ID NO: 17 | RIDPEDGETKYA PEFQG SEQ ID NO: 51 | SQPFTY SEQ ID NO: 94 | SASSSLNYMY SEQ ID NO: 135 | DTSNLAS SEQ ID NO: 174 | QQWTSFPPT SEQ ID NO: 200 |
| TM-17 | DYLIE SEQ ID NO: 18 | VINPGSGGTNYN EKFKG SEQ ID NO: 52 | SSYGVYVAY PMDY SEQ ID NO: 95 | RASQDIGSNLN SEQ ID NO: 133 | ATSSLDS SEQ ID NO: 173 | LQYASSPRT SEQ ID NO: 198 |
| TM-18 | DYYMN SEQ ID NO: 6 | NINPNNGDAFY NQKFKG SEQ ID NO: 53 | EGQLRLRRV YAMDY SEQ ID NO: 96 | RASKSVSISVY TYVH SEQ ID NO: 136 | LASNLES SEQ ID NO: 175 | QHSRELPYT SEQ ID NO: 201 |
| TM-19 | DYYMY SEQ ID NO: 14 | RIDPEDGDTENA PKFRG SEQ ID NO: 54 | RIGNLYHVM DY SEQ ID NO: 97 | RSSQSIVHSNG NTYLE SEQ ID NO: 137 | KVFNRFS SEQ ID NO: 176 | FQGSHVPFT SEQ ID NO: 202 |
| TM-20 | DYYMH SEQ ID NO: 17 | RIDPEDGETKYA PEFQG SEQ ID NO: 51 | SQPFTY SEQ ID NO: 94 | SASSSLNYMY SEQ ID NO: 135 | DTSNLAS SEQ ID NO: 174 | QQWTSFPPT SEQ ID NO: 200 |
| TM-21 | NYAMS SEQ ID NO: 19 | FISDGGGYIYYA DNVKD SEQ ID NO: 55 | DGGTGFTY SEQ ID NO: 98 | RSSKSLLHSNG ITYLF SEQ ID NO: 138 | QMSNLAS SEQ ID NO: 169 | VQNLELPYT SEQ ID NO: 203 |
| TM-22 | SYYIH SEQ ID NO: 20 | WIYPGNGITNYN EKFKG SEQ ID NO: 56 | PYYGIRNCYF DV SEQ ID NO: 99 | RSGQSIVHSNG NTYLE SEQ ID NO: 139 | KVSNRFS SEQ ID NO: 161 | FQGSHVPWT SEQ ID NO: 204 |
| TM-23 | NYLIE SEQ ID NO: 3 | VINPGSGITNYN EKFKG SEQ ID NO: 57 | SDFITTVVAD Y SEQ ID NO: 100 | RSSQSLTNYYG NTYLS SEQ ID NO: 140 | GISNRFS SEQ ID NO: 177 | LQGTHQPRT SEQ ID NO: 205 |

TABLE 4A-continued

Antibody CDR sequences

| Clone ID | CDR-H1 | CDR-H2 | CDR-H3 | CDR-L1 | CDR-L2 | CDR-L3 |
|---|---|---|---|---|---|---|
| TM-24 | DYGVH SEQ ID NO: 13 | VIWNNGNTDYN AAFIS SEQ ID NO: 46 | SLRPLHFDY SEQ ID NO: 89 | KSSQSLLNSNN QQNYLA SEQ ID NO: 141 | FASIRES SEQ ID NO: 171 | QQHYSTPFT SEQ ID NO: 206 |
| TM-25 | GYGMS SEQ ID NO: 11 | TISSGGRYTVYP DSVKG SEQ ID NO: 58 | DNFYSYAMD Y SEQ ID NO: 101 | RSSKSLLHSNG ITYLF SEQ ID NO: 138 | QMSNLAS SEQ ID NO: 169 | AQNLELWT SEQ ID NO: 207 |
| TM-26 | NYLIE SEQ ID NO: 3 | VINPGSGITNYN EKFKG SEQ ID NO: 57 | SDFITTVVAD Y SEQ ID NO: 100 | RSSQSLTNYYG NTYLS SEQ ID NO: 140 | GISNRFS SEQ ID NO: 177 | LQGTHQPRT SEQ ID NO: 205 |
| TM-27 | NYLIE SEQ ID NO: 3 | VINPGSGSTKYN EKFKG SEQ ID NO: 59 | IIYDHDWYED V SEQ ID NO: 102 | SASSSISYMY SEQ ID NO: 142 | RTSTLAS SEQ ID NO: 178 | QQHSYPRT SEQ ID NO: 208 |
| TM-28 | DYYIH SEQ ID NO: 9 | LVYPYNGGTNY NQNFKG SEQ ID NO: 60 | SYFSNPIGY SEQ ID NO: 103 | KSSQSLLNSGN QKNYLA SEQ ID NO: 143 | GASTRES SEQ ID NO: 167 | QNDHSYPLT SEQ ID NO: 192 |
| TM-29 | DYYIN SEQ ID NO: 21 | RIYPGSGYTYYN EKFKG SEQ ID NO: 61 | HYTNPFAY SEQ ID NO: 104 | RSSKSLLHYNG ITYLY SEQ ID NO: 144 | QMSNLAS SEQ ID NO: 169 | AQNLELPYT SEQ ID NO: 209 |
| TM-30 | NYDVN SEQ ID NO: 22 | WIYPRDGTTIYN EKFKG SEQ ID NO: 62 | TLPQAMDY SEQ ID NO: 105 | RSSQTIVHRNG NTYLE SEQ ID NO: 145 | KVSNRFS SEQ ID NO: 161 | FQGSHLPWT SEQ ID NO: 210 |
| TM-31 | SYWMN SEQ ID NO: 12 | YINPTSGYTRYN QKFKD SEQ ID NO: 63 | SPPTVVLIGYF DY SEQ ID NO: 106 | KASQDINSYLS SEQ ID NO: 128 | RGNGLVD SEQ ID NO: 179 | LQYDEFPFT SEQ ID NO: 211 |
| TM-32 | DYYMY SEQ ID NO: 14 | RIDPEDGDTEYV PKFQG SEQ ID NO: 64 | RTWDLYYAV DN SEQ ID NO: 107 | RSSQNIVHSNG NTYLE SEQ ID NO: 146 | KVSNRFS SEQ ID NO: 161 | FQGSHVPFT SEQ ID NO: 202 |
| TM-33 | DYNMN SEQ ID NO: 23 | VINPNYGTTSYN QKFKG SEQ ID NO: 65 | SY SEQ ID NO: 108 | KASQNVGTAV A SEQ ID NO: 147 | SASNRYT SEQ ID NO: 180 | QQYSSYPYT SEQ ID NO: 212 |
| TM-34 | DSGMD SEQ ID NO: 24 | YISSGSSTTHYA DTVKG SEQ ID NO: 66 | RDGNYWYFD V SEQ ID NO: 109 | RATSSVTYMH SEQ ID NO: 148 | ATSNLAS SEQ ID NO: 162 | QQWSSNPYT SEQ ID NO: 213 |
| TM-35 | RHWMQ SEQ ID NO: 25 | EILPGSNNIYYN EKVKG SEQ ID NO: 67 | SLYDYDGVF AY SEQ ID NO: 110 | RSSQSIVHRNG NTYLE SEQ ID NO: 149 | KVSNRFS SEQ ID NO: 161 | FQGSHVPYT SEQ ID NO: 196 |
| TM-37 | SYWMH SEQ ID NO: 26 | YVNPSSGYTKN NQKFKD SEQ ID NO: 68 | EGGSISDWYF DV SEQ ID NO: 111 | RSSKSLLHSNG NTYSY SEQ ID NO: 150 | RMSNLAS SEQ ID NO: 181 | MQHLEYPYT SEQ ID NO: 214 |
| TM-39 | DYWMH SEQ ID NO: 27 | FINPSSGYTKYN QNFKD SEQ ID NO: 69 | EAGSISDWYF DV SEQ ID NO: 112 | RSSKTLLNSNG NTYLY SEQ ID NO: 151 | RMSNLAS SEQ ID NO: 181 | MQHLDYPYT SEQ ID NO: 215 |
| TM-41 | DCYMH SEQ ID NO: 28 | RIDPEDGTTNFA PKFQD SEQ ID NO: 70 | EWDSGAY SEQ ID NO: 113 | KSSQSLLYSSN QKNYLA SEQ ID NO: 152 | WASTRES SEQ ID NO: 182 | QQYSYPYT SEQ ID NO: 216 |
| TM-42 | NYWMH SEQ ID NO: 29 | YINPSSGYTKYN QKFKD SEQ ID NO: 71 | EGGSISDWYF DV SEQ ID NO: 111 | RSSKSLLHSNG NTYLY SEQ ID NO: 153 | RMSNLAS SEQ ID NO: 181 | MQHLEYPYT SEQ ID NO: 214 |
| TM-44 | DYGMH SEQ ID NO: 30 | YISSGSSTIYYAD TVKG SEQ ID NO: 72 | NYGSPYAMD Y SEQ ID NO: 114 | KSSQSLLYSSN QKNYLA SEQ ID NO: 152 | WASTRES SEQ ID NO: 182 | QQYYSYPT SEQ ID NO: 217 |

TABLE 4A-continued

Antibody CDR sequences

| Clone ID | CDR-H1 | CDR-H2 | CDR-H3 | CDR-L1 | CDR-L2 | CDR-L3 |
|---|---|---|---|---|---|---|
| TM-45 | NYWMH SEQ ID NO: 29 | YINPSSGYTKYN QKFKD SEQ ID NO: 71 | EGGSISDWYF DV SEQ ID NO: 111 | RSSKSLLHSNG NTYLY SEQ ID NO: 153 | RMSNLAS SEQ ID NO: 181 | MQHLEYPYT SEQ ID NO: 214 |
| TM-46 | SFWMN SEQ ID NO: 31 | QIYPGDGDTDY NGKFKD SEQ ID NO: 73 | GDGFSYFDY SEQ ID NO: 115 | CASSRVNYMH SEQ ID NO: 154 | DTSKLAS SEQ ID NO: 183 | QQWSSNPPT SEQ ID NO: 218 |
| TM-47 | NYGVH SEQ ID NO: 32 | VIWAGGNTNYN SALMS SEQ ID NO: 74 | EAKLLRSYA MDY SEQ ID NO: 116 | KSSQSLLNSGN QKNYLT SEQ ID NO: 155 | WASTRES SEQ ID NO: 182 | QNDYSYPLT SEQ ID NO: 219 |
| TM-48 | SYDIN SEQ ID NO: 33 | WIYPRDGNTQYI EKLKG SEQ ID NO: 75 | WIFYAMDY SEQ ID NO: 117 | RSSQSIVHGNG NTYLE SEQ ID NO: 156 | KVSNRFS SEQ ID NO: 161 | FQGSHLPYT SEQ ID NO: 220 |
| TM-49 | RFWMH SEQ ID NO: 34 | NIDPSDSQTHYN QKFKD SEQ ID NO: 76 | LITVDYAMD Y SEQ ID NO: 118 | SASSSVSYMY SEQ ID NO: 157 | RTSNLAS SEQ ID NO: 184 | QQYHSYPPT SEQ ID NO: 221 |
| TM-50 | NYGVH SEQ ID NO: 32 | VIWAGGNTNYN SALMS SEQ ID NO: 74 | EAKLLRSYA MDY SEQ ID NO: 116 | RASQDINNYLY SEQ ID NO: 158 | YTSMLHS SEQ ID NO: 185 | QQGSTLMYT SEQ ID NO: 222 |
| TM-51 | TYWID SEQ ID NO: 35 | NMFPGSSRTNY NEKFKS SEQ ID NO: 77 | KEGLWTYGY DGGAWFAY SEQ ID NO: 119 | KSSQSLRNSRT RKNYLA SEQ ID NO: 159 | WASTRES SEQ ID NO: 182 | KQSYNLLT SEQ ID NO: 223 |
| TM-52 | NYWMH SEQ ID NO: 29 | NIDPSDSETHYN QKFKD SEQ ID NO: 78 | RGYYGRSPFA Y SEQ ID NO: 120 | SASSSVSYMH SEQ ID NO: 160 | DTSKLAS SEQ ID NO: 183 | FQGSGYPLT SEQ ID NO: 224 |

TABLE 4B $V_H$ and $V_L$ sequences

| Clone ID | $V_H$: | $V_L$: |
|---|---|---|
| TM-1 | QVQLQQSGAELVRPGTSVKVSCKASGYAFTNYLIEW VKQRPGQGLEWIGVINPGSGGTKYNEKLKGKATLTA DKSSSTAYMQLSSLTSVDSAVYFCARRGYTIYDFYA MDYWGQGTSVTVSS (SEQ ID NO: 225) | DVLMTQTPLSLPVSLGDHASISCRSSQSIVYN NGNTYLEWYLQKPGQSPKLLIYKVSNRFSGVP DRFSGSGSGTDFTLKISRVEAEDLGVYYCFQV SHVPFTFGSGTKLEEK (SEQ ID NO: 269) |
| TM-2 | HIQLVQSGPELKKPGETVKISCKASGYTFTEYPMEE WVKQAPGKGFRWMGMIYTNTGEPTYAAEFKGRFAFS LETSASTGYLQINNLKNEDSATYFCVTAGYWGQGTL VTVSA (SEQ ID NO: 226) | QIVLTQSPAILSASPGEKVTMTCRASSSVSYI HWFLQKPGSSPKPWIYATSNLASGVPFRFIGS GSGTSYSLTISGVEAEDSATYYCQQWSSNPST GFAGTKLELK (SEQ ID NO: 270) |
| TM-3 | QVTLKESGPGIVQPSQTLSLTCSFSGFSLNTLGRGV GWIRQPSGKGLEWLAKIWWNDDKFYYPALKSRLTIS KDTSKNQIFLKIANVDTADSATYYCARIAGGTGAAY WGQGTTLTVSS (SEQ ID NO: 227) | DIVMTQAAFSNPVTLGTSASISCRSSKSLLHS NGITYLYWYLQKPGQSPQLLISQMSSLASGVP DRFSSGGSGTDFTLRISRVEAEDVGVFYCAQN ELLPWTFGGGTKLELK (SEQ ID NO: 271) |
| TM-4 | EVQVQQSGPVLVKPGASVKMSCKASGYTFTDYYMNW VKQSHGKNLEWIGVINPYNGGTSYHQKFKGKATLTV DKSSSTAYMELNSLTSEDSAVYYCARAATVVAGFDY WGQGTTLTVSS (SEQ ID NO: 228) | QAVVTQESALTTSPGETVTLTCRSSTGAVTTS NYANWVQEKPDHLFTGLIGGTNNRAPGVPARF SGSLIGDKAALTITGAQTEDEAIYFCVLWYSN HLVFGGGTKLTVL (SEQ ID NO: 272) |
| TM-5 | QVQLQQSGTELARPGASVKVSCKASGYIFTTYGITW VKQRGGQGLEWIGEIYPRSDNTYYNEKFKDKATLTA DKSSSTAYMELRSLTSEDSAVYFCARSKGSGTGDYW GQGTTVTVSS (SEQ ID NO: 229) | DIQMTQSPASLSASVGETVTITCRASENIYIY LAWYQQKQGKTPQLLVYNGKMLAENVPSRFSG SGSGTQFSLKINSLQPEDFGSYYCQHHYGSPP AFGAGTKLELK (SEQ ID NO: 273) |

TABLE 4B-continued

V$_H$ and V$_L$ sequences

| Clone ID | V$_H$: | V$_L$: |
|---|---|---|
| TM-6 | QVQLQQSGAELVKPGASVKLSCKASGYTFTEYTHEW VKQRSGQGLEWIGWFYPGSTYEDYNEKFKDKATLTA DKSSSTVYLELSRLTSEDSAVYFCARHEEDYSNWFP FWGQGTLVTVSA (SEQ ID NO: 230) | DIQMSQSSSYLSVSLGGRVTITCKASDHINNW LAWYQQKPGNAPRLLISGATSLETGVPSRFSG SGSGKDYTLSITSLQTEDVATYYCQQYWSSPY TFGGGTKLEIK (SEQ ID NO: 274) |
| TM-7 | EVQLQQSGPVLVKPGPPVKISCKASGFTFTDYYIHW VKLSHGKSLEWIGLVYPYNGDTDYNQKFKGKATLTV DTSSSTAYMELNSLTSEDSAVYYCARTYYANSPDYW GQGTTVTVSS (SEQ ID NO: 231) | DIVMTQSPSSLSVSAGEKVTMSCKSSQSLLNS GNQRNYLAWYQQKPGQPPKLLIYGASTRESGV PDRFTGSGSGTDFTLTISNVQAEDLAVYYCQN DHSYPLTFGAGTKLELK (SEQ ID NO: 275) |
| TM-8 | QIQLVQSGPELKKPGETVKISCKASGYTFTDYPMHW VKQAPGKGFKWMGVIYTDTGEPKYAEVFKGRFAFSL ETSASTAYLQINNLKNEDTATYFCVRRLAYWGQGTL VTVSA (SEQ ID NO: 232) | DIKMTQSPSSMYASLGERVTITCKASQDINSY LSWFQQKPGKSPKTLIFRANRLVDGVPSRFSG SGSGQDYSLTISSLEYEDMGIYYCLQYDEFPL TFGAGTKLEMK (SEQ ID NO: 276) |
| TM-9 | EVQLVESGGDLVKPGGSLKLSCVASGFTFSGYGMSW VRQTPDKRLEWVATISSGSFYIYYPDSVKGRLTVSR DNAKNTLYLQMSSLKSEDTAIYYCARQNFYYGCEDY WGQGTTLTVSS (SEQ ID NO: 233) | DIVMTQAAFSNPVTLGTSASISCRSSKSLLHS NGITYLYWYLQKPGQSPQLLIYQMSNLASGVP NRFSSSGSGTDFTLRISRVEAEDVGVYYCAQN LELPWTFGGGTKLEIK (SEQ ID NO: 277) |
| TM-10 | QVQLQQSGAELVKPGASVKISCKGSGYAFSSYWMNW VKQRPGKGLEWIGQIYPGDGDTNYNGKFKGKATLTA DKSSTTAYIEILSSLTSEDSAVYFCARWGHYDEAMD DWGQGTSVTVSS (SEQ ID NO: 234) | DVVMTQTPLSLPVSLGDQASISCRSSQSLVHS NGKTYLHWYVQKPGQSPKLLIYKISNRFSGVP DRFSGSGSGTDFTLKISRVEAEDLGVYFCSQI THVPWTFGGGTKLESK (SEQ ID NO: 278) |
| TM-11 | QVQLKQSGPGQVQPSQSLSITCTVSGFSLSDYGVHW VRQSPGKGLEWLGVIWNNGNTDYNAAFISRLSINKD NSKSQVFFKMTSLQADDTAIYYCVRSLRPLIEFDYW GQGTTVTVSS (SEQ ID NO: 235) | DIVMTQSPSSLTMSVGQKVTMEECKSSQSLLN SNNLQNYLAWYQQKPGQSPTLLVYFASIRESG VPDRFIGSGSGTDFTLTISSVQAEDLADYFCQ QHYNTPFTFGSGTKLEIR (SEQ ID NO: 279) |
| TM-12 | EVQLQQSGAELMRPGASVKLSCTASGFNIQDYYMYW VKQRPEQGLEWIGRIDPEDGDAEYAPKFQGKATMTA DTSSNTAYLQLSSLTSEDTAVYYCSTRVIYDGYYRT MDCWGQGTSVTVSS (SEQ ID NO: 236) | DVLMTQIPLSLPVSLGDQASISCRSSQTIVHS GNNTYLEWYLKKPGQSPKLLEDKISNRFSGVP DRFSGSGSGTDFTLKISRVEAEDLGVYYCFQG HSVPYTFGGGTKLEIK (SEQ ID NO: 280) |
| TM-13 | QVQLQQSGAELVKPGASVKMSCKASGYTETTFPIEW MKQSHGKGLEWIGNFHPYNDDTKYNEKFKGKATLTV DKSSSTVYLDLSRLTSDDSAVYYCARYFYGGMDYWG QGTSVTVSS (SEQ ID NO: 237) | DIQMTQSPASLSVSVGETVTITCRASENIYSS LGWYQQKQGESPQLLVFAATNLADGVPSRFSG SGSGTQYSLKINSLQSEDFGTYYCQHLWSIPW TFGGGTRLEIK (SEQ ID NO: 281) |
| TM-14 | QVQLQQSGPELVRPGTSVKVSCKASGYAFTNYLIEW VKQRPGQGLEWIGVINPGGGNTDYSEKFKDKATLTA DKSSSNTAYIQLSSLTSEDSAVYFCARSPYSSYVGYA VDYWGQGTSVTVSS (SEQ ID NO: 238) | DIQMTQSPSSLSASLGERVSLTCRASQDIGSN LNWLQQEPDGTEKRLIYATSSLDSGVPKRFSG SRSGSDYSLTISSLESEDFVVYYCLQYASSPR TFGGGTRLEIK (SEQ ID NO: 282) |
| TM-15 | QVQLQQPGAEFVRPGASVKLSCKASGYTFTNYWITW VKQRPGHGLEWIGDIYPGSGNSNYNESFKRKATLTV DTSSSTAYMEELSSQTSEDSAVYFCARKAYGGFPYW QGGTLVTVSA (SEQ ID NO: 239) | DIQMTQSPASLSVSVGETVTITCRVSENIYNN LAWYQQKPEKSPQLLVFAATNLADGVPSRFSG SGSGTQFSLKINSLQSEDFGTYYCQHFWDTPF TFGSGTKLEIK (SEQ ID NO: 283) |
| TM-16 | EVQLQQSGAELVRPGASVKLSCTTSGENEKDYYMIE WVKQRTEQGLEWIGREDPEDGETKYAPEFQGKATIT SDTSSNTAFLQLSSLTSEDTAVYYCASSQPFTYWGQ GTLVTVSA (SEQ ID NO: 240) | QIVLTQSPAIMSASPGEKLTMTCSASSSLNYM YWYQQKPGSSPRLLIYDTSNLASGVPRFSGS GSGTSYSLTISRMEAEDGATYYCQQWTSFPPT FGAGTKLELK (SEQ ID NO: 284) |
| TM-17 | QVQLQQSGAELIRPGTSVKVSCKASGYAFTDYLIEW VKQRPGQGLEWIGVINPGSGGTNYNEKFKGKAKLTA DKSSSTAYMQLSSLTSEDSAVYFCVRSSYGVYAYP MDYWGQGTSVTVSS (SEQ ID NO: 241) | DIQMTQSPSSLSASLGERVSLTCRASQDIGSN NLWLQQEPDGTEKRLIYATSSLDSGVPKRFSG SRSGSDYSLTISSLESEDFVDYYCLQYASSPR TFGGGTKLEIK (SEQ ID NO: 285) |

TABLE 4B-continued

V$_H$ and V$_L$ sequences

| Clone ID | V$_H$: | V$_L$: |
|---|---|---|
| TM-18 | EVRLQQSGPELVKPGASVKISCKTSGYTFTDYYMNW<br>VKQSHGKSLEWIVNINPNNGDAFYNQKFKGKATLTV<br>DKSSNTAYLDLRSLTSEDSAVYYCAREGQLRLRRVY<br>AMDYWGQGTSVTVSS<br>(SEQ ID NO: 242) | DIVLAQSPASLAVSLGQRATISCRASKSVSIS<br>YVTYVHWYQQKPGQPPKLLIYLASNLESGVPA<br>RFSGSGSGTDFTLNIEEPVEEEDAATYYCQHS<br>RELPYTFGGGTKLEIK<br>(SEQ ID NO: 286) |
| TM-19 | DVQLQQSGAELVRPGASVKLSCTASGFNEKDYYMYW<br>VKQRPEQGLEWIGRIDPEDGDTENAPKFRGMATMTA<br>DTSSNTAYLQLNSLTSEDTAVYYCTTRIGNLYHVMD<br>YWGHGTSVTVSS<br>(SEQ ID NO: 243) | DVLMTQTPLSLPVSLGDQASISCRSSQSIVHS<br>NGNTYLEWYLQKPGQAPKLLIDKVFNRFSGVP<br>DRFSGSGSGTDFTLKISRVEAEDLGVYYCFQG<br>SHVPFTFGSGTKLEIK<br>(SEQ ID NO: 287) |
| TM-20 | EVQLQQSGAELVRPGASVKLSCTTSGENEKDYYMIE<br>WVKQRTEQGLEWIGREDPEDGETKYAPEFQGKATIT<br>SDTSSNTAFLQLSSLTSEDTAVYYCASSQPFTYWGQ<br>GTLVTVSA<br>(SEQ ID NO: 240) | QIVLTQSPAIMSASPGEKLTMTCSASSSLNYM<br>YWYQQKPGSSPRLLIYDTSNLASGVPVRFRGS<br>GSGTSYSLTISRMEAEDGATYYCQQWTSFPPT<br>FGAGTKLELK<br>(SEQ ID NO: 288) |
| TM-21 | EVQLVESGGGLVKPGGSLKLSCAASGFTFSNYAMSW<br>VRETPEKRLEWVAFISDGGGYIYYADNVKDRFTISR<br>DNAKNNLYLQMRHLKSEDTAMYYCARDGGTGFTYWG<br>QGTLVTVSV<br>(SEQ ID NO: 244) | DIVMTQAAFSNPVTLGTSASISCRSSKSLLHSN<br>GITYLFVVYLQKPGQSPQLLIYQMSNLASGVPD<br>RFSSSGSGTDFTLRISRVEAEDVGVYYCVQNLE<br>LPYTFGGGTKLEIK<br>(SEQ ID NO: 289) |
| TM-22 | QVQLQQSGPELVKPGASVKISCKASGYRFTSYYHEW<br>VKQRPGQGLEWIGWIYPGNGITNYNEKFKGKATLTA<br>DTSSSTAYMQLSSLTSEDSAVYYCASPYYGIRNCYF<br>DVWGTGTTVTVSS<br>(SEQ ID NO: 245) | DVLMTQTPLSLPVSLGDHASISCRSGQSIVHS<br>NGNTYLEWYLQKPGQSPKLLIYKVSNRFSGVP<br>DRFSGSGSGTDFTLKISRVEAEDLGIYYCFQG<br>SHVPWTFGGGTKLEIK<br>(SEQ ID NO: 290) |
| TM-23 | QVQLQQSGAELIRPGTSVKVSCKASGYAFTNYLIEW<br>VKKRPGQGLEWIGVINPGSGITNYNEKFKGKATLTA<br>DKSSSTAYMQLSSLTSEDSAVYFCARSDFITTVVAD<br>YWGQGTTVTVSS<br>(SEQ ID NO: 246) | DIVVTQTPLSLPVSFGDQVSISCRSSQSLTNY<br>YGNTYLSWYLHKPGQSPQLLIYGISNRFSGVP<br>DRFSGSGSGTDFTLKISTIKPEDLGMYYCLQG<br>THQPRTFGGGTKLEIK<br>(SEQ ID NO: 291) |
| TM-24 | QVQLKQSGPGQVQPSQSLSITCTVSGFSLSDYGVHW<br>VRQSPGKGLEWLGVIWNNGNTDYNAAFISRLSINKD<br>NSKSQVFFKMTSLQADDTAIYYCVRSLRPLIEFDYW<br>GQGTTVTVSS<br>(SEQ ID NO: 235) | DIVMTQSPSSLTMSVGQKVTMNCKSSQSLLNS<br>NNQQNYLAWYQQKPGQSPKLLVYFASIRESGV<br>PDRFIGSGSGTDFTLTINSVQAEDLADYFCQQ<br>HYSTPFTFGSGTKLEIR<br>(SEQ ID NO: 292) |
| TM-25 | EVQLVESGGDLVKPGGSLRLSCAASGFTFSGYGMSW<br>IRQTPDKRLEWVATISSGGRYTVYPDSVKGRFTMSR<br>DNVKNTLYLQMSSLKSEDTALYYCARDNFYSYAMDY<br>WGLGTSVTVSA<br>(SEQ ID NO: 247) | DIVMTQAAFSNPVTLGTSASISCRSSKSLLHS<br>NGITYLFVVYLQKPGQSPQLLIYQMSNLASGV<br>PDRFSSSGSGTDFTLRISRVEAEDVGVYYCAQ<br>NLELWTFGGGTKLEIK<br>(SEQ ID NO: 293) |
| TM-26 | QVQLQQSGAELIRPGTSVKVSCKASGYAFTNYLIEW<br>VKKRPGQGLEWIGVINPGSGITNYNEKFKGKATLTA<br>DKSSSTAYMQLSSLTSEDSAVYFCARSDFITTVVAD<br>YWGQGTTVTVSS<br>(SEQ ID NO: 246) | DIVVTQTPLSLPVSFGDQVSISCRSSQSLTNY<br>YGNTYLSWYLHKPGQSPQLLIYGISNRFSGVP<br>DRFSGSGSGTDFTLKISTIKPEDLGMYYCLQG<br>THQPRTFGGGTKLEIK<br>(SEQ ID NO: 291) |
| TM-27 | QVQLQQSGAELVRPGTSVKVSCKASGYALTNYLIEW<br>VKQRPGQGLEWIGVNPGSGSTKYNEKFKGKATLTA<br>DKSSSTAYMQLSSLTSEDSAVYFCARHYDHDWYFDV<br>WGTGTTVTVSS<br>(SEQ ID NO: 248) | QIVLTQSPAIMSASPGEKVTISCSASSSISYM<br>YWYQQKPGSSPKPWIYRTSTLASGVPARFSGS<br>GSGTSYSLTISSMEAEDAATYYCQQYHSYPRT<br>FGGGTKLEIK<br>(SEQ ID NO: 294) |
| TM-28 | EVQLQQSGPVLVKPGPSVKISCMASVFTFNDYYIHW<br>VKQSHGKSLEWIGLVYPYNGGTNYNQNFKGKATLTV<br>DTSSRTAYMELNSLTSEDSAVYYCARSYFSNPIGYW<br>GQGTLVTVSE<br>(SEQ ID NO: 249) | DIVMTQSPSSLSVSVGEKVTVSCKSSQSLLNS<br>GNQKNYLAWYQQKPGQPPKLLIYGASTRESGV<br>PDRFTGSGSGTDFTLTISSVQAEDLAVYYCQN<br>DHSYPLTFGAGTKLELK<br>(SEQ ID NO: 295) |
| TM-29 | QVQLRQSGAELVRPGASVKLSCKASGYTFTDYYINW<br>VKQRPGQGLEWIARIYPGSGYTYYNEKFKGKATLTA<br>EGSSNTAYMQLSSLTSEDSAVYFCANHYTNPFAYWG<br>QGTLVTVSA<br>(SEQ ID NO: 250) | DIVMTQAAFSNPVTLGTSASISCRSSKSLLHY<br>NGITYLYWYLQKPGQSPQLLIYQMSNLASGVP<br>DRFSSSGSGTDFTLRISRVEAEDVGVYYCAQN<br>LELPYTFGGGTKLEIK<br>(SEQ ID NO: 296) |

TABLE 4B-continued

V$_H$ and V$_L$ sequences

| Clone ID | V$_H$: | V$_L$: |
|---|---|---|
| TM-30 | QVQLQQSGPELVKPGASVKLSCKASDNTFTNYDVNW VRQRPGQGLEWIGWIYPRDGTTIYNEKFKGRATLTV DTSSSTAYMELHSLTSEDSAVFFCARTLPQAMDYWG QGTSVTVSS (SEQ ID NO: 251) | DVLMTQSPLSLPVSLGDQVSISCRSSQTIVHR NGNTYLEWYLQKPGQSPKLLIYKVSNRFSGVP DRFSGSGSGTDFTLKISRVEAEDLGVYYCFQG SHLPWTFGGGTKLEIK (SEQ ID NO: 297) |
| TM-31 | QVQLQQSGAELAKPGASVKVSCKASGYTFISYWMNW VKQRPGQGLEWIGYINPTSGYTRYNQKFKDKATLTA DKSSSTAYMQLSSLTYEDSAVYYCARSPPTVVLIGY FDYWGQGTTLTVSS (SEQ ID NO: 252) | DIKMTQSPSSMYASLGERVTFTCKASQDINSY LSWFQQKPGKSPKTLIYRGNGLVDGVPSRFSG SGSGQDYSLTISSLEYEDMGIYYCLQYDEFPF TFASGTKLEIK (SEQ ID NO: 298) |
| TM-32 | EVQLQQSGAELVRPGASVRLSCIASGFNEKDYYMYW VKQRPGQGLEWIGREDPEDGDTEYVPKFQGKATMTA DTSSNTAYLQLSSLTSEDIGVYYCTTRTVVDLYYAV DNVVGQGTSVTVSS (SEQ ID NO: 253) | DVLMTQTPLSLPVSLGDQASISCRSSQNIVHS NGNTYLEWYLQKPGQSPKLLIDKVSNRFSGVP DRFSGSGSGTDFTLKISRVEAEDLGIYYCFQG SHVPFTFGSGTKLEIK (SEQ ID NO: 299) |
| TM-33 | EFQLQQSGPELVKPGASVKISCKASGYSFTDYNMNW VKQSNGKSLEWIGVINPNYGTTSYNQKFKGKATLTV DQSSSTAYMQLNSLTSEDSAVYYCASSYWGQGTLVT VSA (SEQ ID NO: 254) | DIVMTQSQKFMSTTVGDRVSITCKASQNVGTA VAWYQQKPGQSPKLLIYSASNRYTGVPDRFTG SGSGTDFTLTISNMQSEDLADYFCQQYSSYPY TFGGGTKLEIK (SEQ ID NO: 300) |
| TM-34 | EVQLVESGGGLVKPGGSLKLSCAASGFSFSDSGMDW VRQAPEKGLEWFAYISSGSSTTHYADTVKGRFIISR DNAKNTLFLQMTSLRSEDTAMYYCVRRDGNYWYFDV WGTGTTVTVSS (SEQ ID NO: 255) | QIVLSQSPVILSASPGEKVTMTCRATSSVTYM HWYQLKPGSSPKPWIYATSNLASGVPARFSGS GSGTSYSLTISRVEAEDAATYYCQQWSSNPYT FGGGTKLEIK (SEQ ID NO: 301) |
| TM-35 | QVQLQQSGPELVRPGTSVKISCKAPGYTFTRHWMQW VRQRPGQGLEWIGEILPGSNNIYYNEKVKGKATLTV DTSSSTSYMQLSSLTSEDSAVYFCARSLYDYDGVFA YWGQGTLVTVSA (SEQ ID NO: 256) | DVLMTQIPLSLPVSLGDQASISCRSSQSIVHR NGNTYLEWYLQKPGQSPKLLIYKVSNRFSGVP DRFSGSGSGTDFTLKISRVEAEDLGVYYCFQG SHVPYTFGGGTKLEIK (SEQ ID NO: 302) |
| TM-37 | QVQLQQSGAELAKPGASVKLSCKASGYTFTSYWMHW VKQRPGQGLEWIGYVNPSSGYTKNNQKFKDKVTLTA DKSSSTAYMQLSSLTYEDSAVYYCAREGGSISDWYF DVWGTGTTVTVSS (SEQ ID NO: 257) | DIVMTQAAPSVPVTPGESVSISCRSSKSLLHS NGNTYSYWFLQRPGQSPQLLIYRMSNLASGVP DRFSGSGSGTAFTLRISRVEAEDVGVYYCMQH LEYPYTEGGGTKLEIK (SEQ ID NO: 303) |
| TM-39 | HVQRQQSGTELAKPGASVKLSCKTSGYTFTDYWMHW IKQRPGQGLEWIGFINPSSGYTKYNQNFKDKATLTA DKSSSTAYMQLSSLTYEDSAVEYCAREAGSISDWYE DVWGTGTTVTVSS (SEQ ID NO: 258) | DIVMTQAAPSIPVTPGESVSISCRSSKTLLNS NGNTYLYWFLQRPGQPPQLLIYRMSNLASGVP DRFSGSGSGTAFTLRISRVEAEDVGVYYCMQH LDYPYTFGGGTQLEIK (SEQ ID NO: 304) |
| TM-41 | EVQLQQSGAELVKPGASEKLSCTASGENEKDCYMIE WVKQRTEQGLEWIGREDPEDGTTNFAPKFQDRATIT ADTSSNTAYLQLTSLTSEDTAVYYCAREWDSGAYWG QGTLVTVSA (SEQ ID NO: 259) | DIVMSQSPSSLAVSVGQKVTMSCKSSQSLLYS SNQKNYLAWYQQKPGQSPKLLIYWASTRESGV PDRFTGSGSGTDFTLTISSVKTEDLAVYYCQQ YYSYPYTFGGGTKLEIK (SEQ ID NO: 305) |
| TM-42 | QVQLQQSGAELAKPGASVKLSCKASGYTFTNYWMHW VKKRPGQGLEWIGYINPSGYTKYNQKFKDKATLTA DKSSNTAYMQLSSLTYEDSAVYYCTREGGSISDWYF DVWGTGTTVTVSS (SEQ ID NO: 260) | DIVMTQAAPSLPVTPGESVSISCRSSKSLLHS NGNTYLYWFLQRPGQSPQLLIYRMSNLASGVP DRFSGSGSGTAFTLRISRVEAEDVGVYYCMQH LEYPYTFGGGTKLEIK (SEQ ID NO: 306) |
| TM-44 | EVQLVESGGGLVKPGGSLKLSCAASGFTFSDYGMHW VRQAPEKGLEWVAYISSGSSTIYYADTVKGRFTISR DNAKNTLFLQMTSLRSEDTAMYYCARNYGSPYAMDY WGQGTSVTVSS (SEQ ID NO: 261) | DIVMSQSPSSLAVSVGEKVTMSCKSSQSLLYS SNQKNYLAWYQQKPGQSPKLLIYWASTRESGV PDRFTGSGSGTDFTLTISSVKAEDLAVYYCQQ YYSYPTFGGGTKLEIK (SEQ ID NO: 307) |
| TM-45 | QVQLQQSGAELAKPGASVKLSCKASGYTFTNYWMHW VKKRPGQGLEWIGYINPSSGYTKYNQKFKDKATLTA DKSSNTAYMQLSSLTYEDSAVYYCTREGGSISDWYF DVWGTGTTVTVSS (SEQ ID NO: 260) | DIVMTQAAPSLPVTPGESVSISCRSSKSLLHS NGNTYLYWFLQRPGQSPQLLIYRMSNLASGVP DRFSGSGSGTAFTLRISRVEAEDVGVYYCMQH LEYPYTFGGGTKLEIK (SEQ ID NO: 306) |

TABLE 4B-continued

V_H and V_L sequences

| Clone ID | V_H: | V_L: |
|---|---|---|
| TM-46 | QVQLQQSGADLVKPGASVKISCKASGYAFSSFWMNW VKLRPGKGLEWIGQIYPGDGDTDYNGKFKDKATLTA DTSSNTAYMQLSRLTSEDSAVYFCARGDGFSYFDYW GQGTILTVSS (SEQ ID NO: 262) | QIVLTQSPVIMSASPGERVTMTCCASSRVNYM HWYQQKSGSYPKRWIYDTSKLASGVPGRFSGS GSGTSYSLTISSMEAEDAATYYCQQWSSNPPT FGGGTKLEIK (SEQ ID NO: 308) |
| TM-47 | QVQLKESGPVLVAPSQSLSITCTVSGFSLTNYGVHW VRQPPGKGLEWLGVIWAGGNTNYNSALMSRLSISKD NSKSQVFLKMNSLQTDDTAMYYCAKEAKLLRSYAMD YWGQGTSVTVSS (SEQ ID NO: 263) | DIVMTQSPSSLTVTAGEKVTMSCKSSQSLLNS GNQKNYLTVVYQQKPGQPPKLLIYWASTRESG VPDRFTGSGSGTDFTLTISSVQAEDLAVYYCQ NDYSYPLTFGAGTKLEIK (SEQ ID NO: 309) |
| TM-48 | QVQLQQSGPELVKPGASVKLSCKASGYTFTSYDINW VKQRPGQGLEWIGWIYPRDGNTQYIEKLKGKATLTV DTSSSTAYMELHSLTSEDSAVYFCARWIFYAMDYWG QGTSVTVSS (SEQ ID NO: 264) | DVLMTQTPLSLPVSLGNQASISCRSSQSIVHG NGNTYLEWYLQKPGQSPKLLIYKVSNRFSGVP DRFSGSGSGTDFTLKISRVEAEDLGVYYCFQG SHLPYTFGGGTKLEIK (SEQ ID NO: 310) |
| TM-49 | QVQLQQPGAELVRPGSSVKLSCKASGYTFTRFWMHW VKQRPIQGLEWIGNEDPSDSQTHYNQKFKDKATLTV DKSSSTAYMQLSSLTSEDSAVYYCARLITVDYAMDY WGQGTSVTVSS (SEQ ID NO: 265) | QIVLTQSPAIMSASPGEKVTISCSASSSVSYM YWYQQKPGSSPKPWIHRTSNLASGVPVRFSGS GSGTSYSLTISSMEAEDAATYYCQQYHSYPPT FGAGTKLELK (SEQ ID NO: 311) |
| TM-50 | QVQLKESGPVLVAPSQSLSITCTVSGESLTNYGVHW VRQPPGKGLEWLGVIWAGGNTNYNSALMSRLSISKD NSKSQVFLKMNSLQTDDTAMYYCAKEAKLLRSYAMD YWGQGTLVTVSA (SEQ ID NO: 266) | DVQMTQTTSSLSASLGDRVTISCRASQDINNY LYWYQQKPDGTVKLLIYYTSMLHSGVPSRFSG SGSGTDYSLTISNLEQEDIATYFCQQGSTLMY TFGGGTKLEIK (SEQ ID NO: 312) |
| TM-51 | QVQLQQPGAELVKPGASVKLSCKASGYTFTTYWIDW VKQRPGQGLEWIGNMFPGSSRTNYNEKEKSRATLTV DTSSSTAYMQLSSLTSDDSAVYYCARKEGLWTYGYD GGAWFAYWGQGTLVTVSA (SEQ ID NO: 267) | DIVMSQSPSSLAVSVGEKVTMSCKSSQSLRNS RTRKNYLAWYQQKPGQSPKLLIYWASTRESGV PDRFTGSGSGTDFTLTISSVQAEDLAIYYCKQ SYNLLTFGAGTKLELK (SEQ ID NO: 313) |
| TM-52 | QVQLQQPGAELVKPGASVKLSCKASGYTFTNYWMHW VKQRPGQGLDWIGNEDPSDSETHYNQKFKDKATLTV DKVSSTAYMQLSSLTSEDSAVYYCARRGYYGRSPFA YWGQGTLVTVSA (SEQ ID NO: 268) | ENVLTQSPAEVISASPGEKVTMTCSASSSVSY MHWYQQKSNTSPKLWIYDTSKLASGVPGRFSG SGSGNSYSLTISSAEAEDVATYYCFQGSGYPL TFGAGTKLELK (SEQ ID NO: 314) |

Example 12: Kinetic Characterization of Anti-TMEM106B Antibodies

Binding kinetic characterization of the purified antibodies was performed by Carterra using a proprietary array SPR instrument (MX-96) as follows. Briefly, antibodies were prepared by diluting to 5 μg/ml in 10 mM Acetate, pH 4.5 (Carterra), at 150 μL/well and then made an additional dilution at 1:10 from there by titrating 11 μL into 100 μL. The antibodies were printed onto a CMD 50M chip (Xantec #SPMXCMD50M lot #SCCMD50M0416.a exp 31.03.18) using the CFM. The chip was activated with 18 mM EDC (Sigma Bioxtra) and 4.5 mM S-NHS (Thermo Fisher) diluted in 100 mM MES, pH 5.5, for 7 minutes, and then antibodies were coupled for 10 minutes at 45 μL/minute. After coupling, the chip was returned to the MX-96 and quenched for 7 minutes using 1 M Ethanolamine pH 8.5 (Carterra).

Printed antibodies were profiled for their ability to bind GST-TMEM106B (truncated) protein (described above). Briefly, GST-TMEM106B (truncated) antigen was diluted to 18 μg/ml (500 nM of 36 kDa fusion protein) by mixing 2.7 μL of 2.0 mg/ml antigen into 298 μL Running buffer (HBS-EP+, Teknova with 1 mg/ml BSA, Sigma), and titrated 50 μl into 200 μl for 5-fold serial dilutions. In addition, binding to GST (Pierce) was assayed under the same conditions to determine the extent of any non-specific binding of the anti-TMEM106B antibodies to GST portion of the TMEM106B-GST fusion protein. Duplicate measurements for each anti-TMEM106B antibody were taken to ensure reproducibility.

Thirty of the forty-eight anti-TMEM106B antibodies bound to the truncated TMEM106B protein. Eighteen of the anti-TMEM106B antibodies did not bind to the truncated TMEM106B protein, consistent with the binding observed in the ELISA binding analysis as described above. None of the 48 anti-TMEM106B antibodies tested showed any binding to GST protein.

Kon, Koff and KD were calculated for each of the 30 anti-TMEM106B antibodies displaying binding to the truncated TMEM106B protein, the results of which are shown below in Table 5.

TABLE 5

| Ab ID | $K_{on}$ (M-1 s-1) | $K_{off}$ (s-1) | $K_D$ (M) |
|---|---|---|---|
| TM 1 | 4.00E+04 | 5.70E−04 | 1.40E−08 |
| TM 1 | 5.20E+04 | 6.90E−04 | 1.30E−08 |
| TM 5 | 2.30E+04 | 3.30E−05 | 1.40E−09 |
| TM 5 | 2.60E+04 | 4.80E−05 | 1.80E−09 |
| TM 2 | 1.20E+04 | 1.10E−05 | 9.00E−10 |
| TM 2 | 8.30E+03 | 1.00E−05 | 1.20E−09 |

TABLE 5-continued

| Ab ID | $K_{on}$ (M-1 s-1) | $K_{off}$ (s-1) | $K_D$ (M) |
|---|---|---|---|
| TM 6 | N/A | N/A | N/A |
| TM 6 | N/A | N/A | N/A |
| TM 25 | 2.20E+04 | 3.30E-05 | 1.50E-09 |
| TM 25 | 2.20E+04 | 5.80E-05 | 2.60E-09 |
| TM 18 | 9.90E+03 | 7.20E-05 | 7.30E-09 |
| TM 18 | 8.50E+03 | 9.40E-05 | 1.10E-08 |
| TM 4 | N/A | N/A | N/A |
| TM 4 | N/A | N/A | N/A |
| TM 19 | N/A | N/A | N/A |
| TM 19 | N/A | N/A | N/A |
| TM 22 | N/A | N/A | N/A |
| TM 22 | N/A | N/A | N/A |
| TM 32 | 2.90E+04 | 8.60E-05 | 3.00E-09 |
| TM 32 | 4.00E+04 | 3.50E-05 | 8.60E-10 |
| TM 16 | 6.50E+03 | 3.10E-03 | 4.70E-07 |
| TM 16 | 3.30E+04 | 9.50E-04 | 2.90E-08 |
| TM 9 | 2.00E+04 | 8.30E-05 | 4.20E-09 |
| TM 9 | 1.60E+04 | 8.40E-05 | 5.20E-09 |
| TM 20 | 6.50E+03 | 1.10E-03 | 1.70E-07 |
| TM 20 | 4.90E+03 | 1.40E-03 | 2.80E-07 |
| TM 7 | 9.90E+03 | 1.80E-04 | 1.90E-08 |
| TM 7 | 1.00E+04 | 6.60E-04 | 6.40E-08 |
| TM 27 | 3.10E+04 | 4.80E-04 | 1.60E-08 |
| TM 27 | 3.90E+04 | 6.80E-04 | 1.80E-08 |
| TM 28 | N/A | N/A | N/A |
| TM 28 | 1.40E+04 | 7.20E-05 | 5.30E-09 |
| TM 29 | 1.80E+04 | 6.50E-05 | 3.50E-09 |
| TM 29 | 1.50E+04 | 7.80E-05 | 5.20E-09 |
| TM 23 | 3.60E+04 | 4.50E-04 | 1.20E-08 |
| TM 23 | 4.10E+04 | 1.00E-03 | 2.60E-08 |
| TM 12 | 2.10E+04 | 7.20E-05 | 3.40E-09 |
| TM 12 | 2.90E+04 | 1.70E-05 | 5.80E-10 |
| TM 8 | N/A | N/A | N/A |
| TM 8 | N/A | N/A | N/A |
| TM 14 | N/A | N/A | N/A |
| TM 14 | N/A | N/A | N/A |
| TM 15 | N/A | N/A | N/A |
| TM 15 | N/A | N/A | N/A |
| TM 31 | N/A | N/A | N/A |
| TM 31 | N/A | N/A | N/A |
| TM 26 | 3.40E+04 | 4.10E-04 | 1.20E-08 |
| TM 26 | 4.50E+04 | 8.50E-04 | 1.90E-08 |
| TM 13 | 2.90E+04 | 7.00E-05 | 2.40E-09 |
| TM 13 | 4.20E+04 | 8.40E-05 | 2.00E-09 |
| TM 17 | 2.90E+04 | 6.30E-04 | 2.20E-08 |
| TM 17 | 3.50E+04 | 9.70E-04 | 2.80E-08 |
| TM 33 | N/A | N/A | N/A |
| TM 33 | N/A | N/A | N/A |
| TM 34 | N/A | N/A | N/A |
| TM 34 | N/A | N/A | N/A |
| TM 35 | 1.50E+04 | 9.00E-05 | 6.00E-09 |
| TM 35 | 1.60E+04 | 1.10E-04 | 6.80E-09 |
| TM 36 | N/A | N/A | N/A |
| TM 36 | N/A | N/A | N/A |
| TM 37 | 1.90E+04 | 5.10E-05 | 2.60E-09 |
| TM 37 | 1.80E+04 | 1.10E-04 | 6.30E-09 |
| TM 39 | 1.40E+04 | 5.80E-05 | 4.10E-09 |
| TM 39 | 1.40E+04 | 3.00E-05 | 2.20E-09 |
| TM 53 | 1.70E+04 | 8.30E-04 | 5.00E-08 |
| TM 53 | 1.50E+04 | 1.30E-03 | 8.40E-08 |
| TM 41 | N/A | N/A | N/A |
| TM 41 | N/A | N/A | N/A |
| TM 42 | 1.30E+04 | 4.30E-04 | 3.30E-08 |
| TM 42 | 1.80E+04 | 4.20E-04 | 2.40E-08 |
| TM 44 | N/A | N/A | N/A |
| TM 44 | N/A | N/A | N/A |
| TM 45 | 1.10E+04 | 2.10E-04 | 1.90E-08 |
| TM 45 | 1.20E+04 | 2.10E-04 | 1.80E-08 |
| TM 46 | N/A | N/A | N/A |
| TM 46 | N/A | N/A | N/A |
| TM 48 | 1.70E+04 | 5.30E-05 | 3.10E-09 |
| TM 48 | 1.40E+04 | 5.60E-05 | 3.90E-09 |
| TM 49 | N/A | N/A | N/A |
| TM 49 | N/A | N/A | N/A |
| TM 50 | N/A | N/A | N/A |
| TM 50 | N/A | N/A | N/A |
| TM 51 | N/A | N/A | N/A |
| TM 51 | N/A | N/A | N/A |
| TM 52 | N/A | N/A | N/A |
| TM 52 | N/A | N/A | N/A |
| TM 3 | 2.20E+04 | 3.80E-05 | 1.70E-09 |
| TM 3 | 2.30E+04 | 4.80E-05 | 2.10E-09 |
| TM 11 | 2.40E+04 | 5.20E-05 | 2.10E-09 |
| TM 11 | 2.70E+04 | 5.70E-05 | 2.10E-09 |
| TM 21 | 1.80E+04 | 5.20E-05 | 2.90E-09 |
| TM 21 | 1.70E+04 | 7.10E-05 | 4.10E-09 |
| TM 47 | N/A | N/A | N/A |
| TM 47 | N/A | N/A | N/A |
| TM 10 | 3.20E+04 | 5.40E-04 | 1.70E-08 |
| TM 10 | 2.80E+04 | 6.00E-04 | 2.20E-08 |

These results showed that the anti-TMEM106B antibodies displayed a range of affinities, within the range of 1-100 nM for the majority of the clones. TMEM106B antibody TM-2 displayed the strongest binding at approximately 1 nM; the weakest (on average) binder based on these experiments was TMEM106B antibody TM-20, which displayed an affinity of approximately 225 nM.

Example 13: Anti-TMEM106B Antibody Binding to Transiently and Natively-Expressing Cell Lines Purified anti-TMEM106B antibodies were evaluated for their binding affinity to various TMEM106B-expressing cell lines including HEK293 transiently transfected with human/cyno/mouse TMEM106B, as well as HeLa cells and A549 cells. Antibodies tested for this experiment were mouse IgGs purified from hybridoma supernatant. Affinity binding to cells was determined as follows. Briefly, 1×10^5 cells were aliquoted per well in 96-well round bottom plates and incubated with 50 µL of purified anti-TMEM106B antibody at various concentrations (10× dilutions starting at 10 µg/ml) in FACS buffer (PBS+2% FBS+1 mM EDTA). After primary incubation, excess anti-TMEM106B antibody was removed via centrifugation, the cells were washed 2× with 150 µL of ice-cold FACS buffer and incubated with anti-mouse APC (Jackson Labs #115-136-071) diluted 1:200 on ice for 30 minutes. Following the secondary incubation, the cells were again washed 2× with ice-cold FACS buffer and resuspended in a final volume of 50 µL of FACS buffer+0.25 µl/well propidium iodide (BD Biosciences Cat #556463) for live/dead cell gating. Sorting was performed on a iQue (Intellicyt), with sort gates drawn to exclude dead (propidium iodide+) cells. Binding data was analyzed using median fluorescent intensity (MFI) and graphed in Prism. Data from these experiments is shown below in Table 6. Values presented are MFI.

TABLE 6

| Clone ID | A549 10 µg/ml | A549 1 µg/ml | HEK Parental 10 µg/ml | HEK + huTMEM 10 µg/ml | HEK + huTMEM 1.0 µg/ml | HEK + huTMEM 0.1 µg/ml | HEK + huTMEM 0.01 µg/ml |
|---|---|---|---|---|---|---|---|
| TM-1 | 409 | 364 | 525 | 2381 | 2012 | 1330 | 655 |
| TM-2 | 3360 | 1093 | 1802.5 | 55506 | 29275 | 4728 | 1437 |
| TM-3 | 7668 | 4842 | 4174 | 82271 | 89070.5 | 48711 | 7702.5 |

TABLE 6-continued

| Clone ID | A549 10 µg/ml | A549 1 µg/ml | HEK Parental 10 µg/ml | HEK + huTMEM 10 µg/ml | HEK + huTMEM 1.0 µg/ml | HEK + huTMEM 0.1 µg/ml | HEK + huTMEM 0.01 µg/ml |
|---|---|---|---|---|---|---|---|
| TM-4 | 443 | 373 | 640 | 845.5 | 415 | 304 | 282 |
| TM-5 | 4803 | 1969 | 1764 | 59276 | 64535 | 10843 | 2182 |
| TM-6 | 544 | 418 | 927 | 581 | 393 | 327 | 294 |
| TM-7 | 1811 | 883 | 1320 | 40836 | 40003.5 | 9870.5 | 1670 |
| TM-8 | 492 | 393 | 549 | 465 | 317 | 305 | 301 |
| TM-9 | 7090 | 4879 | 3312 | 56360.5 | 62077 | 28349 | 3939 |
| TM-10 | 1093 | 663 | 695 | 36527.5 | 44432 | 20964.5 | 3358 |
| TM-11 | 5581 | 2868 | 2518 | 57940 | 54619 | 16226 | 4281.5 |
| TM-12 | 4950 | 3154 | 2740 | 75345 | 77808.5 | 19666 | 3340 |
| TM-13 | 3886 | 1950 | 2094.5 | 67514 | 67050.5 | 19120 | 2905 |
| TM-14 | 438 | 409 | 418 | 1186.5 | 680 | 364 | 314 |
| TM-15 | 1976 | 650 | 1197 | 63078 | 14273 | 2061 | 584 |
| TM-16 | 557 | 409 | 593 | 5980 | 2138 | 680 | 351 |
| TM-17 | 425 | 379 | 405 | 3958 | 2625 | 1905.5 | 1146 |
| TM-18 | 5188 | 2616.5 | 2236 | 71694 | 67295.5 | 10600 | 1735 |
| TM-19 | 4958 | 3640 | 1994 | 78975 | 66753 | 29812.5 | 3338 |
| TM-20 | 793 | 428 | 707 | 8044 | 2570 | 621 | 352 |
| TM-21 | 4227 | 2027 | 1794 | 69433 | 69362.5 | 15599 | 2347.5 |
| TM-22 | 478 | 399 | 737 | 3575 | 2102.5 | 833 | 500 |
| TM-23 | 757 | 398 | 710 | 12404 | 3899 | 2414 | 1097 |
| TM-24 | 4484 | 2878 | 2085 | 66268 | 64491 | 22042 | 3616.5 |
| TM-25 | 7005 | 4533 | 3123 | 60326 | 64737 | 32839 | 4309 |
| TM-26 | 509 | 380 | 591 | 3854 | 3341 | 1955.5 | 1001 |
| TM-27 | 622 | 431 | 692 | 4138 | 3042 | 1702 | 744.5 |
| TM-28 | 4349 | 2631.5 | 3530.5 | 64821.5 | 66353 | 19819 | 3340 |
| TM-29 | 4202 | 2476 | 2253 | 61240 | 63251 | 24444 | 4050.5 |
| TM-30 | 4040 | 3033 | 2131.5 | 61546 | 63547.5 | 18381.5 | 3073 |
| TM-31 | 527 | 403 | 478 | 6057.5 | 3684 | 1391 | 596 |
| TM-32 | 6097 | 3931 | 2731 | 61067 | 63329.5 | 20345 | 4101 |
| TM-33 | 514 | 366.5 | 637 | 12070 | 5627 | 1750 | 651 |
| TM-34 | 465 | 393 | 420.5 | 389 | 317 | 285 | 295 |
| TM-35 | 4200 | 3272 | 1970 | 48672.5 | 55367.5 | 22616 | 4078 |
| TM-36 | 512 | 406 | 682 | 507 | 323 | 305 | 299 |
| TM-37 | 4213 | 2984 | 1870 | 50479 | 58700.5 | 29395.5 | 3924 |
| TM-38 | 6460 | 4662 | 3036 | 66955 | 69381 | 35294 | 4274 |
| TM-39 | 5332 | 3610 | 2553 | 51940.5 | 55617 | 19216 | 3851 |
| TM-40 | | | | Not determined | | | |
| TM-41 | 441 | 394 | 371 | 403 | 302 | 295 | 306 |
| TM-42 | 3298 | 1779 | 2273 | 60092.5 | 58107 | 16735 | 2069 |
| TM-43 | | | | Not determined | | | |
| TM-44 | 466 | 404 | 631 | 512 | 337 | 309 | 300 |
| TM-45 | 3238 | 1855 | 1831 | 58112.5 | 57551 | 21306 | 2495 |
| TM-46 | 460 | 393 | 1167 | 623 | 361.5 | 310 | 302 |
| TM-47 | 446 | 421 | 389 | 341 | 317 | 288 | 295 |
| TM-48 | 2449 | 1582 | 1303 | 38153 | 39877 | 21551.5 | 4047 |
| TM-49 | 613 | 473 | 603 | 16502 | 15659 | 3032 | 756 |
| TM-50 | 445 | 381 | 463 | 396 | 314 | 305 | 294 |
| TM-51 | 463 | 403 | 411 | 1034 | 292 | 273 | 295 |
| TM-52 | 443 | 401 | 27819 | 7016 | 8205 | 1940 | 451 |
| TM-53 | 1140 | 680 | 942 | 24283 | 23584 | 9472.5 | 1915 |

From these data, equilibrium binding constants to cellular TMEM106B was calculated for many of the anti-TMEM106B clones. Equilibrium affinity to cells was not well correlated with overall levels of maximum cell binding, with some low-binding clones (e.g., TM-1) and many high binding clones (e.g. TM-18 or TM-19) having apparent affinities of roughly 1 nM. Binding to A549 and the transfected HEK293 cells was highly correlated, albeit in a non-linear fashion. From these data, anti-TMEM106B clones were divided into "high" and "low" binders, based on maximum binding signal rather than affinity. The high binding clones included TM-2, TM-3, TM-5. TM-7, TM-9, TM-10, TM-11, TM-112, TM-12, TM-15, TM-18, TM-19. TM-21, TM-24, TM-25, TM-28, TM-29, TM-30, TM-32, TM-35, TM-37, TM-38, TM-39, TM-42, TM-45, TM-48, and were mostly from Fusion A (using the TMEM106B knock-out mice).

Example 14: Epitope Binning of Anti-TMEM106B Antibodies

Epitope binning of the anti-TMEM106B antibodies was performed by Carterra (Salt Lake City, Nevada, USA) using a pre-mix epitope binning approach. Monoclonal anti-TMEM106B antibodies were immobilized to a CMD 50M chip (Xantec #SPMXCMD50M lot #SCCMD50M0416.a exp 31.03.18. The running buffer was HBS-EP+ with 1 mg/ml BSA. The GST-TMEM106B (truncated) antigen was prepared at a final concentration of 55 nM (corresponding to 2 µg/ml) and mixed with the competing analyte anti-TMEM106B antibodies at a final concentration of 333 nM (corresponding to 50 µg/ml) or compared to a buffer control. Samples were injected for 5 minutes over the array and regenerated after every cycle with 1 minute of two parts Pierce IgG-Elution buffer (ThermoFisher Cat #21004) and 1 part of 10 mM Glycine, pH 2.0 (Carterra).

Anti-TMEM106B antibodies sorted into a wide range of competing bins, but were generally sorted to two 'communities' of antibodies showing no ability to block antibodies in the other community. These results of these experiments are shown below in Table 7. Community 3 refers to anti-TMEM106B antibodies displaying no ability to block the binding to any of the other anti-TMEM106B antibodies due to their inability to bind the truncated GST-TMEM106B fusion protein used in these binning experiments. All community 1 anti-TMEM106B antibodies were derived from immunizations of TMEM106B knockout mice, are human/cyno/mouse cross-reactive, and bin together (bin 1). Within Community 2, most anti-TMEM106B antibodies are in a common bin (bin 2), containing a mix of anti-TMEM106B antibodies obtained from both sets of immunizations and having both human/cyno/mouse-cross reactivity and human/cyno cross-reactive antibodies. Within Community 2, a few notable sub-groups comprising either TM-7, TM-10, and TM-28 (bin 3), or TM-5 and TM-29 (bin 4). All anti-TMEM106B antibodies within Community 1 were derived from the TMEM106B knockout mice immunizations. All anti-TMEM106B antibodies within bin 3 and bin 4 were derived from TMEM106B knock-out mouse immunizations and are human/cyno/mouse TMEM106B cross-reactive.

TABLE 7

| Community 1 (Bin 1) | Community 2 (Bins 2/3/4) | Community 3 (Bin 5) |
|---|---|---|
| TM-1, TM-17, TM-22, TM-23, TM-26, TM-27 | Bin 2: TM-2, TM-3, TM-9, TM-10, TM-11, TM-12, TM-13, TM-18, TM-19, TM-21, TM-25, TM-32, TM-35, TM-37, TM-39, TM-42, TM-45, TM-48, TM-53<br>Bin 3: TM-7, TM-10, TM-28<br>Bin 4: TM-5, TM-29 | TM-4, TM-6, TM-8, TM-14, TM-15, TM-16, TM-20, TM-31, TM-33, TM-34, TM-36, TM-41, TM-44, TM-46, TM-47, TM-49, TM-50, TM-51, TM-52 |

Example 15: Epitope Mapping of Anti-TMEM106B Antibodies

Epitope mapping of the anti-TMEM106B antibodies was carried out by Pepscan (Lelystad, Netherlands). Using their proprietary CLIPS technology, Pepscan created a library (>2500) of linear peptides and looped and discontinuous epitope mimics of the human TMEM106B protein. These peptides were made in situ on a proprietary hydrogel of a Pepscan mini-array and binding of anti-TMEM106B antibodies to each peptide was measured using an ELISA-based method.

The linear and CLIPS peptides were synthesized based on the amino acid sequence of the target protein using standard Fmoc-chemistry and deprotected using trifluoric acid with scavengers. The constrained peptides were synthesized on chemical scaffolds in order to reconstruct conformational epitopes, using Chemically Linked Peptides on Scaffolds (CLIPS) technology (Timmerman et al. (2007). For example, the single looped peptides were synthesized containing a dicysteine, which was cyclized by treating with alpha, alpha'-dibromoxylene and the size of the loop was varied by introducing cysteine residues at variable spacing. If other cysteines besides the newly introduced cysteines were present, they were replaced by cysteine-acetamydomethyl. The side-chains of the multiple cysteines in the peptides were coupled to CLIPS templates by reacting onto credit-card format polypropylene PEPSCAN cards (455 peptide formats/card) with a 0.5 mM solution of CLIPS template such as 1,3-bis(bromomethyl) benzene in ammonium bicarbonate (20 mM, pH 7.9)/acetonitrile (1:1 (v/v)). The cards were gently shaken in the solution for 30 to 60 minutes while completely covered in solution. Finally, the cards were washed extensively with excess of H2O and sonicated in disrupt-buffer containing 1% SDS/0.1% beta-mercaptoethanol in PBS (pH 7.2) at 70° C. for 30 minutes, followed by sonication in H2O for another 45 minutes. The binding of antibody to each peptide was tested in a PEPSCAN-based ELISA. The 455-well credit card format polypropylene cards containing the covalently linked peptides were incubated with primary antibody solution, for example, consisting of 1 µg/ml diluted in blocking solution, for example 4% horse serum, 5% ovalbumin (w/v) in PBS/1% Tween. After washing, the peptides were incubated with a 1/1000 dilution of antibody peroxidase conjugate for one hour at 25° C. After washing, the peroxidase substrate 2,2'-azino-di-3-ethylbenzthiazoline sulfonate (ABTS) and 2 µl of 3% H2O2 were added. After one hour, the color development was measured. The color development was quantified with a charge coupled device (CCD)-camera and an image processing system (as first described in Slootstra et al., 1996).

Six sets of synthesized peptides were prepared as follows. Set 1: linear peptides of 15 amino acid residue lengths were synthesized from the amino acid sequence of human TMEM106B with an off-set of 1 amino acid residue. Set 2: linear peptides of 15 amino acid residue lengths were synthesized with residues on positions 10 and 11 replaced with Ala; when a native Ala residue occurred on either position 10 or 11, it was replaced with Gly. Set 3: linear peptides of 15 amino acid residue lengths were synthesized in which native Cys residues were replaced with Cys-acetamidomethyl (Cys-acm). Set 4: constrained peptides of 17 amino acid residue lengths were synthesized, with positions 2-16 being 15-mer peptides derived from the amino acid sequence of human TMEM106B; Cys residues were inserted in positions 1 and 17 and joined by means of mP2 CLIPS to create a looped structure. Native Cys within the 15-mers were replaced by Cys-acm. Set 5: constrained peptides of 22 amino acid length were constructed, in which positions 2-21 being 20-mer peptides derived from the amino acid sequence of human TMEM106B with an offset of one amino acid residue; residues on positions 11 and 12 were replaced by "PG" motif to induce a B-turn formation. Cys residues were inserted on positions 1 and 22 and were joined by means of mP2 CLIPS to create a B-strand like structure. Native Cys in these peptides were replaced by Cys-acm. Set 6: combinatorial peptides of 33 amino acid length, with positions 2-16 and 18-32 being 15-mer peptides derived from the human TMEM106B sequence. Cys residues were inserted on positions 1, 17, and 33 and were joined by means of T3 CLIPS to create a double loop structure. Native Cys in these peptides were replaced by Cys-acm. The synthesized peptides corresponded to both lumenal and cytoplasmic regions of human TMEM106B.

The results of the Pepscan analyses are shown below in Table 8. Most anti-TMEM106b antibodies recognized overlapping epitopes, except for TM-1 and TM-23, which recognized identical epitopes within the lumenal domain of TMEM106B.

TABLE 8

| Antibody | Domain | Epitope Sequences |
|---|---|---|
| TM-1 and TM-23 | Lumenal | $_{151}$NITNNNYYSVEVENI$_{165}$ (SEQ ID NO: 324)<br>$_{185}$TIIGPLDMKQI$_{195}$ (SEQ ID NO: 325) |
| TM-2 | Cytoplasmic | $_{59}$VTCPTCQGTGRIPRG$_{73}$ (SEQ ID NO: 326)<br>$_{80}$ALIPYSDQRLR$_{90}$ (SEQ ID NO: 327) |
| | Lumenal | $_{139}$KRTIYLNITNT$_{149}$ (SEQ ID NO: 328)<br>$_{248}$YQYVDCGRNTT$_{258}$ (SEQ ID NO: 329) |
| TM-3 | Cytoplasmic | $_{15}$EDAYDGVTSE$_{24}$ (SEQ ID NO: 330)<br>$_{33}$SEVHNEDG$_{40}$ (SEQ ID NO: 331) |
| TM-7 | Cytoplasmic | $_{5}$LSHLPLHSSKEDAYD$_{19}$ (SEQ ID NO: 332)<br>$_{30}$LVNSEVHNEDG$_{40}$ (SEQ ID NO: 333) |
| | Lumenal | $_{156}$NYYSVE$_{161}$ (SEQ ID NO: 334)<br>$_{202}$VIAEEM$_{207}$ (SEQ ID NO: 335)<br>$_{219}$IKVHNIVLMMQVTVT$_{233}$ (SEQ ID NO: 336) |
| TM-12 | Lumenal | $_{126}$IGVKSAYVSYDVQKR$_{140}$ (SEQ ID NO: 337)<br>$_{185}$TIIGPLDMKQI$_{195}$ (SEQ ID NO: 325)<br>$_{260}$QLGQSEYLNVLQPQQ$_{274}$ (SEQ ID NO: 338) |
| TM-13 | Cytoplasmic | $_{34}$EVHNEDG$_{40}$ (SEQ ID NO: 339) |
| | Lumenal | $_{202}$VIAEEMSYMYD$_{212}$ (SEQ ID NO: 340) |
| TM-24 | Lumenal | $_{151}$NITNNNYYSVE$_{161}$ (SEQ ID NO: 341)<br>$_{223}$NIVLMMQVTVT$_{233}$ (SEQ ID NO: 342) |
| TM-29 | Cytoplasmic | $_{59}$VTCPTCQGTGR$_{69}$ (SEQ ID NO: 343) |
| | Lumenal | $_{143}$YLNITNTLNIT$_{153}$ (SEQ ID NO: 344)<br>$_{223}$NIVLMM$_{228}$ (SEQ ID NO: 345) |
| TM-30 | Lumenal | $_{133}$VSYDVQKRITYLN$_{145}$ (SEQ ID NO: 346)<br>$_{198}$TVPTVIAEEMSYMYD$_{212}$ (SEQ ID NO: 347) |
| TM-51 | Cytoplasmic | $_{52}$EFTGRDSVTCP$_{62}$ (SEQ ID NO: 348)<br>$_{64}$CQGTGRIPRGQE$_{75}$ (SEQ ID NO: 349) |
| | Lumenal | $_{223}$NIVLMM$_{228}$ (SEQ ID NO: 345) |

Data in Table 8 shows that certain sequences were identified multiple times as being recognized by various anti-TMEM106b antibodies tested. For example, the region spanning amino acid residues 219-233 is exemplified by TM-7 ($_{219}$IKVHNIVLMMQVTVT$_{233}$), TM-24 ($_{223}$NIVLMMQVTVT$_{233}$), TM-29 ($_{223}$NIVLMM$_{228}$), and TM-51 ($_{223}$NIVLMM$_{228}$).

The binding data for TM-1 and TM-23 (both of which fall into Community 1 by epitope binning) combined with structural homology modeling suggested that these two anti-TMEM106b antibodies bind to a discontinuous epitope on TMEM106b, which includes $_{151}$NITNNNYYSVEVENI$_{165}$ and $_{185}$TIIGPLDMKQI$_{195}$.

Example 16: Downregulation of Cellular TMEM106B by Anti-TMEM106B Antibodies in Cell Lines The ability of anti-TMEM106B antibodies to reduce or down-regulate cell surface and total cellular protein levels of TMEM106B in various cell lines is evaluated as follows. Cell lines useful for such down-regulation experiments are those identified in the literature as expressing TMEM106B and confirmed in experiments described above as showing significant binding to anti-TMEM106B antibodies. Experiments are performed using, for example, the following cell lines: adenocarcinoma HeLa cells (ATCC CTL-2), gliablastoma U251cells (Sigma Cat #09063001), A549 human lung carcinoma cells (ATCC CCL-185), and mouse Neuroblastoma cell line Neuro2a (ATCC CCL-131). Preferably, experiments are performed using A549 cells, which display high expression of TMEM106B, as shown above. The cell lines are incubated with various concentrations or amounts of anti-TMEM106B antibodies of the present invention for various time periods and then the levels of TMEM106B remaining associated with the cells is measured using either FACS (for measuring changes in levels of cell surface TMEM106B) or western blot (for measuring changes in levels of total cellular TMEM106B).

HeLa cells, U251 cells, and Neuro2a cells are cultured in Eagle's Minimum Essential Media (EMEM)+10% FBS (fetal bovine serum) and A549 cells are cultured in DMEM+10% FBS, each in either T75 or T150 flasks. When the cells reach >80% confluence, they are detached via application of trypsin-EDTA at 37C, the enzyme is quenched with media (including FBS), washed into fresh media, and distributed into 96-well plates (1×10^5 cells per well in 10 µL) for FACS assays or 24 well plates (4×10^5 cells/well in 1 mL) for western blot readouts. 24 hours after being plated, anti-TMEM106B antibodies are added to the well (using, for example, 0.1-10 µg/ml final antibody concentration) and allowed to incubate overnight with the target cells at 370C. For FACS assays, detection of the remaining TMEM106B is performed using direct-dyelight-650 conjugated, non-competing antibodies identified above. For Western blot detection, A549 cells are detached via removal of media, washed with PBS, and followed by the addition of trypsin-EDTA (10 minutes at 370C). Trypsin-EDTA is then quenched with media (DMEM+10% FBS), and cells removed from the plates into 96-well round-bottomed plates, washed in PBS, and then lysed via addition of 50 µL lysis buffer (RIPA lysis buffer (ThermoFischerScientific Cat #89900)+1:100 HALT protease inhibitor cocktail (ThermoFischerScientific Cat #87786). Total protein levels in the lysate can be determined by BCA assay (Pierce, Cat #23225), and equivalent levels of protein loaded onto SDS-PAGE gels and then transferred to a nitrocellulose membrane for Western blot analysis (chemilumenescence, using the iBright system from ThermoFischerScientific).

For FACS experiments, downregulation of TMEM106B is associated with reduced binding of the 2nd, non-competing dylight-conjugated anti-TMEM106B antibody. Percent down regulation is calculated from the differential of the MFI of binding to A549 cells with and without the presence of an anti-TMEM106b antibody during overnight incubation. For Western blot experiments, total protein levels are directly assayed based on the level of chemiluminescent signal, and percent down regulation determined by the ratio of signal from cells treated with or without anti-TMEM106B antibodies.

Figure 2:
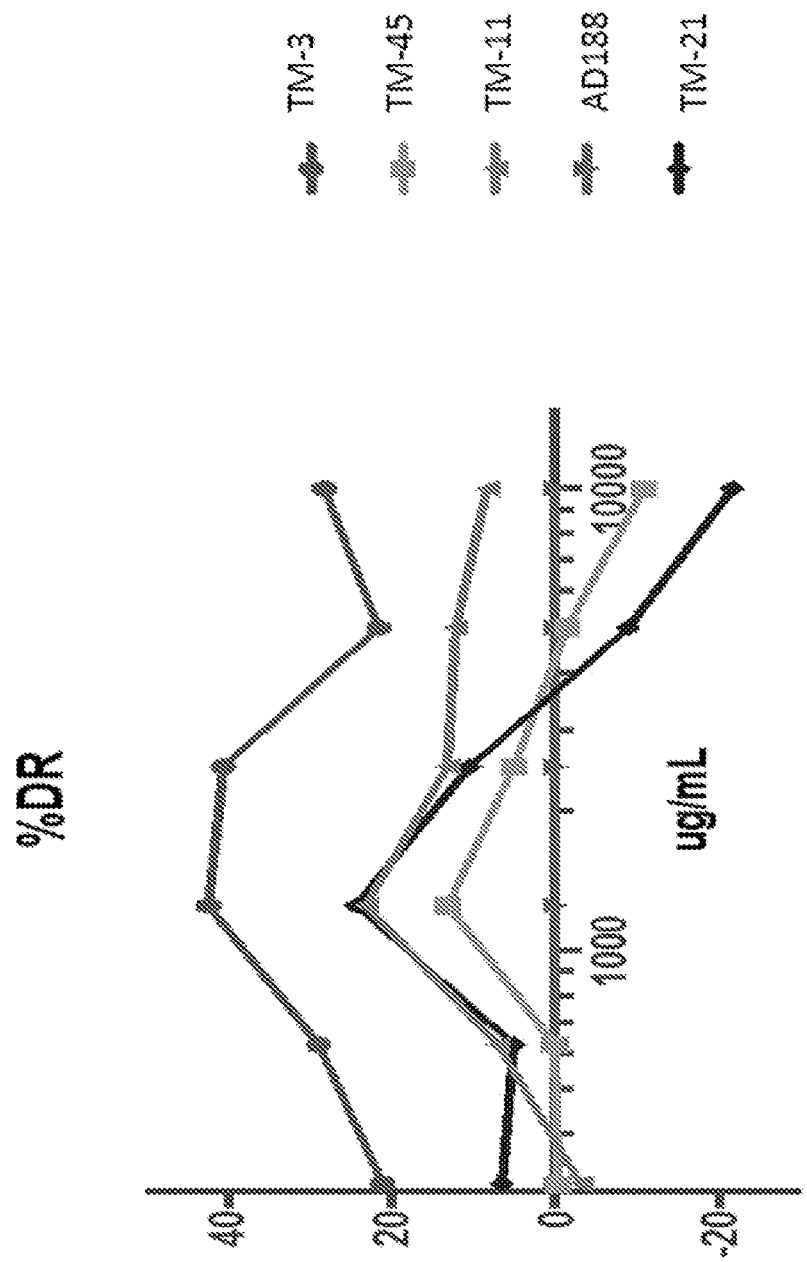
FIG. 2 sets forth data showing percent down regulation of TMEM106B in A549 cells following addition of various anti-TMEM106B antibodies of the present disclosure.

As shown in FIG. 1 and FIG. 2, various anti-TMEM106B antibodies of the present disclosure reduced or down-regulated TMEM106B levels in A549 cells.

Example 17: Downregulation of TMEM106b in Primary Cell Cultures

The ability of anti-TMEM106B antibodies of the present invention to reduce or down-regulate cell surface/cellular expression in primary cell cultures is evaluated as follows. Mouse primary cortical neurons are harvested from early postnatal nice (day 0-3) and cultured according to standard methods in the field (Maximov et al., 2007, J. Neu. Meth., 161 75-87). Cultured neurons are then incubated with anti-TMEM106B antibodies in various conditions (1-20 µg/ml, 2-48 hours), harvested, and total TMEM106B levels are quantified using either FACS (for measuring changes in levels of cell surface TMEM106B) or western blot (for measuring changes in levels of total cellular TMEM106B).

Primary cortical neurons are isolated as follows. Briefly, cells in the cortex, hippocampus, or striatum of P0 mouse pups are dissociated by incubation for 7 minutes at 370C in digestion solution containing 6 mg/ml trypsin (Sigma, Cat #T1005-1G), 0.5 mg/ml DNAse (Sigma, Cat #D5025) and 137 nM NaCl, 5 mM KCl, 7 mM Na2HPO4, and 25 mM HEPES-NaOH, pH 7.2. The dissociated cells containing neurons are then washed once with Hank's balanced salt solution (HBSS) containing 20% fetal bovine serum (FBS) followed by two washes in serum-free HBS, and the further dissociated by gentle pipetting in HBS containing 12 mM MgSO4 and 0.5 mg/ml DNAse. The cell suspension is centrifuged for 10 minutes at 160 g and plated on Matrigel (Collaborative Biomedical Products, Cat #871-275-0004) coated circular glass coverslips (Ø 12 mm) in MEM (Invitrogen) supplemented with B27 (Invitrogen, Cat #17504-044), glucose, transferrin, and 5% fetal bovine serum. For cortical cultures, the cell suspension obtained from the cortex of a single brain is used to plate 12 wells in a 24-well plate. For all cultures, the initial cell density (including glia) at plating varies between 1500 and 2500 cells per square millimeter. When the confluency of glia cells in the culture reaches ~40-50% (usually 2 days after plating), 50% of the conditioned culture medium is replaced with fresh medium containing 4 mM Ara-C (Sigma). The cultures are maintained in medium containing 2 mM Ara-C at 37C and 5% CO2 until experiments (13-18 DIV).

Treatment with anti-TMEM106B antibodies may be carried out for 1-7 days and at concentrations ranging from 0.001-10 µg/ml. Briefly, anti-TMEM106B antibodies are diluted into culture media and added to the cell cultures, followed by a 1-7 day incubation/culture at standard culture conditions. The neural cultures are then disassociated with trypsin-EDTA and prepared for either FACS or Western blot analysis as described above.

The ability of anti-TMEM106B antibodies to down regulate the levels of TMEM106B is determined by showing either lower cell surface TMEM106B levels as determined by FACS analysis using non-blocking TMEM106B antibodies, or lower overall cell TMEM106B levels detected using Western blot analysis.

Example 18: Rescue of HEK293 Cells from TMEM106B Overexpression

TMEM106B overexpression in certain cells lines can result in cell toxicity. On the assumption that this toxicity is due to increased function of TMEM106B associated with overexpression of TMEM106B in these cells, the extent and degree of cell toxicity can provide a useful functional readout for examining anti-TMEM106B antibody activity. Accordingly, an assay is developed using HEK293 cells transfected with TMEM106B expression plasmids under conditions known to promote a cell toxicity. Cell toxicity is measured by various parameters known to be affected by cell toxicity: cell number, cell health, visible cell debris in culture, and overall changes cellular metabolism as measured by the Cell Titer-GLO system (Promega). Transfected HEK293 cells are cultured in the absence or presence of various concentrations of anti-TMEM106B antibodies for various lengths of time (e.g., 24 hours, 48 hours, 72 hours) after which cell number and cell viability are assessed using the CellTiter-GLO system.

HEK293 cells are seeded in 96-well tissue culture plates (Corning Cat #087722C) at a density of $2.5 \times 10^4$ cells per well in 100 µL of DMEM+10% FBS 24 hours prior to transfection; outer wells are filled with media-only in order to reduce potential edge effects. Transfection is carried out using the Lipofectamine 3000 system. Briefly, for each plate (60 wells containing cells), 1-12 µg of TMEM106B expression plasmid DNA is diluted into 600 µL of Optimem media, to which is then added 25 µL of P3000 reagent. Separately, 25 µL of lipofectamine reagent is added to an additional 600 µL of Optimem media. After 5 minutes at room temperature, the two aliquots of Optimem are mixed and allowed to sit at room temperature for 30 minutes to form lipofectamine-DNA complexes, and then 15 µL of lipofectamine-DNA is added per well. Anti-TMEM106B antibodies are then added to the cell cultures at 1-10 µg/ml either prior to, or up to 6 hours following transfection. Transfected cells are then assayed for viability using the CellTiter-GLO system (Promega Cat #G7570) at 24, 48, and 72 hours after transfection. Briefly, the 96-well plate is spun down at 1500 rpm for 3 minutes and supernatant removed, and then 50 µL PBS and 50 µL of CellTiter-GLO reagent are added per well followed by 10 minutes shaking at room temperature. 75 µL of the resulting lysate is transferred to a white, opaque 96-well plate (Costar Cat #3922) and luminescence is read on a BioTek Synergy Microplate Reader using GEN5 2.04 software.

Anti-TMEM106B antibodies that block TMEM106B function are predicted to prevent or reduce cellular toxicity, measured by the number and viability of cells, as detected by an increase in CellTiter-GLO luminescence.

Example 19: In Vivo Downregulation of TMEM106B by Anti-TMEM106B Antibodies

The activity of anti-TMEM106B down-regulating antibodies is further examined using two in vivo mouse model systems. Human/mouse cross-reactive anti-TMEM106B antibodies are tested in wildtype mice, while a BAC transgenic line expressing human TMEM106B under its natural enhancers is used to test human-only and human/cyno cross-reactive anti-TMEM106B antibodies. Anti-TMEM106B antibodies are administered to the mice via intraperitoneal injection and changes in total TMEM106B protein levels subsequently evaluated from different tissue types (liver and frontal cortex isolates) by Western Blot and isolated cells (hepatocytes) via FACS.

Example 20: Characterization of Interactions Between TMEM106B and TMEM106B Binding Partners TMEM106B has been shown to interact with various proteins, including various proteins associated with late endosomal/lysosomal compartments. Use of anti-TMEM106B antibodies to block or inhibit the interaction of TMEM106B with any of its various binding partners, such as but not limited to progranulin protein, other TMEM106 protein family members, such as TMEM106B and TMEM106C, clathrin heavy chain (CLTC), the µl subunit of adipocyte protein 2 (AP2M1), CHMP2B, microtubule-associated protein 6 (MAP6), lysosomal-associated membrane protein 1 (LAMP1), and vacuolar-ATPase subunit accessory protein 1, may be tested. The extent or degree of an anti-TMEM106B antibody blocking the binding of TMEM106B to any of its binding partners is measured by co-immunoprecipitation of TMEM106B protein in the presence or absence of anti-TMEM106B antibodies, followed by Western blot detection of the binding partners. Alternatively, TMEM106B-expressing cell lines are administered anti-TMEM106B antibodies, and then stained for both TMEM106B and binding partner protein levels using a readout such as co-localization or fluorescence resonance energy transfer (FRET).

Example 21: The Effect of Anti-TMEM106B Antibodies on Lysosomal Expression Patterns in TMEM106B Expressing Cell Lines TMEM106B is located in late endosomal/lysosomal cellular compartments. Recent work by Strittmeyer et al (Klein et al. 2017, Neuron, 95:281-296) and others suggests a widespread effect on lysosomal protein levels is caused by TMEM106B genetic knockout. To examine the effects of anti-TMEM106B antibodies on various lysosomal protein expression patterns in cell lines expressing TMEM106B protein, the following experiments are performed. The effects on anti-TMEM106B antibodies may be measured by probing RNA or protein levels of known lysosomal proteins following administration of TMEM106B antibodies to TMEM106B-expressing cell lines. Levels of mRNA of various lysosomal proteins are analyzed by RNA-seq; lysosomal protein levels are determined by label-free quantitation liquid chromatography mass spectrometry (LFQ-LCMS) as described previously (Klein et al. 2017, Neuron 95, 281-296) or by other equivalent approaches.

Example 22: The Effect of Anti-TMEM106B Antibodies on Lysosomal Expression Patterns in a Mouse Model The effects of anti-TMEM106B antibodies on various lysosomal protein expression patterns may be also measured by probing RNA or protein levels of known lysosomal proteins following administration of anti-TMEM106B antibodies to either wildtype TMEM106B+ or TMEM106B BAC transgenic mice. Levels of TMEM106B or other lysosomal protein mRNA may be analyzed by RNA-seq; lysosomal protein levels may be quantified by label-free quantitation liquid chromatography mass spectrometry (LFQ-LCMS) as described previously (Klein et al. 2017, Neuron 95, 281-296) or by other equivalent approaches.

Example 23: The Effect of Anti-TMEM106B Antibodies on Lysosomal Expression Patterns in a Reporter Cell Line The effects of anti-TMEM106B antibodies on various lysosomal expression patterns may also be measured in a luciferase reporter cell assay. Recent reports (Kundu et al., 2016; Nature Commun. 2018; 9:2731) indicated that increased levels of TMEM106B-induced expression of lysosomal genes in the coordinated lysosomal expression and regulation (CLEAR) pathway in lung cancer cells and patient samples. Presumably, this expression acts through the TFEB-CLEAR axis, as TFEB is the master transcriptional regulator of the CLEAR pathway. A 4× CLEAR luciferase reporter cell line has been generated previously (Cortes et al Nat Neurosci. 2014 September; 17 (9): 1180-9). A similar method is used to generate a reporter cell line to measure changes in CLEAR pathway activation upon TMEM106b knock-down, over-expression, or anti-TMEM106B antibody treatment.

Example 24: The Effect of Anti-TMEM106B Antibodies on Pathology Caused by Progranulin Knockout in an FTLD Mouse Model Progranulin (GRN) knockout mice are the closest animal model available for human GRN-dependent FTLD. This mouse model recapitulates several of the phenotypes of this disorder. The mice show progressive development of lysosomal abnormalities, lipofuscin accumulation, retinal degeneration, frontotemporal dementia-like behavior, and neuropathology. The mice also display enhanced activation of microglia and astrocytes, and ubiquitination and cytoplasmic accumulation of phosphorylated transactivation response element DNA binding protein-43 (TDP-43) in hippocampal and thalamic neurons. By eighteen months of age, the mice demonstrate impaired spatial learning and memory. Treatment of these mice with anti-TMEM106B antibodies would be expected to ameliorate the various phenotypes and aspects of this disorder.

GRN-/- mice are grown to 6-12 months, and anti-TMEM106B antibodies are injected via IV weekly for 14 weeks. At various timepoints, the mice are assayed for behavioral and phenotypic abnormalities known to be caused by granulin knockout, which are measured using assays such as Open Field Test or Elevated Water Maze. Successful treatment is associated with either improved performance, or a slower rate of decline in behavioral assays. In addition, the postmortem brains of these mice are examined for microgliosis, lysosomal protein levels, general lysosomal activity, TDP-43 aggregates, and lipofuscin accumulation in neurons, PGRN homozygous mice are also tested in a similar fashion to characterize the effect of anti-TMEM106B antibodies on their behavior and lysosomal phenotypes, which are less severe than that observed in the knockout mouse.

Example 25: The Effect of Anti-TMEM106B Antibodies in Animal Models of Aging, Seizures, Spinal Cord Injury, Retinal Dystrophy, Frontotemporal Dementia, and Alzheimer's Disease The therapeutic utility of anti-TMEM106B antibodies are also tested in animal models of various disorders, such as, for example, animal models of aging, seizures, spinal cord injury, retinal dystrophy, frontotemporal dementia, and Alzheimer disease, as previously described (e.g., Beattie, M S et al., (2002) Neuron 36, 375-386; Volosin, M et al., (2006) J. Neurosci. 26, 7756-7766; Nykjaer, A et al., (2005) Curr. Opin. Neurobiol. 15, 49-57; Jansen, P et al., (2007) Nat. Neurosci. 10, 1449-1457; Volosin, M et al., (2008) J. Neurosci. 28, 9870-9879; Fahnestock, M et al., (2001) Mol. Cell Neurosci. 18, 210-220; Nakamura, K et al., (2007) Cell Death. Differ. 14, 1552-1554; Yune, T et al., (2007) Brain Res. 1183, 32-42; Wei, Y et al., (2007) Neurosci. Lett. 429, 169-174; Provenzano, M J et al., (2008) Laryngoscope 118, 87-93; Nykjaer, A et al., (2004) Nature 427, 843-848; Harrington, A W et al., (2004) Proc. Natl. Acad. Sci. U.S.A. 101, 6226-6230; Teng, H K et al., (2005) J. Neurosci. 25, 5455-5463; Jansen, P et al., (2007) Nat. Neurosci. 10, 1449-1457; Volosin, M et al., (2008) J. Neurosci. 28, 9870-9879; Fan, Y J et al., (2008) Eur. J. Neurosci. 27, 2380-2390;

Al-Shawi, R et al., (2008) Eur. J. Neurosci. 27, 2103-2114; and Yano, H et al., (2009) J. Neurosci. 29, 14790-14802).

Using any one of these animal models, an anti-TMEM106B antibody is administered to the animal in various amounts and over various periods of time. At various timepoints thereafter, the animals are assayed for improvements in behavioral and phenotypic abnormalities associated with each specific animal model of human disease. Successful treatment is associated with either improved performance, or a slower rate of decline in behavioral assays.

Example 26: Antibody Humanization

Antibody humanization is used to transform antibodies generated in a different species to best resemble a human antibody through sequence and structural relationships in order to prevent immunogenicity in human administration. Antibodies from different species share characteristic sequence and structural features that allow the grafting of the specificity-determining regions (SDRs) of the non-human antibody onto a human antibody framework. This results in retention of the specificity of the non-human antibody. The humanization process involves identification of the non-human antibody sequence and features, including the framework regions and SDRs. The following criteria are used to humanize an antibody: 1) percent similarity in framework regions between non-human and known human antibodies, 2) length similarity in SDRs between non-human and known human antibodies, 3) genes used to generate the framework regions of the human antibody, and 4) pervious use of human antibody frameworks in humanizations and as therapeutics. Similarly, in framework regions and SDR lengths are important because differences can generate structural differences in the antibody that can alter the specificity of the antibody. Specific genes used to generate the framework of human antibodies are known to be beneficial or detrimental to the stability or specificity of the antibody and are selectively used or avoided, accordingly. Lastly, previously successful humanization frameworks, including those used in human therapeutics, which are well-tolerated with good half-lives, are likely candidates for future successful humanizations.

Various methods can be used for antibody humanization. For example, the heavy chain variable region (VH) and the light chain variable region (VL) sequences of an anti-TMWM106B antibody of the present disclosure is used as input to the IgBLAST program on the NCBI website (Ye et al, Nucleic Acids Res, 2013, 41: W34-W40). IgBLAST takes a murine VH or VL sequence and compares it to a library of known human germline sequences. The databases to use are IMGT human VH genes (F+ORF, 273 germline sequences) and IMGT human LVkappa genes (F+ORF, 74 germline sequences). An appropriate VH germline and joining region (J gene) and an appropriate VL germline and joining region (J gene) are chosen as good acceptor sequences. Complementary determining regions (CDRs) for the antibody VH and VH are defined according to AbM definition (AbM antibody modeling software). Alteration of human germline framework (i.e., non-CDR residues in the VH and VL) positions to corresponding parental murine sequences may be required to optimize binding to the humanized antibody.

What is claimed is:

1. An isolated nucleic acid comprising a nucleic acid sequence encoding an antibody that binds to human TMEM106B, wherein the antibody comprises a heavy chain variable region and a light chain variable region, wherein the heavy chain variable region and light chain variable region comprise:

(a) an HVR-H1, HVR-H2, HVR-H3, HVR-L1, HVR-L2, and HVR-L3 comprising the amino acid sequences of SEQ ID NOs: 4, 37, 80, 122, 162, and 187, respectively;

(b) an HVR-H1, HVR-H2, HVR-H3, HVR-L1, HVR-L2, and HVR-L3 comprising the amino acid sequences of SEQ ID NOs: 5, 38, 81, 123, 163, and 188, respectively;

(c) an HVR-H1, HVR-H2, HVR-H3, HVR-L1, HVR-L2, and HVR-L3 comprising the amino acid sequences of SEQ ID NOs: 11, 44, 87, 123, 169, and 188, respectively;

(d) an HVR-H1, HVR-H2, HVR-H3, HVR-L1, HVR-L2, and HVR-L3 comprising the amino acid sequences of SEQ ID NOs: 12, 45, 88, 129, 170, and 194, respectively;

(e) an HVR-H1, HVR-H2, HVR-H3, HVR-L1, HVR-L2, and HVR-L3 comprising the amino acid sequences of SEQ ID NOs: 13, 46, 89, 130, 171, and 195, respectively;

(f) an HVR-H1, HVR-H2, HVR-H3, HVR-L1, HVR-L2, and HVR-L3 comprising the amino acid sequences of SEQ ID NOs: 14, 47, 90, 131, 170, and 196, respectively;

(g) an HVR-H1, HVR-H2, HVR-H3, HVR-L1, HVR-L2, and HVR-L3 comprising the amino acid sequences of SEQ ID NOs: 15, 48, 91, 132, 172, and 197, respectively;

(h) an HVR-H1, HVR-H2, HVR-H3, HVR-L1, HVR-L2, and HVR-L3 comprising the amino acid sequences of SEQ ID NOs: 6, 53, 96, 136, 175, and 201, respectively;

(i) an HVR-H1, HVR-H2, HVR-H3, HVR-L1, HVR-L2, and HVR-L3 comprising the amino acid sequences of SEQ ID NOs: 14, 54, 97, 137, 176, and 202, respectively;

(j) an HVR-H1, HVR-H2, HVR-H3, HVR-L1, HVR-L2, and HVR-L3 comprising the amino acid sequences of SEQ ID NOs: 19, 55, 98, 138, 169, and 203, respectively;

(k) an HVR-H1, HVR-H2, HVR-H3, HVR-L1, HVR-L2, and HVR-L3 comprising the amino acid sequences of SEQ ID NOs: 11, 58, 101, 138, 169, and 207, respectively;

(l) an HVR-H1, HVR-H2, HVR-H3, HVR-L1, HVR-L2, and HVR-L3 comprising the amino acid sequences of SEQ ID NOs: 14, 64, 107, 146, 161, and 202, respectively;

(m) an HVR-H1, HVR-H2, HVR-H3, HVR-L1, HVR-L2, and HVR-L3 comprising the amino acid sequences of SEQ ID NOs: 25, 67, 110, 149, 161, and 196, respectively;

(n) an HVR-H1, HVR-H2, HVR-H3, HVR-L1, HVR-L2, and HVR-L3 comprising the amino acid sequences of SEQ ID NOs: 26, 68, 111, 150, 181, and 214, respectively;

(o) an HVR-H1, HVR-H2, HVR-H3, HVR-L1, HVR-L2, and HVR-L3 comprising the amino acid sequences of SEQ ID NOs: 27, 69, 112, 151, 181, and 215, respectively;

(p) an HVR-H1, HVR-H2, HVR-H3, HVR-L1, HVR-L2, and HVR-L3 comprising the amino acid sequences of SEQ ID NOs: 29, 71, 111, 153, 181, and 214, respectively;

(q) an HVR-H1, HVR-H2, HVR-H3, HVR-L1, HVR-L2, and HVR-L3 comprising the amino acid sequences of SEQ ID NOs: 33, 75, 117, 156, 161, and 220, respectively;

(r) an HVR-H1, HVR-H2, HVR-H3, HVR-L1, HVR-L2, and HVR-L3 comprising the amino acid sequences of SEQ ID NOs: 9, 42, 85, 127, 167, and 192, respectively;

(s) an HVR-H1, HVR-H2, HVR-H3, HVR-L1, HVR-L2, and HVR-L3 comprising the amino acid sequences of SEQ ID NOs: 7, 40, 83, 125, 165, and 190, respectively;
(t) an HVR-H1, HVR-H2, HVR-H3, HVR-L1, HVR-L2, and HVR-L3 comprising the amino acid sequences of SEQ ID NOs: 9, 60, 103, 143, 167, and 192, respectively;
(u) an HVR-H1, HVR-H2, HVR-H3, HVR-L1, HVR-L2, and HVR-L3 comprising the amino acid sequences of SEQ ID NOs: 21, 61, 104, 144, 169, and 209, respectively;
(v) an HVR-H1, HVR-H2, HVR-H3, HVR-L1, HVR-L2, and HVR-L3 comprising the amino acid sequences of SEQ ID NOs: 16, 50, 93, 134, 172, and 199, respectively; or
(w) an HVR-H1, HVR-H2, HVR-H3, HVR-L1, HVR-L2, and HVR-L3 comprising the amino acid sequences of SEQ ID NOs: 13, 46, 89, 141, 171, and 206, respectively; or
(x) an HVR-H1, HVR-H2, HVR-H3, HVR-L1, HVR-L2, and HVR-L3 comprising the amino acid sequences of SEQ ID NOs: 22, 62, 105, 145, 161, and 210, respectively.

2. A vector comprising the nucleic acid of claim 1.
3. An isolated host cell comprising the vector of claim 2.
4. A method of producing an antibody that binds to human TMEM106B, comprising culturing the cell of claim 3 so that the antibody is produced.
5. The method of claim 4, further comprising recovering the antibody produced by the cell.
6. The nucleic acid of claim 1, wherein the heavy chain variable region and light chain variable region comprise the amino acid sequences of:
(a) SEQ ID NOs: 226 and 270, respectively;
(b) SEQ ID NOs: 227 and 271, respectively;
(c) SEQ ID NOs: 233 and 277, respectively;
(d) SEQ ID NOs: 234 and 278, respectively;
(e) SEQ ID NOs: 235 and 279, respectively;
(f) SEQ ID NOs: 236 and 280, respectively;
(g) SEQ ID NOs: 237 and 281, respectively;
(h) SEQ ID NOs: 242 and 286, respectively;
(i) SEQ ID NOs: 243 and 287, respectively;
(j) SEQ ID NOs: 244 and 289, respectively;
(k) SEQ ID NOs: 247 and 293, respectively;
(l) SEQ ID NOs: 253 and 299, respectively;
(m) SEQ ID NOs: 256 and 302, respectively;
(n) SEQ ID NOs: 257 and 303, respectively;
(o) SEQ ID NOs: 258 and 304, respectively;
(p) SEQ ID NOs: 260 and 306, respectively;
(q) SEQ ID NOs: 264 and 310, respectively;
(r) SEQ ID NOs: 231 and 275, respectively;
(s) SEQ ID NOs: 229 and 273, respectively;
(t) SEQ ID NOs: 249 and 295, respectively;
(u) SEQ ID NOs: 250 and 296, respectively;
(v) SEQ ID NOs: 239 and 283, respectively;
(w) SEQ ID NOs: 235 and 292, respectively; or
(x) SEQ ID NOs: 251 and 297, respectively.

7. The nucleic acid of claim 1, wherein the antibody is a monoclonal antibody.
8. The nucleic acid of claim 1, wherein the antibody is of the IgG class, the IgM class, or the IgA class.
9. The nucleic acid of claim 8, wherein the antibody is of the IgG class and has an IgG1, IgG2, or IgG4 isotype.
10. The nucleic acid of claim 1, wherein the antibody is an antibody fragment.
11. The nucleic acid of claim 10, wherein the fragment is a Fab, Fab', Fab'-SH, F (ab')2, Fv or scFv fragment.
12. The nucleic acid of claim 1, wherein the antibody further comprises an antigen facilitating transport across the blood-brain-barrier selected from the group consisting of transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30(A), a protein transduction domain, TAT, Syn-B, penetratin, a poly-arginine peptide, an angiopeptide, basigin, Glut1, CD98hc, and ANG1005.
13. The nucleic acid of claim 1, wherein the heavy chain variable region comprises:
an HVR-H1 comprising the amino acid sequence of SEQ ID NO:11;
an HVR-H2 comprising the amino acid sequence of SEQ ID NO:44; and
an HVR-H3 comprising the amino acid sequence of SEQ ID NO:87; and
wherein the light chain variable region comprises:
an HVR-L1 comprising the amino acid sequence of SEQ ID NO:123;
an HVR-L2 comprising the amino acid sequence of SEQ ID NO:169; and
an HVR-L3 comprising the amino acid sequence of SEQ ID NO:188.
14. The nucleic acid of claim 13, wherein the heavy chain variable region and light chain variable region comprise the amino acid sequences of SEQ ID NOs: 233 and 277, respectively.
15. The nucleic acid of claim 14, wherein the antibody is of the IgG class and has an IgG1 isotype.
16. The nucleic acid of claim 13, wherein the antibody further comprises an antigen facilitating transport across the blood-brain-barrier selected from the group consisting of transferring receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30 (A), a protein transduction domain, TAT, Syn-B, penetratin, a poly-arginine peptide, an angiopeptide, basigin, Glut1, CD98hc, and ANG1005.
17. The nucleic acid of claim 14, wherein the antibody further comprises an antigen facilitating transport across the blood-brain-barrier selected from the group consisting of transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30 (A), a protein transduction domain, TAT, Syn-B, penetratin, a poly-arginine peptide, an angiopeptide, basigin, Glut1, CD98hc, and ANG1005.
18. The nucleic acid of claim 1, wherein the heavy chain variable region comprises:
an HVR-H1 comprising the amino acid sequence of SEQ ID NO:5;
an HVR-H2 comprising the amino acid sequence of SEQ ID NO:38; and
an HVR-H3 comprising the amino acid sequence of SEQ ID NO:81; and
wherein the light chain variable region comprises:
an HVR-L1 comprising the amino acid sequence of SEQ ID NO:123;
an HVR-L2 comprising the amino acid sequence of SEQ ID NO: 163; and an HVR-L3 comprising the amino acid sequence of SEQ ID NO: 188.

19. The nucleic acid of claim 18, wherein the heavy chain variable region and light chain variable region comprise the amino acid sequences of SEQ ID NOs: 227 and 271, respectively.

20. The nucleic acid of claim 19, wherein the antibody is of the IgG class and has an IgG1 isotype.

21. The nucleic acid of claim 18, wherein the antibody further comprises an antigen facilitating transport across the blood-brain-barrier selected from the group consisting of transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30 (A), a protein transduction domain, TAT, Syn-B, penetratin, a poly-arginine peptide, an angiopeptide, basigin, Glut1, CD98hc, and ANG1005.

22. The nucleic acid of claim 19, wherein the antibody further comprises an antigen facilitating transport across the blood-brain-barrier selected from the group consisting of transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30 (A), a protein transduction domain, TAT, Syn-B, penetratin, a poly-arginine peptide, an angiopeptide, basigin, Glut1, CD98hc, and ANG1005.

23. The nucleic acid of claim 1,
wherein the heavy chain variable region comprises:
   an HVR-H1 comprising the amino acid sequence of SEQ ID NO:11;
   an HVR-H2 comprising the amino acid sequence of SEQ ID NO:58; and
   an HVR-H3 comprising the amino acid sequence of SEQ ID NO:101; and wherein the light chain variable region comprises:
   an HVR-L1 comprising the amino acid sequence of SEQ ID NO:138;
   an HVR-L2 comprising the amino acid sequence of SEQ ID NO:169; and
   an HVR-L3 comprising the amino acid sequence of SEQ ID NO:207.

24. The nucleic acid of claim 23, wherein the heavy chain variable region and light chain variable region comprise the amino acid sequences of SEQ ID NOs: 247 and 293, respectively.

25. The nucleic acid of claim 24, wherein the antibody is of the IgG class and has an IgG1 isotype.

26. The nucleic acid of claim 23, wherein the antibody further comprises an antigen facilitating transport across the blood-brain-barrier selected from the group consisting of transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30 (A), a protein transduction domain, TAT, Syn-B, penetratin, a poly-arginine peptide, an angiopeptide, basigin, Glut1, CD98hc, and ANG1005.

27. The nucleic acid of claim 24, wherein the antibody further comprises an antigen facilitating transport across the blood-brain-barrier selected from the group consisting of transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30 (A), a protein transduction domain, TAT, Syn-B, penetratin, a poly-arginine peptide, an angiopeptide, basigin, Glut1, CD98hc, and ANG1005.

\* \* \* \* \*